(12) United States Patent
Farady et al.

(10) Patent No.: US 12,168,012 B2
(45) Date of Patent: Dec. 17, 2024

(54) NLRP3 INFLAMMASOME INHIBITORS

(71) Applicant: Novartis AG, Basel (CH)

(72) Inventors: Christopher Farady, Basel (CH); Nina Gommermann, Lörrach (DE); Philipp Janser, Basel (CH); Angela MacKay, Basel (CH); Henri Mattes, Michelbach le Bas (FR); Nikolaus Johannes Stiefl, Lörrach (DE); Juraj Velcicky, Basel (CH)

(73) Assignee: Novartis AG, Basel (CH)

( * ) Notice: Subject to any disclaimer, the term of this patent is extended or adjusted under 35 U.S.C. 154(b) by 779 days.

(21) Appl. No.: 17/259,252

(22) PCT Filed: Jul. 23, 2019

(86) PCT No.: PCT/IB2019/056278
§ 371 (c)(1),
(2) Date: Jan. 11, 2021

(87) PCT Pub. No.: WO2020/021447
PCT Pub. Date: Jan. 30, 2020

(65) Prior Publication Data
US 2021/0308140 A1    Oct. 7, 2021

(30) Foreign Application Priority Data

Jul. 25, 2018 (EP) ................................ 18185580
May 17, 2019 (EP) ................................ 19175246

(51) Int. Cl.
| | | |
|---|---|---|
| A61K 31/53 | (2006.01) | |
| A61K 31/616 | (2006.01) | |
| A61K 45/06 | (2006.01) | |
| C07D 495/14 | (2006.01) | |
| C07D 513/14 | (2006.01) | |
| C07D 515/14 | (2006.01) | |

(52) U.S. Cl.
CPC ............ *A61K 31/53* (2013.01); *A61K 31/616* (2013.01); *A61K 45/06* (2013.01); *C07D 495/14* (2013.01); *C07D 513/14* (2013.01); *C07D 515/14* (2013.01)

(58) Field of Classification Search
CPC ...... A61K 31/53; A61K 31/616; A61K 45/06; A61K 2300/00; C07D 495/14; C07D 513/14; C07D 515/14; A61P 29/00; A61P 37/00
See application file for complete search history.

(56) References Cited

FOREIGN PATENT DOCUMENTS

| EP | 3272739 A1 | 1/2018 |
|---|---|---|
| WO | 2009008906 A2 | 1/2009 |
| WO | 2017/100726 A1 | 6/2017 |
| WO | 2017/184746 A1 | 10/2017 |
| WO | 2019/025467 A1 | 2/2019 |
| WO | 2019/034690 A1 | 2/2019 |
| WO | 2019/034693 A1 | 2/2019 |
| WO | 2019/092170 A1 | 5/2019 |

OTHER PUBLICATIONS

Kim et al., Discovery of thienopyrrolotriazine derivatives to protect mitochondrial function against AÎ²-induced neurotoxicity, Eur. J. Med. Chem., 141, pp. 240-256 (Year: 2017).*
Singh, et al., TNF-α and IL-6 inhibitors: Conjugates of N-substituted indole and aminophenylmorpholin-3-one as anti-inflammatory agents, European Journal of Medicinal Chemistry, Sep. 4, 2017, 92-103, 140.
Bian et al., "Discovery of NAD(P)H: quinone oxidoreductase 1 (NQO1) inhibitors with novel chemical scaffolds by shape-based virtual screening combined with cascade docking"; RSC Advances. 5(61):49471-49479 (2015).
Gupta et al., "Discovery of dual binding site acetylcholinesterase inhibitors identified by pharmacophore modeling and sequential virtual screening techniques," Bioorg Med Chem Lett. 21(4):1105-12 (2011).
Kim et al., "Discovery of thienopyrrolotriazine derivatives to protect mitochondrial function against Aβ-induced neurotoxicity," Eur J Med Chem. 41:240-56 (2017).
International Search Report and Written Opinion for International Patent Application No. PCT/IB2019/056278 mailed Nov. 5, 2019 (10 pages).
Ilyin et al., "Synthesis of heterocyclic compounds possessing the 4H-thieno[3,2-b]pyrrole moiety," J Comb Chem. 9(1):96-106 (2007).
Coll et al. "A small-molecule inhibitor of the NLRP3 inflammasome for the treatment of inflammatory diseases," Nat Med 21(3):248-55 (2015).

(Continued)

*Primary Examiner* — Jeffrey S Lundgren
*Assistant Examiner* — Alexander K. Showalter
(74) *Attorney, Agent, or Firm* — Timothy P. O'Dea

(57) ABSTRACT

The present invention relates to novel thienopyrrolotriazinacetamide compounds of Formula (I): wherein $R^1$, $R^2$ and $R^3$ are defined herein, which inhibit NOD-like receptor protein 3 (NLRP3) inflammasome activity. The invention further relates to the processes for their preparation, pharmaceutical compositions and medicaments containing them, and their use in the treatment of diseases and disorders mediated by NLRP3.

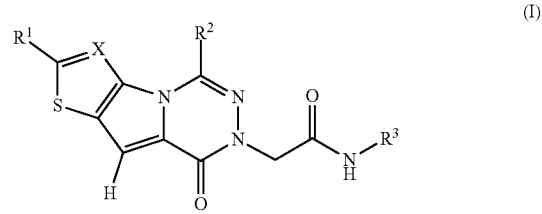

19 Claims, No Drawings

(56) References Cited

OTHER PUBLICATIONS

Cheung et al., "Discovery of Small Molecule Splicing Modulators of Survival Motor Neuron-2 (SMN2) for the Treatment of Spinal Muscular Atrophy (SMA)," J Med Chem. 61(24):11021-11036 (2018).

* cited by examiner

NLRP3 INFLAMMASOME INHIBITORS

FIELD OF THE INVENTION

The present invention relates to novel thienopyrrolotriazinacetamide compounds that are useful as inhibitors of NOD-like receptor protein 3 (NLRP3) inflammasome pathway. The present invention also relates to processes for the preparation of said compounds, pharmaceutical compositions comprising said compounds, methods of using said compounds in the treatment of various diseases and disorders, and medicaments containing them, and their use in diseases and disorders mediated by NLRP3.

BACKGROUND OF THE INVENTION

The NOD-like receptor protein 3 (NLRP3) is a protein-coding gene: the protein belongs to the family of nucleotide-binding and oligomerization domain-like receptors (NLRs) and is also known as "pyrin domain-containing protein 3" (Inoue et al., *Immunology*, 2013, 139, 11-18). This gene encodes a protein containing a pyrin domain, a nucleotide-binding site domain (NBD), and a leucine-rich repeat (LRR) motif. In response to sterile inflammatory danger signals, NLRP3 interacts with an adapter protein, apoptosis-associated speck-like protein (ASC) and procaspase-1 to form the NLRP3 inflammasome. NLRP3 inflammasome activation then leads to the release of the inflammatory cytokines IL-1β and IL-18, and when dysregulated, can drive pathology in a number of disease settings.

NLRP3 inflammasome activation normally requires two steps. The first step involves a priming signal in which pathogen activated molecular patterns (PAMPs) or danger-activated molecular patterns (DAMPs) are recognized by Toll-like receptors, leading to nuclear factor kappa B (NF-κB)-mediated signaling, which in turn up-regulates transcription of inflammasome-related components, including inactive NLRP3 and proIL-1β (pro-interleukin-1β) (Bauernfeind et al., *J. Immunol.* 2009, 183, 787-791; Franchi et al., *Nat. Immunol.* 2012, 13, 325-332; Franchi et al., *J. Immunol.* 2014, 193, 4214-4222). The second step is the oligomerization of NLRP3 and subsequent assembly of NLRP3, ASC, and procaspase-1 into an inflammasome complex. This triggers the transformation of procaspase-1 to caspase-1, and the production and secretion of mature IL-1β and IL-18 (Kim et al., *J. Inflamm.* 2015, 12, 41; Ozaki et al., *J. Inflamm. Res.* 2015, 8, 15-27; Rabeony et al., *Eur. J. Immunol.* 2015, 45, 2847-2857).

NLRP3 inflammasome activation has been linked to various inflammasome-related diseases/disorders, immune diseases, inflammatory diseases, auto-immune disease and auto-inflammatory diseases, for example, autoinflammatory fever syndrome such as cryopyrin-associated periodic syndrome (CAPS) (Mortimer et al., *Nature Immunol.* 2016, 17(10), 1176-1188); sickle cell disease; systemic lupus erythematosus (SLE); liver related diseases/disorders such as chronic liver disease, viral hepatitis, non-alcoholic steatohepatitis (NASH), alcoholic steatohepatitis, and alcoholic liver disease (Petrasek et al., *J. Clin. Invest.* 2012, 122, 3476-89; Petrasek et al., *Nat. Rev. Gastroenterol. Hepatol.* 2015, 12, 387-400; Mridha et al., J. Hepatol. 2017, 66, 1037-46); inflammatory arthritis related disorders, such as gout, pseudogout (chondrocalcinosis), osteoarthritis (Ridker et al., *N. Engl. J. Med.* 2017, 377, 1119-31), and rheumatoid arthritis (Mathews et al., *Ann. Rheum. Dis.* 2014, 73, 1202-10), acute or chronic arthropathy; kidney related diseases such as hyperoxaluria (Knauf et al., *Kidney Int.* 2013, 84, 895-901), lupus nephritis, hypertensive nephropathy (Krishnan et al., *Br. J. Pharmacol.* 2016, 173, 752-65), hemodialysis related inflammation and diabetic nephropathy which is a kidney-related complication of diabetes (Type 1, Type 2 and mellitus diabetes), also called diabetic kidney disease (Shahzad et al., *Kidney Int.* 2015, 87, 74-84). Emerging studies have revealed the involvement of the increased production of IL-1β and IL-18 by the NLRP3 inflammasome can contribute to the onset and progression of various diseases such as neuroinflammation-related disorders, e.g. brain infection, acute injury, multiple sclerosis, Alzheimer's disease, and neurodegenerative diseases (Shao et al., *Front. Pharmacol.* 2015, 6, 262); cardiovascular/metabolic disorders/diseases, e.g. cardiovascular risk reduction (CvRR), atherosclerosis, type I and type II diabetes and related complications (e.g. nephropathy, retinopathy), peripheral artery disease (PAD), acute heart failure and hypertension (Ridker et al., *N. Engl. J. Med.* 2017, 377, 1119-31; Vandanmasgar et al., *Nat. Med.* 2011, 17, 179-88; Hu et al., *Proc. Natl. Acad. Sci.* 2015, 112, 11318-23; Antonopoulos et al., *Curr. Opin. Pharmacol.* 2017, 39, 1-8; Toldo et al., *Nat. Rev. Cardiol.* 2018, 15, 203-214); wound healing and scar formation; inflammatory skin diseases, e.g. acne, hidradenitis suppurativa (Sweeney et al., *Br. J. Dermatol.* 2015, 173, 1361), asthma, sarcoidosis, age-related macular degeneration; cancer related diseases/disorders, e.g. myeloproliferative neoplasms, leukemias, myelodysplastic syndromes (MDS), myelofibrosis, lung cancer, colon cancer (Ridker et al., *Lancet* 2017, 390, 1833-42; Derangere et al., *Cell. Death Differ.* 2014, 21, 1914-24, Gelfo et al., *Oncotarget* 2016, 7, 72167-83, Baiorka et al., *Blood* 2016, 128, 2960-75; Carey et al., *Cell. Rep.* 2017, 18, 3204-18). Those diseases/disorders that are immune or inflammatory in nature usually are difficult to diagnose or treat efficiently. Most treatments include treating of the symptoms, slowing down the progression of the disease/disorder, change in lifestyle and surgery as a last resort (e.g., open heart surgery for advance forms of atherosclerosis). Recent studies have linked mitochondrial dysfunction and NLRP3 activation in neuroinflammation related diseases such as Parkinson's (Sarkar et al., *npj Parkinson's disease* 2017, 3:30; Zhou et al., *Nature*, 2011, 469, 221). One of the major problems associated with the mitochondrial modulators is their poor metabolic stability; thus there is a need for selective and stable inhibitors in neuroinflammation of this nature (Lee et al., *Eur. J. Org. Chem.* 2017, 141, 240).

Therefore, there is a need for inhibitors of the NLRP3 inflammasome pathway to provide new and/or alternative treatments for these inflammasome-related diseases/disorders and others such as autoinflammatory fever syndrome cryopyrin-associated periodic syndrome (e.g. CAPS), sickle cell disease, chronic liver disease, nonalcoholic steatohepatitis (NASH), gout, hyperoxaluria, pseudogout (chondrocalcinosis), Type I/Type II diabetes and related complications (e.g. nephropathy, retinopathy), neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

SUMMARY OF THE INVENTION

The invention provides compounds or pharmaceutically acceptable salts thereof, pharmaceutical compositions thereof and combination thereof, which compounds inhibit the NLRP3 inflammasome pathway. The invention further provides methods of treating, or preventing, disease and/or disorders related to NLRP3, or a pharmaceutically acceptable salt thereof, comprising administering to a subject in need thereof an effective amount of the compounds of the invention.

Various embodiments of the invention are described herein.

Within certain aspects, provided herein is a compound of formula (I), or a pharmaceutically acceptable salt thereof:

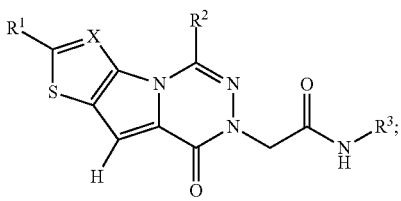

(I)

wherein:
R$^1$ is H, halo or methyl;
R$^2$ is ethyl substituted with OH, C$_1$-C$_4$alkoxy, or with one or more halo groups; or
R$^2$ is C$_3$-C$_6$alkyl optionally substituted with —OH, halo or C$_1$-C$_4$alkoxy; or
R$^2$ is C$_3$-C$_6$cycloalkyl;
R$^3$ is C$_2$-C$_8$alkyl optionally substituted with 1 to 3 substituents independently selected from —NH$_2$, —NH(C$_1$-C$_4$alkyl), —NHC(O)O(C$_1$-C$_4$alkyl), —NHC(O)(C$_1$-C$_4$alkyl), —OH, C$_1$-C$_4$alkoxy, haloC$_1$-C$_4$alkoxy, halo and C$_3$-C$_5$cycloalkyl which is further optionally substituted with OH or halo; or
R$^3$ is C$_3$-C$_{10}$cycloalkyl or C$_3$-C$_5$cycloalkyl-CH$_2$, each of which is optionally substituted with 1 to 3 substituents independently selected from —OH, C$_1$-C$_4$alkyl, C$_3$-C$_6$cycloalkyl, halo, —OC(O)(C$_1$-C$_4$alkyl), —CO$_2$H, haloC$_1$-C$_4$alkyl, —C(O)O(C$_1$-C$_4$alkyl), hydroxyC$_1$-C$_4$alkyl, C$_1$-C$_4$alkoxy, haloC$_1$-C$_4$alkoxy, —NH$_2$, —NH(C$_1$-C$_4$alkyl); or
R$^3$ is mono or bicyclic aryl, or a mono or bicyclic heteroaryl, each of which is optionally substituted with 1 to 3 substituents independently selected from —OH, C$_1$-C$_4$alkyl, C$_3$-C$_6$cycloalkyl, halo, —OC(O)(C$_1$-C$_4$alkyl), haloC$_1$-C$_4$alkyl, —C(O)O(C$_1$-C$_4$alkyl), —CO$_2$H, hydroxyC$_1$-C$_4$alkyl, C$_1$-C$_4$alkoxy, haloC$_1$-C$_4$alkoxy, —NH$_2$, —SO$_2$NH$_2$, —SO$_2$NH(C$_1$-C$_4$alkyl), —NHSO$_2$(C$_1$-C$_4$alkyl), —NH(C$_1$-C$_4$alkyl), —C(O)NH$_2$, C(O)C$_1$-C$_4$alkyl; or
R$^3$ is a mono or bicyclic heterocyclyl optionally substituted with 1 to 3 substituents independently selected from —OH, oxo, C$_3$-C$_6$cycloalkyl, halo, —C(O)O—C$_1$-C$_4$alkyl, —C(O)C$_1$-C$_4$alkyl, and C$_1$-C$_4$alkyl which is further optionally substituted with 1 to 4 substituents independently selected from C$_3$-C$_6$cycloalkyl, halo, C$_1$-C$_4$alkoxy, haloC$_1$-C$_4$alkoxy and —OH;
X is N or CH.

In another aspect, the invention provides a pharmaceutical composition comprising a therapeutically effective amount of a compound according to the definition of compound of formula (I), or subformulae thereof, as disclosed herein, or a pharmaceutically acceptable salt thereof, and one or more pharmaceutically acceptable carriers. The pharmaceutical composition is useful in the treatment of diseases and/or disorders related to the NLRP3 activity.

In another aspect, the invention provides a combination, in particular a pharmaceutical combination, comprising a therapeutically effective amount of a compound according to the definition of compound of formula (I), or subformulae thereof, as disclosed herein, or a pharmaceutically acceptable salt thereof, and one or more therapeutic agents.

In another aspect, the invention provides a combination, in particular a pharmaceutical combination, as disclosed herein, for use as a medicament.

In another aspect, the invention provides a compound of formula (I), or subformulae thereof, as disclosed herein, or a pharmaceutically acceptable salt thereof, for use in the treatment of a disease or disorder in which the NLRP3 signaling contributes to the pathology, and/or symptoms, and/or progression, of said disease or disorder.

In another aspect, the invention provides a method of treating a disease or disorder in which the NLRP3 signaling contributes to the pathology, and/or symptoms, and/or progression, of said disease or disorder, comprising administering a therapeutically effective amount of a compound of formula (I), or subformulae thereof, as disclosed herein, or a pharmaceutically acceptable salt thereof.

In another aspect, the invention provides a method of inhibiting the NLRP3 inflammasome activity in a subject in need thereof, the method comprises administering to the subject in need thereof a therapeutically effective amount of a compound of formula (I), or subformulae thereof, as disclosed herein, or a pharmaceutically acceptable salt thereof.

Another aspect of the invention, relates to the use of a compound of formula (I), or subformulae thereof, as disclosed herein, or a pharmaceutically acceptable salt thereof, as a medicament, in particular for inhibiting NLRP3 inflammasome activity.

Another aspect of the invention, relates to a compound of formula (I), or subformulae thereof, as disclosed herein, or a pharmaceutically acceptable salt thereof, for use as a medicament, in particular for inhibiting NLRP3 inflammasome activity.

Another aspect of the invention, also provides a compound of formula (I), or subformulae thereof, as disclosed herein, or a pharmaceutically acceptable salt thereof, for use in the treatment of a disease or disorder selected from inflammasome-related disease/disorders, immune diseases, inflammatory diseases, auto-immune diseases, or auto-inflammatory diseases.

DETAILED DESCRIPTION OF THE INVENTION

The invention therefore provides a compound of Formula (I):

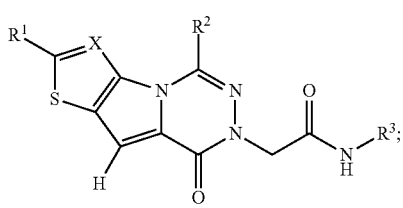

(I)

wherein
R$^1$ is H, halo or methyl;
R$^2$ is ethyl substituted with —OH, C$_1$-C$_4$alkoxy, or with one or more halo groups; or
R$^2$ is C$_3$-C$_6$alkyl optionally substituted with —OH, halo or C$_1$-C$_4$alkoxy; or
R$^2$ is C$_3$-C$_6$cycloalkyl;
R$^3$ is C$_2$-C$_8$alkyl optionally substituted with 1 to 3 substituents independently selected from —NH$_2$, —NH(C$_1$-C$_4$alkyl), —NHC(O)O(C$_1$-C$_4$alkyl), —NHC(O)(C$_1$-C$_4$alkyl), —OH, C$_1$-C$_4$alkoxy, haloC$_1$-C$_4$alkoxy, halo and C$_3$-C$_5$cycloalkyl which is optionally further substituted with —OH or halo; or
R$^3$ is C$_3$-C$_{10}$cycloalkyl or C$_3$-C$_5$cycloalkyl-CH$_2$, each of which is optionally substituted with 1 to 3 substituents independently selected from —OH, C$_1$-C$_4$alkyl, C$_3$-C$_6$cycloalkyl, halo, —OC(O)(C$_1$-C$_4$alkyl), haloC$_1$-C$_4$alkyl, —C(O)O(C$_1$-C$_4$alkyl), —CO$_2$H, hydroxyC$_1$-C$_4$alkyl, C$_1$-C$_4$alkoxy, haloC$_1$-C$_4$alkoxy, —NH$_2$, —NH(C$_1$-C$_4$alkyl); or
R$^3$ is mono or bicyclic aryl, or a mono or bicyclic heteroaryl, each of which is optionally substituted with 1 to 3 substituents independently selected from —OH, C$_1$-C$_4$alkyl, C$_3$-C$_6$cycloalkyl, halo, —OC(O)(C$_1$-C$_4$alkyl), haloC$_1$-C$_4$alkyl, —C(O)O(C$_1$-C$_4$alkyl), —CO$_2$H, hydroxyC$_1$-C$_4$alkyl, C$_1$-C$_4$alkoxy, haloC$_1$-C$_4$alkoxy, —NH$_2$, —SO$_2$NH$_2$, —SO$_2$NH(C$_1$-C$_4$alkyl), —NHSO$_2$(C$_1$-C$_4$alkyl), —NH(C$_1$-C$_4$alkyl), —C(O)NH$_2$, C(O)C$_1$-C$_4$alkyl; or
R$^3$ is a mono or bicyclic heterocyclyl optionally substituted with 1 to 3 substituents independently selected from —OH, oxo, C$_3$-C$_6$cycloalkyl, halo, —C(O)O—C$_1$-C$_4$alkyl, —C(O)C$_1$-C$_4$alkyl, and C$_1$-C$_4$alkyl which is further optionally substituted with 1 to 4 substituents independently selected from C$_3$-C$_6$cycloalkyl, halo, C$_1$-C$_4$alkoxy, haloC$_1$-C$_4$alkoxy and —OH;
X is N or CH.

Unless specified otherwise, the term "compounds of the present invention" refers to compounds of formula (I), and subformulae thereof, and salts thereof, as well as all stereoisomers (including diastereoisomers and enantiomers), rotamers, tautomers and isotopically labeled compounds (including deuterium substitutions), as well as inherently formed moieties.

DEFINITIONS

For purpose of interpreting this specification, the following definitions will apply unless specified otherwise and when appropriate, terms used in the singular will also include the plural and vice versa.

It must be noted that as used herein and in the appended claims, the singular forms "a", "an" and "the" include plural referents unless the context clearly dictates otherwise. Thus, for example, reference to "the compound" includes reference to one or more compounds; and so forth.

As used herein, the term "C$_2$-C$_8$alkyl" refers to a straight or branched hydrocarbon chain radical consisting solely of carbon and hydrogen atoms, containing no unsaturation, having from two to eight carbon atoms, and which is attached to the rest of the molecule by a single bond. The term "C$_1$-C$_4$alkyl" is to be construed accordingly. Examples of C$_2$-C$_8$alkyl include, but are not limited to, ethyl, n-propyl, 1-methylethyl (iso-propyl), n-butyl, n-pentyl, 1,1-dimethylethyl (tert-butyl).

As used herein, the term "C$_1$-C$_4$alkoxy" refers to a radical of the formula —OR$_a$ where R$_a$ is a C$_1$-C$_4$alkyl radical as generally defined above. Examples of "C$_1$-C$_4$alkoxy" include, but are not limited to, methoxy, ethoxy, propoxy, isopropoxy, butoxy, and isobutoxy.

As used herein, the term "C$_3$-C$_{10}$cycloalkyl" refers to a stable monocyclic, bicyclic or tricyclic saturated hydrocarbon radical consisting solely of carbon and hydrogen atoms, having from three to ten carbon atoms. C$_3$-C$_5$cycloalkyl is to be construed the same way. The term bicyclic cycloalkyl also includes spiro bicyclic cycloalkyl. A spiro bicyclic cycloalkyl refers to 2 cycloalkyl rings which are connected through a single carbon atom. Examples of monocyclic C$_3$-C$_{10}$cycloalkyl include, but are not limited to, cyclopropyl, cyclobutyl, cyclopentyl, cyclohexyl, cycloheptyl and cyclooctyl. Preferably, a monocyclic cycloalkyl is C$_3$-C$_5$cycloalkyl. Examples of bicyclic C$_3$-C$_{10}$cycloalkyl include but are not limited to, bicyclo[1.1.1]pentane, bicyclo[2.2.2]octane. Examples of spiro bicyclic C$_3$-C$_{10}$cycloalkyl include, but are not limited to, spiro[3.3]heptyl and spiro[2.2]pentyl. Examples of tricyclic C$_3$-C$_{10}$cycloalkyl include but are not limited to adamantyl.

As used herein, the term "Halogen" or "Halo" refers to bromo, chloro, fluoro or iodo.

As used herein, the term "haloC$_1$-C$_4$alkyl" refers to a C$_1$-C$_4$alkyl radical, as defined above, substituted by one or more halo radicals, as defined above. Examples of halogenC$_1$-C$_4$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

As used herein, the term "haloC$_1$-C$_4$alkoxy" refers to a C$_1$-C$_4$alkoxy radical substituted by one or more halo radicals, as defined above. Examples of haloC$_1$-C$_4$alkoxy include, but are not limited to, trifluoromethoxy, difluoromethoxy, fluoromethoxy, trichloromethoxy, and 2,2,2-trifluoroethoxy.

As used herein, the term "hydroxyC$_1$-C$_4$alkyl" refers to a C$_1$-C$_4$alkyl radical wherein one of the hydrogen atoms of the C$_1$-C$_4$alkyl radical is replaced by OH. Examples of hydroxyC$_1$-C$_4$alkyl include, but are not limited to, hydroxymethyl, 2-hydroxy-ethyl, 2-hydroxy-propyl, 3-hydroxy-propyl and 4-hydroxy-butyl.

As used herein, the term "heterocyclyl" or "heterocyclic" refers to a heterocyclic group that is saturated or partially saturated and is a monocyclic or a polycyclic ring; which has 3 to 24, preferably 4 to 16, most preferably 5 to 10 and most preferably 1 or 4 ring atoms; wherein one or more, preferably one to four, especially one or two ring atoms are a heteroatom selected from oxygen, nitrogen and sulfur (the remaining ring atoms therefore being carbon). The term heterocyclyl excludes heteroaryl. The heterocyclic group can be attached to the rest of the molecule through a heteroatom, selected from oxygen, nitrogen and sulfur, or a carbon atom. The heterocyclyl can include fused or bridged rings as well as spirocyclic rings. A spiro heterocyclyl refers to a bicyclic heterocyclic group wherein the 2 cycles are connected through a single carbon atom. For example, the term "heterocyclyl" can refer to a 5-7 monocyclic ring containing 1 or 2 heteroatoms, selected from oxygen, nitrogen and sulfur. For example, the term "heterocyclyl" can refer to a 6-10 spiro heterocyclyl. Examples of heterocyclyl include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl. A non-limiting example of a spiro heterocyclyl is 2-oxaspiro [3.3]heptyl.

As used herein, the term "heteroaryl" refers to a 5 to 8-membered aromatic monocyclic ring or bicyclic ring system, which comprises 1, 2, or 3 heteroatoms individually selected from nitrogen, oxygen and sulfur. The heteroaryl radical may be bonded via a carbon atom or heteroatom, selected from oxygen, nitrogen and sulfur. Examples of heteroaryl include, but are not limited to, furyl, pyrrolyl, thienyl, pyrazolyl, imidazolyl, indazolyl, thiazolyl, isothiazolyl, oxazolyl, isoxazolyl, triazolyl, tetrazolyl, pyrazinyl, pyridazinyl, pyrimidyl or pyridyl.

As used herein, the term "aryl" refers to an aromatic hydrocarbon group having 6-20 carbon atoms in the ring portion. Typically, aryl is monocyclic, bicyclic or tricyclic aryl having 6-20 carbon atoms. Non-limiting examples include phenyl, naphthyl. In a preferred embodiment, aryl is phenyl.

Unless specified otherwise, the term "compounds of the present invention" refers to compounds of formula (I), and subformulae thereof, and salts thereof, as well as all stereoisomers (including diastereoisomers and enantiomers), rotamers, tautomers and isotopically labeled compounds (including deuterium substitutions). The term "compounds of the (present) invention" or "a compound of the (present) invention" refers to a compound as defined in any one of embodiments mentioned below.

Various embodiments of the invention are described herein, it will be recognized that features specified in each embodiment may be combined with other specified features to provide further embodiments of the present invention.

In embodiment 1, the invention provides a compound of formula (I), or a pharmaceutically acceptable salt thereof, as described above.

In embodiment 2, the invention provides a compound of formula (I) according to embodiment 1, having a formula (II):

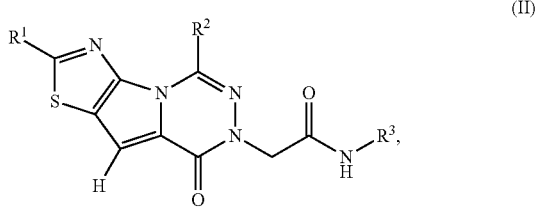

or a pharmaceutically acceptable salt thereof, wherein $R^1$ is methyl or H.

In embodiment 3, the invention provides a compound of formula (I) according to embodiment 1, having a formula (III):

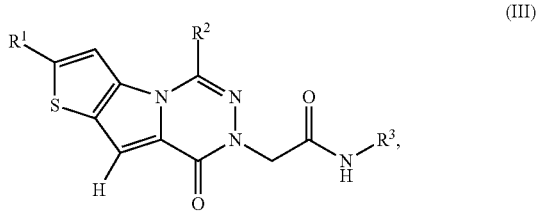

or a pharmaceutically acceptable salt thereof, wherein $R^1$ is halo or methyl.

In embodiment 4, the invention provides a compound of any one of formulae (I) to (III), or a pharmaceutically acceptable salt thereof, according to embodiment 1, 2 or 3, wherein $R^3$ is $C_2$-$C_8$alkyl optionally substituted with 1 to 3 substituents independently selected from $NH_2$, $NH(C_1$-$C_4$alkyl), $NHC(O)O(C_1$-$C_4$alkyl), $NHC(O)(C_1$-$C_4$alkyl), OH, $C_1$-$C_4$alkoxy, halo$C_1$-$C_4$alkoxy, halo and $C_3$-$C_5$cycloalkyl which is optionally further substituted with OH, or halo.

In embodiment 5, the invention provides for a compound of any one of formulae (I) to (III), or a pharmaceutically acceptable salt thereof, according to any one of the previous embodiments, wherein $R^3$ is $C_2$-$C_5$alkyl optionally substituted with 1 to 2 substituents independently selected from OH, $NH_2$, $NHC(O)(C_1$-$C_4$alkyl), halo, and $C_3$-$C_5$cycloalkyl which is optionally further substituted with OH, or halo.

In embodiment 5a, and according to embodiment 5, the invention relates to a compound of any one of formulae (I) to (III), or a pharmaceutically acceptable salt thereof, wherein $R^3$ is $C_2$-$C_8$alkyl substituted with OH or $NH_2$. In a particular embodiment, the $C_2$-$C_5$alkyl is further optionally substituted with 1 to 3 halo, or with a $C_3$-$C_5$cycloalkyl which is optionally substituted with OH, or halo. In a particular embodiment, the $C_2$-$C_5$alkyl is further optionally substituted with a $C_3$-$C_5$cycloalkyl which is optionally further substituted with OH.

In embodiment 6, the invention provides for a compound of any one of formulae (I) to (III), or a pharmaceutically acceptable salt thereof, according to any one of the previous embodiments 1, 2 or 3, wherein $R^3$ is $C_3$-$C_{10}$cycloalkyl or $C_3$-$C_5$cycloalkyl-$CH_2$, each of which is optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), $CO_2H$, hydroxy$C_1$-$C_4$alkyl, $C_1$-$C_4$alkoxy, halo$C_1$-$C_4$alkoxy, —$NH_2$, —$NH(C_1$-$C_4$alkyl).

In embodiment 6a, the invention relates to a compound of any one of formulae (I) to (III), or a pharmaceutically acceptable salt thereof, wherein $R^3$ is $C_3$-$C_{10}$cycloalkyl or $C_3$-$C_5$cycloalkyl-$CH_2$, each of which is optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, —$CO_2H$, —$NH_2$.

In embodiment 6b, and according to embodiment 6, or 6a, the invention relates to a compound of any one of formulae (I) to (III), or a pharmaceutically acceptable salt thereof, wherein $R^3$ is $C_3$-$C_{10}$cycloalkyl or $C_3$-$C_5$cycloalkyl-$CH_2$, each of which is optionally substituted with 1 to 2 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, —$CO_2H$, —$NH_2$.

In embodiment 6c, and according to embodiment 6, 6a, or 6b, the invention relates to a compound of any one of formulae (I) to (III), or a pharmaceutically acceptable salt thereof, wherein $R_3$ is $C_3$-$C_{10}$cycloalkyl optionally with 1 to 2 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, —$CO_2H$, —$NH_2$.

In embodiment 6d, and according to embodiment 6, 6a, 6b, or 6c, the invention relates to a compound of any one of formulae (I) to (III), or a pharmaceutically acceptable salt thereof, wherein $R_3$ is $C_3$-$C_{10}$cycloalkyl optionally with 1 to 2 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, $CO_2H$, —$NH_2$.

In embodiment 6e, and according to embodiment 6, 6a, or 6b, the invention relates to a compound of any one of formulae (I) to (III), or a pharmaceutically acceptable salt thereof, wherein $R_3$ is $C_3$-$C_5$cycloalkyl-$CH_2$ optionally with 1 to 2 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, —$NH_2$.

In embodiment 6f, and according to embodiment 6, 6a, 6b, or 6e, the invention relates to a compound of any one of formulae (I) to (III), or a pharmaceutically acceptable salt thereof, wherein $R_3$ is $C_3$-$C_5$cycloalkyl-$CH_2$ optionally with 1 to 2 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, —$CO_2H$, —$NH_2$.

In embodiment 7, the invention provides for a compound of any one of formulae (I) to (III), or a pharmaceutically acceptable salt thereof, according to embodiment 6, and embodiments 6, 6a, 6b, 6c or 6d, wherein $R^3$ is selected from the following:

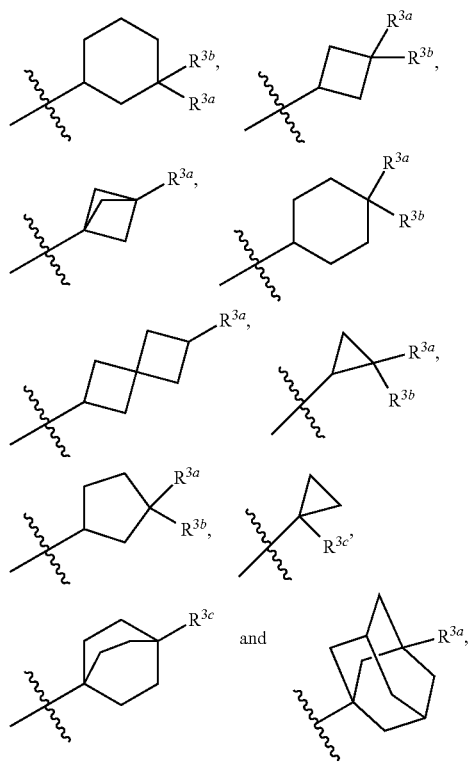

wherein $R^{3a}$, $R^{3b}$ and $R^{3c}$ are independently selected from H, —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —$CO_2H$, —$NH_2$, —NH($C_1$-$C_4$alkyl).

In embodiment 7a, and according to embodiment 7, the invention relates to a compound of any one of formulae (I) to (III), or a pharmaceutically acceptable salt thereof, wherein $R^3$ is selected from the following:

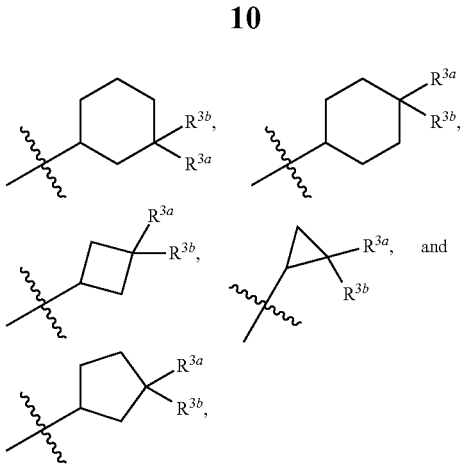

wherein $R^{3a}$, and $R^{3b}$ are independently selected from H, —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —$CO_2H$, —$NH_2$, —NH($C_1$-$C_4$alkyl).

In embodiment 7b, and according to embodiment 7, or 7a, the invention relates to a compound of any one of formulae (I) to (III), or a pharmaceutically acceptable salt thereof, wherein $R^{3a}$, and $R^{3b}$ are independently selected from H, —OH, $C_1$-$C_4$alkyl, $C_3$-$C_6$cycloalkyl, halo, halo$C_1$-$C_4$alkyl, hydroxy$C_1$-$C_4$alkyl, $C_1$-$C_4$alkoxy, —$NH_2$.

In embodiment 7c, according to embodiment 7, 7a, or 7b, the invention relates to a compound of any one of formulae (I) to (III), or a pharmaceutically acceptable salt thereof, wherein $R^3$ is $C_3$-$C_{10}$cycloalkyl selected from the group consisting of:

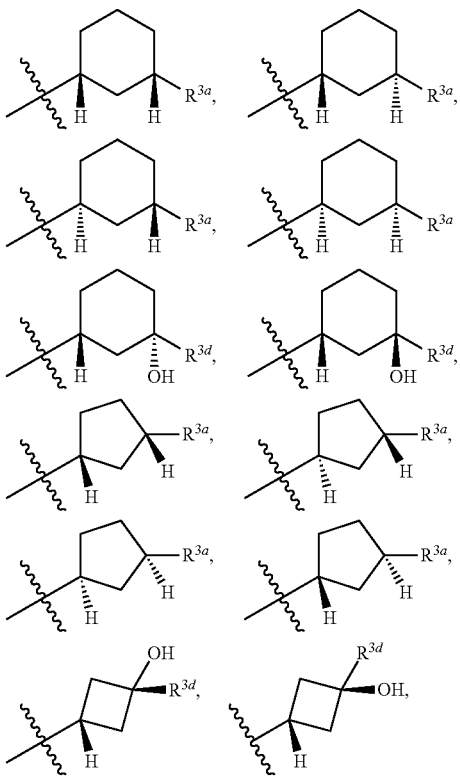

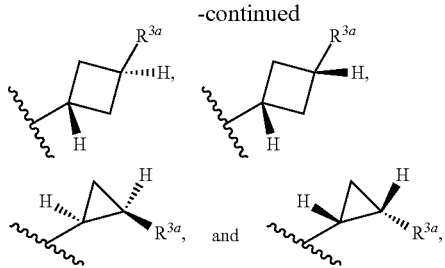

wherein $R^{3a}$ is selected from the group consisting of —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —NH($C_1$-$C_4$alkyl); and $R^{3d}$ is selected from the group consisting of $C_1$-$C_4$alkyl, $C_3$-$C_6$cycloalkyl, halo, halo$C_1$-$C_4$alkyl, —C(O)O($C_1$-$C_4$alkyl), hydroxy$C_1$-$C_4$alkyl.

In embodiment 7d, and according to embodiment 7, 7a, 7b, or 7c, the invention relates to a compound of any one of formulae (I) to (III), or a pharmaceutically acceptable salt thereof, wherein $R^3$ is $C_3$-$C_{10}$cycloalkyl selected from the group consisting of:

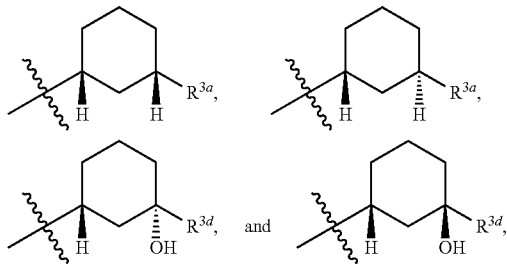

wherein $R^{3a}$ is selected from the group consisting of —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —NH($C_1$-$C_4$alkyl); and $R^{3d}$ is selected from the group consisting of $C_1$-$C_4$alkyl, $C_3$-$C_6$cycloalkyl, halo, halo$C_1$-$C_4$alkyl, —C(O)O($C_1$-$C_4$alkyl), hydroxy$C_1$-$C_4$alkyl.

In embodiment 7e, according to embodiments 7, 7a, 7b, 7c, or 7d, the invention relates to a compound of any one of formulae (I) to (III), or a pharmaceutically acceptable salt thereof, wherein $R^3$ is $C_3$-$C_{10}$cycloalkyl preferably selected from the group consisting of:

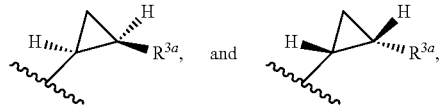

wherein $R^{3a}$ is selected from the group consisting of —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —NH($C_1$-$C_4$alkyl).

In embodiment 7f, and according to embodiments 7, 7a, 7b, 7c, 7d, or 7e, the invention relates to a compound of any one of formulae (I) to (III), or a pharmaceutically acceptable salt thereof, wherein $R^3$ is $C_3$-$C_{10}$cycloalkyl preferably selected from the group consisting of:

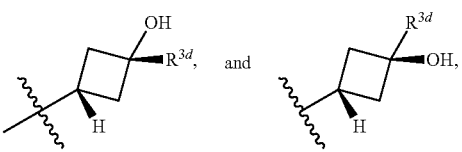

wherein $R^{3d}$ is selected from the group consisting of $C_1$-$C_4$alkyl, $C_3$-$C_6$cycloalkyl, halo, halo$C_1$-$C_4$alkyl, —C(O)O($C_1$-$C_4$alkyl), hydroxy$C_1$-$C_4$alkyl.

In embodiment 7g, and according to embodiment 7, 7a, 7b, 7c, 7d or 7e, the invention relates to a compound of any one of formulae (I) to (III), or a pharmaceutically acceptable salt thereof, $R^{3a}$ is selected from the group consisting of OH, CH$_3$, —OC(O)CH$_3$, F, CF$_3$, CHF$_2$, —C(O)OCH$_3$, —COCH$_3$ or NH$_2$. Preferably, $R^{3a}$ is OH or F.

In embodiment 7h, and according to embodiment 7c or 7d, the invention relates to a compound of any one of formulae (I) to (III), or a pharmaceutically acceptable salt thereof, $R^{3d}$ is CH$_3$.

In embodiment 8, the invention provides a compound of any one of formulae (I) to (III), or a pharmaceutically acceptable salt thereof, according to embodiment 1, 2 or 3, wherein $R^3$ is mono or bicyclic aryl, a mono or bicyclic heteroaryl, each of which is optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —SO$_2$NH$_2$, —SO$_2$NH($C_1$-$C_4$alkyl), —NHSO$_2$($C_1$-$C_4$alkyl), —NH($C_1$-$C_4$alkyl), —C(O)NH$_2$, CO$_2$H, C(O)$C_1$-$C_4$alkyl.

In a particular aspect of embodiment 8, the invention relates to a compound of any one of formulae (I) to (III), or a pharmaceutically acceptable salt thereof, $R^3$ is phenyl or monocyclic heteroaryl, each of which is optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —SO$_2$NH$_2$, —SO$_2$NH($C_1$-$C_4$alkyl), —NHSO$_2$($C_1$-$C_4$alkyl), —NH($C_1$-$C_4$alkyl), —C(O)NH$_2$, CO$_2$H, C(O)$C_1$-$C_4$alkyl.

In embodiment 9, the invention provides for a compound of any one of formulae (I) to (III), or a pharmaceutically acceptable salt thereof, according to embodiment 8, wherein $R^3$ is selected from the following:

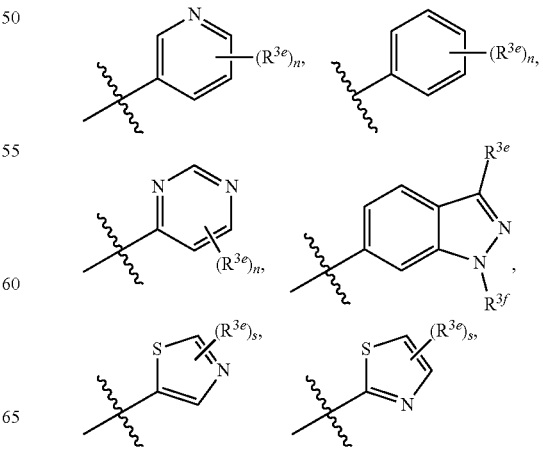

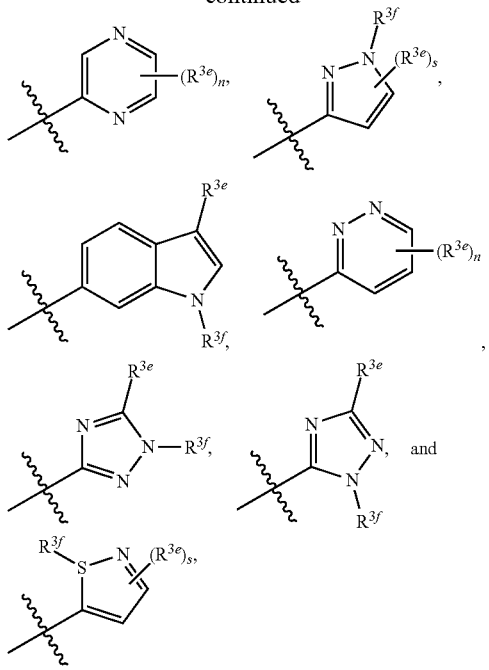

wherein R$^{3e}$ is independently selected from H, —OH, C$_1$-C$_4$alkyl, C$_3$-C$_6$cycloalkyl, halo, —OC(O)(C$_1$-C$_4$alkyl), haloC$_1$-C$_4$alkyl, —C(O)O(C$_1$-C$_4$alkyl), hydroxyC$_1$-C$_4$alkyl, C$_1$-C$_4$alkoxy, haloC$_1$-C$_4$alkoxy, —NH$_2$, —SO$_2$NH$_2$, —SO$_2$NH(C$_1$-C$_4$alkyl), —NHSO$_2$(C$_1$-C$_4$alkyl), —NH(C$_1$-C$_4$alkyl), —C(O)NH$_2$, C(O)C$_1$-C$_4$alkyl, CO$_2$H; R$^{3f}$ is H or C$_1$-C$_4$alkyl; n is 1, 2 or 3; and s is 1 or 2.

In embodiment 9a, and embodiment 9, the invention relates to a compound of any one of formulae (I) to (III), or a pharmaceutically acceptable salt thereof, wherein R$^3$ is selected from the following:

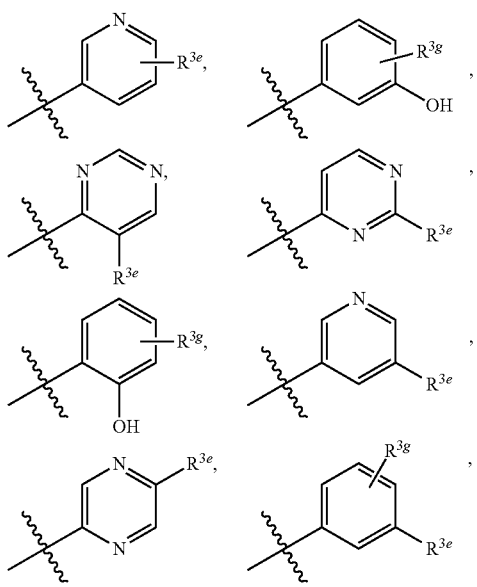

wherein R$^{3e}$ is independently selected from —OH, C$_1$-C$_4$alkyl, C$_3$-C$_6$cycloalkyl, halo, —OC(O)(C$_1$-C$_4$alkyl), haloC$_1$-C$_4$alkyl, —C(O)O(C$_1$-C$_4$alkyl), hydroxyC$_1$-C$_4$alkyl, C$_1$-C$_4$alkoxy, haloC$_1$-C$_4$alkoxy, —NH$_2$, —SO$_2$NH$_2$, —SO$_2$NH(C$_1$-C$_4$alkyl), —NHSO$_2$(C$_1$-C$_4$alkyl), —NH(C$_1$-C$_4$alkyl), —C(O)NH$_2$, CO$_2$H; and R$^{3g}$ is selected from H, C$_1$-C$_4$alkyl, C$_3$-C$_6$cycloalkyl, halo and haloC$_1$-C$_4$alkyl.

In embodiment 9b, and according to embodiment 9a, the invention relates to a compound of any one of formulae (I) to (III), or a pharmaceutically acceptable salt thereof, wherein preferably R$^{3e}$ is selected from the group consisting of halo, OH, CH$_3$, CH$_2$OH, —NHS(O)$_2$CH$_3$, CF$_3$, CHF$_2$, C(O)CH$_3$, C(O)NH$_2$, CO$_2$H; and R$^{3g}$ is H, CH$_3$ or halo.

In embodiment 9c, and according to embodiment 9a, or 9b, the invention relates to a compound of any one of formulae (I) to (III), or a pharmaceutically acceptable salt thereof, wherein R$^{3e}$ is independently selected from halo, OH, CH$_3$, CH$_2$OH, —NHS(O)$_2$CH$_3$, CF$_3$, NH$_2$; and R$^{3g}$ is H, CH$_3$ or halo.

In embodiment 10, the invention provides a compound of any one of formulae (I) to (III), or a pharmaceutically acceptable salt thereof, according to embodiments 1, 2 or 3, wherein R$^3$ is a mono or bicyclic heterocyclyl optionally substituted with 1 to 3 substituents independently selected from —OH, oxo, C$_3$-C$_6$cycloalkyl, halo, —C(O)O—C$_1$-C$_4$alkyl, —C(O)C$_1$-C$_4$alkyl, and C$_1$-C$_4$alkyl which is further optionally substituted with 1 to 4 substituents independently selected from C$_3$-C$_6$cycloalkyl, halo, C$_1$-C$_4$alkoxy, haloC$_1$-C$_4$alkoxy and OH.

In embodiment 10a, and according to embodiment 10, the invention provides a compound of any one of formulae (I) to (III), or a pharmaceutically acceptable salt thereof, according to embodiments 1, 2, or 3, wherein R$^3$ is a mono or bicyclic heterocyclyl optionally substituted with 1 to 2 substituents independently selected from —OH, oxo, C$_3$-C$_6$cycloalkyl, halo, —C(O)O—C$_1$-C$_4$alkyl, —C(O)C$_1$-C$_4$alkyl, and C$_1$-C$_4$alkyl which is further optionally substituted with 1 to 4 substituents independently selected from C$_3$-C$_6$cycloalkyl, halo, haloC$_1$-C$_4$alkoxy and OH.

In embodiment 11, the invention provides a compound of any one of formulae (I) to (III), or a pharmaceutically acceptable salt thereof, according to embodiments 10, or 10a wherein R$^3$ is selected from the following:

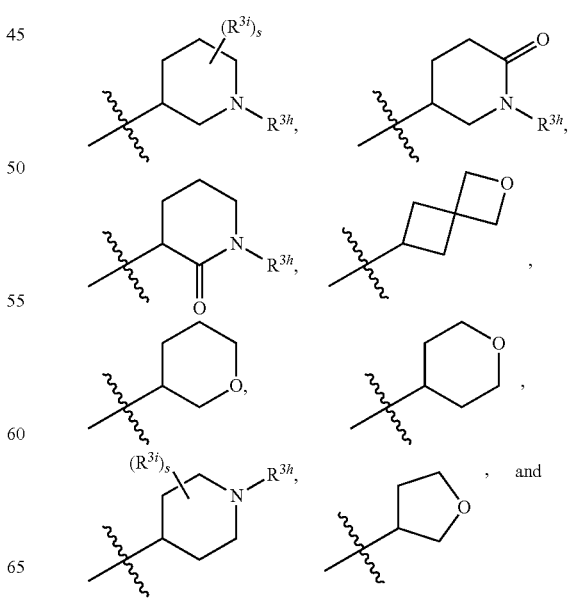

-continued

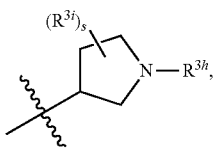

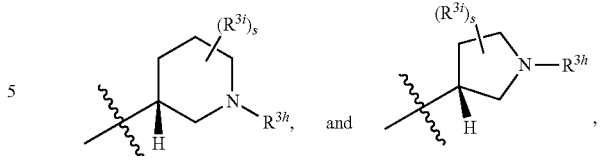

wherein $R^{3h}$ is selected from H, $C_3$-$C_6$cycloalkyl; —C(O)O—$C_1$-$C_4$alkyl; —C(O)$C_1$-$C_4$alkyl; and $C_1$-$C_4$alkyl which is further optionally substituted with 1 to 4 substituents independently selected from $C_3$-$C_6$cycloalkyl, halo, $C_1$-$C_4$alkoxy, halo$C_1$-$C_4$alkoxy and OH; $R^{3i}$ is H, halo, OH, or alkyl; and s is 1, or 2.

In embodiment 11a, and according to embodiment 11, the invention relates to a compound of any one of formulae (I) to (III), or a pharmaceutically acceptable salt thereof, $R^{3h}$ is selected from H, $C_3$-$C_5$cycloalkyl, $C_3$-$C_5$cycloalkylCH$_2$—, hydroxy$C_1$-$C_4$alkyl, halo$C_1$-$C_4$alkyl, $C_1$-$C_4$alkyl optionally substituted with $C_3$-$C_5$cycloalkyl and optionally further substituted with OH, $C_1$-$C_4$alkyl substituted with halo$C_1$-$C_4$alkoxy, C(O)$C_1$-$C_4$alkyl, and C(O)O—$C_1$-$C_4$alkyl.

In embodiment 11b, and according to embodiment 11, or 11a, the invention relates to a compound of any one of formulae (I) to (III), or a pharmaceutically acceptable salt thereof, $R^{3i}$ is H, halo, or CH$_3$.

In embodiment 11c, and according to embodiment 11, 11a, or 11b, the invention relates to a compound of any one of formulae (I) to (III), or a pharmaceutically acceptable salt thereof, wherein $R^3$ is selected from the following:

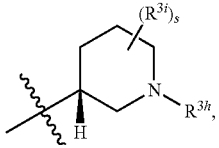 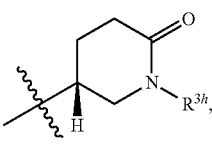

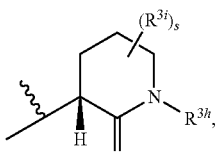 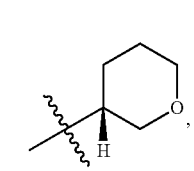

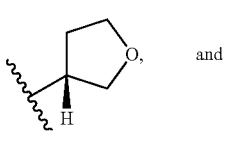 and 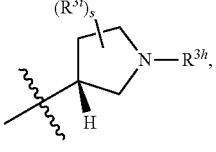

wherein $R^{3h}$ is selected from H, $C_3$-$C_6$cycloalkyl, —C(O)O—$C_1$-$C_4$alkyl, —C(O)$C_1$-$C_4$alkyl, and $C_1$-$C_4$alkyl which is further optionally substituted with 1 to 4 substituents independently selected from $C_3$-$C_6$cycloalkyl; $R^{3i}$ is H, halo, OH, or alkyl; and s is 1, or 2.

In embodiment 11d, and according to embodiment 11, 11a, 11b, or 11c, the invention relates to a compound of any one of formulae (I) to (III), or a pharmaceutically acceptable salt thereof, wherein $R^3$ is preferably the following structure wherein $R^{3h}$ is selected from H, $C_3$-$C_6$cycloalkyl, —C(O)O—$C_1$-$C_4$alkyl, —C(O)$C_1$-$C_4$alkyl, and $C_1$-$C_4$alkyl which is further optionally substituted with 1 to 4 substituents independently selected from $C_3$-$C_6$cycloalkyl, halo, $C_1$-$C_4$alkoxy, halo$C_1$-$C_4$alkoxy and OH; $R^{3i}$ is H, halo, OH, or alkyl; and s is 1, or 2.

In embodiment 12, the invention provides for a compound of any one of formulae (I) to (III), or a pharmaceutically acceptable salt thereof, according to any one of the preceding embodiments (i.e. any one of embodiments 1 to 5, 5a, 6, 6a-6f, 7, 7a-7h, 8, 9, 9a-9c, 10, 10a, 11 and 11a-11d), wherein $R^1$ is chloro, or a pharmaceutically acceptable salt thereof.

In embodiment 13, the invention provides for a compound of any one of formulae (I) to (III), or a pharmaceutically acceptable salt thereof, according to any one of the preceding embodiments (i.e. any one of embodiments 1 to 5, 5a, 6, 6a-6f, 7, 7a-7h, 8, 9, 9a-9c, 10, 10a, 11, 11a-11 d and 12), wherein $R^2$ is selected from:

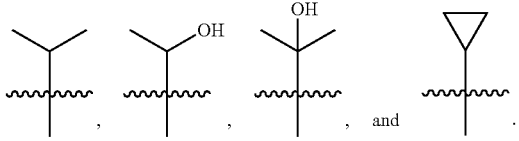

In embodiment 14, the invention provides for a compound of any one of formulae (I) to (III), or a pharmaceutically acceptable salt thereof, according to embodiment 1, wherein the compound is selected from:
2-(2-Chloro-5-isopropyl-8-oxothieno[2',3':4,5]pyrrolo[1,2-d][1,2,4]triazin-7(8H)-yl)-N-(pyrimidin-4-yl)acetamide;
2-(2-Chloro-5-isopropyl-8-oxothieno[2',3':4,5]pyrrolo[1,2-d][1,2,4]triazin-7(8H)-yl)-N-(pyridin-3-yl)acetamide;
2-(2-Chloro-5-(1-hydroxyethyl)-8-oxothieno[2',3':4,5]pyrrolo[1,2-d][1,2,4]triazin-7(8H)-yl)-N-(pyrimidin-4-yl)acetamide;
2-(5-Cyclopropyl-8-oxothiazolo[5',4':4,5]pyrrolo[1,2-d][1,2,4]triazin-7(8H)-yl)-N-(pyridin-3-yl)acetamide;
2-(2-Fluoro-5-isopropyl-8-oxothieno[2',3':4,5]pyrrolo[1,2-d][1,2,4]triazin-7(8H)-yl)-N-(pyridin-3-yl)acetamide;
2-(2-Fluoro-5-isopropyl-8-oxothieno[2',3':4,5]pyrrolo[1,2-d][1,2,4]triazin-7(8H)-yl)-N-(pyrimidin-4-yl)acetamide;
2-(5-Isopropyl-2-methyl-8-oxothieno[2',3':4,5]pyrrolo[1,2-d][1,2,4]triazin-7(8H)-yl)-N-(pyridin-3-yl)acetamide;
2-(2-Chloro-5-(2-hydroxypropan-2-yl)-8-oxothieno[2',3':4,5]pyrrolo[1,2-d][1,2,4]triazin-7(8H)-yl)-N-(pyridin-3-yl)acetamide;
2-(2-Chloro-5-(2-hydroxypropan-2-yl)-8-oxothieno[2',3':4,5]pyrrolo[1,2-d][1,2,4]triazin-7(8H)-yl)-N-(pyrimidin-4-yl)acetamide;
(R)-2-(2-Chloro-5-isopropyl-8-oxothieno[2',3':4,5]pyrrolo[1,2-d][1,2,4]triazin-7(8H)-yl)-N-(piperidin-3-yl)acetamide;
2-(2-Chloro-5-isopropyl-8-oxothieno[2',3':4,5]pyrrolo[1,2-d][1,2,4]triazin-7(8H)-yl)-N-(thiazol-2-yl)acetamide;

2-(2-Chloro-5-isopropyl-8-oxothieno[2',3':4,5]pyrrolo[1,2-d][1,2,4]triazin-7(8H)-yl)-N-(thiazol-5-yl)acetamide;

2-(2-Chloro-5-isopropyl-8-oxothieno[2',3':4,5]pyrrolo[1,2-d][1,2,4]triazin-7(8H)-yl)-N-(2-chloropyridin-3-yl)acetamide;

2-(2-Chloro-5-isopropyl-8-oxothieno[2',3':4,5]pyrrolo[1,2-d][1,2,4]triazin-7(8H)-yl)-N-(6-fluoropyridin-3-yl)acetamide;

2-(2-Chloro-5-isopropyl-8-oxothieno[2',3':4,5]pyrrolo[1,2-d][1,2,4]triazin-7(8H)-yl)-N-(5-fluoropyrimidin-4-yl)acetamide;

2-(2-Chloro-5-isopropyl-8-oxothieno[2',3':4,5]pyrrolo[1,2-d][1,2,4]triazin-7(8H)-yl)-N-(5-chloropyrimidin-4-yl)acetamide;

(R)-2-(2-Chloro-5-isopropyl-8-oxothieno[2',3':4,5]pyrrolo[1,2-d][1,2,4]triazin-7(8H)-yl)-N-(1-methylpiperidin-3-yl)acetamide;

(S)-2-(2-Chloro-5-isopropyl-8-oxothieno[2',3':4,5]pyrrolo[1,2-d][1,2,4]triazin-7(8H)-yl)-N-(1-methylpiperidin-3-yl)acetamide;

(R)-2-(2-Chloro-5-isopropyl-8-oxothieno[2',3':4,5]pyrrolo[1,2-d][1,2,4]triazin-7(8H)-yl)-N-(6-oxopiperidin-3-yl)acetamide;

2-(2-Chloro-5-isopropyl-8-oxothieno[2',3':4,5]pyrrolo[1,2-d][1,2,4]triazin-7(8H)-yl)-N-(3-hydroxy-2,2-dimethylpropyl)acetamide;

2-(2-Chloro-5-isopropyl-8-oxothieno[2',3':4,5]pyrrolo[1,2-d][1,2,4]triazin-7(8H)-yl)-N-((1R,3R)-3-hydroxycyclohexyl)acetamide;

N-((1R,3R)-3-Aminocyclopentyl)-2-(2-chloro-5-isopropyl-8-oxothieno[2',3':4,5]pyrrolo[1,2-d][1,2,4]triazin-7(8H)-yl)acetamide;

2-(2-Chloro-5-isopropyl-8-oxothieno[2',3':4,5]pyrrolo[1,2-d][1,2,4]triazin-7(8H)-yl)-N-((1 r,3r)-3-hydroxy-1-methylcyclobutyl) acetamide;

2-(2-Chloro-5-isopropyl-8-oxothieno[2',3':4,5]pyrrolo[1,2-d][1,2,4]triazin-7(8H)-yl)-N-(2-oxaspiro[3.3]heptan-6-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-(3,3-dimethylcyclobutyl)acetamide;

2-(2-Chloro-5-(2-hydroxypropan-2-yl)-8-oxothieno[2',3':4,5]pyrrolo[1,2-d][1,2,4]triazin-7(8H)-yl)-N-(2-oxaspiro[3.3]heptan-6-yl)acetamide;

2-(2-Chloro-5-isopropyl-8-oxothieno[2',3':4,5]pyrrolo[1,2-d][1,2,4]triazin-7(8H)-yl)-N-((1R,3R)-3-hydroxy-3-methylcyclohexyl)acetamide;

(R)-2-(2-Chloro-5-isopropyl-8-oxothieno[2',3':4,5]pyrrolo[1,2-d][1,2,4]triazin-7(8H)-yl)-N-(1-(2-fluoroethyl)piperidin-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-methyl-6-oxopiperidin-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-(2-fluoroethyl)piperidin-3-yl)acetamide;

(R)-2-(2-Fluoro-5-isopropyl-8-oxothieno[2',3':4,5]pyrrolo[1,2-d][1,2,4]triazin-7(8H)-yl)-N-(piperidin-3-yl)acetamide hydrochloride;

(R)-2-(2-Fluoro-5-isopropyl-8-oxothieno[2',3':4,5]pyrrolo[1,2-d][1,2,4]triazin-7(8H)-yl)-N-(1-methylpiperidin-3-yl)acetamide;

(R)-2-(2-Fluoro-5-isopropyl-8-oxothieno[2',3':4,5]pyrrolo[1,2-d][1,2,4]triazin-7(8H)-yl)-N-(6-oxopiperidin-3-yl)acetamide;

(R)-2-(5-Cyclopropyl-2-fluoro-8-oxothieno[2',3':4,5]pyrrolo[1,2-d][1,2,4]triazin-7(8H)-yl)-N-(piperidin-3-yl)acetamide;

(R)-2-(5-Cyclopropyl-2-fluoro-8-oxothieno[2',3':4,5]pyrrolo[1,2-d][1,2,4]triazin-7(8H)-yl)-N-(1-methylpiperidin-3-yl)acetamide;

(R)-2-(2-Chloro-5-cyclopropyl-8-oxothieno[2',3':4,5]pyrrolo[1,2-d][1,2,4]triazin-7(8H)-yl)-N-(piperidin-3-yl)acetamide hydrochloride;

(R)-2-(2-Chloro-5-cyclopropyl-8-oxothieno[2',3':4,5]pyrrolo[1,2-d][1,2,4]triazin-7(8H)-yl)-N-(1-methylpiperidin-3-yl)acetamide;

(R)-2-(5-Isopropyl-2-methyl-8-oxothieno[2',3':4,5]pyrrolo[1,2-d][1,2,4]triazin-7(8H)-yl)-N-(piperidin-3-yl)acetamide;

(R)-2-(5-Isopropyl-2-methyl-8-oxothieno[2',3':4,5]pyrrolo[1,2-d][1,2,4]triazin-7(8H)-yl)-N-(6-oxopiperidin-3-yl)acetamide;

(R)-2-(5-Isopropyl-2-methyl-8-oxothieno[2',3':4,5]pyrrolo[1,2-d][1,2,4]triazin-7(8H)-yl)-N-(1-methylpiperidin-3-yl)acetamide;

N-Cyclopropyl-2-(5-isopropyl-2-methyl-8-oxothieno[2',3':4,5]pyrrolo[1,2-d][1,2,4]triazin-7(8H)-yl)acetamide;

2-(2-Chloro-5-(1-hydroxyethyl)-8-oxothieno[2',3':4,5]pyrrolo[1,2-d][1,2,4]triazin-7(8H)-yl)-N-(pyridin-3-yl)acetamide;

2-(2-Chloro-5-(1-hydroxyethyl)-8-oxothieno[2',3':4,5]pyrrolo[1,2-d][1,2,4]triazin-7(8H)-yl)-N—((R)-piperidin-3-yl)acetamide hydrochloride;

2-(2-Chloro-5-(1-hydroxyethyl)-8-oxothieno[2',3':4,5]pyrrolo[1,2-d][1,2,4]triazin-7(8H)-yl)-N—((R)-1-methylpiperidin-3-yl)acetamide;

2-(2-Chloro-5-(1-hydroxyethyl)-8-oxothieno[2',3':4,5]pyrrolo[1,2-d][1,2,4]triazin-7(8H)-yl)-N-((1R,3R)-3-hydroxy-3-methylcyclohexyl)acetamide;

(R)-2-(5-Isopropyl-8-oxothiazolo[5',4':4,5]pyrrolo[1,2-d][1,2,4]triazin-7(8H)-yl)-N-(6-oxopiperidin-3-yl)acetamide;

N-((1R,3R)-3-Hydroxycyclohexyl)-2-(5-isopropyl-8-oxothiazolo[5',4':4,5]pyrrolo[1,2-d][1,2,4]triazin-7(8H)-yl)acetamide;

(R)-2-(5-Isopropyl-8-oxothiazolo[5',4':4,5]pyrrolo[1,2-d][1,2,4]triazin-7(8H)-yl)-N-(1-methylpiperidin-3-yl)acetamide;

(R)-2-(5-Isopropyl-8-oxothiazolo[5',4':4,5]pyrrolo[1,2-d][1,2,4]triazin-7(8H)-yl)-N-(1-methyl-6-oxopiperidin-3-yl)acetamide;

(R)-2-(5-Isopropyl-2-methyl-8-oxothiazolo[5',4':4,5]pyrrolo[1,2-d][1,2,4]triazin-7(8H)-yl)-N-(piperidin-3-yl)acetamide;

N-Cyclopropyl-2-(5-isopropyl-8-oxothiazolo[5',4':4,5]pyrrolo[1,2-d][1,2,4]triazin-7(8H)-yl)acetamide;

2-(2-Chloro-5-isopropyl-8-oxothieno[2',3':4,5]pyrrolo[1,2-d][1,2,4]triazin-7(8H)-yl)-N-((1R,2S)-2-fluorocyclopropyl)acetamide;

(1 r,4r)-4-(2-(2-Chloro-5-isopropyl-8-oxothieno[2',3':4,5]pyrrolo[1,2-d][1,2,4]triazin-7(8H)-yl)acetamido)cyclohexane-1-carboxylic acid;

(1s,4s)-4-(2-(2-Chloro-5-isopropyl-8-oxothieno[2',3':4,5]pyrrolo[1,2-d][1,2,4]triazin-7(8H)-yl)acetamido)cyclohexane-1-carboxylic acid;

(1R,3S)-3-(2-(2-Chloro-5-isopropyl-8-oxothieno[2',3':4,5]pyrrolo[1,2-d][1,2,4]triazin-7(8H)-yl)acetamido)cyclohexane-1-carboxylic acid;

tert-Butyl((1R,3S)-3-(2-(2-chloro-5-isopropyl-8-oxothieno[2',3':4,5]pyrrolo[1,2-d][1,2,4]triazin-7(8H)-yl)acetamido)cyclohexyl)carbamate;

2-(2-Chloro-5-isopropyl-8-oxothieno[2',3':4,5]pyrrolo[1,2-d][1,2,4]triazin-7(8H)-yl)-N-(1-methyl-1H-pyrazol-5-yl)acetamide;

2-(2-Chloro-5-isopropyl-8-oxothieno[2',3':4,5]pyrrolo[1,2-d][1,2,4]triazin-7(8H)-yl)-N-(2,4-difluorophenyl)acetamide;

(R)-2-(2-Chloro-5-isopropyl-8-oxothieno[2',3':4,5]pyrrolo[1,2-d][1,2,4]triazin-7(8H)-yl)-N-(tetrahydro-2H-pyran-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-methylpiperidin-3-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-((1 r,3r)-3-hydroxy-3-methylcyclobutyl)acetamide;

2-(2-Chloro-5-(2-hydroxypropan-2-yl)-8-oxothieno[2',3':4,5]pyrrolo[1,2-d][1,2,4]triazin-7(8H)-yl)-N-cyclopropylacetamide;

2-(2-Chloro-5-(2-hydroxypropan-2-yl)-8-oxothieno[2',3':4,5]pyrrolo[1,2-d][1,2,4]triazin-7(8H)-yl)-N-((1s,3s)-3-hydroxy-3-methyl cyclobutyl) acetamide;

2-(2-Chloro-5-(2-hydroxypropan-2-yl)-8-oxothieno[2',3':4,5]pyrrolo[1,2-d][1,2,4]triazin-7(8H)-yl)-N-((1R,3R)-3-hydroxy cyclohexyl)acetamide;

2-(2-Chloro-5-(2-hydroxypropan-2-yl)-8-oxothieno[2',3':4,5]pyrrolo[1,2-d][1,2,4]triazin-7(8H)-yl)-N-(1H-indazol-6-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-(3-methyl-1H-indazol-6-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-(1H-indol-6-yl)acetamide;

2-(2-Chloro-5-isopropyl-8-oxothieno[2',3':4,5]pyrrolo[1,2-d][1,2,4]triazin-7(8H)-yl)-N-(2-hydroxyethyl)acetamide;

(S)-2-(2-Chloro-5-isopropyl-8-oxothieno[2',3':4,5]pyrrolo[1,2-d][1,2,4]triazin-7(8H)-yl)-N-(2-hydroxy propyl)acetamide;

(R)-2-(2-Chloro-5-isopropyl-8-oxothieno[2',3':4,5]pyrrolo[1,2-d][1,2,4]triazin-7(8H)-yl)-N-(2-hydroxypropyl)acetamide;

2-(2-Chloro-5-isopropyl-8-oxothieno[2',3':4,5]pyrrolo[1,2-d][1,2,4]triazin-7(8H)-yl)-N-((1 r,3r)-3-hydroxy-3-methylcyclobutyl)acetamide;

2-(2-Chloro-5-isopropyl-8-oxothieno[2',3':4,5]pyrrolo[1,2-d][1,2,4]triazin-7(8H)-yl)-N-((1s,3s)-3-hydroxy-3-methylcyclobutyl)acetamide;

2-(2-Chloro-5-isopropyl-8-oxothieno[2',3':4,5]pyrrolo[1,2-d][1,2,4]triazin-7(8H)-yl)-N-(6-hydroxyspiro[3.3]heptan-2-yl)acetamide;

2-(2-Chloro-5-isopropyl-8-oxothieno[2',3':4,5]pyrrolo[1,2-d][1,2,4]triazin-7(8H)-yl)-N-((1s,3s)-3-hydroxy-3-(trifluoromethyl)cyclobutyl)acetamide;

2-(2-Chloro-5-isopropyl-8-oxothieno[2',3':4,5]pyrrolo[1,2-d][1,2,4]triazin-7(8H)-yl)-N-(tetrahydro-2H-pyran-4-yl)acetamide;

2-(2-Chloro-5-isopropyl-8-oxothieno[2',3':4,5]pyrrolo[1,2-d][1,2,4]triazin-7(8H)-yl)-N-(4-hydroxybicyclo[2.2.2]octan-1-yl)acetamide;

2-(2-Chloro-5-isopropyl-8-oxothieno[2',3':4,5]pyrrolo[1,2-d][1,2,4]triazin-7(8H)-yl)-N-(3-hydroxy-3-methyl butyl)acetamide;

(R)-2-(2-Chloro-5-isopropyl-8-oxothieno[2',3':4,5]pyrrolo[1,2-d][1,2,4]triazin-7(8H)-yl)-N-(1-(2-(trifluoromethoxy) ethyl)piperidin-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(piperidin-3-yl)acetamide;

(2-(2-Chloro-5-(2-hydroxypropan-2-yl)-8-oxothieno[2',3':4,5]pyrrolo[1,2-d][1,2,4]triazin-7(8H)-yl)-N-(3-hydroxy-3-methylbutyl)acetamide;

2-(2-Chloro-5-(2-hydroxypropan-2-yl)-8-oxothieno[2',3':4,5]pyrrolo[1,2-d][1,2,4]triazin-7(8H)-yl)-N-((1R,3S)-3-hydroxycyclohexyl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-(2,2,2-trifluoroethyl)piperidin-3-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-((1R,3R)-3-hydroxy-3-methyl cyclohexyl)acetamide;

2-(2-Fluoro-5-isopropyl-8-oxothieno[2',3':4,5]pyrrolo[1,2-d][1,2,4]triazin-7(8H)-yl)-N-(3-hydroxy-3-methyl butyl)acetamide;

(R)-2-(2-Fluoro-5-isopropyl-8-oxothieno[2',3':4,5]pyrrolo[1,2-d][1,2,4]triazin-7(8H)-yl)-N-(2-hydroxy propyl)acetamide;

2-(2-Fluoro-5-isopropyl-8-oxothieno[2',3':4,5]pyrrolo[1,2-d][1,2,4]triazin-7(8H)-yl)-N-((1 r,3r)-3-hydroxy-3-methylcyclobutyl)acetamide;

2-(2-Fluoro-5-isopropyl-8-oxothieno[2',3':4,5]pyrrolo[1,2-d][1,2,4]triazin-7(8H)-yl)-N-((1s,3s)-3-hydroxy-3-methyl cyclobutyl)acetamide;

(R)-2-(5-Isopropyl-8-oxothiazolo[5',4':4,5]pyrrolo[1,2-d][1,2,4]triazin-7(8H)-yl)-N-(piperidin-3-yl)acetamide;

(R)—N-(1-(2-Fluoroethyl)piperidin-3-yl)-2-(5-isopropyl-8-oxothiazolo[5',4':4,5]pyrrolo[1,2-d][1,2,4]triazin-7(8H)-yl)acetamide;

N-((1R,3R)-3-Hydroxy-3-methylcyclohexyl)-2-(5-isopropyl-8-oxothiazolo[5',4':4,5]pyrrolo[1,2-d][1,2,4]triazin-7(8H)-yl)acetamide;

N-((1R,3S)-3-Hydroxycyclohexyl)-2-(5-isopropyl-8-oxothiazolo[5',4':4,5]pyrrolo[1,2-d][1,2,4]triazin-7(8H)-yl)acetamide;

(R)-2-(5-Isopropyl-2-methyl-8-oxothiazolo[5',4':4,5]pyrrolo[1,2-d][1,2,4]triazin-7(8H)-yl)-N-(1-methylpiperidin-3-yl)acetamide;

N-((1s,3s)-3-Hydroxy-3-methylcyclobutyl)-2-(5-isopropyl-8-oxothiazolo[5',4':4,5]pyrrolo[1,2-d][1,2,4]triazin-7(8H)-yl)acetamide;

N-(3-Hydroxy-3-methylbutyl)-2-(5-isopropyl-8-oxothiazolo[5',4':4,5]pyrrolo[1,2-d][1,2,4]triazin-7(8H)-yl)acetamide;

(R)—N-(2-Hydroxypropyl)-2-(5-isopropyl-8-oxothiazolo[5',4':4,5]pyrrolo[1,2-d][1,2,4]triazin-7(8H)-yl)acetamide;

N-Cyclopropyl-2-(5-isopropyl-2-methyl-8-oxothiazolo[5',4':4,5]pyrrolo[1,2-d][1,2,4]triazin-7(8H)-yl)acetamide;

(R)-2-(5-Isopropyl-8-oxothiazolo[5',4':4,5]pyrrolo[1,2-d][1,2,4]triazin-7(8H)-yl)-N-(1-methyl-6-oxopiperidin-3-yl)acetamide;

N-Cyclopentyl-2-(5-isopropyl-8-oxothiazolo[5',4':4,5]pyrrolo[1,2-d][1,2,4]triazin-7(8H)-yl)acetamide;

(S)-2-(2-Chloro-5-isopropyl-8-oxothieno[2',3':4,5]pyrrolo[1,2-d][1,2,4]triazin-7(8H)-yl)-N-(tetrahydrofuran-3-yl)acetamide;

(R)-2-(2-Chloro-5-isopropyl-8-oxothieno[2',3':4,5]pyrrolo[1,2-d][1,2,4]triazin-7(8H)-yl)-N-(tetrahydrofuran-3-yl)acetamide;

2-(2-Chloro-5-Isopropyl-8-oxothieno[2',3':4,5]pyrrolo[1,2-d][1,2,4]triazin-7(8H)-yl)-N-cyclopentylacetamide;

(S)-2-(2-Chloro-5-isopropyl-8-oxothieno[2',3':4,5]pyrrolo[1,2-d][1,2,4]triazin-7(8H)-yl)-N-(pyrrolidin-3-yl)acetamide;
(R)-2-(2-Chloro-5-isopropyl-8-oxothieno[2',3':4,5]pyrrolo[1,2-d][1,2,4]triazin-7(8H)-yl)-N-(pyrrolidin-3-yl)acetamide;
(R)-2-(2-Chloro-5-isopropyl-8-oxothieno[2',3':4,5]pyrrolo[1,2-d][1,2,4]triazin-7(8H)-yl)-N-(1-methylpyrrolidin-3-yl)acetamide;
(S)-2-(2-Chloro-5-isopropyl-8-oxothieno[2',3':4,5]pyrrolo[1,2-d][1,2,4]triazin-7(8H)-yl)-N-(1-methylpyrrolidin-3-yl)acetamide;
(R)-2-(2-Chloro-5-(2-hydroxypropan-2-yl)-8-oxothieno[2',3':4,5]pyrrolo[1,2-d][1,2,4]triazin-7(8H)-yl)-N-(pyrrolidin-3-yl)acetamide;
(S)-2-(2-Chloro-5-(2-hydroxypropan-2-yl)-8-oxothieno[2',3':4,5]pyrrolo[1,2-d][1,2,4]triazin-7(8H)-yl)-N-(pyrrolidin-3-yl)acetamide;
2-(2-Chloro-5-isopropyl-8-oxothieno[2',3':4,5]pyrrolo[1,2-d][1,2,4]triazin-7(8H)-yl)-N-((1r,3r)-3-hydroxycyclobutyl)acetamide;
2-(2-Chloro-5-isopropyl-8-oxothieno[2',3':4,5]pyrrolo[1,2-d][1,2,4]triazin-7(8H)-yl)-N-((1s,3s)-3-hydroxycyclobutyl)acetamide;
2-(2-Chloro-5-isopropyl-8-oxothieno[2',3':4,5]pyrrolo[1,2-d][1,2,4]triazin-7(8H)-yl)-N-(2-(1-hydroxycyclopropyl)ethyl)acetamide;
2-(2-Chloro-5-isopropyl-8-oxothieno[2',3':4,5]pyrrolo[1,2-d][1,2,4]triazin-7(8H)-yl)-N-(1-(hydroxymethyl)cyclopropyl)acetamide;
2-(2-Chloro-5-isopropyl-8-oxothieno[2',3':4,5]pyrrolo[1,2-d][1,2,4]triazin-7(8H)-yl)-N-(6-(difluoromethyl)pyrimidin-4-yl)acetamide;
Methyl 3-(2-(2-chloro-5-isopropyl-8-oxothieno[2',3':4,5]pyrrolo[1,2-d][1,2,4]triazin-7(8H)-yl)acetamido)bicyclo[1.1.1]pentane-1-carboxylate;
2-(2-Chloro-5-isopropyl-8-oxothieno[2',3':4,5]pyrrolo[1,2-d][1,2,4]triazin-7(8H)-yl)-N-((1S,3R,5S)-3-hydroxyadamantan-1-yl)acetamide;
N-(3-Aminobicyclo[1.1.1]pentan-1-yl)-2-(2-chloro-5-isopropyl-8-oxothieno[2',3':4,5]pyrrolo[1,2-d][1,2,4]triazin-7(8H)-yl)acetamide;
2-(2-Chloro-5-(2-hydroxypropan-2-yl)-8-oxothieno[2',3':4,5]pyrrolo[1,2-d][1,2,4]triazin-7(8H)-yl)-N-(3-(methylsulfonamido)phenyl)acetamide;
2-(2-Chloro-5-isopropyl-8-oxothieno[2',3':4,5]pyrrolo[1,2-d][1,2,4]triazin-7(8H)-yl)-N-(1,3,4-thiadiazol-2-yl)acetamide;
(1r,4r)-4-(2-(5-Isopropyl-2-methyl-8-oxothiazolo[5',4':4,5]pyrrolo[1,2-d][1,2,4]triazin-7(8H)-yl)acetamido)cyclohexane-1-carboxylic acid;
(1r,4r)-4-(2-(5-Isopropyl-8-oxothiazolo[5',4':4,5]pyrrolo[1,2-d][1,2,4]triazin-7(8H)-yl)acetamido)cyclohexane-1-carboxylic acid;
(1r,4r)-4-(2-(2-Fluoro-5-isopropyl-8-oxothieno[2',3':4,5]pyrrolo[1,2-d][1,2,4]triazin-7(8H)-yl)acetamido)cyclohexane-1-carboxylic acid;
(1r,4r)-4-(2-(2-Chloro-5-cyclopropyl-8-oxothieno[2',3':4,5]pyrrolo[1,2-d][1,2,4]triazin-7(8H)-yl)acetamido)cyclohexane-1-carboxylic acid;
(1r,4r)-4-(2-(2-Chloro-5-(2-hydroxypropan-2-yl)-8-oxothieno[2',3':4,5]pyrrolo[1,2-d][1,2,4]triazin-7(8H)-yl)acetamido)cyclohexane-1-carboxylic acid;
3-(2-(2-Chloro-5-isopropyl-8-oxothieno[2',3':4,5]pyrrolo[1,2-d][1,2,4]triazin-7(8H)-yl)acetamido)bicyclo[1.1.1]pentane-1-carboxylic acid;
(R)-2-(2-Chloro-5-isopropyl-8-oxothieno[2',3':4,5]pyrrolo[1,2-d][1,2,4]triazin-7(8H)-yl)-N-(1-cyclopropylpiperidin-3-yl)acetamide;
(R)-2-(2-Chloro-5-isopropyl-8-oxothieno[2',3':4,5]pyrrolo[1,2-d][1,2,4]triazin-7(8H)-yl)-N-(1-cyclobutylpiperidin-3-yl)acetamide;
(R)-2-(2-Chloro-5-(2-hydroxypropan-2-yl)-8-oxothieno[2',3':4,5]pyrrolo[1,2-d][1,2,4]triazin-7(8H)-yl)-N-(1-cyclopropylpiperidin-3-yl)acetamide;
(R)—N-(1-Cyclopropylpiperidin-3-yl)-2-(5-isopropyl-8-oxothiazolo[5',4':4,5]pyrrolo[1,2-d][1,2,4]triazin-7(8H)-yl)acetamide;
2-(2-Chloro-5-isopropyl-8-oxothieno[2',3':4,5]pyrrolo[1,2-d][1,2,4]triazin-7(8H)-yl)-N—((R)-1-((R)-2-hydroxypropyl)piperidin-3-yl)acetamide;
2-(2-Chloro-5-isopropyl-8-oxothieno[2',3':4,5]pyrrolo[1,2-d][1,2,4]triazin-7(8H)-yl)-N—((R)-1-((S)-2-hydroxypropyl)piperidin-3-yl)acetamide;
(R)-2-(2-Chloro-5-isopropyl-8-oxothieno[2',3':4,5]pyrrolo[1,2-d][1,2,4]triazin-7(8H)-yl)-N-(1-(2-hydroxy-2-methylpropyl)piperidin-3-yl)acetamide;
(R)-2-(2-Chloro-5-isopropyl-8-oxothieno[2',3':4,5]pyrrolo[1,2-d][1,2,4]triazin-7(8H)-yl)-N-(1-((1-hydroxycyclobutyl)methyl)piperidin-3-yl)acetamide;
(R)-2-(2-Chloro-5-(2-hydroxypropan-2-yl)-8-oxothieno[2',3':4,5]pyrrolo[1,2-d][1,2,4]triazin-7(8H)-yl)-N-(1-ethylpiperidin-3-yl)acetamide;
(R)-2-(2-Chloro-5-isopropyl-8-oxothieno[2',3':4,5]pyrrolo[1,2-d][1,2,4]triazin-7(8H)-yl)-N-(1-(2-hydroxyethyl)piperidin-3-yl)acetamide; and
(R)-2-(2-Chloro-5-isopropyl-8-oxothieno[2',3':4,5]pyrrolo[1,2-d][1,2,4]triazin-7(8H)-yl)-N-(1-(cyclopropylmethyl)piperidin-3-yl)acetamide.

In embodiment 14a, the invention relates to a compound of formula (I), wherein the compound is 2-(2-fluoro-5-isopropyl-8-oxothieno[2',3':4,5]pyrrolo[1,2-d][1,2,4]triazin-7(8H)-yl)-N-(pyrimidin-4-yl)acetamide, or a pharmaceutically acceptable salt thereof.

In embodiment 14b, the invention relates to a compound of formula (I), wherein the compound is (R)-2-(2-chloro-5-(2-hydroxypropan-2-yl)-8-oxothieno[2',3':4,5]pyrrolo[1,2-d][1,2,4]triazin-7(8H)-yl)-N-(1-methylpiperidin-3-yl)acetamide, or a pharmaceutically acceptable salt thereof.

In embodiment 14c, the invention relates to a compound of formula (I), wherein the compound is 2-(2-chloro-5-isopropyl-8-oxothieno[2',3':4,5]pyrrolo[1,2-d][1,2,4]triazin-7(8H)-yl)-N-((1s,3s)-3-hydroxy-3-methylcyclobutyl) acetamide, or a pharmaceutically acceptable salt thereof.

In embodiment 14d, the invention relates to a compound of formula (I), wherein the compound is (R)-2-(5-isopropyl-8-oxothiazolo[5',4':4,5]pyrrolo[1,2-d][1,2,4]triazin-7(8H)-yl)-N-(piperidin-3-yl)acetamide, or a pharmaceutically acceptable salt thereof.

In embodiment 14e, the invention relates to a compound of formula (I), wherein the compound is N-((1s,3s)-3-hydroxy-3-methylcyclobutyl)-2-(5-isopropyl-8-oxothiazolo[5',4':4,5]pyrrolo[1,2-d][1,2,4]triazin-7(8H)-yl)acetamide, or a pharmaceutically acceptable salt thereof.

In embodiment 14f, the invention relates to a compound of formula (I), wherein the compound is (R)-2-(2-chloro-5-isopropyl-8-oxothieno[2',3':4,5]pyrrolo[1,2-d][1,2,4]triazin-7(8H)-yl)-N-(1-cyclobutylpiperidin-3-yl)acetamide, or a pharmaceutically acceptable salt thereof.

In embodiment 14g, the invention relates to a compound of formula (I), wherein the compound is 2-(2-fluoro-5-isopropyl-8-oxothieno[2',3':4,5]pyrrolo[1,2-d][1,2,4]triazin- 7(8H)-yl)-N-((1s,3s)-3-hydroxy-3-methylcyclobutyl) acetamide, or a pharmaceutically acceptable salt thereof.

In embodiment 14h, the invention relates to a compound of formula (I), wherein the compound is 2-(2-chloro-5-(2-hydroxypropan-2-yl)-8-oxothieno[2',3':4,5]pyrrolo[1,2-d][1,2,4]triazin-7(8H)-yl)-N-((1s,3s)-3-hydroxy-3-methylcyclobutyl) acetamide, or a pharmaceutically acceptable salt thereof.

In embodiment 14i, the invention relates to a compound of formula (I), wherein the compound is N-((1R,3R)-3-hydroxycyclohexyl)-2-(5-isopropyl-8-oxothiazolo[5',4':4,5]pyrrolo[1,2-d][1,2,4]triazin-7(8H)-yl)acetamide, or a pharmaceutically acceptable salt thereof.

In embodiment 14j, the invention relates to a compound of formula (I), wherein the compound is (1 r,4r)-4-(2-(2-fluoro-5-isopropyl-8-oxothieno[2',3':4,5]pyrrolo[1,2-d][1,2,4]triazin-7(8H)-yl)acetamido)cyclohexane-1-carboxylic acid, or a pharmaceutically acceptable salt thereof.

In embodiment 15, the invention relates to a pharmaceutical composition comprising a therapeutically effective amount of a compound of formulae (I) to (III), or a pharmaceutically acceptable salt thereof, according to any one of embodiments 1, 2, 3, 4, 5, 5a, 6, 6a, 6b, 6c, 6d, 6e, 6f, 7, 7a, 7b, 7c, 7d, 7e, 7f, 7g, 7h, 8, 9, 9a, 9b, 9c, 10, 10a, 11, 11a, 11b, 11c, 11d, 12, 13, 14, 14a, 14b, 14c, 14d, 14e, 14f, 14g, 14h, 14i and 14j, and one or more pharmaceutically acceptable carriers.

In embodiment 16, the invention relates to a combination comprising a therapeutically effective amount of a compound of formulae (I) to (III), or a pharmaceutically acceptable salt thereof, according to any one of embodiments 1, 2, 3, 4, 5, 5a, 6, 6a, 6b, 6c, 6d, 6e, 6f, 7, 7a, 7b, 7c, 7d, 7e, 7f, 7g, 7h, 8, 9, 9a, 9b, 9c, 10, 10a, 11, 11a, 11b, 11c, 11d, 12, 13, 14, 14a, 14b, 14c, 14d, 14e, 14f, 14g, 14h, 14i and 14j, and one or more therapeutic agents.

In embodiment 17, the invention relates to a combination comprising a therapeutically effective amount of a compound of formulae (I) to (III), or a pharmaceutically acceptable salt thereof, according to embodiment 16, wherein one or more therapeutic agents are independently selected from farnesoid X receptor (FXR) agonists; anti-steatotics; anti-fibrotics; JAK inhibitors; checkpoint inhibitors including anti-PD1 inhibitors, anti-LAG-3 inhibitors, anti-TIM-3 inhibitors, or anti-PDL1 inhibitors; chemotherapy, radiation therapy and surgical procedures; urate-lowering therapies; anabolics and cartilage regenerative therapy; blockade of IL-17; complement inhibitors; Bruton's tyrosine Kinase inhibitors (BTK inhibitors); Toll Like receptor inhibitors (TLR7/8 inhibitors); CAR-T therapy; anti-hypertensive agents; cholesterol lowering agents; leukotriene A4 hydrolase (LTAH4) inhibitors; SGLT2 inhibitors; β2-agonists; anti-inflammatory agents; nonsteroidal anti-inflammatory drugs ("NSAIDs"); acetylsalicylic acid drugs (ASA) including aspirin; paracetamol; regenerative therapy treatments; cystic fibrosis treatments; or atherosclerotic treatment.

In one embodiment, the invention relates to a method of inhibiting NLRP3 activity in a subject, wherein the method comprises administering to the subject a therapeutically effective amount of a compound of formulae (I) to (III), or a pharmaceutically acceptable salt thereof, according to any one of embodiments 1, 2, 3, 4, 5, 5a, 6, 6a, 6b, 6c, 6d, 6e, 6f, 7, 7a, 7b, 7c, 7d, 7e, 7f, 7g, 7h, 8, 9, 9a, 9b, 9c, 10, 10a, 11, 11a, 11b, 11c, 11d, 12, 13, 14, 14a, 14b, 14c, 14d, 14e, 14f, 14g, 14h, 14i and 14j.

In one embodiment, the invention relates to a method of treating a disease or disorder selected from inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, hyperoxaluria, pseudogout (chondrocalcinosis), osteoarthritis, rheumatoid arthritis, acute or chronic arthropathy, kidney related diseases (e.g. lupus nephritis, diabetic nephropathy, hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis), wherein the method comprises administering to the subject a therapeutically effective amount of a compound of formulae (I) to (III), or a pharmaceutically acceptable salt thereof, according to any one of embodiments 1, 2, 3, 4, 5, 5a, 6, 6a, 6b, 6c, 6d, 6e, 6f, 7, 7a, 7b, 7c, 7d, 7e, 7f, 7g, 7h, 8, 9, 9a, 9b, 9c, 10, 10a, 11, 11a, 11b, 11c, 12, 13, 14, 14a, 14b, 14c, 14d, 14e, 14f, 14g, 14h, 14i and 14j. In particular the disease or disorder is preferably selected from autoinflammatory fever syndromes (e.g. CAPS), sickle cell disease, Type I/Type II diabetes and related complications (e.g. nephropathy, retinopathy), gout, hyperoxaluria, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In embodiment 18, the invention relates to a compound of formulae (I) to (III), or a pharmaceutically acceptable salt thereof, according to any one of embodiments 1, 2, 3, 4, 5, 5a, 6, 6a, 6b, 6c, 6d, 6e, 6f, 7, 7a, 7b, 7c, 7d, 7e, 7f, 7g, 7h, 8, 9, 9a, 9b, 9c, 10, 10a, 11, 11a, 11b, 11c, 12, 13, 14, 14a, 14b, 14c, 14d, 14e, 14f, 14g, 14h, 14i and 14j, or a combination according to embodiments 16 to 17, for use as a medicament, in particular for inhibiting NLRP3 activity. In particular, the invention relates to a compound of formulae (I) to (III), or a pharmaceutically acceptable salt thereof, according to any one of embodiments 1 to 14j, for use as a medicament. In particular, the invention relates to a compound of formulae (I) to (III), or a pharmaceutically acceptable salt thereof, according to any one of embodiments 1 to 14j, for use as a medicament for inhibiting NLRP3 pathway. In another particular embodiment, the invention relates to a combination according to any one of embodiments 16 to 17, for use as a medicament.

In embodiment 19, the invention relates to a compound of formulae (I) to (III), or a pharmaceutically acceptable salt thereof, according to any one of embodiments 1 to 14j, for use in the treatment of a disease or disorder in which the NLRP3 signaling contributes to the pathology, and/or symptoms, and/or progression, of said disease or disorder.

In embodiment 20, the invention relates to a method of treating a disease or disorder in which the NLRP3 signaling contributes to the pathology, and/or symptoms, and/or progression, of said disease or disorder, comprising administering a therapeutically effective amount of a compound of formulae (I) to (III), or a pharmaceutically acceptable salt thereof, according to any one of embodiments 1 to 14j.

In embodiment 21, the invention relates to a compound of formulae (I) to (III), or a pharmaceutically acceptable salt thereof, according to any one of embodiments 1, 2, 3, 4, 5, 5a, 6, 6a, 6b, 6c, 6d, 6e, 6f, 7, 7a, 7b, 7c, 7d, 7e, 7f, 7g, 7h, 8, 9, 9a, 9b, 9c, 10, 10a, 11, 11a, 11b, 11c, 12, 13, 14, 14a, 14b, 14c, 14d, 14e, 14f, 14g, 14h, 14i and 14j, for use according to embodiment 19, or to a method of treating according to embodiment 20, wherein the disease or disorder is selected from inflammasome-related diseases/disorders, immune diseases, inflammatory diseases, auto-immune diseases, or auto-inflammatory diseases, for example, auto-inflammatory fever syndromes (e.g cryopyrin-associated periodic syndrome), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukaemia, myelodysplastic syndromes (MDS), myelofibrosis). In a particular aspect, the invention relates to a compound of any one of formula (I), (II), (III), and (Ill-A), or a pharmaceutically acceptable salt thereof, wherein the disease or disorder is preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In one embodiment, the invention relates to a compound of formulae (I) to (III), or a pharmaceutically acceptable salt thereof, according to any one of embodiments 1, 2, 3, 4, 5, 5a, 6, 6a, 6b, 6c, 6d, 6e, 6f, 7, 7a, 7b, 7c, 7d, 7e, 7f, 7g, 7h, 8, 9, 9a, 9b, 9c, 10, 10a, 11, 11a, 11b, 11c, 12, 13, 14, 14a, 14b, 14c, 14d, 14e, 14f, 14g, 14h, 14i and 14j, for use in the treatment of a disease or disorder selected from inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis).

In a particular aspect of embodiment 21, the invention relates to a compound of formulae (I) to (III), or a pharmaceutically acceptable salt thereof, wherein the disease or disorder is preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In embodiment 22, the invention relates to a method of inhibiting the NLRP3 inflammasome activity in a subject in need thereof, the method comprising administering to a subject in need thereof a therapeutically effective amount of a compound of formulae (I) to (III), or a pharmaceutically acceptable salt thereof, according to any one of embodiments 1 to 14j.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diastereoisomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. The invention is also meant to include any pseudo-asymmetric carbon atom, represented herein as (r)- and (s)-, and which are invariant on reflection in a mirror but are reversed by exchange of any two entities, (PAC 1996, 68, 2193, *Basic terminology of stereochemistry IUPAC recommandations* 1996).

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups, or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine, and tromethamine.

In another aspect, the present invention provides compounds of any one of formulae (I) to (III) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate, or xinafoate salt form.

In another aspect, the present invention provides compounds of any one of formulae (I) to (III) in sodium, potassium, ammonium, calcium, magnesium, iron, silver, zinc, copper, isopropylamine, benzathine, cholinate, diethanolamine, diethylamine, lysine, meglumine, piperazine, or tromethamine salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of formula (I). The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

In another aspect, the invention provides a compound of formula (I),

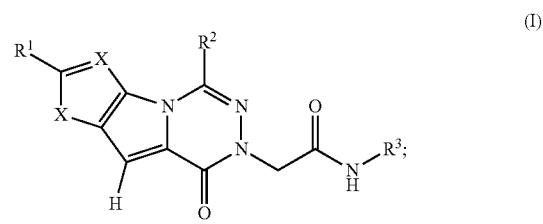

or a pharmaceutically acceptable salt thereof, wherein when $R^3$ is selected from the following:

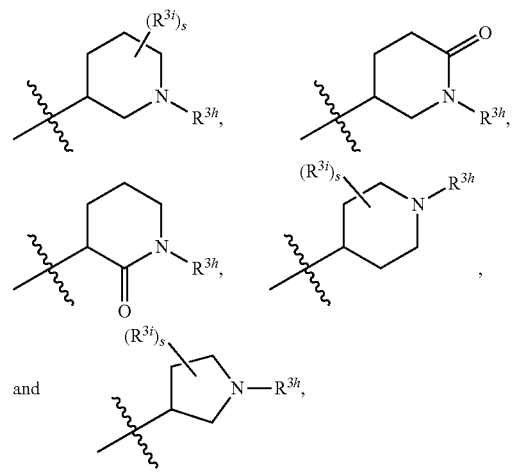

and with $R^{3i}$ and $R^{3h}$ are as defined in embodiment 11, 11a, 11b, or 11c, and one or more hydrogen atoms present in $R^{3i}$ and/or $R^{3h}$ can be replaced with a deuterium atom (including $R^{3i}$ or $R^{3h}$ being a deuterium atom). For example, but not limited to, the deuterium can be incorporated as follows:

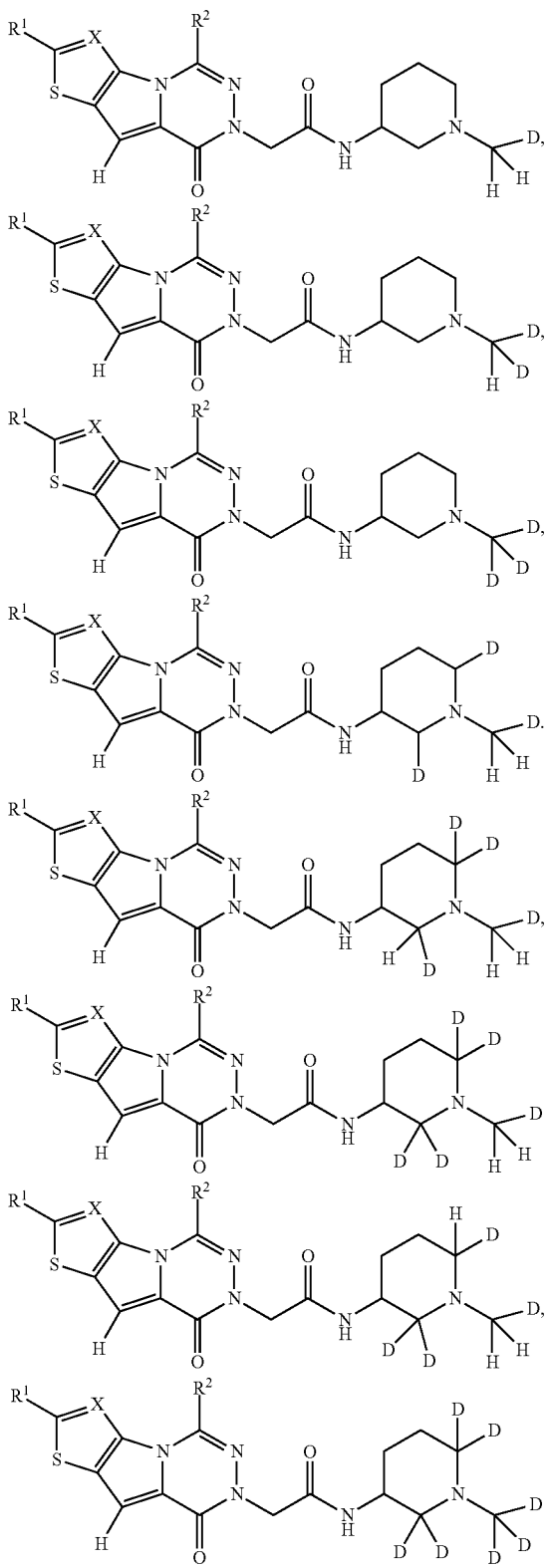

Other examples of isotopes that can be incorporated into compounds of the invention include isotopes of hydrogen, carbon, nitrogen, oxygen, phosphorous, fluorine, chlorine, and iodine, such as $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. Accordingly, it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutical Composition

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by NLRP3, or (ii) associated with NLRP3 activity, or (iii) characterized by activity (normal or abnormal) of NLRP3; or (2) reduce or inhibit the activity of NLRP3; or (3) reduce or inhibit the expression of NLRP3. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of NLRP3; or at least partially reduce or inhibit the expression of NLRP3.

As used herein, the term "subject" refers to primates (e.g., humans, male or female), dogs, rabbits, guinea pigs, pigs, rats and mice. In certain embodiments, the subject is a primate. In yet another embodiment, the subject is a human.

As used herein, the term "inhibit", "inhibition" or "inhibiting" refers to the reduction or suppression of a given condition, symptom, or disorder, or disease, or a significant decrease in the baseline activity of a biological activity or process. Specifically, inhibiting NLRP3 or inhibiting NLRP3 inflammasome pathway comprises reducing the ability of NLRP3 or NLRP3 inflammasome pathway to induce the production of IL-1β and/or IL-18. This can be achieved by mechanisms including, but not limited to, inactivating, destabilizing, and/or altering distribution of NLRP3.

As used herein, the term "NLRP3" is meant to include, without limitation, nucleic acids, polynucleotides, oligonucleotides, sense and anti-sense polynucleotide strands, complementary sequences, peptides, polypeptides, proteins, homologous and/or orthologous NLRP molecules, isoforms, precursors, mutants, variants, derivatives, splice variants, alleles, different species, and active fragments thereof.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates, or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) using a chiral adsorbent.

Method of Synthesizing the Compounds of the Invention

The compounds of the present invention may be prepared in accordance to the definition of compound of formula (I), by the routes described in the following Schemes or the Examples. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. In the following general methods, $R^1$, $R^2$, $R^3$, halo and X are as previously defined in the above embodiments, or limited to designations in the Schemes. Unless otherwise stated, starting materials are either commercially available or are prepared by known methods.

Reaction Scheme 1

Compounds of the present invention, as described herein, may be prepared by a reaction sequence shown in Scheme 1 (below), whereby an appropriately substituted bicyclic pyrrole-5-carbohydrazide (M1) is reacted with the hydrochloride salt of an appropriate imidate (M2) wherein R is $C_1$-$C_4$alkyl, followed by base-induced cyclization, e.g. with KOtBu, to give triazinone (M3) which is then either alkylated with an appropriate haloacetamide (Path A) and a base, e.g. $Cs_2CO_3$ or LiHMDS, to provide a target compound of formula (I), or a pharmaceutically acceptable salt thereof, directly, or is alkylated with an appropriate alkyl haloacetate wherein R is $C_1$-$C_4$alkyl (Path B) and a base, e.g. $Cs_2CO_3$, to provide ester (M4) which is typically cleaved e.g. under basic conditions, e.g. aqueous LiOH in THF to yield the acid intermediate (M5), followed by amidation with $R^3$—$NH_2$ (wherein if $R^3$ has a functional group such as OH, $NH_2$, $CO_2H$, such group is optionally protected) using standard coupling conditions, e.g. HATU or EDC/HOBt and base, e.g. Hunig's base, optionally followed by an additional deprotection step to provide a compound of formula (I), or a pharmaceutically acceptable salt thereof.

Scheme 1

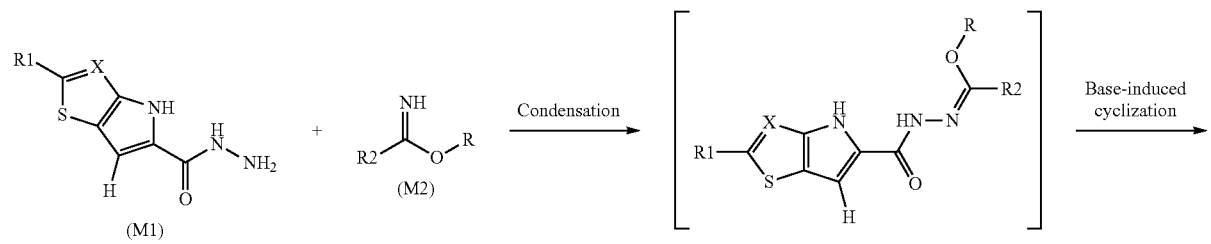

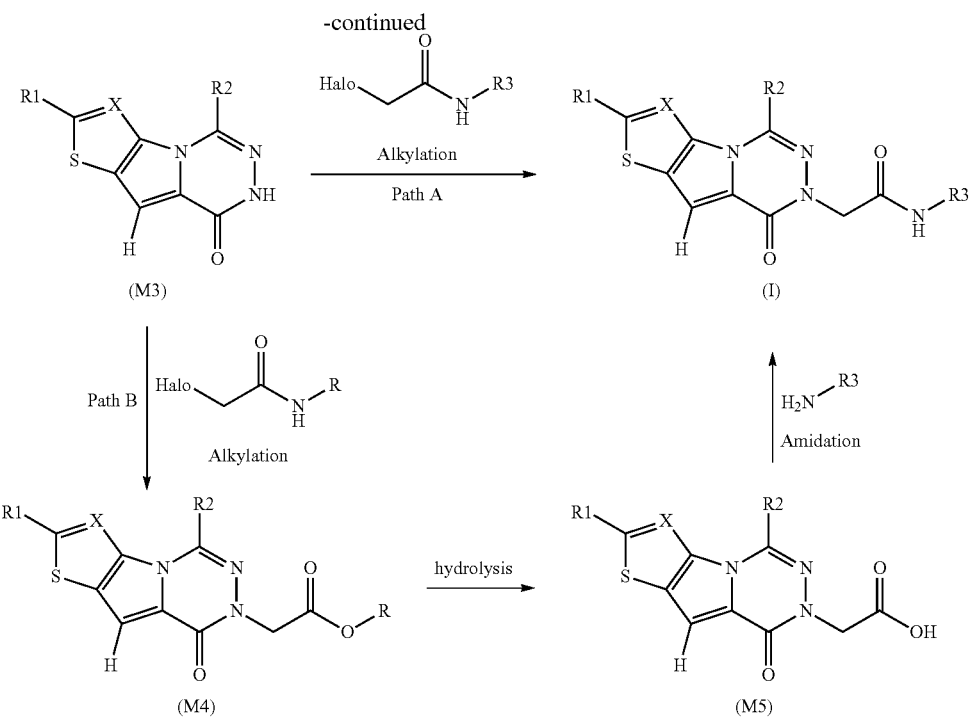

Reaction Scheme 2

Alternatively, compounds of the present invention, as described herein, may be prepared by a reaction sequence whereby an appropriately substituted bicyclic pyrrole-5-carbohydrazide (M6) is reacted with the hydrochloride salt of an appropriate imidate wherein R is $C_1$-$C_4$alkyl (M2) followed by base-induced cyclization, e.g. with KOtBu, to give triazinone (M7) which is either halogenated (Path A), e.g. with NCS, NBS in THF, to give intermediate (M8) which is then alkylated with an appropriate haloacetamide wherein R is $C_1$-$C_4$alkyl, and a base, e.g. $Cs_2CO_3$ or LiHMDS, to provide a target compound of formula (I), or a pharmaceutically acceptable salt thereof, directly. Alternatively, (M7) is is alkylated with an appropriate alkyl haloacetate (Path B) and a base, e.g. $Cs_2CO_3$, to provide ester (M9) which is halogenated, e.g. with NCS, to yield intermediate (M10) which is typically cleaved e.g. under basic conditions, e.g. aqueous LiOH in THF to yield the acid intermediate (M11), followed by amidation with $R^3$—$NH_2$ (wherein if $R^3$ has a fundamental group such as OH, $NH_2$, $CO_2H$, such group is optionally protected)standard coupling conditions, e.g. HATU or EDC/HOBt and base, e.g. Hunig's base, optionally followed by an additional deprotection step to provide a compound of formula (I), or a pharmaceutically acceptable salt thereof, as shown in Scheme 2 (below).

Scheme 2

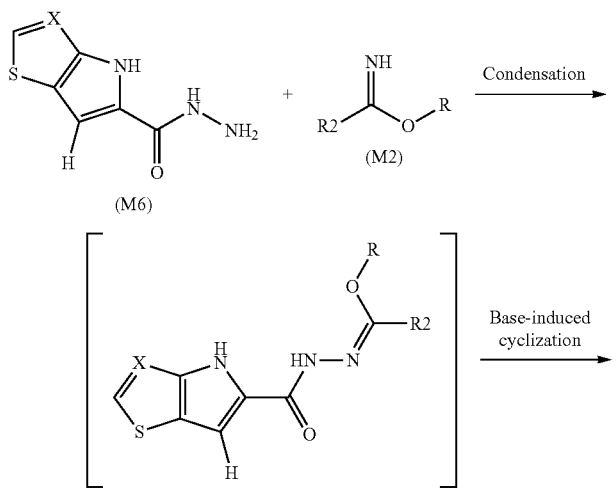

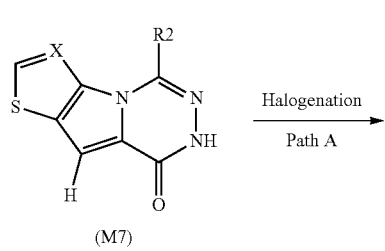 (M7)

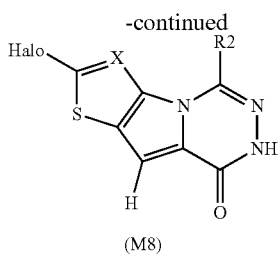 (M8)

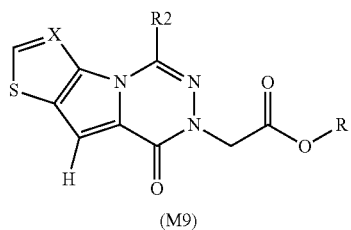 (M9)

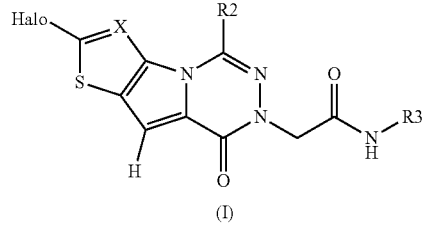 (I)

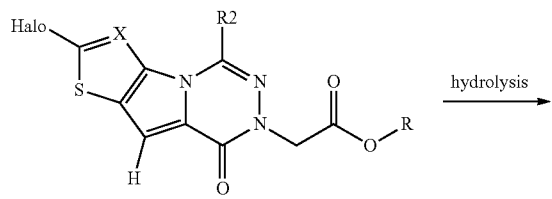

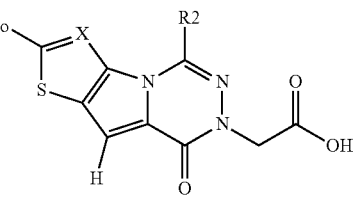

Reaction Scheme 3

Alternatively, compounds of the present invention wherein R² is —C(CH₃)₂OH, as defined herein, may be prepared by a reaction sequence whereby an appropriately substituted bicyclic pyrrole-5-carbohydrazide (M1) is reacted with the hydrochloride salt of an appropriate alkyl 2-hydroxypropanimidate (M12) wherein R is $C_1$-$C_4$alkyl (M12) followed by base-induced cyclization, e.g. with KOtBu, to give triazinone (M13) which is oxidized, e.g. with Dess-Martin periodinane, to provide ketone (M14), which is subjected to a Grignard-type addition reaction, typically facilitated with e.g lanthanide derivatives e.g. CeCl₃ or LaCl₃, to give intermediate (M15) followed by alkylation with an appropriate haloacetate wherein R is $C_1$-$C_4$alkyl and a base, e.g. Cs₂CO₃ or LiHMDS, to yield ester (M16), which is either hydrolyzed (Path A) e.g. under basic conditions, e.g. aqueous LiOH in THF to yield the acid intermediate (M17), followed by amidation with R³—NH₂ (wherein if R³ has a fundamental group such as OH, NH₂, CO₂H, such group is optionally protected) using standard coupling conditions, e.g. HATU or EDC/HOBt and base, e.g. Hunig's base, optionally followed by an additional deprotection step to provide a compound of formula (I), or a pharmaceutically acceptable salt thereof or is halogenated (Path B) e.g. with NCS or NBS, to yield intermediate (M18) which is typically cleaved e.g. under basic conditions, e.g. aqueous LiOH in THF to yield the acid intermediate (M19), followed by amidation with appropriately protected amines using standard coupling conditions, e.g. HATU or EDC/HOBt and base, e.g. Hunig's base, optionally followed by an additional deprotection step to provide a compound of formula (I), or a pharmaceutically acceptable salt thereof, as shown in Scheme 3 (below):

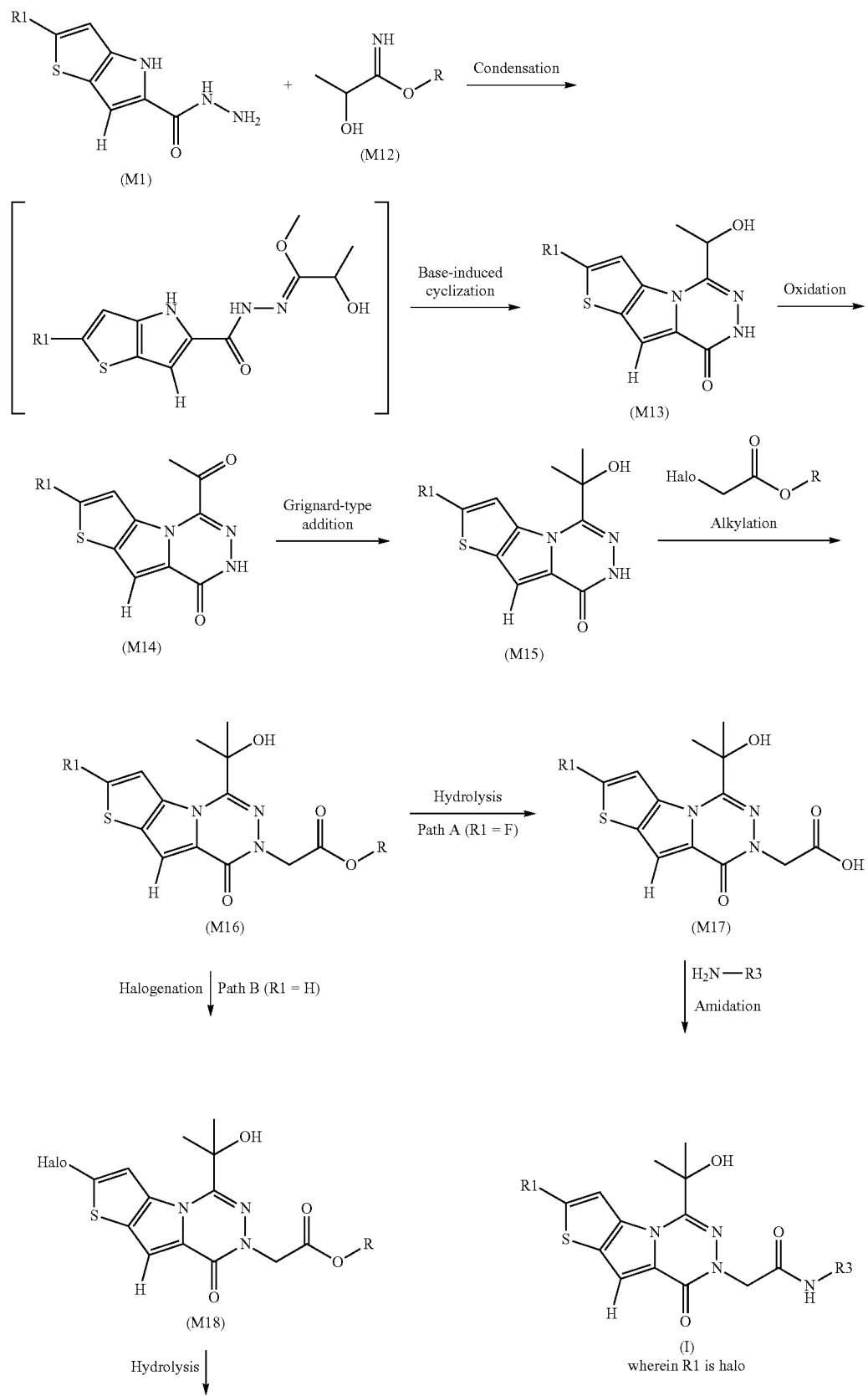

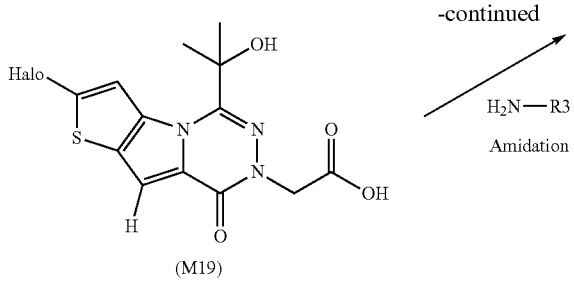

(M19)

Reaction Scheme 4

Bicyclic pyrrole-5-carbohydrazides (M1), if not commercially available, may be prepared by a reaction sequence shown in Scheme 4 (below), whereby an appropriately substituted aldehyde (M20) is reacted with an alkyl 2-azidoacetate and a base, e.g. NaOEt, to give azido-acrylate wherein R is $C_1$-$C_4$alkyl (M21) followed by thermal cyclization to give bicycle (M22) which is transformed into the desired hydrazide (M1) by reaction with hydrazide.

Scheme 4

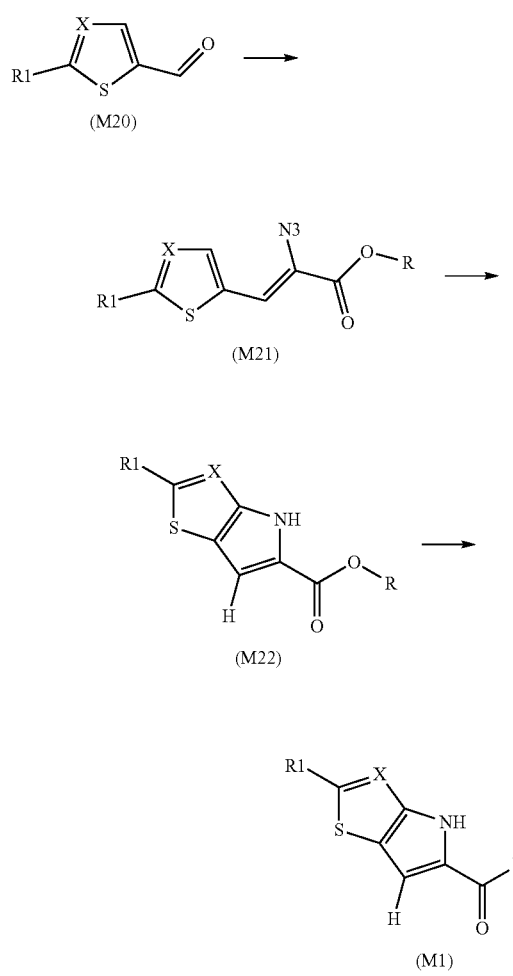

In another embodiment, the invention relates to a compound, or a pharmaceutically acceptable salt thereof, selected from the group consisting of:

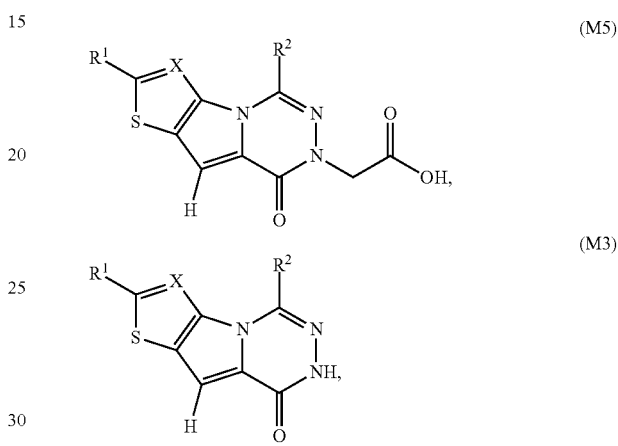

wherein X, $R^1$ and $R^2$ are as defined in embodiment 1.

In another embodiment, the invention relates to a process for preparing a compound of formula (I), or a pharmaceutically acceptable salt thereof, as described in Scheme 1, Scheme 2, Scheme 3 or Scheme 4 above, the process comprising reacting a compound of formula (M3) with a compound of formula halo-$CH_2$—C(O)$NHR_3$, wherein $R_3$ is as defined herein, to obtain a compound of formula (I), or pharmaceutical acceptable salt thereof.

In another embodiment, the invention relates to a process for preparing a compound of formula (I), or a pharmaceutically acceptable salt thereof, as described in Scheme 1, Scheme 2, Scheme 3 or Scheme 4 above, the process comprising the steps of:
 (i) preparing a compound of formula (M3),
 (ii) reacting said compound of formula (M3) with a compound of formula halo-$CH_2$—C(O)$NHR_3$, wherein $R_3$ is as defined herein, to obtain a compound of formula (I), or pharmaceutically acceptable salt thereof.

In yet another embodiment, the invention relates to an alternative process for preparing a compound of formula (I), or a pharmaceutically acceptable salt thereof, as described in Scheme 1, Scheme 2, Scheme 3 or Scheme 4 above, the process comprising the steps of:
 (i) reacting a compound of formula (M3) with a compound of formula halo-$CH_2$—C(O)OR wherein R is $C_1$-$C_4$alkyl,
 (ii) cleaving the ester group to obtain a compound of formula (M5), or a pharmaceutically acceptable salt thereof,
 (iii) reacting said compound of formula (M5) with an amide of formula $NH_2$—$R_3$, wherein $R_3$ is as defined herein, to obtain a compound of formula (I), or pharmaceutically acceptable salt thereof, wherein the compound of formula (M3), or a pharmaceutically acceptable salt thereof, is optionally prepared prior to be reacted.

The processes can be extended to prepare any one of compound of formulae (I) to (III), or a pharmaceutically acceptable salt thereof, as described herein. Depending on the starting materials and the selected route, as mentioned in Scheme 1, Scheme 2, Scheme 3 or Scheme 4 above, a skilled person would know how to prepare compound of formula (I), or a pharmaceutically acceptable salt thereof. Certain variants or alternative processes are described herein below in the experimental section.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Method of Use of the Invention

There is evidence for a role of NLRP3-induced IL-1 and IL-18 in the inflammatory responses occurring in connection with, or as a result of, a multitude of different disorders (Menu et al., *Clinical and Experimental Immunology*, 2011, 166, 1-15; Strowig et al., *Nature*, 2012, 481, 278-286). NLRP3 mutations have been found to be responsible for a set of rare autoinflammatory diseases known as CAPS (Ozaki et al., *J. Inflammation Research*, 2015, 8, 15-27; Schroder et al., *Cell*, 2010, 140: 821-832; Menu et al., *Clinical and Experimental Immunology*, 2011, 166, 1-15).

CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1 beta. NLRP3 has also been implicated in a number of autoinflammatory diseases, including pyogenic arthritis, pyoderma gangrenosum and acne (PAPA), Sweet's syndrome, chronic nonbacterial osteomyelitis (CNO), and acne vulgaris (Cook et al., *Eur. J. Immunol.*, 2010, 40, 595-653).

A number of autoimmune diseases have been shown to involve NLRP3 including, in particular, multiple sclerosis, type-1 diabetes (TID), psoriasis, rheumatoid arthritis (RA), Behcet's disease, Schnitzler syndrome, macrophage activation syndrome (Braddock et al., *Nat. Rev. Drug Disc.* 2004, 3, 1-10; Inoue et al., *Immunology*, 2013, 139, 11-18; Coll et al., *Nat. Med.* 2015, 21(3), 248-55; Scott et al., *Clin. Exp. Rheumatol.* 2016, 34(1), 88-93), systemic lupus erythematosus and its complications such as lupus nephritis (Lu et al., *J. Immunol.*, 2017, 198(3), 1119-29), and systemic sclerosis (Artlett et al., *Arthritis Rheum.* 2011, 63(11), 3563-74). NLRP3 has also been shown to play a role in a number of lung diseases including chronic obstructive pulmonary disorder (COPD), asthma (including steroid-resistant asthma), asbestosis, and silicosis (De Nardo et al., *Am. J. Pathol.*, 2014, 184: 42-54; Kim et al., *Am. J. Respir. Crit. Care Med*, 2017, 196(3), 283-97). NLRP3 has also been suggested to have a role in a number of central nervous system conditions, including Multiple Sclerosis (MS), Parkinson's disease (PD), Alzheimer's disease (AD), dementia, Huntington's disease, cerebral malaria, brain injury from pneumococcal meningitis (Walsh et al., *Nature Reviews*, 2014, 15, 84-97; and Dempsey et al., Brain. Behav. Immun. 2017, 61, 306-16), intracranial aneurysms (Zhang et al., *J. Stroke and Cerebrovascular Dis.*, 2015, 24, 5, 972-9), and traumatic brain injury (Ismael et al., *J. Neurotrauma.*, 2018, 35(11), 1294-1303). NRLP3 activity has also been shown to be involved in various metabolic diseases including type 2 diabetes (T2D) and its organ-specific complications, atherosclerosis, obesity, gout, pseudo-gout, metabolic syndrome (Wen et al., *Nature Immunology*, 2012, 13, 352-357; Duewell et al., *Nature*, 2010, 464, 1357-1361; Strowig et al., *Nature*, 2014, 481, 278-286), and non-alcoholic steatohepatitis (Mridha et al., *J. Hepatol.* 2017, 66(5), 1037-46). A role for NLRP3 via IL-1 beta has also been suggested in atherosclerosis, myocardial infarction (van Hout et al., *Eur. Heart J.* 2017, 38(11), 828-36), heart failure (Sano et al., *J. Am. Coll. Cardiol.* 2018, 71(8), 875-66), aortic aneurysm and dissection (Wu et al., *Arterioscler. Thromb. Vase. Biol.*, 2017, 37(4), 694-706), and other cardiovascular events (Ridker et al., *N. Engl. J. Med.*, 2017, 377(12), 1119-31).

Other diseases in which NLRP3 has been shown to be involved include: ocular diseases such as both wet and dry age-related macular degeneration (Doyle et al., *Nature Medicine*, 2012, 18, 791-798; Tarallo et al., *Cell* 2012, 149(4), 847-59), diabetic retinopathy (Loukovaara et al., *Acta Ophthalmol.*, 2017, 95(8), 803-8), non-infectious uveitis and optic nerve damage (Puyang et al., *Sci. Rep.* 2016, 6, 20998); liver diseases including non-alcoholic steatohepatitis (NASH) and acute alcoholic hepatitis (Henao-Meija et al., *Nature*, 2012, 482, 179-185); inflammatory reactions in the lung and skin (Primiano et al., *J.*

Immunol. 2016, 197(6), 2421-33) including contact hypersensitivity (such as bullous pemphigoid (Fang et al., *J Dermatol Sci.* 2016, 83(2), 116-23)), atopic dermatitis (Niebuhr et al., *Allergy,* 2014, 69(8), 1058-67), Hidradenitis suppurativa (Alikhan et al., *J. Am. Acad. Dermatol.,* 2009, 60(4), 539-61), and sarcoidosis (Jager et al., *Am. J. Respir. Crit. Care Med.,* 2015, 191, A5816); inflammatory reactions in the joints (Braddock et al., *Nat. Rev. Drug Disc,* 2004, 3, 1-10); amyotrophic lateral sclerosis (Gugliandolo et al., *Int. J. Mol. Sci.,* 2018, 19(7), E1992); cystic fibrosis (Iannitti et al., *Nat. Commun.,* 2016, 7, 10791); stroke (Walsh et al., *Nature Reviews,* 2014, 15, 84-97); chronic kidney disease (Granata et al., *PLoS One* 2015, 10(3), eoi22272); and inflammatory bowel diseases including ulcerative colitis and Crohn's disease (Braddock et al., *Nat. Rev. Drug Disc,* 2004, 3, 1-10; Neudecker et al., *J. Exp. Med.* 2017, 214(6), 1737-52; Lazaridis et al., *Dig. Dis. Sci.* 2017, 62(9), 2348-56). The NLRP3 inflammasome has been found to be activated in response to oxidative stress. NLRP3 has also been shown to be involved in inflammatory hyperalgesia (Dolunay et al., *Inflammation,* 2017, 40, 366-86).

Activation of the NLRP3 inflammasome has been shown to potentiate some pathogenic infections such as influenza and Leishmaniasis (Tate et al., *Sci Rep.,* 2016, 10(6), 27912-20; Novias et al., *PLOS Pathogens* 2017, 13(2), e1006196).

NLRP3 has also been implicated in the pathogenesis of many cancers (Menu et al., *Clinical and Experimental Immunology,* 2011, 166, 1-15). For example, several previous studies have suggested a role for IL-1 beta in cancer invasiveness, growth and metastasis, and inhibition of IL-1 beta with canakinumab has been shown to reduce the incidence of lung cancer and total cancer mortality in a randomised, double-blind, placebo-controlled trial (Ridker et al., *Lancet.,* 2017, 390(10105), 1833-42). Inhibition of the NLRP3 inflammasome or IL-1 beta has also been shown to inhibit the proliferation and migration of lung cancer cells in vitro (Wang et al., *Oncol Rep.,* 2016, 35(4), 2053-64). A role for the NLRP3 inflammasome has been suggested in myelodysplastic syndromes, myelofibrosis and other myeloproliferative neoplasms, and acute myeloid leukemia (AML) (Basiorka et al., *Blood,* 2016, 128(25), 2960-75.) and also in the carcinogenesis of various other cancers including glioma (Li et al., *Am. J. Cancer Res.* 2015, 5(1), 442-9), inflammation-induced tumors (Allen et al., *J. Exp. Med.* 2010, 207(5), 1045-56; Hu et al., *PNAS.,* 2010, 107(50), 21635-40), multiple myeloma (Li et al., *Hematology,* 2016 21(3), 144-51), and squamous cell carcinoma of the head and neck (Huang et al., *J. Exp. Clin. Cancer Res.,* 2017, 36(1), 116). Activation of the NLRP3 inflammasome has also been shown to mediate chemoresistance of tumor cells to 5-Fluorouracil (Feng et al., *J. Exp. Clin. Cancer Res.,* 2017, 36(1), 81), and activation of NLRP3 inflammasome in peripheral nerve contributes to chemotherapy-induced neuropathic pain (Jia et al., *Mol. Pain.,* 2017, 13, 1-11). NLRP3 has also been shown to be required for the efficient control of viruses, bacteria, and fungi.

The activation of NLRP3 leads to cell pyroptosis and this feature plays an important part in the manifestation of clinical disease (Yan-gang et al., *Cell Death and Disease,* 2017, 8(2), 2579; Alexander et al., *Hepatology,* 2014, 59(3), 898-910; Baldwin et al., *J. Med. Chem.,* 2016, 59(5), 1691-1710; Ozaki et al., *J. Inflammation Research,* 2015, 8, 15-27; Zhen et al., *Neuroimmunology Neuroinflammation,* 2014, 1(2), 60-65; Mattia et al., *J. Med. Chem.,* 2014, 57(24), 10366-82; Satoh et al., *Cell Death and Disease,* 2013, 4, 644). Therefore, it is anticipated that inhibitors of NLRP3 will block pyroptosis, as well as the release of pro-inflammatory cytokines (e.g. IL-1 beta) from the cell.

The compounds of any one of formulae (I) to (III), or a compound according to any one of the preceding embodiments, or a compound according to any one of the exemplified examples (e.g. Ex 001 to Ex 134 as disclosed herein) in free form or in pharmaceutically acceptable salt form, exhibit valuable pharmacological properties, e.g. NRLP3 inhibiting properties on the NLRP3 inflammasome pathway e.g. as indicated in vitro tests as provided in the next sections, and are therefore indicated for therapy or for use as research chemicals, e.g. as tool compounds.

Compounds of the invention may be useful in the treatment of an indication selected from: inflammasome-related disease/disorders, immune diseases, inflammatory diseases, auto-immune diseases, or auto-inflammatory diseases, for example, of diseases, disorders or conditions in which NLRP3 signaling contributes to the pathology, and/or symptoms, and/or progression, and which may be responsive to NLRP3 inhibition and which may be treated or prevented, according to any one of embodiments 1 to 23, or a compound according to any one of the exemplified examples (e.g. Ex 001 to Ex 134 as disclosed herein), of the present invention include:

I. Inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity. Examples of inflammation that may be treated or prevented include inflammatory responses occurring in connection with, or as a result of:

(a) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(b) a joint condition such as osteoarthritis, systemic juvenile idiopathic arthritis, adult-onset Still's disease, relapsing polychondritis, rheumatoid arthritis, juvenile chronic arthritis, crystal induced arthropathy (e.g. pseudo-gout, gout), or a seronegative spondyloarthropathy (e.g. ankylosing spondylitis, psoriatic arthritis or Reiter's disease);

(c) a muscular condition such as polymyositis or myasthenia gravis;

(d) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(e) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;
(f) a vascular condition such as atherosclerosis, Behcet's disease, vasculitides, or Wegener's granulomatosis;
(g) an immune condition, e.g. autoimmune condition, such as systemic lupus erythematosus (SLE), Sjogren's syndrome, systemic sclerosis, Hashimoto's thyroiditis, type I diabetes, idiopathic thrombocytopenia purpura, or Graves disease;
(h) an ocular condition such as uveitis, allergic conjunctivitis, or vernal conjunctivitis;
(i) a nervous condition such as multiple sclerosis or encephalomyelitis;
(j) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *legionella*, Lyme disease, influenza A, epstein-barr virus, viral encephalitis/aseptic meningitis, or pelvic inflammatory disease;
(k) a renal condition such as mesangial proliferative glomerulonephritis, nephrotic syndrome, nephritis, glomerular nephritis, acute renal failure, uremia, or nephritic syndrome;
(l) a lymphatic condition such as Castleman's disease;
(m) a condition of, or involving, the immune system, such as hyper IgE syndrome, lepromatous leprosy, familial hemophagocytic lymphohistiocytosis, or graft versus host disease;
(n) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;
(o) a cancer, including those cancers listed herein below;
(p) a burn, wound, trauma, haemorrhage or stroke;
(q) radiation exposure; and/or
(r) obesity; and/or
(s) pain such as inflammatory hyperalgesia;
II. Inflammatory disease, including inflammation occurring as a result of an inflammatory disorder, e.g. an autoinflammatory disease, such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD);
III. Immune diseases, e.g. auto-immune diseases, such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barre syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjogren's syndrome, systemic sclerosis a systemic connective tissue disorder, Takayasu's arteritis, temporal arteritis, warm autoimmune hemolytic anemia, Wegener's granulomatosis, alopecia universalis, Beliefs disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, giant cell arteritis, vitiligo or vulvodynia;

IV. Cancer including lung cancer, renal cell carcinoma, non-small cell lung carcinoma (NSCLC), Langerhans cell histiocytosis (LCH), myeloproliferative neoplams (MPN), pancreatic cancer, gastric cancer, myelodysplastic syndrome (MDS), leukaemia including acute lymphocytic leukaemia (ALL) and acute myeloid leukaemia (AML), promyelocytic leukemia (APML, or APL), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

V. Infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocyto-* genes, *Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *schistosoma*, roundworms, tapeworms or flukes), and prion infections;

VI. Central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, multiple sclerosis, and amyotrophic lateral sclerosis;

VII. Metabolic diseases such as type 2 diabetes (T2D), atherosclerosis, obesity, gout, and pseudo-gout;

VIII. Cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, cardiovascular risk reduction (CvRR), and pericarditis including Dressler's syndrome;

IX. Respiratory diseases including chronic obstructive pulmonary disorder (COPD), asthma such as allergic asthma and steroid-resistant asthma, asbestosis, silicosis, nanoparticle induced inflammation, cystic fibrosis, and idiopathic pulmonary fibrosis;

X. Liver diseases including non-alcoholic fatty liver disease (NAFLD) and nonalcoholic steatohepatitis (NASH) including advanced fibrosis stages F3 and F4, alcoholic fatty liver disease (AFLD), and alcoholic steatohepatitis (ASH);

XI. Renal diseases including acute kidney disease, hyperoxaluria, chronic kidney disease, oxalate nephropathy, nephrocalcinosis, glomerulonephritis, and diabetic nephropathy;

XII. Ocular diseases including those of the ocular epithelium, age-related macular degeneration (AMD) (dry and wet), uveitis, corneal infection, diabetic retinopathy, optic nerve damage, dry eye, and glaucoma;

XIII. Skin diseases including dermatitis such as contact dermatitis and atopic dermatitis, contact hypersensitivity, sunburn, skin lesions, hidradenitis suppurativa (HS), other cyst-causing skin diseases, and acne conglobata;

XIV. Lymphatic conditions such as lymphangitis, and Castleman's disease;

XV. Psychological disorders such as depression, and psychological stress;

XVI. Graft versus host disease;

XVII. Bone diseases including osteoporosis, osteopetrosis;

XVIII. Blood disease including sickle cell disease;

XVIX. Allodynia including mechanical allodynia; and

XVX. Any disease where an individual has been determined to carry a germline or somatic non-silent mutation in NLRP3.

More specifically the compounds of the invention may be useful in the treatment of an indication selected from: inflammasome-related disease/disorders, immune diseases, inflammatory diseases, auto-immune diseases, or auto-inflammatory diseases, for example, autoinflammatory fever syndromes (e.g., cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In particular, compounds of the invention, or a pharmaceutically acceptable salt thereof, may be useful in the treatment of a disease or disorder preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).Thus, as a further aspect, the present invention provides the use of a compound of formula (I), (II) or (III), or a compound according to any one of the preceding embodiments (i.e. according to any one of embodiments 1 to 14j), or a compound according to any one of the exemplified examples (e.g. Ex 001 to Ex 134 as disclosed herein), or a pharmaceutically acceptable salt thereof, in therapy. In a further embodiment, the therapy is selected from a disease, which may be treated by inhibition of NLRP3 inflammasome. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy) hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

Thus, as a further aspect, the present invention provides a compound of any one of formulae (I) to (III), or a compound according to any one of the preceding embodiments (i.e. according to any one of embodiments 1 to 14j), or a compound according to any one of the exemplified examples (e.g. Ex 001 to Ex 134 as disclosed herein), or a pharmaceutically acceptable salt thereof, for use in therapy. In a further embodiment, the therapy is selected from a disease, which may be treated by inhibition of NLRP3 inflammasome. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another aspect, the invention provides a method of treating a disease which is treated by inhibiting NLRP3 comprising administration of a therapeutically effective amount of a compound of any one of formulae (I) to (III), or a compound according to any one of the preceding embodiments (i.e. according to any one of embodiments 1 to 14j), or a compound according to any one of the exemplified examples (e.g. Ex 001 to Ex 134 as disclosed herein), or a pharmaceutically acceptable salt thereof. In a further embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

Thus, as a further aspect, the present invention provides the use of a compound of any one of formulae (I) to (III), or a compound according to any one of the preceding embodiments (i.e. according to any one of embodiments 1 to 14j), or a compound according to any one of the exemplified examples (e.g. Ex 001 to Ex 134 as disclosed herein), or a pharmaceutically acceptable salt thereof, for the manufacture of a medicament. In a further embodiment, the medicament is for treatment of a disease, which is treated by inhibition of NLRP3 inflammasome. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 2-(2-fluoro-5-isopropyl-8-oxothieno[2',3':4,5]pyrrolo[1,2-d][1,2,4]triazin-7(8H)-yl)-N-(pyrimidin-4-yl)acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In one embodiment of the present invention, there is provided (R)-2-(2-chloro-5-(2-hydroxypropan-2-yl)-8-oxothieno[2',3':4,5]pyrrolo[1,2-d][1,2,4]triazin-7(8H)-yl)-N-(1-methyl piperidin-3-yl) acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 2-(2-chloro-5-isopropyl-8-oxothieno[2',3':4,5]pyrrolo[1,2-d][1,2,4]triazin-7(8H)-yl)-N-((1s,3s)-3-hydroxy-3-methylcyclobutyl) acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided (R)-2-(5-isopropyl-8-oxothiazolo[5',4':4,5]pyrrolo[1,2-d][1,2,4]triazin-7(8H)-yl)-N-(piperidin-3-yl)acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided N-((1s,3s)-3-hydroxy-3-methylcyclobutyl)-2-(5-isopropyl-8-oxothiazolo[5',4':4,5]pyrrolo[1,2-d][1,2,4]triazin-7(8H)-yl) acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided (R)-2-(2-chloro-5-isopropyl-8-oxothieno[2',3':4,5]

pyrrolo[1,2-d][1,2,4]triazin-7(8H)-yl)-N-(1-cyclobutylpiperidin-3-yl)acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 2-(2-fluoro-5-isopropyl-8-oxothieno[2',3':4,5]pyrrolo[1,2-d][1,2,4]triazin-7(8H)-yl)-N-((1s,3s)-3-hydroxy-3-methylcyclobutyl) acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 2-(2-chloro-5-(2-hydroxypropan-2-yl)-8-oxothieno[2',3':4,5]pyrrolo[1,2-d][1,2,4]triazin-7(8H)-yl)-N-((1s,3s)-3-hydroxy-3-methylcyclobutyl)acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided N-((1R,3R)-3-hydroxycyclohexyl)-2-(5-isopropyl-8-oxothiazolo[5',4':4,5]pyrrolo[1,2-d][1,2,4]triazin-7(8H)-yl) acetamide, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided (1r,4r)-4-(2-(2-fluoro-5-isopropyl-8-oxothieno[2',3':4,5]pyrrolo[1,2-d][1,2,4]triazin-7(8H)-yl)acetamido)cyclohexane-1-carboxylic acid, or a pharmaceutically acceptable salt thereof, for use in the treatment of a disease or disorder selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, Type I and Type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

The pharmaceutical composition or combination of the present invention can be in unit dosage of about 1-1000 mg of active ingredient(s) for a subject of about 50-70 kg, or about 1-500 mg, or about 1-250 mg, or about 1-150 mg, or about 1-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^3$ molar and $10^9$ molar concentrations. A therapeutically effective amount in vivo may range depending on the route of administration, between about 0.1-500 mg/kg, or between about 1-100 mg/kg.

Combination Product and Combination Therapy of the Invention

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g. powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g. tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of any one formula (I) to (III), or a pharmaceutically acceptable salt thereof, and at least one other therapeutic agent as a combined preparation for simultaneous, separate or sequential use in therapy. In one embodiment, the therapy is the treatment of a disease or condition mediated by NLRP3. Products provided as a combined preparation include a composition comprising the compound of any one of formulae (I) to (III), or a pharmaceutically acceptable salt thereof and the other therapeutic agent(s) together in the same pharmaceutical composition, or the compound of any one of formulae (I) to (III) and the other therapeutic agent(s) in separate form, e.g. in the form of a kit.

In one embodiment, the invention provides a pharmaceutical combination comprising a compound of any one of formulae (I) to (III), or a compound according to any one of the preceding embodiments (i.e. according to any one of embodiments 1 to 14j), or a pharmaceutically acceptable salt thereof, and another therapeutic agent(s). Optionally, the pharmaceutical combination may comprise a pharmaceutically acceptable carrier, as described above.

In one embodiment, the invention provides a kit comprising two or more separate pharmaceutical compositions, at least one of which contains a compound of any one of formulae (I) to (III), or a compound according to any one of the preceding embodiments (i.e. according to any one of embodiments 1 to 14j), or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of any one of formulae (I) to (III) for treating a disease or condition mediated by NLRP3, wherein the medicament is prepared for administration with another therapeutic agent. The invention also provides the use of another therapeutic agent for treating a disease or condition mediated by NLRP3 wherein the medicament is administered with a compound of any one of formulae (I) to (III), or a compound according to any one of the preceding embodiments (i.e. according to any one of embodiments 1 to 14j), or a pharmaceutically acceptable salt thereof.

The invention also provides a compound of any one of formulae (I) to (III), or a compound according to any one of the preceding embodiments (i.e. according to any one of embodiments 1 to 14j), or a pharmaceutically acceptable salt thereof, for use in a method of treating a disease or condition mediated by NLRP3, wherein the compound of formula (I), (II), or (III), or a compound according to any one of the preceding embodiments (i.e. according to any one of embodiments 1 to 14j), or pharmaceutically acceptable salt thereof, is prepared for administration with another therapeutic agent. The invention also provides another therapeutic agent for use in a method of treating a disease or condition mediated by NLRP3, wherein the other therapeutic agent is prepared for administration with a compound of formulae (I), (II), or (III), or a compound according to any one of the preceding embodiments (i.e. according to any one of embodiments 1 to 14j), or pharmaceutically acceptable salt thereof. The invention also provides a compound of any one of formulae (I) to (III), or a compound according to any one of the preceding embodiments (i.e. according to any one of embodiments 1 to 14j), or pharmaceutically acceptable salt thereof, for use in a method of treating a disease or condition mediated by NLRP3, wherein the compound of formulae (I), (II), or (III), or a compound according to any one of the preceding embodiments (i.e. according to any one of embodiments 1 to 14j), or pharmaceutically acceptable salt thereof, is administered with another therapeutic agent. The invention also provides another therapeutic agent for use in a method of treating a disease or condition mediated by NLRP3, wherein the other therapeutic agent is administered with a compound of formula (I), (II), or (III), or a compound according to any one of the preceding embodiments (i.e. according to any one of embodiments 1 to 14j), or a pharmaceutically acceptable salt thereof.

The invention also provides the use of a compound of any one of formulae (I) to (III), or a compound according to any one of the preceding embodiments (i.e. according to any one of embodiments 1 to 14j), or pharmaceutically acceptable salt thereof, for treating a disease or condition mediated by NLRP3, wherein the patient has previously (e.g. within 24 hours) been treated with another therapeutic agent. The invention also provides the use of another therapeutic agent for treating a disease or condition mediated by NLRP3 inflammasome, wherein the patient has previously (e.g. within 24 hours) been treated with a compound of formulae (I), (II), or (III), or a compound according to any one of the preceding embodiments (i.e. according to any one of embodiments 1 to 14j), or a pharmaceutically acceptable salt thereof.

In one embodiment, the other therapeutic agent is a therapeutic agent useful in the treatment of inflammasome-related diseases/disorders, immune diseases, inflammatory diseases, auto-immune diseases, or auto-inflammatory diseases, as disclosed herein.

In one embodiment, the other therapeutic agent useful in the combination therapy is selected from farnesoid X receptor (FXR) agonists; anti-steatotics; anti-fibrotics; JAK inhibitors; checkpoint inhibitors; chemotherapy, radiation therapy and surgical procedures; urate-lowering therapies; anabolics and cartilage regenerative therapy; blockade of IL-17; complement inhibitors; Bruton's tyrosine Kinase inhibitors (BTK inhibitors); Toll Like receptor inhibitors (TLR7/8 inhibitors); CAR-T therapy; anti-hypertensive agents; cholesterol lowering agents; leukotriene A4 hydrolase (LTAH4) inhibitors; SGLT2 inhibitors; β2-agonists; anti-inflammatory agents; nonsteroidal anti-inflammatory drugs ("NSAIDs"); acetylsalicylic acid drugs (ASA) including aspirin; paracetamol; regenerative therapy treatments; cystic fibrosis treatments; and atherosclerotic treatment.

Suitable leukotriene A4 hydrolase (LTA4H) inhibitors for use in the combination include, but are not limited to, compounds disclosed in WO2015/092740.

Suitable sodium-dependent glucose transporter 2 (SGLT2) inhibitors for use in the combination include, but are not limited to, compounds disclosed in U.S. Pat. No. 8,163,704, WO2011/048112, WO2011/048148, or in WO2010/128152.

Suitable β2-agonists for use in the combination include, but are not limited to, arformoterol, bambuterol, bitolterol, broxaterol, carbuterol, clenbuterol, dopexamine, fenoterol, formoterol, hexoprenaline, ibuterol, Isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, GSK-159797, GSK-678007, GSK-642444, GSK-159802, HOKU-81, (−)-2-[7(S)-[2(R)-Hydroxy-2-(4-hydroxyphenyl)ethylamino]-5, 6,7, 8-tetrahydro-2-naphthyloxy]-N,N-dimethylacetamide hydrochloride monohydrate, carmoterol, QAB-149 and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy) propyl]sulfonyl}ethyl]amino}ethyl]-2(3H)-benzothiazolone, 1-(1-fluoro-4-hydroxy phenyl)-2-[4-(1-benzimidazolyl)-2-methyl-2-butylamino]ethanol, 1-[3-(4-methoxybenzylamino)-4-hydroxyphenyl]-2-[4(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino] ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol,5-hydroxy-8-(1-hydroxy-2-isopropylaminobutyl)-2H-1,4benzoxazin-3-(4H)-one, 1-(4-amino-3-chloro-5trifluoromethylphenyl)-2-tert-butylamino) ethanol, 1-(4-ethoxycarbonylamino-3-cyano-5-fluorophenyl)-2-(tert-butylamino)ethanol, and combinations thereof, each of which is optionally in the form of a racemate, enantiomer, diastereomer, or mixtures thereof, and also optionally in the form of a pharmacologically-compatible acid addition salt.

Suitable cartilage regenerative therapy for use in the combination includes, but are not limited to, ANGPTL3 peptidomimetics disclosed in WO2014/138687, or a chondrogenesis activator disclosed in WO2015/175487.

Suitable checkpoint inhibitors for use in the combination include, but are not limited to, anti-PD1 inhibitors, anti-LAG-3 inhibitors, anti-TIM-3 inhibitors, anti-PDL1 inhibitors. Suitable anti-PD1 inhibitors, include, but are not limited to, an antibody molecule disclosed in WO2015/112900. Suitable anti-LAG-3 inhibitors, include, but are not limited to, an antibody molecule disclosed in WO2015/138920. Suitable anti-TIM-3 inhibitors include, but are not limited to, an antibody molecule disclosed in WO2015/117002. Suitable anti-TIM-3 inhibitors include, but are not limited to, an antibody molecule disclosed in WO2015/117002. Suitable anti PDL1 inhibitors include, but are not limited to, an antibody molecule disclosed in WO2016/061142.

Suitable Toll Like receptor inhibitors (TLR7/8 inhibitors) for use in the combination include, but are not limited to, a compound disclosed in WO2018/04081.

Suitable FXR agonists for use in the combination include, but are not limited to, obeticholic acid (OCA), GS9674, elafibranor (GFT505), GW4064, UPF987, FXR-450, fexaramine, methylcolate, methyl deoxycholate, 5β-cholanic acid, 5β-chloanic acid 7α, 12α diol, NIHS700, marchantin A, marchantin E, MFA-1 INT767 (also called 6α-ethyl-CDCA disclosed in WO2014/085474), MET409 (Metacrine), EDP-305 (Enanta), 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid (also known under the name Tropifexor), or a pharmaceutically acceptable salt thereof, or a compound disclosed in WO2012/087519, or a compound disclosed in WO2015/069666.

Suitable JAK inhibitors for use in the combination include, but are not limited to Ruxolitinib.

Suitable NSAIDs for use in the combination include, but are not limited to, Aceclofenac, acemetacin, acetylsalicylic acid, alclofenac, alminoprofen, amfenac, Ampiroxicam, Antolmetinguacil, Anirolac, antrafenine, azapropazone, benorylate, Bermoprofen, bindarit, bromfenac, bucloxic acid, Bucolom, Bufexamac, Bumadizon, butibufen, Butixirat, Carbasalatcalcium, carprofen, choline magnesium trisalicylate, celecoxib, Cinmetacin, Cinnoxicam, clidanac Clobuzarit Deboxamet, dexibuprofen, Dexketoprofen, diclofenac, diflunisal, droxicam, Eltenac, Enfenaminsaure, Etersalat, etodolac, etofenamate, etoricoxib, Feclobuzon, felbinac, fenbufen, fenclofenac, fenoprofen, fentiazac, Fepradinol, Feprazon, Flobufen, floctafenine, flufenamic acid, flufenisal, Flunoxaprofen, flurbiprofen, Flurbiprofenaxetil, Furofenac, Furprofen, Glucametacin, ibufenac, ibuprofen, Indobufen, indomethacin, Indometacinfarnesil, indoprofen, Isoxepac, Isoxicam, ketoprofen, ketorolac, lobenzarit, Lonazolac, lornoxicam, Loxoprofen, lumiracoxib, meclofenamic, Meclofen, mefenamic acid, meloxicam, mesalazine, Miro Profen, Mofezolac, nabumetone, naproxen, niflumic acid, olsalazine, oxaprozin, Oxipinac, oxyphenbutazone, parecoxib, phenylbutazone, Pelubiprofen, Pimeprofen, Pirazolac, Priroxicam, pirprofen, Pranoprofen, Prifelon, Prinomod, Proglumetacin, Proquazon, Protizininsaure, rofecoxib, Romazarit, salicylamide, salicylic acid, Salmi Stein, Salnacedin, salsalate, sulindac, sudoxicam, suprofen, Talniflumate, tenidap, Tenosal, tenoxicam, tepoxalin, tiaprofenic acid, Taramid, Tilnoprofenarbamel, timegadine, Tinoridin, Tiopinac, tolfenamic acid, tolmetin, Ufenamat, valdecoxib, Ximoprofen, zaltoprofen, Zoliprofen and combinations thereof.

Suitable BTK inhibitors include for example Ibrutinib, Acalabrutinib (ACP-196), Evobrutinib; Fenebrutinib; Tirabrutinib (ONO-4059, GS-4059); Zanubrutinib (BGB-3111), Spebrutinib (CC-292, AVL-292), Poseltinib (HM-71224, LY3337641), Vecabrutinib (SNS-062), BMS-986142; BMS986195; PRN2246; PRN1008, M7583, CT1530, B11B068, AC-0058TA, ARQ-531, TAK-020, TG1701 or a compound described in WO2015/079417, WO2015/083008, WO2015/110923, WO2014/173289, WO2012/021444, WO2013/081016, WO2013/067274, WO2012/170976, WO2011/162515, US2017/119766, WO2016/065226, U.S. Pat. No. 9,688,676, WO2016/201280, WO2017/059702, U.S. Pat. No. 9,630,968, US2014/0256734, WO2017/118277, WO2014/039899, WO/16/105531, WO2018/005849, WO2013/185082 or in *J. Med. Chem.*, 2016, 59(19), 9173-9200.

Of particular interest, BTK inhibitors include compound of example 31 described in WO2014/039899, compound of the following structure:

described as compound 14f in *Journal of Medicinal Chemistry*, 2016, 59 (19), 9173-9200; compound of example 2 described in US2017/119766, compound of example 223 described in WO2016/065226 which is:

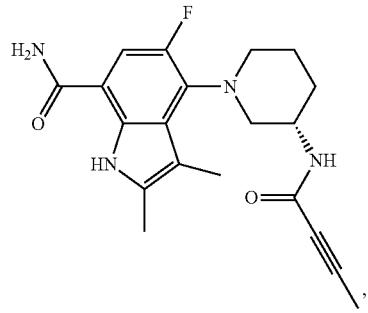 [SMILES: CC#CC(=O)N[C@H]1CCCN(c2c(F)cc(C(N)=O)c3[nH]c(C)c(C)c23)C1]

or compound 1 described in WO2016/201280, compound 1 described in WO2017/059702, or compound 1 described in WO2017/118277; or a pharmaceutically acceptable salt thereof. Of other particular interest, BTK inhibitors include a compound described in WO2015/079417, for example a compound selected from N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloyl azetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclo propyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-yn amido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido) propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclo propyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof.

EXAMPLES

Exemplification of the Invention

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (2014) Protective Groups in Organic Synthesis, 5th edition, John Wiley & Sons). These groups are removed at a convenient stage of the compound synthesis using methods that are readily apparent to those skilled in the art.

Unless otherwise noted, reagents and solvents were used as received from commercial suppliers.

The chemical names were generated using ChemBioDraw Ultra v14 from CambridgeSoft.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Abbreviations

AcOH Acetic acid
ASC Apoptosis-associated speck-like protein
ATCC American Type Culture Collection
CAPS Cryopyrin-Associated Periodic Syndromes
DAMPs Danger-activated molecular patterns
DCM Dichloromethane
DIPEA N-Diisopropylethylamine
DMF N,N-Dimethylformamide
DMSO Dimethylsulfoxide
EDC N-(3-Dimethylaminopropyl)-N'-ethylcarbodiimide hydrochloride
EtOAc Ethyl acetate
EtOH Ethanol
HATU 2-(3H-[1,2,3]triazolo[4,5-b]pyridin-3-yl)-1,1,3,3-tetramethyluronium hexafluorophosphate
HOBt 1H-benzo[d][1,2,3]triazol-1-ol
HTRF homogeneous time resolved fluorescence
Hz/MHz Hertz/Mega Hertz
$IC_{50}$ Half maximal inhibitory concentration
IL-1β Interleukin 1 beta
IR Infrared
LC-MS Liquid chromatography—mass spectrometry
LPS Lipopolysaccharides from *Escherichia coli* 0111:B4
LRR Leucine-rich repeat
M Molar
MEK Methyl ethyl ketone; Butan-2-one
MeOH Methanol
min Minute
mL Millilitre
mmol Millimol
NaOEt Sodium ethoxide
NASH Non-alcoholic steatohepatitis
NBD Nucleotide-binding site domain
NCS N-Chlorosuccinimide
NLRs NOD-like receptors
NMR Nuclear magnetic resonance
PAD Peripheral artery disease
PAMPs Pathogen activated molecular patterns
Pd/C Palladium on carbon
PMA Phorbol 12-myristate 13-acetate
ppm parts per million
RPMI Roswell Park Memorial Institute
RT Room temperature—in Celsius
Rt Retention time
SLE systemic lupus erythematosus
TBAB Tetrabutylammonium bromide
TFA Trifluoroacetic acid
THF Tetrahydrofuran
TMS tetramethylsilane
TNF-α Tumor necrosis factor-α

Analytical Details

NMR: Measurements were performed on a Bruker Ultrashield™ 400 (400 MHz) spectrometer using or not tetramethylsilane (TMS) as an internal standard. Chemical shifts (δ) are reported in ppm downfield from TMS, spectra splitting pattern are designated as singlet (s), doublet (d), triplet (t), quartet (q), quintet (quint), septet (sept), multiplet, unresolved or overlapping signals (m), broad signal (br). Deuterated solvents are given in parentheses and have a chemical shifts of dimethyl sulfoxide (δ 2.50 ppm), methanol (δ 3.31 ppm), chloroform (δ 7.26 ppm), or other solvent as indicated in NMR spectral data.

Preparative and Analytic Methods

LC-MS: System: Waters Acquity UPLC with Waters SQ detector.

Column: Acquity HSS T3 1.8 μm 2.1×50 mm, column temperature: 60° C.

Gradient: from 5 to 98% B in 1.4 min, A=water+0.05% formic acid+3.75 mM ammonium acetate, B=acetonitrile+0.04% formic acid, flow: 1.0 mL/min.

Mass spectrometry results are reported as the ratio of mass over charge.

Flash Column Chromatography System:

System: Teledyne ISCO, CombiFlash Rf.

Columns: pre-packed RediSep Rf cartridges.

Samples were typically adsorbed on Isolute.

Reverse Phase (RP) Chromatography:

System: Waters Autopurification-MS System

XBridge C18 OBD 5 um 30×100 mm column.

Detection: Waters 2998 Photodiode Array Detector

Waters MS Single Quadrupole Detection

Column temperature: RT

Eluent A: water+0.1% TFA

Eluent B: acetonitrile+0.1% TFA

Flow: 49 mL/min

Gradient:

| Time [min] | % A (Eluent A) | % B (Eluent B) |
|---|---|---|
| 0.0 | 82 | 18 |
| 2.0 | 82 | 18 |
| 9.0 | 52 | 48 |
| 9.2 | 0 | 100 |
| 10.5 | 0 | 100 |

All starting materials, building blocks, reagents, acids, bases, dehydrating agents, solvents, and catalysts utilized to synthesis the compounds of the present invention are either commercially available or can be produced by organic synthesis methods known to one of ordinary skill in the art.

SYNTHESIS OF INTERMEDIATES 2-(2-Chloro-5-isopropyl-8-oxothieno[2',3':4,5]pyrrolo[1,2-d][1,2,4]triazin-7(8H)-yl)acetic Acid, Int 1

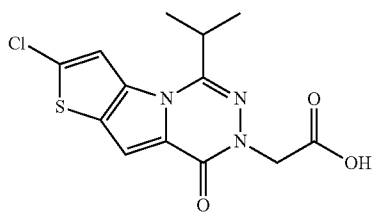 [SMILES: CC(C)c1nn(CC(=O)O)c(=O)c2cc3sc(Cl)cc3n12]

(1) 5-Isopropylthieno[2',3':4,5]pyrrolo[1,2-d][1,2,4]triazin-8(7H)-one, Int 2

A suspension of methyl isobutyrimidate hydrochloride (1.822 g, 13.24 mmol) and 4H-thieno[3,2-b]pyrrole-5-carbohydrazide (2 g, 11.04 mmol) in DMF (15 mL) was vigorously stirred at RT for 20 minutes. Conversion to the intermediate methyl (Z)—N-(4H-thieno[3,2-b]pyrrole-5-carbonyl)isobutyrohydrazonate was complete. Then, solid KOtBu (2.72 g, 24.28 mmol) was added and the mixture was placed in a preheated oil bath at 90° C. and stirred for 1 hour. The dark brown mixture was cooled to 0° C. in an ice-bath, diluted with water (50 mL) and acidified with 2M HCl to pH 5. A precipitate formed which was filtered off and washed thoroughly with water and DCM to give the title compound as a beige solid which was used without further purification. $^1$H-NMR (400 MHz, DMSO-d$_6$): δ (ppm) 11.77 (s, 1H), 7.79 (d, 1H), 7.56 (dd, 1H), 7.47 (d, 1H), 3.63 (sept, 1H), 1.32 (d, 6H). LC-MS: Rt=0.81 min; MS m/z [M+H]$^+$ 234.1

(2) Ethyl 2-(5-isopropyl-8-oxothieno[2',3':4,5]pyrrolo[1,2-d][1,2,4]triazin-7(8H)-yl)acetate, Int 3

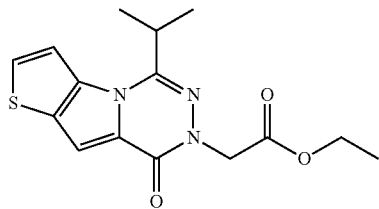 [SMILES: CCOC(=O)Cn1nc(C(C)C)n2c(cc3sccc32)c1=O]

A suspension of Int 2 (0.928g, 3.98 mmol) and Cs$_2$CO$_3$ (3.89 g, 11.93 mmol) in DMF (10 mL) was treated with ethyl 2-iodoacetate (0.470 mL, 3.98 mmol). The mixture was stirred at RT for 20 minutes. The reaction mixture was diluted with water, acidified with 2M HCl and extracted twice with EtOAc. The combined organic extracts were washed with 10% NaHCO$_3$ solution and brine, dried over Na$_2$SO$_4$, filtered and evaporated to provide the crude title compound which was used without further purification. $^1$H NMR (400 MHz, DMSO-d6) δ (ppm) 7.84 (d, 1H), 7.59 (d, 1H), 7.55 (s, 1H), 4.75 (s, 2H), 4.20-4.14 (m, 2H), 3.71-3.63 (m, 1H), 1.32 (d, 6H), 1.21 (dd, 3H). LC-MS: Rt=1.07 min; MS m/z [M+H]$^+$ 320.1

(3) Ethyl 2-(2-chloro-5-isopropyl-8-oxothieno[2',3':4,5]pyrrolo[1,2-d][1,2,4]triazin-7(8H)-yl)acetate, Int 4

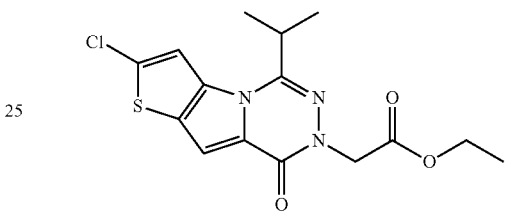

A solution of Int 3 (1.2 g, 3.76 mmol) in THF (20 mL) was treated with solid NCS (0.502 g, 3.76 mmol) and heated at 55° C. for 3 hours. Another portion of NCS (0.151 g, 1.127 mmol) was added and heating continued for 1 hour. The solution was quenched with 10% Na$_2$CO$_3$ solution and extracted twice with EtOAc. The combined organic extracts were washed with brine, dried over Na$_2$SO$_4$, filtered and evaporated. The residue was purified by column chromatography on silica gel using cyclohexane and EtOAc (from 0% to 30%) to give the title compound as a white solid. $^1$H NMR (400 MHz, CDCl$_3$) δ 7.41 (d, 1H), 7.22 (d, 1H), 4.81 (s, 2H), 4.27 (q, 2H), 3.39 (sept, 1H), 1.44 (d, 6H), 1.31 (t, 3H). LC-MS: Rt=1.2 min; MS m/z [M+H]$^+$ 354.1

(4) 2-(2-Chloro-5-isopropyl-8-oxothieno[2',3':4,5]pyrrolo[1,2-d][1,2,4]triazin-7(8H)-yl)acetic Acid, Int 1

A solution of Int 4 (1.1 g, 3.11 mmol) in THF (100 mL) was treated with 1 M LiOH (12.44 mL, 12.44 mmol) and stirred at RT for 1 hour. Another portion of 1 M LiOH (6.22 mL, 6.22 mmol) was added and stirring continued for another hour. A thick white slurry had formed. Water was added and some of the THF was evaporated. The mixture was acidified with 2M HCl and extracted twice with EtOAc. The combined extracts were washed with brine, dried over Na$_2$SO$_4$, filtered and evaporated to provide the title compound as an off-white solid which was used without further purification. $^1$H NMR (400 MHz, DMSO-d6) δ (ppm) 13.03 (s, 1H), 7.81 (s, 1H), 7.50 (s, 1H), 4.64 (s, 2H), 3.61 (sept, 1H), 1.29 (d, 6H). LC-MS: Rt=0.93 min; MS m/z [M+H]$^+$ 326.0

2-Chloro-5-isopropylthieno[2',3':4,5]pyrrolo[1,2-d][1,2,4]triazin-8(7H)-one, Int 5

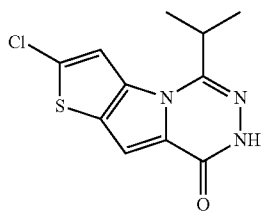 [SMILES: CC(C)c1n[nH]c(=O)c2cc3sc(Cl)cc3n12]

A solution of Int 2 (100 mg, 0.429 mmol) in 10 mL of THF was treated with NCS (57.2 mg, 0.429 mmol) and stirred at RT overnight. Two more portions of NCS (19 mg, 0.142 mmol) were added in intervals of 4 hours. The reaction mixture was partitioned between EtOAc and saturated NaHCO$_3$ solution. The organic layer was dried over Na$_2$SO$_4$, filtered and evaporated. The crude product was purified by column chromatography on silica gel using cyclohexane and EtOAc from 0% to 50% to provide the title compound as a pale yellow solid. $^1$H NMR (400 MHz, DMSO-d6) δ (ppm) 11.83 (s, 1H), 7.79 (d, 1H), 7.44 (d, 1H), 3.59 (sept, 1H), 1.31 (d, 6H). LC-MS: Rt=0.97 min; MS m/z [M+H]$^+$ 268.1

2-(2-Chloro-5-cyclopropyl-8-oxothieno[2',3':4,5]pyrrolo[1,2-d][1,2,4]triazin-7(8H)-yl)acetic acid, Int 6

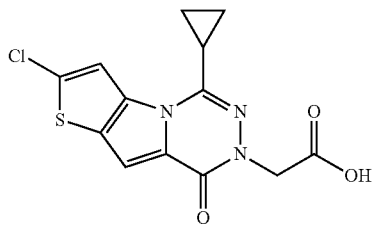 [SMILES: O=C(O)Cn1nc(C2CC2)n2c(cc3sc(Cl)cc32)c1=O]

(1) 5-Cyclopropylthieno[2',3':4,5]pyrrolo[1,2-d][1,2,4]triazin-8(7H)-one, Int 7

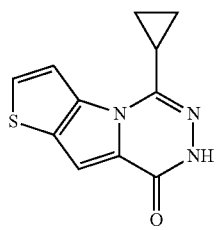

A suspension of ethyl cyclopropanecarbimidate hydrochloride (0.99 g, 6.62 mmol) and 4H-thieno[3,2-b]pyrrole-5-carbohydrazide (1 g, 5.52 mmol) in DMF (20 mL) was vigorously stirred at RT. After 1 hour the conversion to the intermediate ethyl (Z)—N-(4H-thieno[3,2-b]pyrrole-5-carbonyl)cyclopropanecarbohydrazonate was complete. Solid KOtBu (2.17 g, 19.31 mmol) was added and the resulting mixture was placed in a preheated oil bath at 100° C. and stirred for 18 hours. The mixture was cooled to RT, diluted with EtOAc and washed with 10% NaHCO$_3$ solution. The organic layer was dried over Na$_2$SO$_4$, filtered and evaporated to provide the title product. LC-MS: Rt=0.75 min; MS m/z [M+H]$^+$ 232.1

(2) Ethyl 2-(5-cyclopropyl-8-oxothieno[2',3':4,5]pyrrolo[1,2-d][1,2,4]triazin-7(8H)-yl)acetate, Int 8

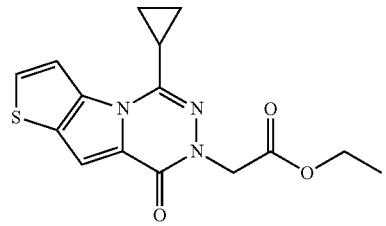 [SMILES: CCOC(=O)Cn1nc(C2CC2)n2c(cc3sccc32)c1=O]

To a suspension of Int 7 (1.30 g, 2.92 mmol) and Cs$_2$CO$_3$ (2.38 g, 7.31 mmol) in DMF (30 mL) was added ethyl 2-iodoacetate (0.45 mL, 3.22 mmol). The resulting mixture was stirred at RT for 18 hours. It was diluted with EtOAc and washed with water. The organic layer was dried over Na$_2$SO$_4$, filtered and evaporated to afford title product. LC-MS: Rt=1.00 min; MS m/z [M+H]$^+$ 318.2

(3) Ethyl 2-(2-chloro-5-cyclopropyl-8-oxothieno[2',3':4,5]pyrrolo[1,2-d][1,2,4]triazin-7(8H)-yl)acetate, Int 9

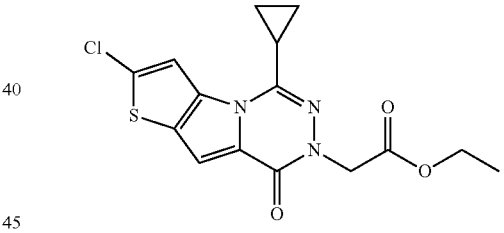

A solution of Int 8 (550 mg, 1.73 mmol) in THF (50 mL) was heated to 60° C. and treated with NCS (1.25 g, 9.36 mmol) added in 4 portions over a period of 5.5 hours. The mixture was cooled to RT, diluted with EtOAc and washed with 10% NaHCO$_3$ solution. The organic layer was dried over Na$_2$SO$_4$, filtered and evaporated. The crude was purified by column chromatography on silica gel using cyclohexane and EtOAc (from 0% to 45%) to afford the title product as a white solid. $^1$H-NMR (400 MHz, DMSO-d6) δ (ppm) 7.93 (s, 1H), 7.49 (s, 1H), 4.71 (s, 2H), 4.16 (q, 2H), 2.53 (m, 1H overlapping with DMSO signal), 1.21 (t, 3H), 1.18-1.12 (m, 2H), 1.02-0.95 (m, 2H). LC-MS: Rt=1.14 min; MS m/z [M+H]$^+$ 352.1

(4) 2-(2-Chloro-5-cyclopropyl-8-oxothieno[2',3':4,5]pyrrolo[1,2-d][1,2,4]triazin-7(8H)-yl)acetic Acid, Int 6

To a solution of Int 9 (445 mg, 1.27 mmol) in THF (3 mL) was added 1M LiOH solution (1.27 mL, 1.27 mmol). The mixture was stirred at RT for 45 minutes. It was then acidified with 2M HCl (2 mL) and extracted with EtOAc. The organic extract was dried over Na$_2$SO$_4$, filtered and evaporated to afford the crude title product as a white solid. $^1$H-NMR (400 MHz, DMSO-d6) δ (ppm) 12.99 (br s, 1H), 7.93 (s, 1H), 7.47 (s, 1H), 4.61 (s, 2H), 2.53 (m, 1H overlapping with DMSO signal), 1.25-1.08 (m, 2H), 1.04-0.95 (m, 2H). LC-MS: Rt=0.88 min; MS m/z [M+H]$^+$ 324.0

2-(5-Isopropyl-2-methyl-8-oxothieno[2',3':4,5]pyrrolo[1,2-d][1,2,4]triazin-7(8H)-yl)acetic Acid, Int 10

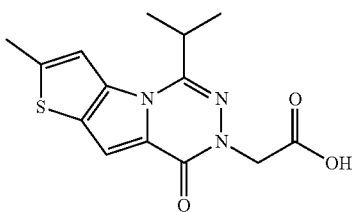 [SMILES: Cc1cc2c(cc3c(=O)n(CC(=O)O)nc(C(C)C)n32)s1]

(1) 5-Isopropyl-2-methylthieno[2',3':4,5]pyrrolo[1,2-d][1,2,4]triazin-8(7H)-one, Int 11

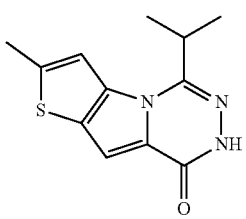 [SMILES: Cc1cc2c(cc3c(=O)[nH]nc(C(C)C)n32)s1]

A suspension of methyl isobutyrimidate hydrochloride (284 mg, 2.064 mmol) and 2-methyl-4H-thieno[3,2-b]pyrrole-5-carbohydrazide (310 mg, 1.588 mmol) in DMF (5 mL) was stirred at RT for 20 minutes. Conversion to the intermediate methyl (Z)—N-(2-methyl-4H-thieno[3,2-b]pyrrole-5-carbonyl)isobutyrohydrazonate was complete. Then, KOtBu (410 mg, 3.65 mmol) was added and the mixture was placed in a preheated oil bath at 90° C. and was stirred for 2 hours. The dark brown mixture was cooled to 5° C. in an ice bath, diluted with water (~15 mL) and the pH was adjusted to ~5 with 2M HCl (~1.5 mL). A brownish precipitate formed which was filtered off and washed thoroughly with water. It was then dissolved in DCM and slowly evaporated. Upon evaporation, the title compound crystallized as fine off-white needles which were filtered off. The mother liquor was further purified by column chromatography on silica gel using cyclohexane and EtOAc (from 0% to 40%) to provide more of the title compound. $^1$H NMR (400 MHz, CDCl$_3$) δ (ppm) 9.24 (s, 1H), 7.46 (d, 1H), 6.99 (s, 1H), 3.49 (sept, 1H), 2.67 (d, 3H), 1.45 (d, 7H). LC-MS: Rt=0.57 min; MS m/z [M+H]$^+$ 236.1

(2) Ethyl 2-(5-isopropyl-2-methyl-8-oxothieno[2',3':4,5]pyrrolo[1,2-d][1,2,4]triazin-7(8H)-yl)acetate, Int 12

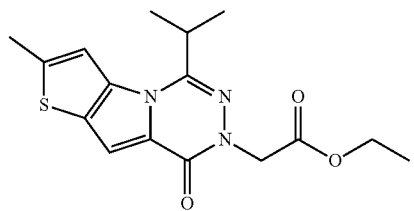 [SMILES: CCOC(=O)Cn1nc(C(C)C)n2c(cc3sc(C)cc32)c1=O]

To a solution of Int 11 (180 mg, 0.728 mmol) in DMF (3 mL) was added Cs$_2$CO$_3$ (1.186 g, 3.64 mmol) followed by a solution of ethyl 2-iodoacetate (0.103 mL, 0.873 mmol) in DMF (2 mL). The mixture was stirred at RT for 3 hours, then quenched with water and extracted twice with EtOAc. The organic extracts were washed with brine, dried over Na$_2$SO$_4$, filtered and evaporated to provide the title compound as a light yellow solid. $^1$H NMR (400 MHz, CDCl$_3$) δ (ppm) 7.41 (s, 1H), 6.96 (s, 1H), 4.80 (s, 2H), 4.25 (q, 2H), 3.45 (sept, 1H), 2.65 (s, 3H), 1.42 (d, 6H), 1.30 (t, 3H). LC-MS: Rt=1.15 min; MS m/z [M+H]$^+$ 334.1

(3) 2-(5-Isopropyl-2-methyl-8-oxothieno[2',3':4,5]pyrrolo[1,2-d][1,2,4]triazin-7(8H)-yl)acetic Acid, Int 10

A solution of Int 12 (225 mg, 0.675 mmol) in THF (7 mL) was treated with 1M LiOH (3.4 mL, 3.4 mmol) and stirred at RT for 16 hours. The mixture was acidified with 0.1M HCl and extracted with EtOAc. The organic layer was washed with brine, dried over Na$_2$SO$_4$, filtered and evaporated to provide the title compound as a white solid. $^1$H NMR (400 MHz, DMSO-d6) δ (ppm) 12.97 (br s, 1H), 7.45 (s, 1H), 7.36 (s, 1H), 4.63 (s, 2H), 3.61 (sept, 1H), 2.63 (s, 3H), 1.32 (d, 6H). LC-MS: Rt=0.89 min; MS m/z [M+H]$^+$ 306.1

2-(2-Chloro-5-(2-hydroxypropan-2-yl)-8-oxothieno[2',3':4,5]pyrrolo[1,2-d][1,2,4]triazin-7(8H)-yl)acetic Acid, Int 13

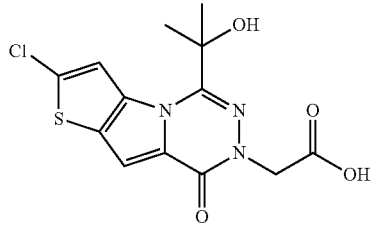 [SMILES: CC(C)(O)c1nn(CC(=O)O)c(=O)c2cc3sc(Cl)cc3n12]

(1) Ethyl 2-hydroxypropanimidate, Int 14

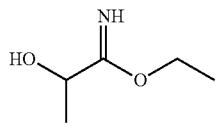

A solution of 2-hydroxypropanenitrile (50 g, 703 mmol) in Et$_2$O (200 mL) and EtOH (45 mL, 774 mmol) was cooled in a dry-ice bath to about 0-5° C. This solution was purged with HCl gas until saturated. The solution was stored at 5° C. for 2 days. A crystalline precipitate formed which was filtered off, washed with Et$_2$O and dried to provide the HCl salt of the title compound. This was used without further purification. $^1$H NMR (400 MHz, DMSO-d6) δ (ppm) 11.40 (s, 2H), 4.58-4.46 (m, 3H), 1.39-1.31 (m, 6H).

(2) 5-(1-Hydroxyethyl)thieno[2',3':4,5]pyrrolo[1,2-d][1,2,4]triazin-8(7H)-one, Int 15

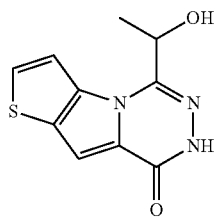 [SMILES: CC(O)c1n[nH]c(=O)c2cc3sccc3n12]

To a suspension of Int 14 hydrochloride (1.297g, 8.44 mmol) in DMF (10 mL) was added 4H-thieno[3,2-b]pyrrole-5-carbohydrazide (1.02 g, 5.63 mmol). After 20 minutes of stirring at RT, KOtBu (1.579 g, 14.07 mmol) was added in small portions (exothermic reaction) over a period of 5 minutes. The mixture was placed in an oil bath, preheated to 90° C., and was stirred for 90 minutes. The reaction mixture was placed in an ice bath and the pH was adjusted to 5 with 2M HCl (~5 mL). It was further diluted with 50 mL of water while stirring. A precipitate formed, which was filtered off and washed thoroughly with water and DCM to provide the title compound as a light brown solid. $^1$H NMR (400 MHz, DMSO-d6) δ (ppm) 11.83 (s, 1H), 7.73 (d, 1H), 7.60 (d, 1H), 7.48 (s, 1H), 5.80 (d, 1H), 5.19 (qd, 1H), 1.56 (d, 3H). LC-MS: Rt=0.57 min; MS m/z [M+H]$^+$ 236.1

(3) 5-Acetylthieno[2',3':4,5]pyrrolo[1,2-d][1,2,4]triazin-8(7H)-one, Int 16

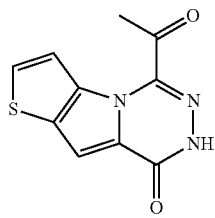 [SMILES: CC(=O)c1n[nH]c(=O)c2cc3sccc3n12]

A suspension of Int 15 (45 mg, 0.191 mmol) and Dess-Martin periodinane (122 mg, 0.287 mmol) in DMF (2 mL) was stirred at RT for 30 minutes. The reaction mixture was carefully quenched with saturated NaHCO$_3$ solution (~10 mL) while stirring. A beige precipitate formed which was filtered off and washed with little DCM to provide the title compound. $^1$H NMR (400 MHz, DMSO-d6) δ (ppm) 12.42 (s, 1H), 7.69 (d, 1H), 7.59 (s, 1H), 7.50 (d, 1H), 2.63 (s, 3H). LC-MS: Rt=0.78 min; MS m/z [M+H]$^+$ 234.1

(4) 5-(2-Hydroxypropan-2-yl)thieno[2',3':4,5]pyrrolo[1,2-d][1,2,4]triazin-8(7H)-one, Int 17

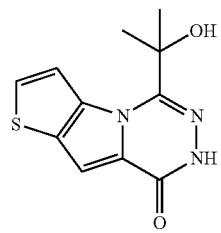 [SMILES: CC(C)(O)c1n[nH]c(=O)c2cc3sccc3n12]

To a solution of Int 16 (1 g, 4.29 mmol) in THF (20 mL) was added LaCl$_3$-2LiCl complex (0.6M in THF, 28.6 mL, 17.15 mmol) and the mixture was stirred at RT for 30 min. This solution was then slowly introduced by pipette into an ice-cold solution of CH$_3$MgCl (3M in THF, 17.15 mL, 51.4 mmol) and THF (20 mL) over a period of 15 minutes, so that the temperature was kept between 5-8° C. After complete addition, the ice-bath was removed and stirring continued for 1 hour. The reaction was carefully quenched with 10% NH$_4$Cl solution and acidified with 2M HCl before extracting 3 times with DCM. The combined organic extracts were dried over Na$_2$SO$_4$, filtered and evaporated to provide the title compound as a brown solid. LC-MS: Rt=0.68 min; MS m/z [M+H]$^+$ 250.1

(5) Ethyl 2-(5-(2-hydroxypropan-2-yl)-8-oxothieno[2',3':4,5]pyrrolo[1,2-d][1,2,4]triazin-7(8H)-yl)acetate, Int 18

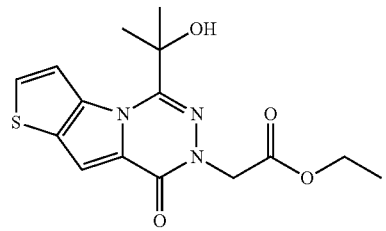 [SMILES: CCOC(=O)Cn1nc(C(C)(C)O)n2c(cc3sccc32)c1=O]

A suspension of Int 17 (235 mg, 0.943 mmol), Cs$_2$CO$_3$ (921 mg, 2.83 mmol) and ethyl 2-iodoacetate (0.111 mL, 0.943 mmol) in DMF (4 mL) was stirred at RT for 10 minutes. The reaction mixture was diluted with water, acidified with 2M HCl and extracted with EtOAc. The organic extract was washed with brine, dried over Na$_2$SO$_4$, filtered and evaporated. The crude was further purified by column chromatography on silica gel using cyclohexane and EtOAc (from 0% to 30%) to provide the title compound as an off-white solid. $^1$H NMR (400 MHz, CDCl$_3$) δ (ppm) 7.88 (dd, 1H), 7.45 (d, 1H), 7.42 (d, 1H), 4.70 (s, 2H), 4.25 (q, 2H), 2.67 (s, 1H), 1.78 (s, 6H), 1.30 (t, 3H). LC-MS: Rt=0.94 min; MS m/z [M+H]$^+$ 336.1

(6) Ethyl 2-(2-chloro-5-(2-hydroxypropan-2-yl)-8-oxothieno[2',3':4,5]pyrrolo[1,2-d][1,2,4]triazin-7(8H)-yl)acetate, Int 19

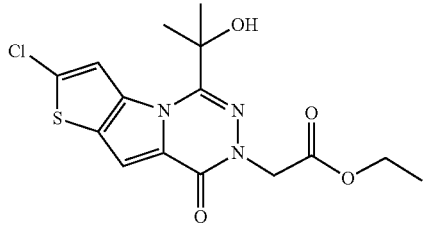 [SMILES: CCOC(=O)Cn1nc(C(C)(C)O)n2c(cc3sc(Cl)cc32)c1=O]

A solution of Int 18 (218 mg, 0.650 mmol) in THF (10 mL) was treated with NCS (87 mg, 0.650 mmol) and stirred at RT for 30 minutes, then at 50° C. for 3 hours and finally at RT over the weekend. Another portion of NCS (26.0 mg, 0.195 mmol) was added and stirring continued at 50° C. for 90 minutes. Another 5 mg of NCS were added and stirring continued for 30 minutes. The fluorescent orange solution was quenched with 10% $Na_2CO_3$ solution and extracted with EtOAc. The organic extract was washed with brine, dried over $Na_2SO_4$, filtered and evaporated. The crude was further purified by column chromatography on silica gel using cyclohexane and EtOAc (from 0% to 25%) to provide the title compound as a white solid. $^1$H NMR (400 MHz, $CDCl_3$) δ (ppm) 7.84 (s, 1H), 7.29 (s, 1H), 4.72 (s, 2H), 4.25 (q, 2H), 2.79 (s, 1H), 1.75 (s, 6H), 1.31 (t, 3H). LC-MS: Rt=1.09 min; MS m/z $[M+H]^+$ 370.1

(7) 2-(2-Chloro-5-(2-hydroxypropan-2-yl)-8-oxothieno[2',3':4,5]pyrrolo[1,2-d][1,2,4]triazin-7(8H)-yl)acetic Acid, Int 13

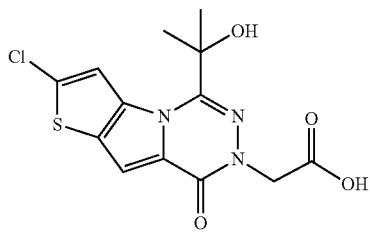 [SMILES: CC(C)(O)c1nn(CC(=O)O)c(=O)c2cc3sc(Cl)cc3n12]

A solution of Int 19 (196 mg, 0.530 mmol) in THF (10 mL) was treated with 1M LiOH (1.590 mL, 1.590 mmol) and stirred at RT overnight. The solution was acidified with 2M HCl, diluted with water and extracted twice with DCM. The combined organic extracts were dried over $Na_2SO_4$, filtered and evaporated to provide the title compound Int 13 as a white solid. $^1$H NMR (400 MHz, DMSO-d6) δ (ppm) 13.05 (s, 1H), 7.93 (d, 1H), 7.57 (d, 1H), 6.10 (s, 1H), 4.66 (s, 2H), 1.60 (s, 6H). LC-MS: Rt=0.83 min; MS m/z $[M+H]^+$ 342.1

2-Chloro-5-(2-hydroxypropan-2-yl)thieno[2',3':4,5]pyrrolo[1,2-d][1,2,4]triazin-8(7H)-one Int 20

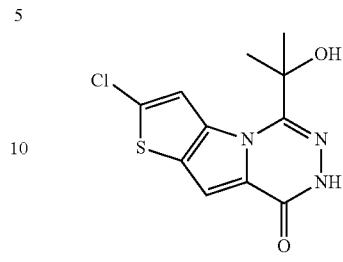

A solution of Int 17 (200 mg, 0.562 mmol) in THF (10 mL) was treated with NCS (75.0 mg, 0.562 mmol) and stirred at RT for 90 minutes. Another portion of NCS (75.0 mg, 0.562 mmol) was added and stirring continued for 4 hours. The fluorescent orange solution was quenched with 10% $NaHCO_3$ solution and water, followed by extraction with EtOAc. The organic extract was further washed with water and brine, dried over $Na_2SO_4$, filtered and evaporated. The crude was triturated with DCM, filtered and dried to give the title compound. LC-MS: Rt=0.85 min; MS m/z $[M+H]^+$ 284.1

2-(2-Chloro-5-(1-hydroxyethyl)-8-oxothieno[2',3':4,5]pyrrolo[1,2-d][1,2,4]triazin-7(8H)-yl)acetic Acid, Int 21

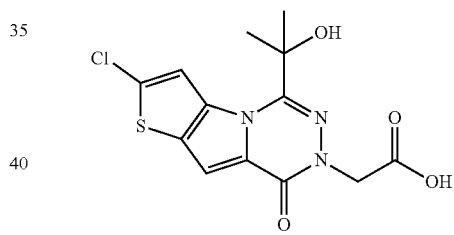

(1) 2-Chloro-5-(1-hydroxyethyl)thieno[2',3':4,5]pyrrolo[1,2-d][1,2,4]triazin-8(7H)-one, Int 22

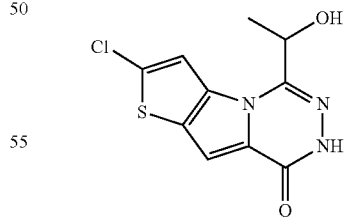

A fine suspension of Int 15 (88 mg, 0.374 mmol) in THF (14 mL) was treated with NCS (54.9 mg, 0.411 mmol) and stirred at 60° C. for 1 hour. Another portion of NCS (54.9 mg, 0.411 mmol) was added and heating continued for 2.5 hours. The reaction was diluted with EtOAc and washed with 10% $NaHCO_3$ solution, water and brine. The organic layer was dried over $Na_2SO_4$, filtered and evaporated. The crude was triturated with a 4/1 mixture of DCM/MeOH to give the title compound as a grey solid. $^1$H NMR (400 MHz, DMSO-d6) δ (ppm) 11.91 (s, 1H), 7.68 (s, 1H), 7.45 (s, 1H), 5.91-5.73 (m, 1H), 5.22-5.11 (m, 1H), 1.54 (d, 3H). LC-MS: Rt=0.74 min; MS m/z [M+H]$^+$ 270.1

(2) Ethyl 2-(2-chloro-5-(1-hydroxyethyl)-8-oxothieno[2',3':4,5]pyrrolo[1,2-d][1,2,4]triazin-7(8H)-yl)acetate, Int 23

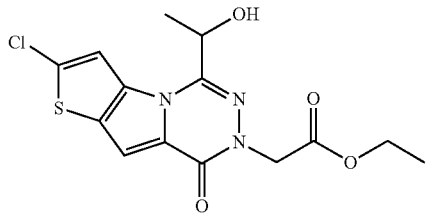 [SMILES: CCOC(=O)Cn1nc(C(C)O)n2c(cc3sc(Cl)cc32)c1=O]

A suspension of Int 22 (110 mg, 0.408 mmol), Cs$_2$CO$_3$ (399 mg, 1.224 mmol) and ethyl 2-iodoacetate (0.053 mL, 0.449 mmol) in DMF (4 mL) was heated at 60° C. for 30 minutes. It was then diluted with water and 1 mL of 2M HCl, followed by extraction with EtOAc. The organic extract was washed with water and brine, dried over Na$_2$SO$_4$, filtered and evaporated. The crude was purified by column chromatography on silica gel using cyclohexane and EtOAc to afford the title compound Int 23 as an off-white solid. $^1$H NMR (400 MHz, CDCl$_3$) δ (ppm) 7.41 (s, 1H), 7.39 (s, 1H), 5.17 (dq, 1H), 4.88-4.74 (m, 2H), 4.27 (q, 2H), 2.70 (d, 1H), 1.72 (d, 3H), 1.32 (t, 3H). LC-MS: Rt=0.97 min; MS m/z [M+H]$^+$ 356.1

(3) 2-(2-Chloro-5-(1-hydroxyethyl)-8-oxothieno[2',3':4,5]pyrrolo[1,2-d][1,2,4]triazin-7(8H)-yl)acetic Acid, Int 21

A solution of Int 23 (79 mg, 0.222 mmol) in THF (3 mL) and MeOH (1 mL) was treated with 1 M LiOH (0.7 mL, 0.7 mmol). It was stirred at RT for 30 minutes. The milky solution was acidified with 2M HCl and extracted with EtOAc. The organic extract was washed with brine, dried over Na$_2$SO$_4$, filtered and evaporated to give the title compound as a white solid. $^1$H NMR (400 MHz, DMSO-d6) δ 13.06 (s, 1H), 7.71 (s, 1H), 7.51 (s, 1H), 5.96 (d, 1H), 5.18 (dq, 1H), 4.73-4.61 (m, 2H), 1.53 (d, 3H). LC-MS: Rt=0.72 min; MS m/z [M+H]$^+$ 328.1

2-(2-Fluoro-5-isopropyl-8-oxothieno[2',3':4,5]pyrrolo[1,2-d][1,2,4]triazin-7(8H)-yl)acetic Acid, Int 24

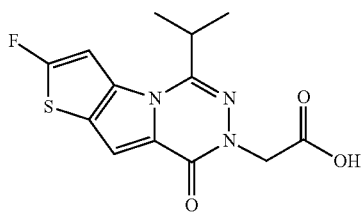 [SMILES: CC(C)c1nn(CC(=O)O)c(=O)c2cc3sc(F)cc3n12]

(1) Ethyl (Z)-2-azido-3-(5-fluorothiophen-2-yl)acrylate, Int 25

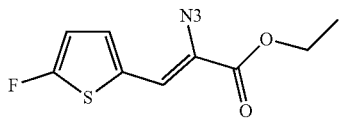 [SMILES: CCOC(=O)/C(=C/c1ccc(F)s1)N=[N+]=[N-]]

A solution of NaOEt (21% in EtOH, 7.9 mL, 21.15 mmol) was diluted with EtOH (40 mL) and cooled in an ice bath to 0° C. To this was added dropwise a mixture of 5-fluorothiophene-2-carbaldehyde (688 mg, 5.29 mmol) and ethyl 2-azidoacetate (30% in DCM, 10.6 mL, 21.15 mmol) while stirring. After 1 hour, the ice bath was removed and stirring continued for 1 hour. The reaction mixture was quenched with saturated NH$_4$Cl solution and extracted with Et$_2$O. The organic layer was dried over Na$_2$SO$_4$, filtered and evaporated. The crude was purified by column chromatography on silica gel using cyclohexane and EtOAc (from 0% to 25%) to provide the title compound. $^1$H NMR (400 MHz, CDCl$_3$) δ (ppm) 7.01 (d, 1H), 6.95 (t, 1H), 6.50 (dd, 1H), 4.38 (q, 2H), 1.41 (t, 3H).

(2) Ethyl 2-fluoro-4H-thieno[3,2-b]pyrrole-5-carboxylate, Int 26

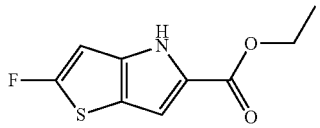

A solution of Int 25 (880 mg, 3.65 mmol) in xylene (10 mL) was stirred at 140° C. for 16 hours. The reaction mixture was evaporated to provide the crude title compound which was used without further purification. $^1$H NMR (400 MHz, CDCl$_3$) δ (ppm) 9.04 (br s, 1H), 7.07 (d, 1H), 6.55 (d, 1H), 4.38 (q, 2H), 1.40 (t, 3H). LC-MS: Rt=1.01 min; MS m/z [M+H]$^+$ 214.0

(3) 2-Fluoro-4H-thieno[3,2-b]pyrrole-5-carbohydrazide, Int 27

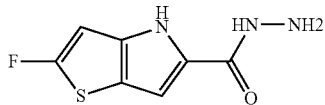

A solution of Int 26 (775 mg, 3.63 mmol) in EtOH (10 mL) and hydrazine monohydrate (1.78 mL, 36.3 mmol) was heated at 80° C. overnight. A white solid formed which was filtered off, washed with water and dried to provide the crude title compound which was used without further purification. $^1$H NMR (400 MHz, DMSO-d6) δ (ppm) 11.83 (br s, 1H), 9.44 (s, 1H), 7.00 (s, 1H), 6.75 (d, 1H), 4.37 (br s, 2H). LC-MS: Rt=0.58 min; MS m/z [M+H]$^+$ 200.1

(4) 2-Fluoro-5-isopropylthieno[2',3':4,5]pyrrolo[1,2-d][1,2,4]triazin-8(7H)-one, Int 28

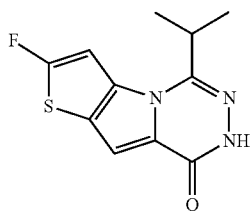 [SMILES: CC(C)c1n[nH]c(=O)c2cc3sc(F)cc3n12]

To a suspension of Int 27 (575 mg, 2.89 mmol) in DMF (5 mL) was added methyl isobutyrimidate hydrochloride (477 mg, 3.46 mmol) and the mixture was stirred for 20 minutes at RT. Then, KOtBu (551 mg, 4.91 mmol) was added and the mixture was placed in a preheated oil bath at 90° C. It was stirred for 30 minutes. The reaction mixture was cooled to RT, diluted with water and extracted with EtOAc. The organic extract was dried over Na$_2$SO$_4$, filtered and evaporated. The crude was purified by column chromatography on silica gel using DCM and MeOH (from 0% to 10%) to give the title compound. $^1$H NMR (400 MHz, DMSO-d6) δ (ppm) 11.77 (s, 1H), 7.54 (d, 1H), 7.45 (s, 1H), 3.53 (sept, 1H), 1.30 (d, 6H). LC-MS: Rt=0.88 min; MS m/z [M+H]$^+$ 252.1

(5) Ethyl 2-(2-fluoro-5-isopropyl-8-oxothieno[2',3':4,5]pyrrolo[1,2-d][1,2,4]triazin-7(8H)-yl)acetate, Int 29

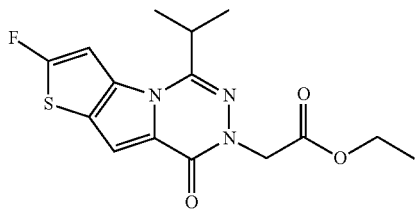 [SMILES: CCOC(=O)Cn1nc(C(C)C)n2c(cc3sc(F)cc32)c1=O]

A solution of Int 28 (470 mg, 1.870 mmol) in DMF (15 mL) was cooled in an ice bath and LiHMDS (1M in THF, 3.29 mL, 3.29 mmol) was added dropwise to keep the temperature between 0 and 2° C. The mixture was stirred for 10 minutes, then a solution of ethyl 2-iodoacetate (0.22 mL, 1.87 mmol) in DMF (7 mL) was added dropwise. The ice bath was removed and stirring continued for 30 minutes. The reaction mixture was evaporated and partitioned between water and EtOAc. The organic layer was washed with brine, dried over Na$_2$SO$_4$, filtered and evaporated. The crude was purified by column chromatography on silica gel using cyclohexane and EtOAc (from 0% to 40%) to give the title compound. $^1$H NMR (400 MHz, DMSO-d6) δ (ppm) 7.56 (br d, 1H), 7.53 (s, 1H), 4.75 (s, 2H), 4.17 (q, 2H), 3.56 (sept, 1H), 1.3 (d, 6H), 1.22 (t, 3H). LC-MS: Rt=1.13 min; MS m/z [M+H]$^+$ 338.1

(6) 2-(2-Fluoro-5-isopropyl-8-oxothieno[2',3':4,5]pyrrolo[1,2-d][1,2,4]triazin-7(8H)-yl)acetic Acid, Int 24

A mixture of Int 29 (370 mg, 1.097 mmol) in THF (10 mL) and 1 M LiOH (5.48 mL, 5.48 mmol) was stirred at RT for 16 hours. The solution was acidified with 0.1 M HCl, diluted with water and extracted with EtOAc. Upon extraction, a solid formed which was filtered off. The organic extract was dried over Na$_2$SO$_4$, filtered, evaporated and combined with the above solid to provide the title compound. $^1$H NMR (400 MHz, DMSO-d6) δ (ppm) 13.0 (br s, 1H), 7.56 (d, 1H), 7.51 (s, 1H), 4.65 (s, 2H), 3.56 (sept, 1H), 1.30 (d, 6H). LC-MS: Rt=0.86 min; MS m/z [M+H]$^+$ 310.1

2-(5-Cyclopropyl-2-fluoro-8-oxothieno[2',3':4,5]pyrrolo[1,2-d][1,2,4]triazin-7(8H)-yl)acetic Acid, Int 30

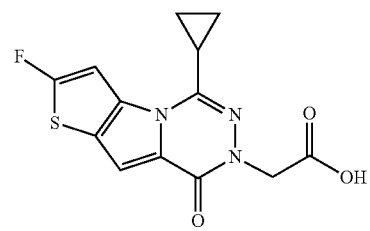 [SMILES: O=C(O)Cn1nc(C2CC2)n2c(cc3sc(F)cc32)c1=O]

(1) 5-Cyclopropyl-2-fluorothieno[2',3':4,5]pyrrolo[1,2-d][1,2,4]triazin-8(7H)-one, Int 31

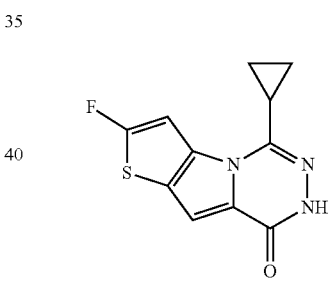

A suspension of Int 27 (107 mg, 0.537 mmol) in DMF (3 mL) was treated with (trimethoxymethyl)cyclopropane (0.135 mL, 0.645 mmol) and heated at 100° C. After 30 minutes, the conversion to the intermediate, methyl (Z)—N-(2-fluoro-4H-thieno[3,2-b]pyrrole-5-carbonyl)cyclopropanecarbohydrazonate, was complete. The solution was allowed to cool to RT and KOtBu (60.3 mg, 0.537 mmol) was added. The mixture was stirred at RT for 10 minutes, then it was placed in an oil bath at 100° C. After 1 hour, the reaction mixture was cooled in an ice-bath, diluted with water (~10 mL) and acidified by addition of 0.2M HCl (3 mL). The brown precipitate was filtered off and washed with water. The mother liquor was extracted with EtOAc. The organic extract was washed with brine, dried over Na$_2$SO$_4$, filtered and evaporated and combined with the above precipitate to give the title compound. LC-MS: Rt=0.82 min; MS m/z [M+H]$^+$ 250.1

(2) Ethyl 2-(5-cyclopropyl-2-fluoro-8-oxothieno[2',3':4,5]pyrrolo[1,2-d][1,2,4]triazin-7(8H)-yl)acetate, Int 32

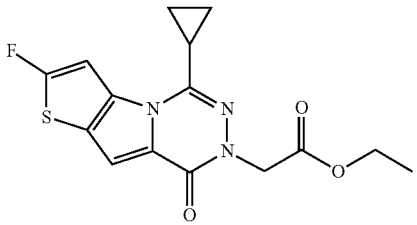 [SMILES: CCOC(=O)Cn1nc(C2CC2)n2c(cc3sc(F)cc32)c1=O]

A suspension of Int 31 (48 mg, 0.193 mmol), Cs$_2$CO$_3$ (188 mg, 0.578 mmol) and ethyl 2-iodoacetate (0.023 mL, 0.193 mmol) in DMF (5 mL) was stirred at RT for 15 minutes. The reaction mixture was diluted with water and acidified with 2M HCl and extracted with EtOAc. The organic extract was washed with water and brine, dried over Na$_2$SO$_4$, filtered and evaporated. The crude was purified by column chromatography on silica gel using cyclohexane and EtOAc (from 0% to 15%) to give the title compound. LC-MS: Rt=1.07 min; MS m/z [M+H]$^+$ 336.1

(3) 2-(5-Cyclopropyl-2-fluoro-8-oxothieno[2',3':4,5]pyrrolo[1,2-d][1,2,4]triazin-7(8H)-yl)acetic Acid, Int 30

A solution of Int 32 (69 mg, 0.206 mmol) in THF (6 mL) was treated with 1 M LiOH (0.62 mL, 0.62 mmol) and stirred at RT for 2 hours. A white precipitate deposited along the flask walls, thus, more THF (6 mL) was added, along with another portion of 1 M LiOH (0.62 mL, 0.62 mmol) and stirring continued for 3 hours. The reaction mixture was acidified with 0.2M HCl and extracted twice with DCM. The combined organic extracts were dried over Na$_2$SO$_4$, filtered and evaporated to give the title compound as a white solid $^1$H NMR (400 MHz, DMSO-d6) δ (ppm) 12.97 (s, 1H), 7.65 (d, 1H), 7.48 (s, 1H), 4.60 (s, 2H), 2.48-2.40 (m, 1H overlapping with DMSO signal), 1.18-1.10 (m, 2H), 1.01-0.94 (m, 2H). LC-MS: Rt=0.80 min; MS m/z [M+H]$^+$ 308.1

2-(2-Fluoro-5-(2-hydroxypropan-2-yl)-8-oxothieno[2',3':4,5]pyrrolo[1,2-d][1,2,4]triazin-7(8H)-yl)acetic Acid, Int 33

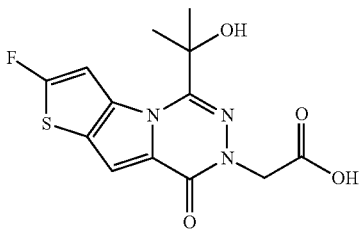 [SMILES: CC(C)(O)c1nn(CC(=O)O)c(=O)c2cc3sc(F)cc3n12]

(1) 2-Fluoro-5-(1-hydroxyethyl)thieno[2',3':4,5]pyrrolo[1,2-d][1,2,4]triazin-8(7H)-one, Int 34

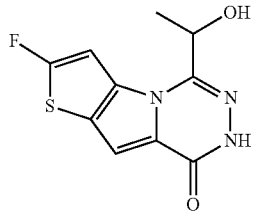 [SMILES: CC(O)c1n[nH]c(=O)c2cc3sc(F)cc3n12]

A solution of Int 27 (620 mg, 3.11 mmol) and Int 15 (717 mg, 4.67 mmol) in DMF (15 mL) was vigorously stirred at RT for 30 minutes. Then, KOtBu (873 mg, 7.78 mmol) was added and the mixture was placed in a preheated oil bath at 90° C. and was stirred for 4 hour. The reaction mixture was cooled in an ice bath to 0° C., diluted with 75 ml water, and acidified with 2M HCl. A precipitate formed which was filtered off and washed thoroughly with water to provide the title compound as beige solid. $^1$H NMR (400 MHz, DMSO-d6) δ (ppm) 11.84 (s, 1H), 7.45 (s, 1H), 7.37 (d, 1H), 5.80 (d, 1H), 5.17-5.02 (m, 1H), 1.52 (d, 3H). LC-MS: Rt=0.75 min; MS m/z [M+H]$^+$ 422.2

(2) 5-Acetyl-2-fluorothieno[2',3':4,5]pyrrolo[1,2-d][1,2,4]triazin-8(7H)-one, Int 35

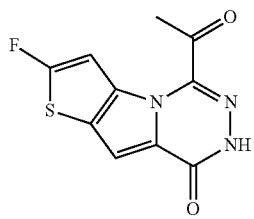 [SMILES: CC(=O)c1n[nH]c(=O)c2cc3sc(F)cc3n12]

A solution of Int 34 (110 mg, 0.434 mmol) in DMF (5 mL) was treated with Dess-Martin periodinane (221 mg, 0.521 mmol). The suspension was stirred at RT overnight, then quenched with 10% NaHCO$_3$ solution (10 mL). The fine suspension was filtered and the filter cake was purified by preparative RP chromatography to provide the title compound. $^1$H NMR (400 MHz, DMSO-d6) δ (ppm) 12.45 (s, 1H), 7.57 (s, 1H), 7.21 (d, 1H), 2.60 (s, 3H). LC-MS: Rt=0.85 min; MS m/z [M+H]$^+$ 252.2

(3) 2-Fluoro-5-(2-hydroxypropan-2-yl)thieno[2',3':4,5]pyrrolo[1,2-d][1,2,4]triazin-8(7H)-one, Int 36

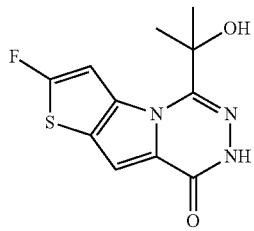 [SMILES: CC(C)(O)c1n[nH]c(=O)c2cc3sc(F)cc3n12]

A suspension of Int 35 (70 mg, 0.279 mmol) in 2-methyltetrahydrofuran (10 mL) was treated with LiCl solution (0.5M in THF, 5.57 mL, 2.79 mmol) and stirred for 1 hour. To this solution was added cerium(III) chloride CeCl$_3$ "ultra dry" from ABCR GmbH (76 mg, 0.306 mmol) and the suspension was stirred at RT overnight. The fine suspension was then cooled in an ice bath and CH$_3$MgBr in (3.4M in 2-methyltetrahydrofuran, 0.41 mL, 1.393 mmol) was added dropwise. Initial gas formation ceased after a few minutes. Four more portions of 3.4M CH$_3$MgBr in 2-methyltetrahydrofuran (0.410 mL, 1.393 mmol) were added at intervals of 30 minutes. The solution was then quenched carefully with 10% NH$_4$Cl solution at 0° C., followed by extraction with EtOAc. The organic extract was washed with water and brine, dried over Na$_2$SO$_4$, filtered and evaporated to afford the title compound as pale brown solid which was contaminated with 15% of starting material. This crude was used without further purification. LC-MS: Rt=0.79 min; MS m/z [M+H]$^+$ 268.1

(4) Ethyl 2-(2-fluoro-5-(2-hydroxypropan-2-yl)-8-oxothieno[2',3':4,5]pyrrolo[1,2-d][1,2,4]triazin-7(8H)-yl)acetate, Int 37

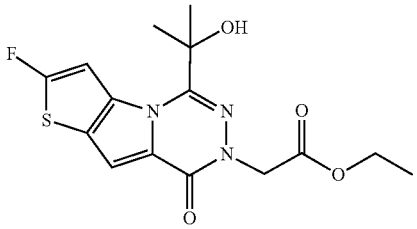 [SMILES: CCOC(=O)Cn1nc(C(C)(C)O)n2c(cc3sc(F)cc32)c1=O]

To a suspension of Int 36 (90 mg, 0.337 mmol) and Cs$_2$CO$_3$ (219 mg, 0.673 mmol) in DMF (5 mL) was added ethyl 2-iodoacetate (0.048 mL, 0.404 mmol). This mixture was stirred at RT for 1 hour, then quenched with water and extracted with EtOAc. The organic extract was dried over Na$_2$SO$_4$, filtered and evaporated. The crude was purified by column chromatography on silica gel using cyclohexane and EtOAc (from 0% to 30%) to provide the title compound as a white solid. $^1$H NMR (400 MHz, CDCl$_3$) δ (ppm) 7.51 (d, 1H), 7.37 (s, 1H), 4.74 (s, 2H), 4.2 (q, 2H), 2.57 (s, 1H), 1.75 (s, 6H), 1.31 (t, 3H). LC-MS: Rt=1.02 min; MS m/z [M+H]$^+$ 354.2

(5) 2-(2-Fluoro-5-(2-hydroxypropan-2-yl)-8-oxothieno[2',3':4,5]pyrrolo[1,2-d][1,2,4]triazin-7(8H)-yl)acetic acid, Int 33

A solution of Int 37 (36 mg, 0.102 mmol) in THF (1 mL) and 1M LiOH (0.2 mL, 0.2 mmol) was stirred at RT for 2 hours. It was then acidified with 1 M HCl (2 mL) and extracted with EtOAc. The organic layer was dried over Na$_2$SO$_4$, filtered and evaporated to afford the title compound as pale yellow solid which was used without further purification. LC-MS: Rt=0.77 min; MS m/z [M+H]$^+$ 326.1

5-Cyclopropylthiazolo[5',4':4,5]pyrrolo[1,2-d][1,2,4]triazin-8(7H)-one, Int 38

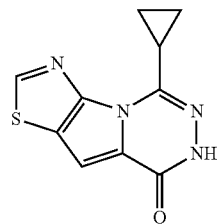 [SMILES: O=c1[nH]nc(C2CC2)n2c1cc1scnc12]

(1) 4H-Pyrrolo[2,3-d]thiazole-5-carbohydrazide, Int 39

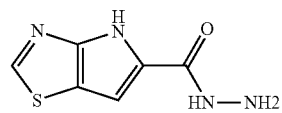

To a solution of methyl 4H-pyrrolo[2,3-d]thiazole-5-carboxylate (Enamine EN300-175043; 300 mg, 1.65 mmol) in EtOH (3 mL) was added hydrazine hydrate (3.42 mL, 69.2 mmol) and the mixture was heated at 80° C. for 72 hours. The suspension was cooled to RT and the solid was filtered off, washed with EtOH and dried to afford the title compound as a white solid. $^1$H-NMR (400 MHz, DMSO-d$_6$): δ (ppm) 12.39 (s, 1H), 9.52 (s, 1H), 8.92 (s, 1H), 7.09 (s, 1H), 4.42 (s, 2H). LC-MS: Rt=0.38 min; MS m/z [M+H]$^+$ 183.2

(2) 5-Cyclopropylthiazolo[5',4':4,5]pyrrolo[1,2-d][1,2,4]triazin-8(7H)-one, Int 38

A suspension of methyl cyclopropanecarbimidate hydrochloride (128 mg, 0.94 mmol) and Int 39 (120 mg, 0.66 mmol) in DMF (4 mL) was vigorously stirred at RT for 2.5 hours. Then, KOtBu (103 mg, 0.922 mmol) was added and the mixture was placed in an oil bath at 90° C. and stirred for 72 hours. The mixture was cooled to RT and partitioned between EtOAc and water. The organic layer was dried over Na$_2$SO$_4$, filtered and evaporated. The crude was purified by column chromatography on silica gel using cyclohexane and EtOAc (from 0% to 100%) to provide the title compound as a brown solid. LC-MS: Rt=0.71 min; MS m/z [M+H]$^+$ 233.2

2-(5-Isopropyl-8-oxothiazolo[5',4':4,5]pyrrolo[1,2-d][1,2,4]triazin-7(8H)-yl)acetic Acid, Int 40

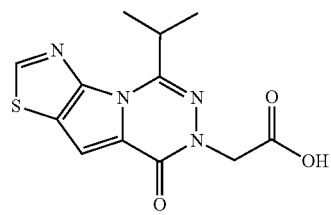 [SMILES: CC(C)c1nn(CC(=O)O)c(=O)c2cc3scnc3n12]

(1) 5-Isopropylthiazolo[5',4':4,5]pyrrolo[1,2-d][1,2,4]triazin-8(7H)-one, Int 41

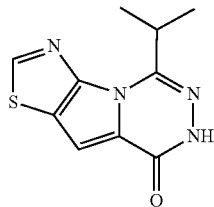 [SMILES: CC(C)c1n[nH]c(=O)c2cc3scnc3n12]

A suspension of methyl isobutyrimidate hydrochloride (344 mg, 2.50 mmol) and Int 39 (380 mg, 2.09 mmol) in DMF (5 mL) was vigorously stirred at RT for 30 minutes. Then, KOtBu (398 mg, 3.55 mmol) was added and the mixture was placed in a preheated oil bath at 90° C. and stirred for 2 hours. The solvent was evaporated and the residue was purified by column chromatography on silica gel using cyclohexane and EtOAc (from 0% to 80%) to provide the title compound as colorless solid. $^1$H-NMR (400 MHz, DMSO-d6) δ (ppm) 11.87 (s, 1H), 9.30 (s, 1H), 7.49 (s, 1H), 4.2 (sept, 1H), 1.35 (d, 6H). LC-MS: Rt=0.76 min; MS m/z [M+H]$^+$ 235.2

(2) Ethyl 2-(5-isopropyl-8-oxothiazolo[5'4':4,5]pyrrolo[1,2-d][1,2,4]triazin-7(8H)-yl)acetate, Int 42

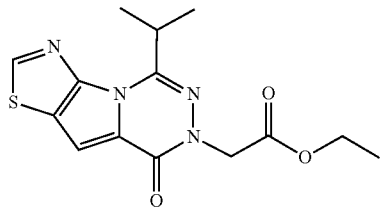 [SMILES: CCOC(=O)Cn1nc(C(C)C)n2c(cc3scnc32)c1=O]

To a suspension of Int 41 (340 mg, 1.45 mmol) and Cs$_2$CO$_3$ (2.36 g, 7.26 mmol) in DMF (3 mL) was added ethyl 2-iodoacetate (0.206 mL, 1.742 mmol) in DMF (2 mL). The mixture was stirred at RT for 10 minutes, then quenched with water and extracted twice with EtOAc. The combined organic extracts were washed with water and brine, dried over Na$_2$SO$_4$, filtered and evaporated. Purification by column chromatography on silica gel using cyclohexane and EtOAc (from 0% to 50%) provided the title compound. LC-MS: Rt=1.04 min; MS m/z [M+H]$^+$ 321.2

(3) 2-(5-Isopropyl-8-oxothiazolo[5',4':4,5]pyrrolo[1,2-d][1,2,4]triazin-7(8H)-yl)acetic acid, Int To a solution of Int 42 (378 mg, 1.18 mmol) in THF (10 mL) was added 1M LiOH (5.90 ml, 5.90 mmol) and the mixture was stirred at RT for 72 hours. It was then acidified with 0.1M HCl and extracted with EtOAc. A precipitate formed between the layers and was filtered off. The organic layer of the mother liquor was separated and washed with brine, dried over Na$_2$SO$_4$, filtered and evaporated. This residue was combined with the precipitate from above to afford the title compound. $^1$H-NMR (400 MHz, DMSO-d6) δ (ppm) 13.05 (br s, 1H), 9.33 (s, 1H), 7.55 (s, 1H), 4.68 (s, 2H), 4.21 (sept, 1H), 1.35 (d, 6H). LC-MS: Rt=0.74 min; MS m/z [M+H]$^+$ 293.1

2-(5-Isopropyl-2-methyl-8-oxothiazolo[5',4':4,5]pyrrolo[1,2-d][1,2,4]triazin-7(8H)-yl)acetic acid, Int 43

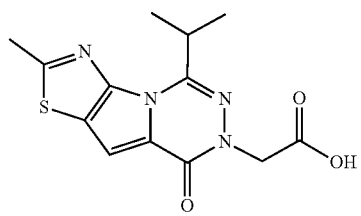 [SMILES: Cc1nc2c(cc3c(=O)n(CC(=O)O)nc(C(C)C)n32)s1]

(1) Ethyl (Z)-2-azido-3-(2-methylthiazol-5-yl)acrylate, Int 44

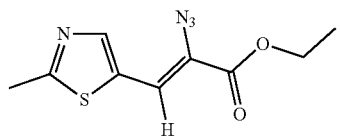 [SMILES: CCOC(=O)/C(=C/c1cnc(C)s1)N=[N+]=[N-]]

A solution of 2-methylthiazole-5-carbaldehyde (1 g, 7.86 mmol) and ethyl 2-azidoacetate (30% in DCM, 15.8 mL, 31.5 mmol) was added dropwise to a solution of NaOEt (21% in EtOH, 11.7 mL, 31.5 mmol) and EtOH (40 mL) at 0°. After stirring for 1 hour at 0° C., the temperature was allowed to come to RT and the stirring was continued for another hour. The mixture was quenched with a saturated solution of NH$_4$Cl and extracted with Et$_2$O. The organic extract was dried over Na$_2$SO$_4$, filtered and evaporated. Purification by column chromatography on silica gel using cyclohexane and EtOAc (from 0% to 30%) provided the title compound as brown solid. $^1$H NMR (400 MHz, DMSO-d6) δ (ppm) 8.07 (d, 1H), 7.27 (d, 1H), 4.31 (q, 2H), 2.69 (s, 3H), 1.32 (t, 3H). LC-MS: Rt=1.05 min; MS m/z [M+H]$^+$ 239.1

(2) Ethyl 2-methyl-4H-pyrrolo[2,3-d]thiazole-5-carboxylate, Int 45

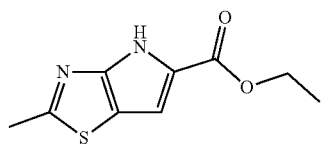

A solution of Int 44 (550 mg, 2.31 mmol) in xylene (10 mL) was stirred at 140° C. for 4 hours. The solvent was evaporated to afford the crude title compound as beige solid. $^1$H-NMR (400 MHz, DMSO-d6) δ (ppm) 12.62 (s, 1H), 7.04 (s, 1H), 4.28 (q, 2H), 2.73 (s, 3H), 1.30 (t, 3H). LC-MS: Rt=0.86 min; MS m/z [M+H]$^+$ 211.1

(3) 2-Methyl-4H-pyrrolo[2,3-d]thiazole-5-carbohydrazide, Int 46

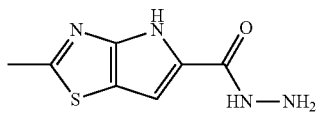

A suspension of Int 45 (798 mg, 3.80 mmol) and hydrazine monohydrate (3.72 mL, 76.0 mmol) was stirred at RT for 2 hours, then at 80° C. for 1 hour. It was allowed to cool to RT and the precipitate was filtered off and dried to provide the title compound. $^1$H NMR (400 MHz, DMSO-d6) δ (ppm) 11.86 (br s, 1H), 9.43 (s, 1H), 6.98 (s, 1H), 4.37 (br s, 2H), 2.69 (s, 3H). LC-MS: Rt=0.46 min; MS m/z [M+H]$^+$ 197.0

(4) 5-Isopropyl-2-methylthiazolo[5',4':4,5]pyrrolo[1,2-d][1,2,4]triazin-8(7H)-one, Int 47

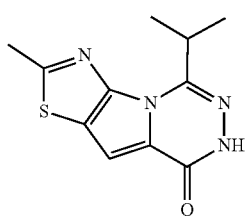 [SMILES: Cc1nc2c(cc3c(=O)[nH]nc(C(C)C)n32)s1]

A suspension of methyl isobutyrimidate hydrochloride (353 mg, 2.57 mmol) and Int 46 (420 mg, 2.14 mmol) in DMF (20 mL) was vigorously stirred at RT for 15 minutes. Then, KOtBu (408 mg, 3.64 mmol) was added and the mixture was heated at 90° C. for 3 hours. It was cooled in an ice bath to 0° C., diluted with water (20 mL) and acidified with 2M HCl (5 mL). The suspension was filtered and the precipitate washed with water and dried to provide the title compound as a beige solid. $^1$H NMR (400 MHz, DMSO-d6) δ (ppm) 11.80 (s, 1H), 7.39 (s, 1H), 4.15 (sept, 1H), 2.84 (s, 3H), 1.32 (d, 6H). LC-MS: Rt=0.88 min; MS m/z [M+H]$^+$ 249.1

(5) Ethyl 2-(5-isopropyl-2-methyl-8-oxothiazolo[5',4':4,5]pyrrolo[1,2-d][1,2,4]triazin-7(8H)-yl)acetate, Int 48

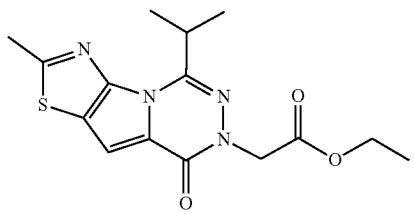 [SMILES: CCOC(=O)Cn1nc(C(C)C)n2c(cc3sc(C)nc32)c1=O]

To a solution of Int 47 (390 mg, 1.571 mmol) in DMF (15 mL) was added Cs$_2$CO$_3$ (2.56 g, 7.85 mmol), followed by the dropwise addition of ethyl 2-iodoacetate (0.223 mL, 1.885 mmol) in DMF (10 mL). The mixture was stirred at RT for 30 minutes, then quenched with water and extracted twice with EtOAc. The combined organic extracts were washed with water and brine, dried over Na$_2$SO$_4$, filtered and evaporated. Purification by column chromatography on silica gel using cyclohexane and EtOAc (from 0% to 50%) provided the title compound as white solid. LC-MS: Rt=1.15 min; MS m/z [M+H]$^+$ 335.2

(6) 2-(5-Isopropyl-2-methyl-8-oxothiazolo[5',4':4,5]pyrrolo[1,2-d][1,2,4]triazin-7(8H)-yl)acetic Acid, Int 43

To a solution of Int 48 (401 mg, 1.199 mmol) in THF (10 mL) was added 1M LiOH (6 mL, 6 mmol). The resulting mixture was stirred at RT overnight, then acidified with 2M HCl and extracted with EtOAc. The organic extract was washed with brine, dried over Na$_2$SO$_4$, filtered and evaporated to afford the title compound as white solid. $^1$H NMR (400 MHz, DMSO-d6) δ (ppm) 13.02 (br s, 1H), 7.46 (s, 1H), 4.65 (s, 2H), 4.16 (sept, 1H), 2.86 (s, 3H), 1.33 (d, 6H). MS: Rt=0.86 min; MS m/z [M+H]$^+$ 307.1

Synthesis of Examples

Example 1

2-(2-Chloro-5-isopropyl-8-oxothieno[2',3':4,5]pyrrolo[1,2-d][1,2,4]triazin-7(8H)-yl)-N-(pyrimidin-4-yl)acetamide

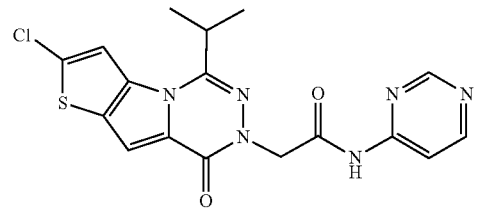 [SMILES: CC(C)c1nn(CC(=O)Nc2ccncn2)c(=O)c2cc3sc(Cl)cc3n12]

A solution of Int 5 (70 mg, 0.261 mmol) in DMF (5 mL) was cooled to 0° C. in an ice bath and LiHMDS (1 M in THF, 0.680 mL, 0.680 mmol) was added dropwise. The mixture was stirred at 0° C. for 20 minutes, then a solution of 2-chloro-N-(pyrimidin-4-yl)acetamide (65.3 mg, 0.314 mmol) in DMF (1 mL) was added slowly. The ice bath was removed and the solution was stirred at RT overnight. The reaction mixture was partitioned between EtOAc and water. The organic layer was dried over Na$_2$SO$_4$, filtered and evaporated. The residue was purified by preparative RP chromatography to give the title compound as a white solid. $^1$H NMR (400 MHz, DMSO-d6) δ (ppm) 11.24 (s, 1H), 8.92 (d, 1H), 8.67 (d, 1H), 8.00 (dd, 1H), 7.82 (s, 1H), 7.50 (s, 1H), 4.90 (s, 2H), 3.62 (sept, 1H), 1.31 (d, 6H). LC-MS: Rt=1.0 min; MS m/z [M+H]$^+$ 403.2

The following examples were synthesized analogous to the procedure of Example 1, using the appropriate intermediates and 2-chloro-acetamides:

| Ex No. | Structure | Name | ¹H NMR | LC/MS (min; m/z) | Int |
|---|---|---|---|---|---|
| Ex 2 | 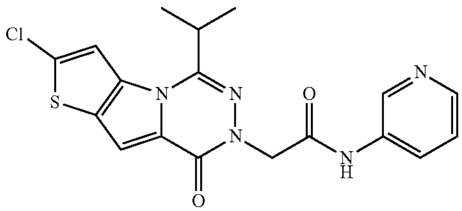 [SMILES: CC(C)c1nn(CC(=O)Nc2cccnc2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(pyridin-3-yl)acetamide | (400 MHz, DMSO-d6) δ (ppm) 10.41 (s, 1H), 8.74 (s, 1H), 8.29 (d, 1H), 8.02 (d, 1H), 7.83 (s, 1H), 7.51 (s, 1H), 7.43-7.29 (m, 1H), 4.83 (s, 2H), 3.72-3.51 (m, 1H), 1.32 (d, 6H). | Rt = 1.0; [M + H]⁺ 402.2 | 5 |
| Ex 3 | 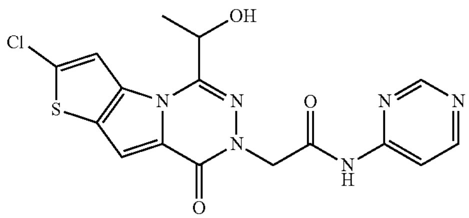 [SMILES: CC(O)c1nn(CC(=O)Nc2ccncn2)c(=O)c2cc3sc(Cl)cc3n12] | 2-(2-Chloro-5-(1-hydroxyethyl)-8-oxothieno[2',3':4,5]pyrrolo[1,2-d][1,2,4]triazin-7(8H)-yl)-N-(pyrimidin-4-yl)acetamide | (400 MHz, DMSO-d6) δ (ppm) 11.27 (s, 1H), 8.93 (d, 1H), 8.68 (d, 1H), 8.0 (dd, 1H), 7.72 (s, 1H), 7.52 (s, 1H), 5.18 (q, 1H), 4.93 (s, 2H), 1.52 (d, 3H). | Rt = 0.81 [M + H]⁺ 405.1 | 22 |
| Ex 4 | 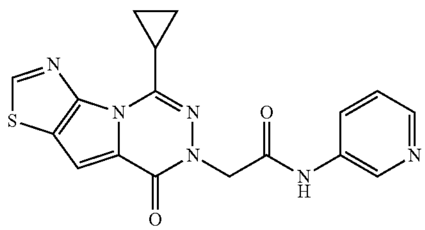 [SMILES: O=C(Cn1nc(C2CC2)n2c(cc3scnc32)c1=O)Nc1cccnc1] | 2-(5-Cyclopropyl-8-oxothiazolo[5',4':4,5]pyrrolo[1,2-d][1,2,4]triazin-7(8H)-yl)-N-(pyridin-3-yl)acetamide | (400 MHz, DMSO-d6) δ (ppm) 10.92 (s, 1H), 9.35 (s, 1H), 9.02 (s, 1H), 8.50 (d, 1H), 8.31 (d, 1H), 7.76 (dd, 1H), 7.56 (s, 1H), 4.85 (s, 2H), 3.27-3.16 (m, 1H), 1.23-1.02 (m, 4H). | Rt = 0.75 [M + H]⁺ 367.3 | 38 |

Example 5

2-(2-Fluoro-5-isopropyl-8-oxothieno[2,3':4,5]pyrrolo[1,2-d][1,2,4]triazin-7(8H)-yl)-N-(pyridin-3-yl)acetamide

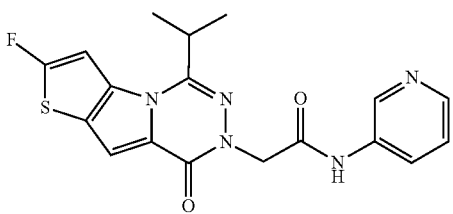 [SMILES: CC(C)c1nn(CC(=O)Nc2cccnc2)c(=O)c2cc3sc(F)cc3n12]

To a solution of Int 28 (40 mg, 0.148 mmol) in DMF (3 ml) was added Cs₂CO₃ (241 mg, 0.740 mmol) followed by a solution of 2-chloro-N-(pyridin-3-yl)acetamide hydrochloride (36.8 mg, 0.178 mmol) in DMF (2 mL). The mixture was stirred at 60° C. for 1 hour, then quenched with water and extracted twice with EtOAc. The combined organic extracts were washed with water then brine, dried over Na₂SO₄, filtered and evaporated. The crude was purified by column chromatography on silica gel using DCM and MeOH (from 0% to 10%) to give the title compound as a yellow solid. ¹H NMR (400 MHz, DMSO-d6) δ (ppm) 10.39 (s, 1H), 8.73 (s, 1H), 8.29 (m, 1H), 8.01 (m, 1H), 7.56 (s, 1H), 7.51 (s, 1H), 7.36 (m, 1H), 4.81 (s, 2H), 3.73-3.51 (m, 1H), 1.30 (d, 6H). LC-MS: Rt=0.89 min; MS m/z [M+H]⁺ 386.2

The following examples were synthesized analogous to the procedure of Example 5, using the appropriate intermediates and 2-chloro-acetamides:

| Ex No. | Structure | Name | ¹H NMR | LC/MS (min; m/z) | Int |
|---|---|---|---|---|---|
| Ex 6 | 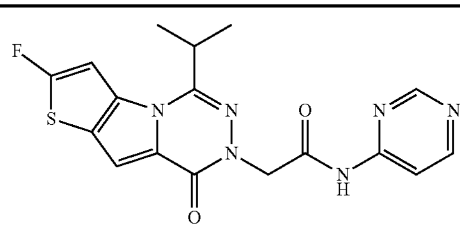 | 2-(2-Fluoro-5-isopropyl-8-oxothieno[2',3':4,5]pyrrolo[1,2-d][1,2,4]triazin-7(8H)-yl)-N-(pyrimidin-4-yl)acetamide | (400 MHz, DMSO-d6) δ (ppm) 11.22 (s, 1H), 8.91 (d, 1H), 8.66 (d, 1H), 7.99 (dd, 1H), 7.56 (d, 1H), 7.51 (s, 1H), 4.89 (s, 2H), 3.56 (sept, 1H), 1.29 (d, 6H). | Rt = 0.93; [M + H]⁺ 387.2 | 28 |

| Ex No. | Structure | Name | ¹H NMR | LC/MS (min; m/z) | Int |
|---|---|---|---|---|---|
| Ex 7 | 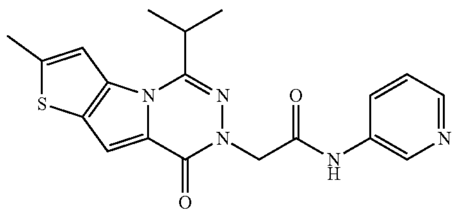 [SMILES: Cc1cc2c(cc3c(=O)n(CC(=O)Nc4cccnc4)nc(C(C)C)n32)s1] | 2-(5-Isopropyl-2-methyl-8-oxothieno[2',3':4,5]pyrrolo[1,2-d][1,2,4]triazin-7(8H)-yl)-N-(pyridin-3-yl)acetamide | (400 MHz, DMSO-d6) (ppm) 10.38 (s, 1H), 8.73 (d, 1H), 8.28 (d, 1H), 8.0 (d, 1H), 7.44 (s, 1H), 7.35 (m, 2H), 4.80 (s, 2H), 3.60 (sept, 1H), 2.61 (s, 3H), 1.32 (d, 6H). | Rt = 0.91 [M + H]$^+$ 382.2 | 11 |
| Ex 8 | 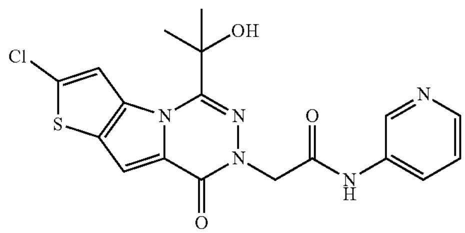 [SMILES: CC(C)(O)c1nn(CC(=O)Nc2cccnc2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-(pyridin-3-yl)acetamide | (400 MHz, DMSO-d6) δ (ppm) 10.45 (s, 1H), 8.74 (d, 1H), 8.29 (dd, 1H), 8.01 (ddd, J = 8.3, 2.6, 1.5 Hz, 1H), 7.93 (s, 1H), 7.57 (s, 1H), 7.36 (dd, 1H), 6.10 (s, 1H), 4.82 (s, 2H), 1.61 (s, 6H). | Rt = 0.88 [M + H]$^+$ 418.2 | 20 |
| Ex 9 | 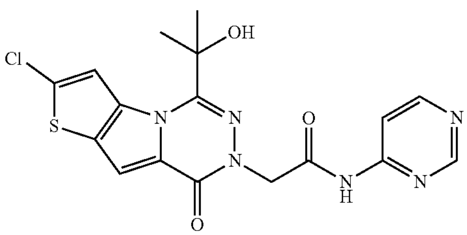 [SMILES: CC(C)(O)c1nn(CC(=O)Nc2ccncn2)c(=O)c2cc3sc(Cl)cc3n12] | 2-(2-Chloro-5-(2-hydroxypropan-2-yl)-8-oxothieno [2',3':4,5]pyrrolo[1,2-d][1,2,4]triazin-7(8H)-yl)-N-(pyrimidin-4-yl)acetamide | (400 MHz, DMSO-d6) δ (ppm) 11.26 (s, 1H), 8.91 (d, 1H), 8.66 (d, 1H), 7.99 (dd, 1H), 7.93 (d, 1H), 7.57 (s, 1H), 6.10 (s, 1H), 4.90 (s, 2H), 1.60 (s, 6H). | Rt = 0.9 [M + H]$^+$ 419.1 | 20 |

Example 10

(R)-2-(2-Chloro-5-isopropyl-8-oxothieno[2',3':4,5]pyrrolo[1,2-d][1,2,4]triazin-7(8H)-yl)-N-(piperidin-3-yl)acetamide

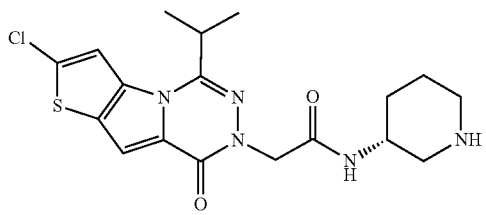 [SMILES: CC(C)c1nn(CC(=O)N[C@@H]2CCCNC2)c(=O)c2cc3sc(Cl)cc3n12]

(1) Tert-Butyl (R)-3-(2-(2-chloro-5-isopropyl-8-oxothieno[2',3':4,5]pyrrolo[1,2-d][1,2,4]triazin-7(8H)-yl)acetamido)piperidine-1-carboxylate, Int 49

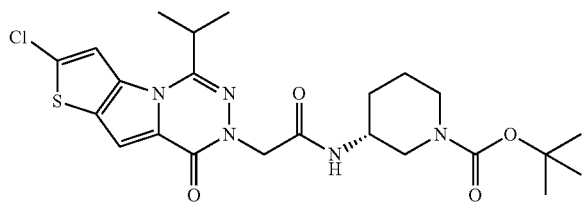 [SMILES: CC(C)c1nn(CC(=O)N[C@@H]2CCCN(C(=O)OC(C)(C)C)C2)c(=O)c2cc3sc(Cl)cc3n12]

To a solution of Int 1 (100 mg, 0.307 mmol) and (R)-tert-butyl 3-aminopiperidine-1-carboxylate (61.5 mg, 0.307 mmol) in DMF (2 mL) was added DIPEA (0.161 mL, 0.921 mmol) followed by HATU (140 mg, 0.368 mmol). The solution was stirred at RT for 1 hour. The reaction mixture was diluted with EtOAc and washed with brine. The organic extract was dried over Na$_2$SO$_4$, filtered and evaporated. The crude was purified by column chromatography on silica gel using DCM and MeOH (from 0% to 10%) to yield the title compound as white powder. LC-MS: Rt=1.20 min; MS m/z [M+H]$^+$ 525.2

(2) (R)-2-(2-chloro-5-isopropyl-8-oxothieno[2',3':4,5]pyrrolo[1,2-d][1,2,4]triazin-7(8H)-yl)-N-(piperidin-3-yl)acetamide To a solution of Int 49 (159 mg, 0.297 mmol) in DCM (5 mL) was added 4M HCl in dioxane (0.743 mL, 2.97 mmol). The reaction mixture was stirred at RT for 16 hours, followed by evaporation to dryness. The crude was partitioned between DCM and saturated NaHCO$_3$ solution. The organic layer was separated, dried over Na$_2$SO$_4$, filtered and evaporated to give the title compound as a colorless solid. ¹H NMR (400 MHz, CDCl$_3$) δ (ppm) 7.43 (d, 1H), 7.22 (d, 1H), 6.56 (br s, 1H), 4.87-4.61 (m, 2H), 4.03-3.92 (m, 1H), 3.40 (sept, 1H), 2.99 (dd, 1H), 2.82-2.69 (m, 2H), 2.61 (dd, 1H), 1.81-1.48 (m, 4H, overlapping with water signal), 1.45 (d, 6H). LC-MS: Rt=0.75 min; MS m/z [M+H]$^+$ 408.2

The following examples were synthesized analogous to the above coupling procedure (Example 10, step 1) using the appropriate amines and carboxylic acid intermediates, optionally followed by a deprotection step:

| Ex No. | Structure | Name | ¹H NMR | LC/MS (min; m/z) | Int |
|---|---|---|---|---|---|
| Ex 11 | 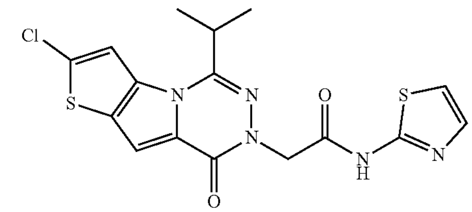 [SMILES: CC(C)c1nn(CC(=O)Nc2nccs2)c(=O)c2cc3sc(Cl)cc3n12] | 2-(2-Chloro-5-isopropyl-8-oxo thieno[2',3':4,5] pyrrolo[1,2-d] [1,2,4] triazin-7(8H)-yl)-N-(thiazol-2-yl)acetamide | (400 MHz, CDCl₃) δ (ppm) 10.34 (s, 1H), 7.48-7.42 (overlapping s and d, 1 + 1H), 7.21 (s, 1H), 6.98 (d, 1H), 5.0 (s, 2H), 3.38 (sept, 1H), 1.44 (d, 6H). | Rt = 1.08 [M + H]⁺ 408.1 | 1 |
| Ex 12 | 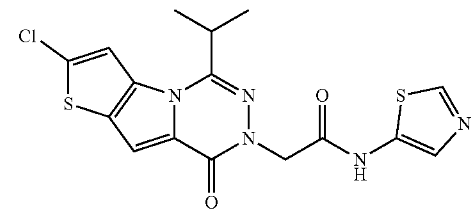 [SMILES: CC(C)c1nn(CC(=O)Nc2cncs2)c(=O)c2cc3sc(Cl)cc3n12] | 2-(2-Chloro-5-isopropyl-8-oxo thieno[2',3':4,5] pyrrolo[1,2-d] [1,2,4] triazin-7(8H)-yl)-N-(thiazol-5-yl)acetamide | (400 MHz, CDCl₃) δ (ppm) 10.04 (s, 1H), 8.38 (s, 1H), 7.59 (s, 1H), 7.37 (s, 1H), 7.15 (s, 1H), 4.95 (s, 2H), 3.36 (sept, 1H), 1.43 (d, 6H). | Rt = 1.02 [M + H]⁺ 408.1 | 1 |
| Ex 13 | 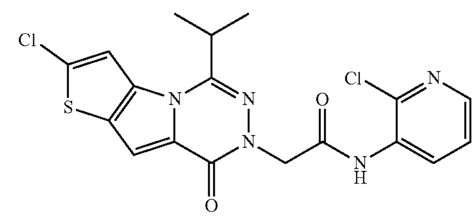 [SMILES: CC(C)c1nn(CC(=O)Nc2cccnc2Cl)c(=O)c2cc3sc(Cl)cc3n12] | 2-(2-Chloro-5-isopropyl-8-oxo thieno[2',3':4,5] pyrrolo[1,2-d] [1,2,4] triazin-7(8H)-yl)-N-(2-chloropyridin-3-yl)acetamide | (400 MHz, DMSO-d6) δ (ppm) 9.96 (s, 1H), 8.22 (d, 1H), 8.16 (d, 1H), 7.82 (br s, 1H), 7.50 (br s, 1H), 7.44 (dd, 1H), 4.89 (s, 2H), 3.62 (sept, 1H), 1.31 (d, 6H). | Rt = 1.11 [M + H]⁺ 436.0 | 1 |
| Ex 14 | 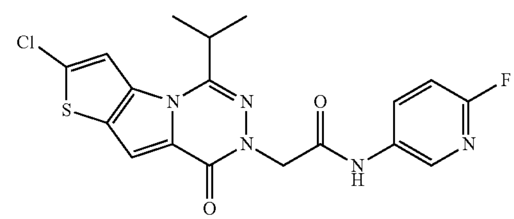 [SMILES: CC(C)c1nn(CC(=O)Nc2ccc(F)nc2)c(=O)c2cc3sc(Cl)cc3n12] | 2-(2-Chloro-5-isopropyl-8-oxo thieno[2',3':4,5] pyrrolo[1,2-d] [1,2,4] triazin-7(8H)-yl)-N-(6-fluoropyridin-3-yl)acetamide | (400 MHz, DMSO-d6) δ (ppm) 10.48 (s, 1H), 8.40 (s, 1H), 8.17-8.08 (m, 1H), 7.82 (s, 1H), 7.50 (s, 1H), 7.22-7.13 (m, 1H), 4.80 (s, 2H), 3.67-3.57 (m, 1H), 1.30 (d, 6H). | Rt = 1.09 [M + H]⁺ 420.1 | 1 |
| Ex 15 | 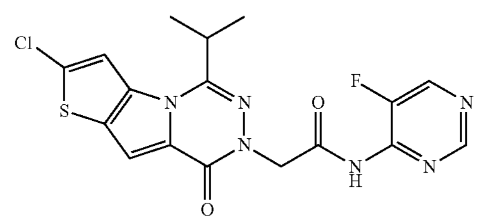 [SMILES: CC(C)c1nn(CC(=O)Nc2ncncc2F)c(=O)c2cc3sc(Cl)cc3n12] | 2-(2-Chloro-5-isopropyl-8-oxo thieno[2',3':4,5] pyrrolo[1,2-d] [1,2,4] triazin-7(8H)-yl)-N-(5-fluoro pyrimidin-4-yl)acetamide | (400 MHz, DMSO-d6) δ (ppm) 11.09 (s, 1H), 8.84-8.79 (m, 2H), 7.82 (s, 1H), 7.51 (s, 1H), 4.97 (s, 2H), 3.62 (sept, 1H), 1.30 (d, 6H). | Rt = 1.01 [M + H]⁺ 421.1 | 1 |
| Ex 16 | 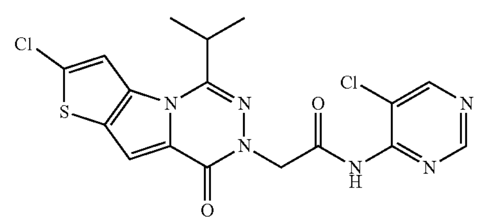 | 2-(2-Chloro-5-isopropyl-8-oxo thieno[2',3':4,5] pyrrolo[1,2-d] [1,2,4] triazin-7(8H)-yl)-N-(5-chloro pyrimidin-4-yl)acetamide | (400 MHz, CDCl₃) δ (ppm) 8.84 (s, 1H), 8.64 (br s, 1H), 8.60 (s, 1H), 7.44 (s, 1H), 7.21 (s, 1H), 5.36 (s, 2H), 3.39 (sept, 1H), 1.43 (d, 6H). | Rt = 1.04 [M + H]⁺ 437.0 | 1 |
| Ex 17 | 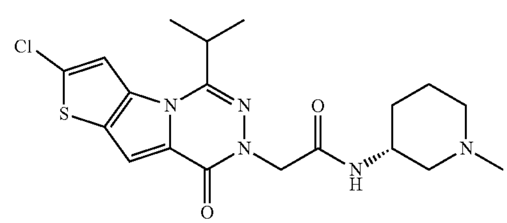 [SMILES: CC(C)c1nn(CC(=O)N[C@@H]2CCCN(C)C2)c(=O)c2cc3sc(Cl)cc3n12] | (R)-2-(2-Chloro-5-isopropyl-8-oxothieno[2',3':4,5] pyrrolo[1,2-d][1,2,4]triazin-7(8H)-yl)-N-(1-methylpiperidin-3-yl)acetamide | (400 MHz, DMSO-d6) δ (ppm) 7.91 (d, 1H), 7.8 (s, 1H), 7.46 (s, 1H), 4.61-4.47 (m, 2H), 3.79-3.69 (m, 1H), 3.59 (sept, 1H), 2.65-2.57 (m, 1H), 2.13 (s, 3H) 1.95-1.86 (m, 1H), 1.85-1.74 (m, 1H), 1.70-1.58 (m, 2H), 1.50-1.39 (m, 1H), 1.28 (d, 6H), 1.25-1.11 (m, 2H). | Rt = 0.76; [M + H]⁺ 422.2 | 1 |

-continued

| Ex No. | Structure | Name | ¹H NMR | LC/MS (min; m/z) | Int |
|---|---|---|---|---|---|
| Ex 18 | 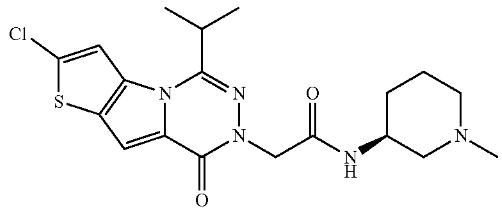 [SMILES: CC(C)c1nn(CC(=O)N[C@H]2CCCN(C)C2)c(=O)c2cc3sc(Cl)cc3n12] | (S)-2-(2-Chloro-5-isopropyl-8-oxothieno[2',3':4,5]pyrrolo[1,2-d][1,2,4]triazin-7(8H)-yl)-N-(1-methylpiperidin-3-yl)acetamide | (400 MHz, DMSO-d6) δ (ppm) 7.91 (d, 1H), 7.8 (s, 1H), 7.46 (s, 1H), 4.61-4.47 (m, 2H), 3.79-3.69 (m, 1H), 3.59 (sept, 1H), 2.65-2.57 (m, 1H), 2.13 (s, 3H) 1.95-1.86 (m, 1H), 1.85-1.74 (m, 1H), 1.70-1.58 (m, 2H), 1.50-1.39 (m, 1H), 1.28 (d, 6H), 1.25-1.11 (m, 2H). | Rt = 0.76; [M + H]⁺ 422.2 | 1 |
| Ex 19 | 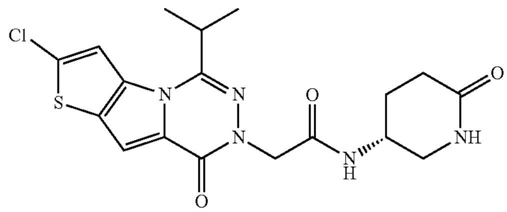 [SMILES: CC(C)c1nn(CC(=O)N[C@@H]2CCC(=O)NC2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(6-oxopiperidin-3-yl)acetamide | (400 MHz, DMSO-d6) δ (ppm) 8.20 (d, 1H), 7.80 (s, 1H), 7.47 (s, 1H), 7.38 (s, 1H), 4.57 (s, 2H), 3.99 (br s, 1H), 3.59 (sept, 1H), 2.98 (dd, 1H), 2.35-2.17 (m, 2H), 1.91-1.69 (m, 2H), 1.34-1.20 (m, 1H) overlapping with 1.29 (d, 6H). | Rt = 0.83 [M + H]⁺ 422.2 | 1 |
| Ex 20 | 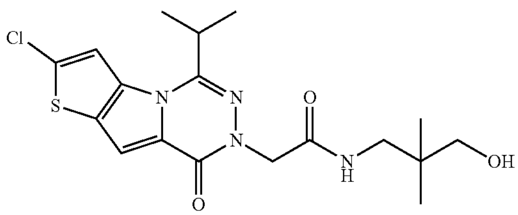 [SMILES: CC(C)c1nn(CC(=O)NCC(C)(C)CO)c(=O)c2cc3sc(Cl)cc3n12] | 2-(2-Chloro-5-isopropyl-8-oxo thieno[2',3':4,5]pyrrolo[1,2-d][1,2,4]triazin-7(8H)-yl)-N-(3-hydroxy-2,2-dimethylpropyl)acetamide | (400 MHz, DMSO-d6) δ (ppm) 7.96 (br s, 1H), 7.80 (br s, 1H), 7.47 (br s, 1H), 4.58 (br s 2H), 4.43 (br s, 1H), 3.58 (br m, 1H), 3.16-2.80 (m, 4H), 1.29 (br s, 6H), 0.77 (br s, 6H). | Rt = 1.01 [M + H]⁺ 411.1 | 1 |
| Ex 21 | 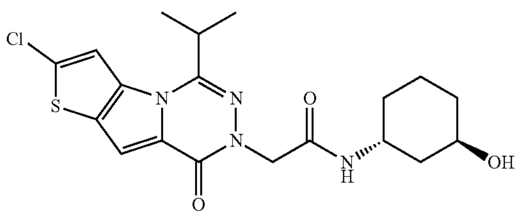 [SMILES: CC(C)c1nn(CC(=O)N[C@@H]2CCC[C@@H](O)C2)c(=O)c2cc3sc(Cl)cc3n12] | 2-(2-Chloro-5-isopropyl-8-oxo thieno[2',3':4,5]pyrrolo[1,2-d][1,2,4]triazin-7(8H)-yl)-N-((1R,3R)-3-hydroxycyclohexyl)acetamide | (400 MHz, DMSO-d6) δ (ppm) 7.80 (br s, 2H), 7.46 (br s, 1H), 4.52 (br s, 2H), 4.41 (br s, 1H), 4.0 (br s, 1H), 3.90 (br s, 1H), 3.59 (br s, 1H), 1.74-1.54 (br m, 4H), 1.53-1.38 (br m, 4H), 1.27 (br m, 6H). | Rt = 0.96 [M + H]⁺ 423.2 | 1 |
| Ex 22 | 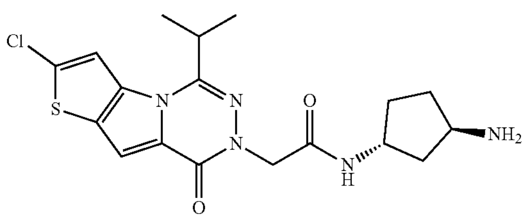 [SMILES: CC(C)c1nn(CC(=O)N[C@@H]2CC[C@@H](N)C2)c(=O)c2cc3sc(Cl)cc3n12] | N-((1R,3R)-3-Aminocyclopentyl)-2-(2-chloro-5-isopropyl-8-oxo thieno[2',3':4,5]pyrrolo[1,2-d][1,2,4]triazin-7(8H)-yl)acetamide | (400 MHz, DMSO-d6) δ (ppm) 8.09 (d, 1H), 7.81 (s, 1H), 7.68 (br s, 3H), 7.47 (s, 1H), 4.52 (s, 2H), 4.28-4.22 (m, 1H), 3.63-3.56 (m, 2H), 2.12-1.97 (m, 2H), 1.91-1.76 (m, 2H), 1.55-1.44 (m, 2H), 1.29 (d, 6H). | Rt = 0.76 [M + H]⁺ 408.1 | 1 |
| Ex 23 | 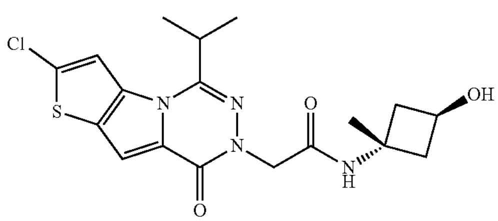 [SMILES: CC(C)c1nn(CC(=O)N[C@]2(C)C[C@@H](O)C2)c(=O)c2cc3sc(Cl)cc3n12] | 2-(2-Chloro-5-isopropyl-8-oxo thieno[2',3':4,5]pyrrolo[1,2-d][1,2,4]triazin-7(8H)-yl)-N-((1r,3r)-3-hydroxy-1-methyl cyclobutyl)acetamide | (400 MHz, DMSO-d6) (ppm) 8.02 (s, 1H), 7.80 (s, 1H), 7.46 (s, 1H), 4.96 (d, 1H), 4.48 (s, 2H), 4.14-4.09 (m, 1H), 3.62-3.56 (m, 1H), 2.57-2.52 (m, 2H), 1.76-1.71 (m, 2H), 1.35 (s, 3H), 1.29 (d, 6H). | Rt = 0.94 [M + H]⁺ 409.3 | 1 |
| Ex 24 | 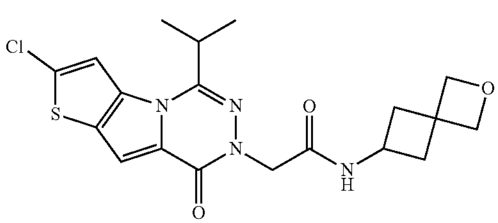 [SMILES: CC(C)c1nn(CC(=O)NC2CC3(COC3)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(2-oxaspiro[3.3]heptan-6-yl)acetamide | (400 MHz, DMSO-d6) δ (ppm) 8.17 (d, 1H), 7.81 (s, 1H), 7.46 (s, 1H), 4.58 (s, 2H), 4.48 (s, 2H), 4.46 (s, 2H), 4.02 (ttd, 1H), 3.59 (sept, 1H), 2.54-2.45 (m, 2H, overlapping with DMSO signal), 2.13-2.02 (m, 2H), 1.28 (d, 6H). | Rt = 0.96 [M + H]⁺ 421.1 | 1 |

| Ex No. | Structure | Name | ¹H NMR | LC/MS (min; m/z) | Int |
|---|---|---|---|---|---|
| Ex 25 | 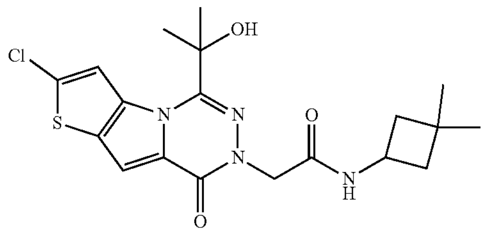 [SMILES: CC1(C)CC(NC(=O)Cn2nc(C(C)(C)O)n3c(cc4sc(Cl)cc43)c2=O)C1] | 2-(2-Chloro-5-(2-hydroxypropan-2-yl)-8-oxothieno[2',3':4,5]pyrrolo[1,2-d][1,2,4]triazin-7(8H)-yl)-N-(3,3-dimethylcyclobutyl)acetamide | (400 MHz, DMSO-d6) δ (ppm) 8.25 (d, 1H), 7.91 (s, 1H), 7.53 (s, 1H), 6.08 (s, 1H), 4.50 (s, 2H), 4.20 (ttd, 1H), 2.07-1.98 (m, 2H), 1.76-1.68 (m, 2H), 1.58 (s, 6H), 1.10 (s, 3H), 1.08 (s, 3H). | Rt = 1.11 [M + H]⁺ 423.1 | 13 |
| Ex 26 | 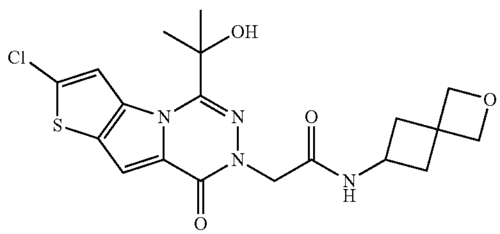 [SMILES: CC(C)(O)c1nn(CC(=O)NC2CC3(COC3)C2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-(2-oxaspiro[3.3]heptan-6-yl)acetamide | (400 MHz, DMSO-d6) δ (ppm) 8.25 (d, 1H), 7.91 (s, 1H), 7.53 (s, 1H), 6.07 (s, 1H), 4.58 (s, 2H), 4.49 (s, 2H), 4.47 (s, 2H), 4.02 (ttd, 1H), 2.54-2.45 (m, 2H, overlapping with DMSO signal), 2.13-2.0 (m, 2H), 1.58 (s, 6H). | Rt = 0.87 [M + H]⁺ 437.1 | 13 |
| Ex 27 | 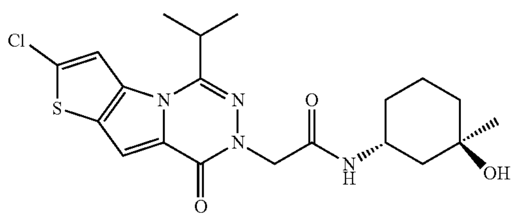 [SMILES: CC(C)c1nn(CC(=O)N[C@@H]2CCC[C@@](C)(O)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((1R,3R)-3-hydroxy-3-methylcyclohexyl)acetamide | (400 MHz, DMSO-d6) δ (ppm) 7.8 (s, 1H), 7.72 (d, 1H), 7.46 (s, 1H), 4.49 (s, 2H), 4.08 (s, 1H), 3.99-3.85 (m, 1H), 3.67-3.53 (m, 1H), 1.78-1.37 (m, 5H), 1.29 (d, 6H), 1.21-0.93 (m, 3 + 3H). | Rt = 1.03 [M + H]⁺ 437.2 | 1 |
| Ex 28 | 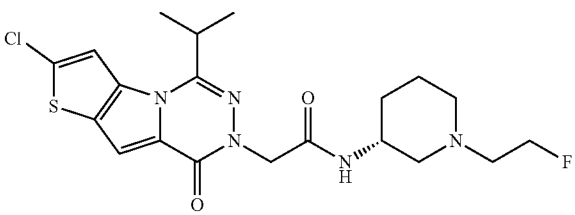 [SMILES: CC(C)c1nn(CC(=O)N[C@@H]2CCCN(CCF)C2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(1-(2-fluoroethyl)piperidin-3-yl)acetamide | (400 MHz, CDCl₃) δ (ppm) 7.42 (s, 1H), 7.21 (s, 1H), 6.61 (br d, 1H), 4.82-4.63 (m, 2H), 4.35 (dt, 2H), 4.16-4.07 (m, 1H), 3.40 (sept, 1H), 2.65-2.44 (m, 5H), 2.34-2.23 (m, 1H), 1.75-1.64 (m, 2H), 1.55-1.49 (m, 2H, overlapping with water peak), 1.44 (d, 6H). | Rt = 0.78 [M + H]⁺ 454.2 | 1 |
| Ex 29 | 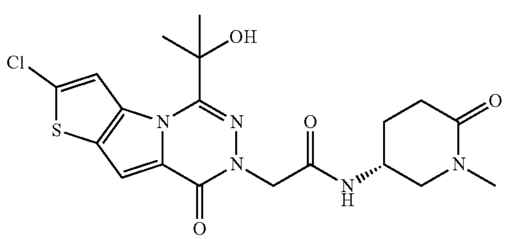 [SMILES: CN1C[C@H](NC(=O)Cn2nc(C(C)(C)O)n3c(cc4sc(Cl)cc43)c2=O)CCC1=O] | (R)-2-(2-Chloro-5-(2-hydroxypropan-2-yl)-8-oxothieno[2',3':4,5]pyrrolo[1,2-d][1,2,4]triazin-7(8H)-yl)-N-(1-methyl-6-oxopiperidin-3-yl)acetamide | (400 MHz, DMSO-d6) δ (ppm) 8.34 (d, 1H), 7.91 (s, 1H), 7.54 (s, 1H), 6.08 (s, 1H), 4.58 (s, 2H), 4.14-4.03 (br m, 1H), 3.53-3.38 (m, 1H, overlapping with water peak), 3.15-3.03 (m, 1H), 2.79 (s, 3H), 2.42-2.20 (m, 2H), 1.93-1.74 (m, 2H), 1.58 (s, 6H). | Rt = 0.80 [M + H]⁺ 452.1 | 13 |
| Ex 30 | 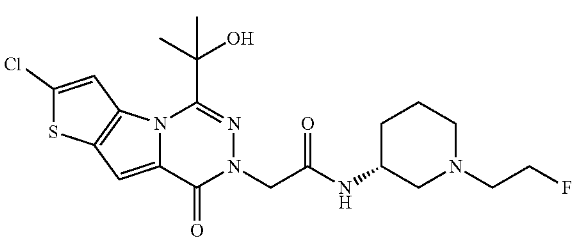 [SMILES: CC(C)(O)c1nn(CC(=O)N[C@@H]2CCCN(CCF)C2)c(=O)c2cc3sc(Cl)cc3n12] | (R)-2-(2-Chloro-5-(2-hydroxypropan-2-yl)-8-oxothieno[2',3':4,5]pyrrolo[1,2-d][1,2,4]triazin-7(8H)-yl)-N-(1-(2-fluoroethyl)piperidin-3-yl)acetamide | (400 MHz, DMSO-d6) δ (ppm) 7.94 (d, 1H), 7.91 (s, 1H), 7.53 (s, 1H), 6.07 (s, 1H), 4.63-4.39 (m, 4H), 3.8-3.67 (br m, 1H), 2.91-2.57 (m, 4H), 2.11-1.86 (m, 2H), 1.76-1.39 (m, 4H) overlapping with 1.58 (s, 6H). | Rt = 0.72 [M + H]⁺ 470.2 | 13 |

| Ex No. | Structure | Name | ¹H NMR | LC/MS (min; m/z) | Int |
|---|---|---|---|---|---|
| Ex 31 | 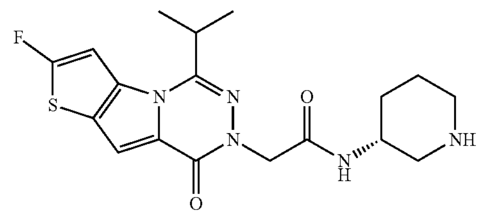 [SMILES: CC(C)c1nn(CC(=O)N[C@@H]2CCCNC2)c(=O)c2cc3sc(F)cc3n12] | (R)-2-(2-Fluoro-5-isopropyl-8-oxothieno[2',3':4,5]pyrrolo[1,2-d][1,2,4]triazin-7(8H)-yl)-N-(piperidin-3-yl)acetamide hydrochloride | (400 MHz, DMSO-d6) δ (ppm) 9.02 (br s, 2H), 8.28 (d, 1H), 7.55 (s, 1H), 7.48 (s, 1H), 4.57 (s, 2H), 4.05-3.91 (m, 1H), 3.54-3.49 (m, 1H), 3.23-3.07 (m, 2H), 2.87-2.70 (m, 2H), 1.92-1.76 (m, 2H), 1.74-1.60 (m, 1H), 1.56-1.41 (m, 1H), 1.28 (d, 6H). | Rt = 0.70 [M + H]⁺ 392.3 | 28 |
| Ex 32 | 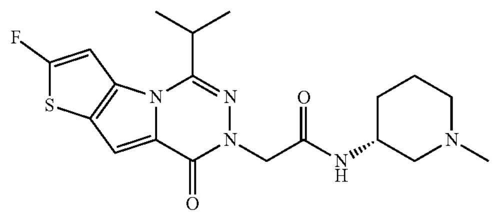 [SMILES: CC(C)c1nn(CC(=O)N[C@@H]2CCCN(C)C2)c(=O)c2cc3sc(F)cc3n12] | (R)-2-(2-Fluoro-5-isopropyl-8-oxothieno[2',3':4,5]pyrrolo[1,2-d][1,2,4]triazin-7(8H)-yl)-N-(1-methylpiperidin-3-yl)acetamide | (400 MHz, DMSO-d6) δ (ppm) 8.05 (d, 1H), 7.55 (s, 1H), 7.47 (s, 1H), 4.55 (s, 2H), 3.92-3.80 (m, 1H), 3.57-3.47 (m, 1H), 3.06-2.80 (m, 2H), 2.46 (s, 3H), 2.41-2.17 (m, 2H), 1.82-1.69 (m, 2H), 1.65-1.50 (m, 1H), 1.38-1.22 (m, 1H) overlapping with 1.29 (d, 6H). | Rt = 0.71 [M + H]⁺ 406.2 | 28 |
| Ex 33 | 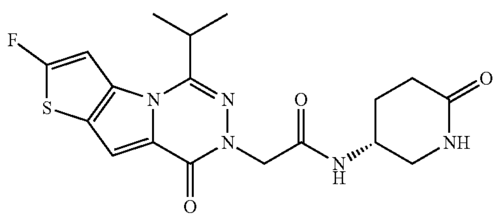 [SMILES: CC(C)c1nn(CC(=O)N[C@@H]2CCC(=O)NC2)c(=O)c2cc3sc(F)cc3n12] | (R)-2-(2-Fluoro-5-isopropyl-8-oxothieno[2',3':4,5]pyrrolo[1,2-d][1,2,4]triazin-7(8H)-yl)-N-(6-oxopiperidin-3-yl)acetamide | (400 MHz, DMSO-d6) δ (ppm) 8.19 (d, 1H), 7.55 (d, 1H), 7.48 (s, 1H), 7.38 (s, 1H), 4.56 (s, 2H), 4.04-3.92 (br m, 1H), 3.53 (sept, 1H), 3.02-2.92 (m, 1H), 2.30-2.14 (m, 2H), 1.90-1.69 (m, 2H), 1.33-1.23 (m, 1H) overlapping with 1.28 (d, 6H). | Rt = 0.77 [M + H]⁺ 406.2 | 28 |
| Ex 34 | 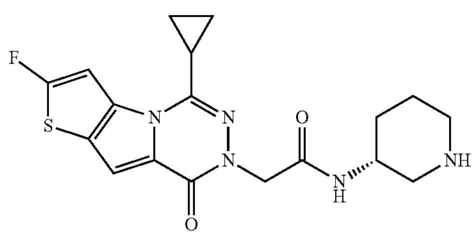 [SMILES: O=C(Cn1nc(C2CC2)n2c(cc3sc(F)cc32)c1=O)N[C@@H]1CCCNC1] | (R)-2-(5-Cyclopropyl-2-fluoro-8-oxothieno[2',3':4,5]pyrrolo[1,2-d][1,2,4]triazin-7(8H)-yl)-N-(piperidin-3-yl)acetamide | (400 MHz, DMSO-d6) δ (ppm) 7.78 (d, 1H), 7.65 (d, 1H), 7.45 (s, 1H), 4.49 (s, 2H), 3.75-3.65 (m, 1H), 3.63-3.59 (br m, 1H), 2.89-2.82 (m, 1H), 2.77-2.69 (m, 1H), 2.46-2.35 (m, 2H), 2.28 (dd, 1H), 1.79-1.70 (m, 1H), 1.62-1.54 (m, 1H), 1.39-1.28 (m, 2H), 1.17-1.08 (m, 2H), 1.0-0.92 (m, 2H). | Rt = 0.67 [M + H]⁺ 390.2 | 30 |
| Ex 35 | 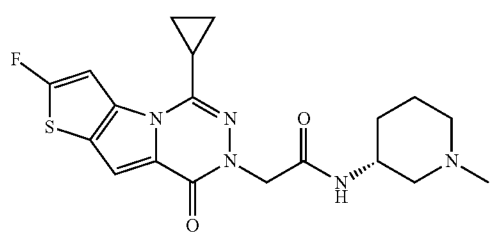 [SMILES: CN1CCC[C@@H](NC(=O)Cn2nc(C3CC3)n3c(cc4sc(F)cc43)c2=O)C1] | (R)-2-(5-Cyclopropyl-2-fluoro-8-oxothieno[2',3':4,5]pyrrolo[1,2-d][1,2,4]triazin-7(8H)-yl)-N-(1-methylpiperidin-3-yl)acetamide | (400 MHz, DMSO-d6) HPF6⁻ salt δ (ppm) 9.53 (s, 1H), 8.22 (d, 1H), 7.65 (d, 1H), 7.46 (s, 1H), 4.52 (s, 2H), 4.00-3.88 (m, 1H), 3.47-3.30 (m, 2H, overlapping with water signal), 2.87-2.76 (m, 1H + 3H), 2.71-2.57 (m, 1H), 2.47-2.40 (m, 1H, overlapping with DMSO signal), 1.96-1.81 (m, 2H), 1.75-1.59 (m, 1H), 1.46-1.32 (m, 1H), 1.18-1.11 (m, 2H), 1.03-0.93 (m, 2H). | Rt = 0.65 [M + H]⁺ 404.2 | 30 |
| Ex 36 | 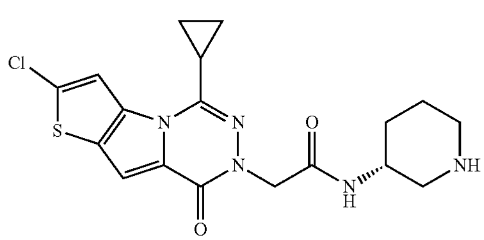 [SMILES: O=C(Cn1nc(C2CC2)n2c(cc3sc(Cl)cc32)c1=O)N[C@@H]1CCCNC1] | (R)-2-(2-Chloro-5-cyclopropyl-8-oxothieno[2',3':4,5]pyrrolo[1,2-d][1,2,4]triazin-7(8H)-yl)-N-(piperidin-3-yl)acetamide hydrochloride | (400 MHz, DMSO-d6) δ (ppm) 9.09 (d, 2H), 8.27 (d, 1H), 7.93 (s, 1H), 7.45 (s, 1H), 4.54 (s, 2H), 4.04-3.90 (m, 1H), 3.2-3.06 (m, 2H), 2.87-2.65 (m, 3H), 1.91-1.77 (m, 2H), 1.75-1.60 (m, 1H), 1.56-1.43 (m, 1H), 1.19-1.09 (m, 2H), 1.03-0.92 (m, 2H). | Rt = 0.71 [M + H]⁺ 406.1 | 6 |

-continued

| Ex No. | Structure | Name | ¹H NMR | LC/MS (min; m/z) | Int |
|---|---|---|---|---|---|
| Ex 37 | 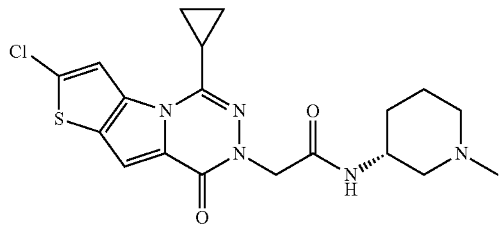 [SMILES: CN1CCC[C@@H](NC(=O)Cn2nc(C3CC3)n3c(cc4sc(Cl)cc43)c2=O)C1] | (R)-2-(2-Chloro-5-cyclopropyl-8-oxothieno[2',3':4,5]pyrrolo[1,2-d][1,2,4]triazin-7(8H)-yl)-N-(1-methylpiperidin-3-yl)acetamide | (400 MHz, DMSO-d6) δ (ppm) 8.17 (d, 1H), 7.92 (s, 1H), 7.44 (s, 1H), 4.53 (s, 2H), 4.03-3.82 (m, 1H), 3.27-3.14 (m, 2H, overlapping with water signal), 2.84-2.65 (m, 6H), 1.96-1.76 (m, 2H), 1.74-1.58 (m, 2H), 1.49-1.33 (m, 1H), 1.20-1.09 (m, 2H), 1.03-0.90 (m, 2H). | Rt = 0.72 [M + H]⁺ 420.2 | 6 |
| Ex 38 | 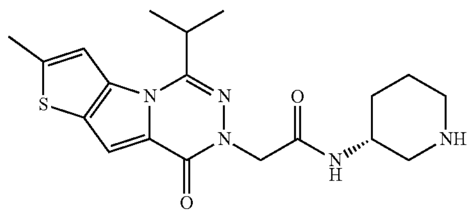 [SMILES: Cc1cc2c(cc3c(=O)n(CC(=O)N[C@@H]4CCCNC4)nc(C(C)C)n32)s1] | (R)-2-(5-Isopropyl-2-methyl-8-oxothieno[2',3':4,5]pyrrolo[1,2-d][1,2,4]triazin-7(8H)-yl)-N-(piperidin-3-yl)acetamide | (400 MHz, DMSO-d6) δ (ppm) 7.85 (d, 1H), 7.41 (s, 1H), 7.35 (s, 1H), 4.52 (s, 2H), 3.67-3.53 (m, 2H), 2.92-2.84 (m, 1H), 2.80-2.71 (m, 1H), 2.69 (s, 1H), 2.62 (s, 3H), 2.45-2.35 (m, 1H), 2.35-2.25 (m, 1H), 1.79-1.71 (m, 1H), 1.64-1.55 (m, 1H), 1.41-1.26 (m, 2H) overlapping with 1.32 (d, 6H). | Rt = 0.7 [M + H]⁺ 388.2 | 10 |
| Ex 39 | 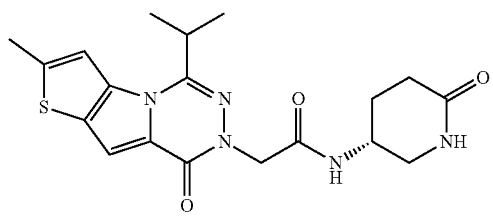 [SMILES: Cc1cc2c(cc3c(=O)n(CC(=O)N[C@@H]4CCC(=O)NC4)nc(C(C)C)n32)s1] | (R)-2-(5-Isopropyl-2-methyl-8-oxothieno[2',3':4,5]pyrrolo[1,2-d][1,2,4]triazin-7(8H)-yl)-N-(6-oxopiperidin-3-yl)acetamide | (400 MHz, DMSO-d6) δ (ppm) 8.19 (s, 1H), 7.57-7.13 (br m, 3H), 4.56 (s, 2H), 4.12-3.90 (br m, 1H), 3.65-3.50 (br m, 1H), 3.09-2.92 (br m, 1H), 2.62 (s, 3H), 2.34-2.13 (br m, 2H), 1.92-1.66 (br m, 2H), 1.30 (br s, 6H). | Rt = 0.79 [M + H]⁺ 402.2 | 10 |
| Ex 40 | 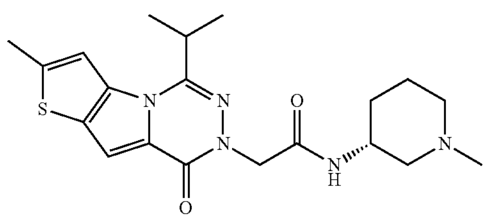 | (R)-2-(5-Isopropyl-2-methyl-8-oxothieno[2',3':4,5]pyrrolo[1,2-d][1,2,4]triazin-7(8H)-yl)-N-(1-methylpiperidin-3-yl)acetamide | (400 MHz, DMSO-d6) δ (ppm) 8.15 (br d, 1H), 7.42 (s, 1H), 7.35 (s, 1H), 4.55 (s, 2H), 3.97-3.84 (br m, 1H), 3.65-3.53 (m, 1H), 3.25-2.95 (br m, 2H overlapping with water signal), 2.72-2.56 (m, 8H), 1.93-1.52 (m, 3H), 1.40-1.26 (m, 1H) overlapping with 1.30 (d, 6H). | Rt = 0.71 [M + H]⁺ 402.2 | 10 |
| Ex 41 | 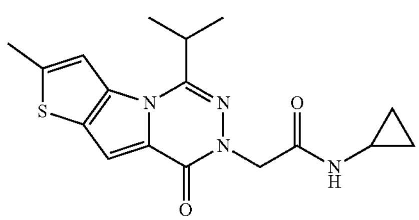 [SMILES: Cc1cc2c(cc3c(=O)n(CC(=O)NC4CC4)nc(C(C)C)n32)s1] | N-Cyclopropyl-2-(5-isopropyl-2-methyl-8-oxothieno[2',3':4,5]pyrrolo[1,2-d][1,2,4]triazin-7(8H)-yl)acetamide | (400 MHz, DMSO-d6) δ (ppm) 8.11 (s, 1H), 7.41 (s, 1H), 7.35 (s, 1H), 4.48 (s, 2H), 3.65-3.51 (m, 1H), 2.69-2.59 (m, 1H) overlapping with 2.62 (s, 3H), 1.30 (d, 6H), 0.66-0.53 (m, 2H), 0.45-0.36 (m, 2H). | Rt = 0.94 [M + H]⁺ 345.1 | 10 |
| Ex 42 | 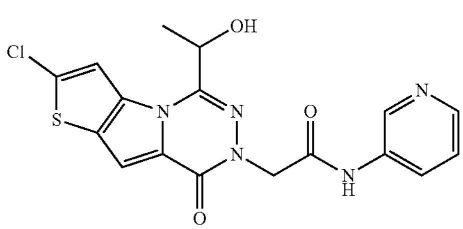 [SMILES: CC(O)c1nn(CC(=O)Nc2cccnc2)c(=O)c2cc3sc(Cl)cc3n12] | 2-(2-Chloro-5-(1-hydroxyethyl)-8-oxothieno[2',3':4,5]pyrrolo[1,2-d][1,2,4]triazin-7(8H)-yl)-N-(pyridin-3-yl)acetamide | (400 MHz, DMSO-d6) δ (ppm) 10.45 (s, 1H), 8.74 (s, 1H), 8.29 (d, 1H), 8.01 (d, 1H), 7.71 (s, 1H), 7.51 (s, 1H), 7.36 (dd, 1H), 5.98 (d, 1H), 5.25-5.07 (m, 1H), 4.94-4.74 (m, 2H), 1.53 (d, 3H). | Rt = 0.77 [M + H]⁺ 404.2 | 21 |

| Ex No. | Structure | Name | ¹H NMR | LC/MS (min; m/z) | Int |
|---|---|---|---|---|---|
| Ex 43 | 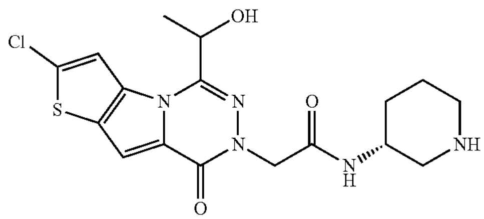 [SMILES: CC(O)c1nn(CC(=O)N[C@@H]2CCCNC2)c(=O)c2cc3sc(Cl)cc3n12] | 2-(2-Chloro-5-(1-hydroxyethyl)-8-oxothieno[2',3':4,5]pyrrolo[1,2-d][1,2,4]triazin-7(8H)-yl)-N-((R)-piperidin-3-yl)acetamide hydrochloride | (400 MHz, DMSO-d6) 1:1 mixture of diastereomers δ (ppm) 8.87 (br d, 2H), 8.32 (d, 1H), 7.72 (s, 1H), 7.48 (s, 1H), 5.99 (d, 1H), 5.22-5.09 (m, 1H), 4.69-4.50 (m, 2H), 4.02-3.88 (br m, 1H), 3.26-3.10 (m, 2H), 2.89-2.71 (m, 2H), 1.92-1.78 (m, 2H), 1.74-1.59 (m, 1H), 1.56-1.45 (m, 1H) overlapping with 1.51 (s, 3H). | Rt = 0.64 [M + H]⁺ 410.2 | 21 |
| Ex 44 | 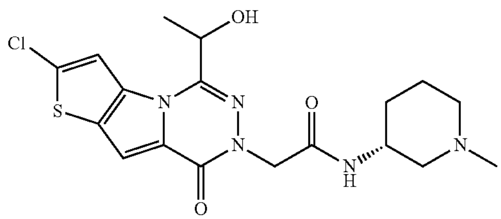 [SMILES: CC(O)c1nn(CC(=O)N[C@@H]2CCCN(C)C2)c(=O)c2cc3sc(Cl)cc3n12] | 2-(2-Chloro-5-(1-hydroxyethyl)-8-oxothieno[2',3':4,5]pyrrolo[1,2-d][1,2,4]triazin-7(8H)-yl)-N-((R)-1-methylpiperidin-3-yl)acetamide | (400 MHz, DMSO-d6) 1:1 mixture of diastereomers δ (ppm) 7.98 (d, 1H), 7.71 (s, 1H), 7.48 (s, 1H), 5.15 (q, 1H), 4.65-4.47 (m, 2H), 3.80-3.69 (m, 1H), 2.67-2.60 (m, 1H), 2.48 (m, 1H, overlapping with DMSO signal), 2.15 (s, 3H), 2.00-1.90 (m, 1H), 1.86-1.79 (m, 1H), 1.72-1.60 (m, 2H), 1.55-1.40 (m, 1H) overlapping with 1.51 (d, 3H), 1.27-1.15 (m, 1H), OH-proton not observed. | Rt = 0.63 [M + H]⁺ 424.2 | 21 |
| Ex 45 | 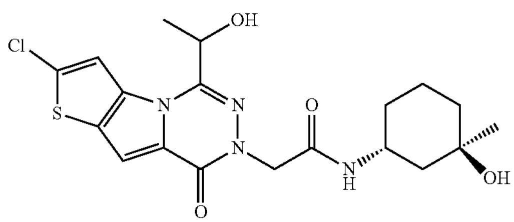 [SMILES: CC(O)c1nn(CC(=O)N[C@@H]2CCC[C@@](C)(O)C2)c(=O)c2cc3sc(Cl)cc3n12] | 2-(2-Chloro-5-(1-hydroxyethyl)-8-oxothieno[2',3':4,5]pyrrolo[1,2-d][1,2,4]triazin-7(8H)-yl)-N-((1R,3R)-3-hydroxy-3-methylcyclohexyl)acetamide | (400 MHz, DMSO-d6) 1:1 mixture of diastereomers δ (ppm) 7.79 (2 d, 1H), 7.71 (s, 1H), 7.48 (s, 1H), 5.15 (q, 1H), 4.60-4.40 (m, 2H), 4.00-3.86 (m, 1H), 1.79-1.55 (m, 3H), 1.53-1.39 (m, 2H) overlapping with 1.52 (d, 3H), 1.20-1.08 (m, 2H) overlapping with 1.11 (s, 3H), 1.06-0.94 (m, 1H), OH-protons not observed. | Rt = 0.83 [M + H]⁺ 439.2 | 21 |
| Ex 46 | 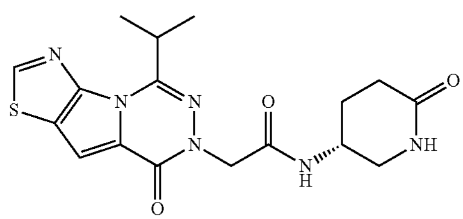 [SMILES: CC(C)c1nn(CC(=O)N[C@@H]2CCC(=O)NC2)c(=O)c2cc3scnc3n12] | (R)-2-(5-Isopropyl-8-oxothiazolo[5',4':4,5]pyrrolo[1,2-d][1,2,4]triazin-7(8H)-yl)-N-(6-oxopiperidin-3-yl)acetamide | (400 MHz, DMSO-d6) δ (ppm) 9.31 (s, 1H), 8.20 (d, 1H), 7.51 (s, 1H), 7.39 (s, 1H), 4.60 (s, 2H), 4.18 (sept, 1H), 4.06-3.94 (m, 1H), 3.02-2.93 (m, 1H), 2.36-2.13 (m, 2H), 1.92-1.65 (m, 2H), 1.46-1.19 (m, 1H) overlapping with 1.34 (d, 6H). | Rt = 0.67 [M + H]⁺ 389.2 | 40 |
| Ex 47 | 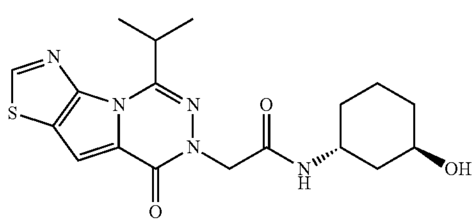 [SMILES: CC(C)c1nn(CC(=O)N[C@@H]2CCC[C@@H](O)C2)c(=O)c2cc3scnc3n12] | N-((1R,3R)-3-Hydroxycyclohexyl)-2-(5-isopropyl-8-oxothiazolo[5',4':4,5]pyrrolo[1,2-d][1,2,4]triazin-7(8H)-yl)acetamide | (400 MHz, DMSO-d6) δ (ppm) 9.31 (s, 1H), 7.78 (d, 1H), 7.50 (s, 1H), 4.58-4.52 (m, 2H), 4.41 (d, 1H), 4.18 (sept, 1H), 4.06-3.96 (m, 1H), 3.95-3.83 (m, 1H), 1.69-1.56 (m, 2H), 1.51-1.16 (m, 6H) overlapping with 1.33 (d, 6H). | Rt = 0.79 [M + H]⁺ 390.2 | 40 |
| Ex 48 | 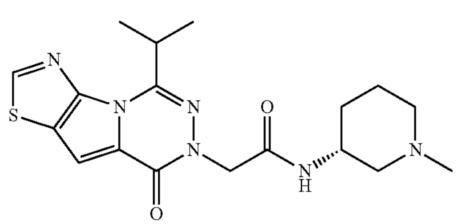 [SMILES: CC(C)c1nn(CC(=O)N[C@@H]2CCCN(C)C2)c(=O)c2cc3scnc3n12] | (R)-2-(5-Isopropyl-8-oxothiazolo[5',4':4,5]pyrrolo[1,2-d][1,2,4]triazin-7(8H)-yl)-N-(1-methylpiperidin-3-yl)acetamide | (400 MHz, DMSO-d6) δ (ppm) 9.32 (s, 1H), 7.99 (br d, 1H), 7.51 (s, 1H), 4.58 (br s, 2H), 4.19 (sept, 1H), 3.88-3.75 (br m, 1H), 2.93-2.62 (m, 2H), 2.32 (s, 3H), 2.23-1.97 (m, 2H), 1.79-1.62 (m, 2H), 1.62-1.45 (m, 1H), 1.43-1.18 (m, 1H) overlapping with 1.33 (d, 6H). | Rt = 0.63 [M + H]⁺ 389.3 | 40 |

-continued

| Ex No. | Structure | Name | ¹H NMR | LC/MS (min; m/z) | Int |
|---|---|---|---|---|---|
| Ex 49 | 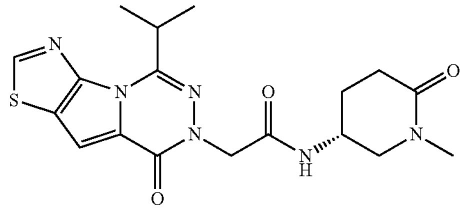 [SMILES: CC(C)c1nn(CC(=O)N[C@@H]2CCC(=O)N(C)C2)c(=O)c2cc3scnc3n12] | (R)-2-(5-Isopropyl-8-oxothiazolo[5',4':4,5]pyrrolo[1,2-d][1,2,4]triazin-7(8H)-yl)-N-(1-methyl-6-oxopiperidin-3-yl)acetamide | (400 MHz, CDCl₃) δ (ppm) 8.87 (s, 1H), 7.49 (s, 1H), 6.65 (d, 1H), 4.88-4.67 (m, 2H), 4.43-4.32 (m, 1H), 4.27 (sept, 1H), 3.58 (ddd, 1H), 3.16 (dd, 1H), 2.90 (s,3H), 2.46 (td, 2H), 2.08-1.98 (m, 1H), 1.94-1.82 (m, 1H), 1.44 (d, 6H). | Rt = 0.72 [M + H]⁺ 403.2 | 40 |
| Ex 50 | 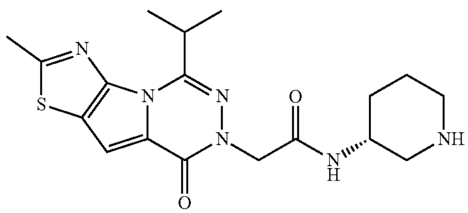 [SMILES: Cc1nc2c(cc3c(=O)n(CC(=O)N[C@@H]4CCCNC4)nc(C(C)C)n32)s1] | (R)-2-(5-Isopropyl-2-methyl-8-oxothiazolo[5',4':4,5]pyrrolo[1,2-d][1,2,4]triazin-7(8H)-yl)-N-(piperidin-3-yl)acetamide | (400 MHz, DMSO-d6) δ (ppm) 7.84 (d, 1H), 7.42 (s, 1H), 5.75 (s, 1H), 4.54 (s, 2H), 4.26-4.04 (m, 1H), 3.65-3.55 (br m, 1H), 2.85 (br s, 3 + 1H), 2.77-2.66 (m, 1H), 2.42-2.23 (m, 2H), 1.79-1.69 (m, 1H), 1.64-1.52 (m, 1H), 1.39-1.19 (m, 2H) overlapping with 1.32 (d, 6H). | Rt = 0.68 [M + H]⁺ 389.2 | 43 |
| Ex 51 | 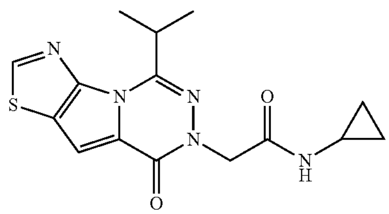 [SMILES: CC(C)c1nn(CC(=O)NC2CC2)c(=O)c2cc3scnc3n12] | N-Cyclopropyl-2-(5-isopropyl-8-oxo thiazolo[5',4':4,5]pyrrolo[1,2-d][1,2,4]triazin-7(8H)-yl)acetamide | (400 MHz, DMSO-d6) δ (ppm) 9.31 (s, 1H), 8.07 (s, 1H), 7.51 (s, 1H), 4.51 (s, 2H), 4.26-4.05 (m, 1H), 2.73-2.62 (br m, 1H), 1.33 (d, 6H), 0.69-0.54 (m, 2H), 0.48-0.35 (m, 2H). | Rt = 0.82 [M + H]⁺ 332.1 | 40 |
| Ex 52 | 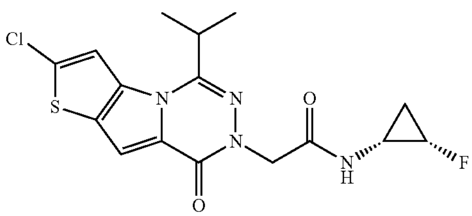 [SMILES: CC(C)c1nn(CC(=O)N[C@@H]2C[C@@H]2F)c(=O)c2cc3sc(Cl)cc3n12] | 2-(2-Chloro-5-isopropyl-8-oxo thieno[2',3':4,5]pyrrolo[1,2-d][1,2,4]triazin-7(8H)-yl)-N-((1R,2S)-2-fluoro cyclopropyl)acetamide | (400 MHz, DMSO-d6) δ (ppm) 8.24 (d, 1H), 7.80 (s, 1H), 7.47 (s, 1H), 4.81-4.74 (m, 0.5H), 4.64-4.53 (m, 2.5H), 3.58 (sept, 1H), 2.73-2.63 (m, 1H), 1.28 (d, 6H), 1.11-0.99 (m, 1H), 0.96-0.82 (m, 1H). | Rt = 1.0 [M + H]⁺ 383.1 | 1 |
| Ex 53 | 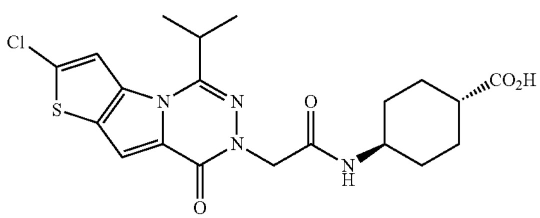 [SMILES: CC(C)c1nn(CC(=O)N[C@H]2CC[C@H](C(=O)O)CC2)c(=O)c2cc3sc(Cl)cc3n12] | (1r,4r)-4-(2-(2-Chloro-5-isopropyl-8-oxothieno[2',3':4,5]pyrrolo[1,2-d][1,2,4]triazin-7(8H)-yl)acetamido)cyclohexane-1-carboxylic acid | (400 MHz, DMSO-d6) δ (ppm): 12.04 (br s, 1H), 7.89 (d, 1H), 7.81 (s, 1H), 7.46 (s, 1H), 4.51 (s, 2H), 3.62-3.47 (m, 2H), 2.16-2.09 (m, 1H), 1.92-1.87 (m, 2H), 1.82-1.78 (m, 2H), 1.40-1.16 (m, 4H), 1.29 (d, 6H). | Rt = 0.96 [M + H]⁺ 451.2 | 1 |
| Ex 54 | 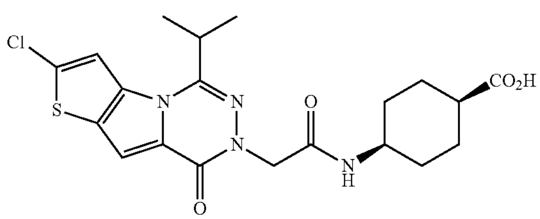 [SMILES: CC(C)c1nn(CC(=O)N[C@H]2CC[C@@H](C(=O)O)CC2)c(=O)c2cc3sc(Cl)cc3n12] | (1s,4s)-4-(2-(2-Chloro-5-isopropyl-8-oxothieno[2',3':4,5]pyrrolo[1,2-d][1,2,4]triazin-7(8H)-yl)acetamido)cyclohexane-1-carboxylic acid | (400 MHz, DMSO-d6) δ (ppm): 12.12 (br s, 1H), 7.93 (d, 1H), 7.80 (s, 1H), 7.46 (s, 1H), 4.53 (s, 2H), 3.75-3.67 (m, 1H), 3.51 (sept, 1H), 3.29-3.27 (m, 2H), 1.90-1.83 (m, 2H), 1.58-1.43 (m, 6H), 1.28 (d, 6H). | Rt = 0.97 [M + H]⁺ 451.3 | 1 |
| Ex 55 | 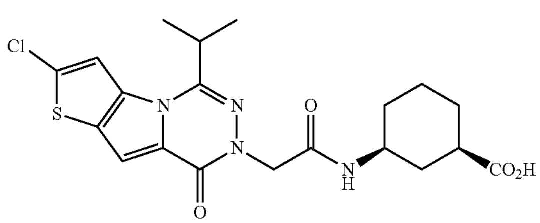 [SMILES: CC(C)c1nn(CC(=O)N[C@H]2CCC[C@@H](C(=O)O)C2)c(=O)c2cc3sc(Cl)cc3n12] | (1R,3S)-3-(2-(2-Chloro-5-isopropyl-8-oxothieno[2',3':4,5]pyrrolo[1,2-d][1,2,4]triazin-7(8H)-yl)acetamido)cyclohexane-1-carboxylic acid | (400 MHz, DMSO-d6) δ (ppm): 12.06 (br s, 1H), 7.91 (d, 1H), 7.81 (s, 1H), 7.47 (s, 1H), 4.51 (s, 2H), 3.65-3.55 (m, 2H), 3.33-3.24 (m, 1H), 1.97-1.94 (m, 2H), 1.83-1.72 (m, 3H), 1.37-1.09 (m, 4H), 1.28 (d, 6H). | Rt = 0.99 [M + H]⁺ 451.2 | 1 |

| Ex No. | Structure | Name | ¹H NMR | LC/MS (min; m/z) | Int |
|---|---|---|---|---|---|
| Ex 56 | 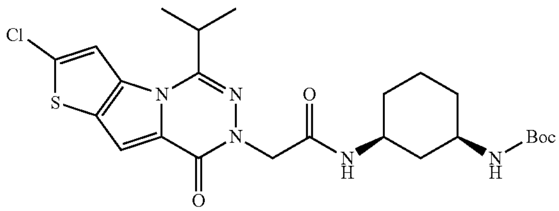 [SMILES: CC(C)c1nn(CC(=O)N[C@H]2CCC[C@@H](NC(=O)OC(C)(C)C)C2)c(=O)c2cc3sc(Cl)cc3n12] | tert-Butyl ((1R,3S)-3-(2-(2-chloro-5-isopropyl-8-oxothieno[2',3':4,5]pyrrolo[1,2-d][1,2,4]triazin-7(8H)-yl)acetamido)cyclohexyl)carbamate | (400 MHz, DMSO-d6) δ (ppm): 7.91 (d, 1H), 7.81 (s, 1H), 7.46 (s, 1H), 6.79 (d, 1H), 4.50 (s, 2H), 3.64-3.52 (m, 2H), 3.27-3.16 (m, 1H), 1.91-1.83 (m, 1H), 1.72-1.64 (m, 3H), 1.37 (s, 9H), 1.31-1.21 (m, 2H) overlapping with 1.28 (d, 6H), 1.12-1.02 (m, 2H). | Rt = 1.20 [M + H]⁺ 522.3 | 1 |
| Ex 57 | 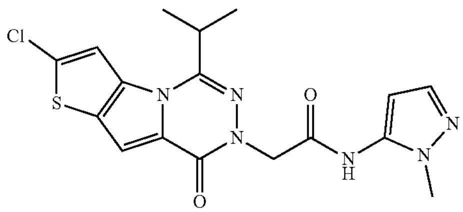 [SMILES: CC(C)c1nn(CC(=O)Nc2ccnn2C)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(1-methyl-1H-pyrazol-5-yl)acetamide | (400 MHz, CDCl₃) δ 8.97 (s, 1H), 7.46 (s, 1H), 7.38 (d, 1H), 7.22 (s, 1H), 6.35 (d, 1H), 4.90 (s, 2H), 3.75 (s, 3H), 3.40 (sept, 1H), 1.44 (d, 6H). | Rt = 0.98 [M + H]⁺ 405.1 | 1 |
| Ex 58 | 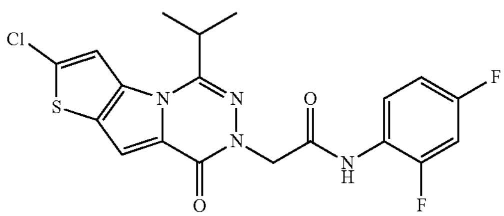 [SMILES: CC(C)c1nn(CC(=O)Nc2ccc(F)cc2F)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(2,4-difluorophenyl)acetamide | (400 MHz, DMSO-d6) δ 9.98 (s, 1H), 7.82 (s, 1H), 7.81-7.71 (m, 1H), 7.50 (s, 1H), 7.41-7.23 (m, 1H), 7.11-7.00 (m, 1H), 4.82 (s, 2H), 3.67-3.56 (m, 1H), 1.30 (d, 6H). | Rt = 1.20 [M + H]⁺ 437.1 | 1 |
| Ex 59 | 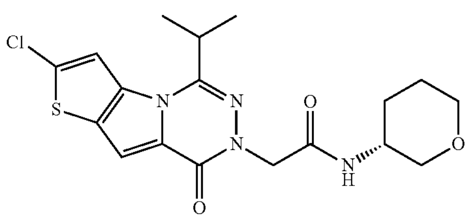 [SMILES: CC(C)c1nn(CC(=O)N[C@@H]2CCCOC2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(tetrahydro-2H-pyran-3-yl)acetamide | (400 MHz, DMSO-d6) δ 8.00 (d, 1H), 7.80 (s, 1H), 7.47 (s, 1H), 4.60-4.48 (m, 2H), 3.76-3.64 (m, 3H), 3.50 (sept, 1H), 3.35 (m, 1H, overlapping with water signal), 3.15-3.06 (m, 1H), 1.87-1.78 (m, 1H), 1.74-1.63 (m, 1H), 1.57-1.41 (m, 2H), 1.28 (d, 6H). | Rt = 1.01 [M + H]⁺ 409.1 | 1 |

Example 60

(R)-2-(2-Chloro-5-(2-hydroxypropan-2-yl)-8-oxothieno[2',3':4,5]pyrrolo[1,2-d][1,2,4]triazin-7(8H)-yl)-N-(1-methylpiperidin-3-yl)acetamide

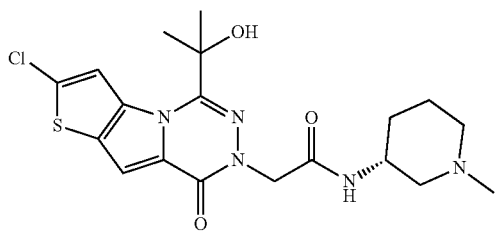 [SMILES: CN1CCC[C@@H](NC(=O)Cn2nc(C(C)(C)O)n3c(cc4sc(Cl)cc43)c2=O)C1]

To a solution of Int 13 (342 mg, 1.001 mmol) and (R)-1-methylpiperidin-3-amine (149 mg, 1.301 mmol) in DMF (8 mL) was added DIPEA (0.524 mL, 3.00 mmol), HOBt (169 mg, 1.101 mmol) and EDC (249 mg, 1.301 mmol). The solution was stirred at RT overnight. The reaction mixture was diluted with 5% Na₂CO₃ solution and extracted with EtOAc. The organic layer was washed twice with 5% Na₂CO₃ solution, then brine. A white precipitate which formed between the layers was filtered off. The remaining organic extract was dried over Na₂SO₄, filtered and evaporated to give an off-white solid after trituration with DCM. This crude product was combined with the first precipitate and further purified by crystallization from hot MEK to provide the title compound as white crystalline solid. ¹H NMR (400 MHz, DMSO-d6) δ (ppm) 7.98 (d, J=8.0 Hz, 1H), 7.91 (s, 1H), 7.53 (s, 1H), 6.09 (s, 1H), 4.54 (d, J=1.9 Hz, 2H), 3.81-3.66 (m, 1H), 2.66-2.57 (m, 1H), 2.48-2.45 (m, overlapping with DMSO signal, 1H) 2.13 (s, 3H), 1.98-1.87 (m, 1H), 1.86-1.76 (m, 1H), 1.71-1.60 (m, 2H), 1.58 (s, 6H), 1.52-1.38 (m, 1H), 1.27-1.11 (m, 1H). LC-MS: Rt=0.69 min; MS m/z [M+H]⁺ 438.2

The following examples were synthesized analogous to the above coupling procedure (Example 60) using the appropriate amines and carboxylic acid intermediates, optionally followed by a deprotection step:

| Ex No. | Structure | Name | ¹H NMR | LC/MS (min; m/z) | Int |
|---|---|---|---|---|---|
| Ex 61 | 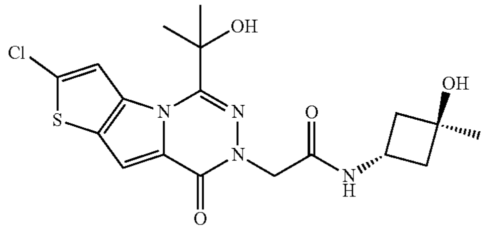 [SMILES: CC(C)(O)c1nn(CC(=O)N[C@H]2C[C@](C)(O)C2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-((1r,3r)-3-hydroxy-3-methylcyclobutyl)acetamide | (400 MHz, DMSO-d6) δ (ppm) 8.26 (d, J = 7.1 Hz, 1H), 7.92 (d, 1H), 7.53 (s, 1H), 6.07 (s, 1H), 4.82 (s, 2H), 4.51 (s, 2H), 4.26 (p, 1H), 2.32-2.14 (m, 2H), 1.98-1.83 (m, 2H), 1.58 (s,6H), 1.25 (s, 3H). | Rt = 0.85 [M + H]⁺ 425.1 | 13 |
| 62 | 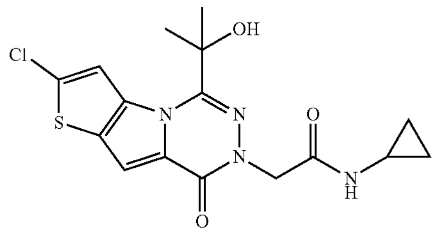 [SMILES: CC(C)(O)c1nn(CC(=O)NC2CC2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-cyclopropylacetamide | (400 MHz, DMSO-d6) δ (ppm) 8.14 (d, 1H), 7.91 (s, 1H), 7.53 (s, 1H), 6.07 (s, 1H), 4.49 (s, 2H), 2.72-2.58 (m, 1H), 1.58 (s, 6H), 0.68-0.57 (m, 2H), 0.45-0.35 (m, 2H). | Rt = 0.89 [M + H]⁺ 381.1 | 13 |
| Ex 63 | 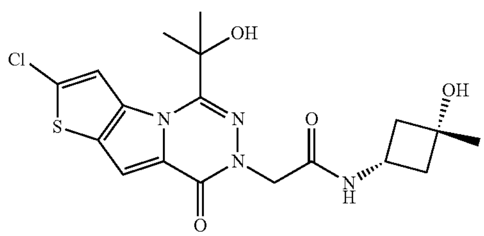 [SMILES: CC(C)(O)c1nn(CC(=O)N[C@H]2C[C@@](C)(O)C2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-((1s,3s)-3-hydroxy-3-methyl cyclobutyl)acetamide | (400 MHz, DMSO-d6) δ (ppm) 8.25 (d, 1H), 7.91 (s, 1H), 7.52 (s, 1H), 6.07 (s, 1H), 4.96 (s, 1H), 4.51 (s, 2H), 3.78 (h, 1H), 2.22 (ddt, 2H), 2.04-1.85 (m, 2H), 1.58(s, 6H), 1.21 (s, 3H). | Rt = 0.82 [M + H]⁺ 425.1 | 13 |
| Ex 64 | 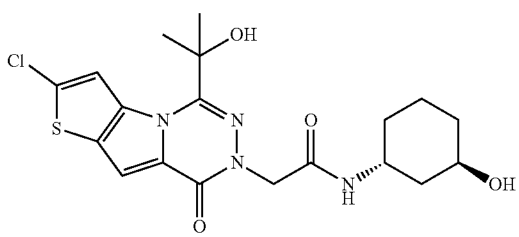 [SMILES: CC(C)(O)c1nn(CC(=O)N[C@@H]2CCC[C@@H](O)C2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-((1R,3R)-3-hydroxy cyclohexyl)acetamide | (400 MHz, DMSO-d6) δ (ppm) 8.05-7.78 (m, 2H), 7.52 (s, 1H), 6.08 (s, 1H), 4.49 (d, 3H), 3.94 (d, 2H), 1.50 (d, 14H). | Rt = 0.87 [M + H]⁺ 439.1 | 13 |
| Ex 65 | 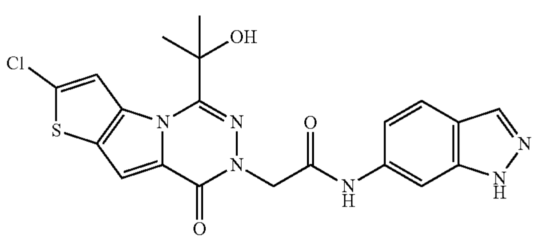 [SMILES: CC(C)(O)c1nn(CC(=O)Nc2ccc3cn[nH]c3c2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-(1H-indazol-6-yl)acetamide | (400 MHz, DMSO-d6) δ (ppm) 12.90 (s, 1H), 10.36 (s, 1H), 8.06 (s, 1H), 7.97 (d, 1H), 7.94 (s, 1H), 7.68 (d, 1H), 7.57 (s, 1H), 7.12 (dd, 1H), 6.11 (s, 1H), 4.83 (s, 2H), 1.61 (s, 6H). | Rt = 0.84 [M + H]⁺ 457.1 | 13 |
| Ex 66 | 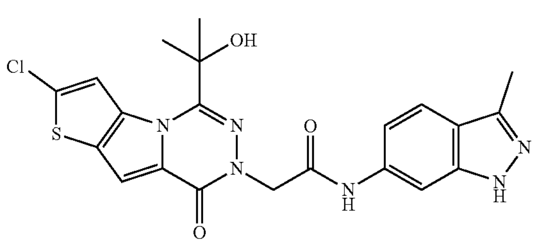 [SMILES: Cc1n[nH]c2cc(NC(=O)Cn3nc(C(C)(C)O)n4c(cc5sc(Cl)cc54)c3=O)ccc12] | 2-(2-Chloro-5-(2-hydroxypropan-2-yl)-8-oxothieno[2',3':4,5]pyrrolo[1,2-d][1,2,4]triazin-7(8H)-yl)-N-(3-methyl-1H-indazol-6-yl)acetamide | (400 MHz, DMSO-d6) δ (ppm) 12.46 (s, 1H), 10.33 (s, 1H), 7.96-7.93 (m, 2H), 7.62 (d, 1H), 7.57 (s, 1H), 7.09 (dd, 1H), 6.11 (s, 1H), 4.82 (s, 2H), 2.44 (s, 3H), 1.61 (s, 6H). | Rt = 0.97 [M + H]⁺ 471.2 | 13 |

-continued

| Ex No. | Structure | Name | ¹H NMR | LC/MS (min; m/z) | Int |
|---|---|---|---|---|---|
| Ex 67 | 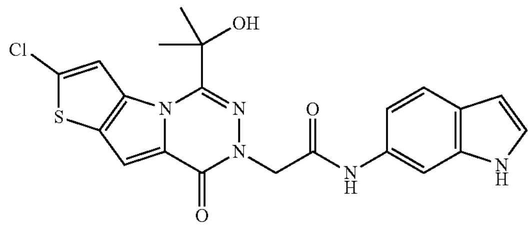 [SMILES: CC(C)(O)c1nn(CC(=O)Nc2ccc3cc[nH]c3c2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-(1H-indol-6-yl)acetamide | (400 MHz, DMSO-d6) δ (ppm) 11.01 (s, 1H), 10.09 (s, 1H), 7.93 (s, 1H), 7.88 (s, 1H), 7.57 (s, 1H), 7.45 (d, 1H, J = 8.5 Hz), 7.26 (t, 1H, J = 2.8 Hz), 7.05 (dd, 1H, J = 8.5, 1.8 Hz), 6.35 (s, 1H), 6.11 (s, 1H), 4.79 (s, 2H), 1.61 (s, 6H). | Rt = 1.04 [M + H]⁺ 456.2 | 13 |
| Ex 68 | 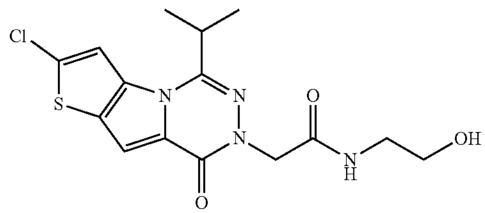 [SMILES: CC(C)c1nn(CC(=O)NCCO)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(2-hydroxyethyl)acetamide | (400 MHz, DMSO-d6) δ (ppm) 8.03 (br t, 1H), 7.80 (s, 1H), 7.46 (s, 1H), 4.74 (br s, 1H), 4.54 (s, 2H), 3.58 (sept, 1H), 3.4 (t, 2H), 3.18-3.10 (m, 2H), 1.29 (d, 6H). | Rt = 0.85 [M + H]⁺ 369.0 | 1 |
| Ex 69 | 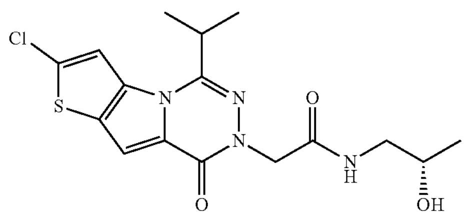 [SMILES: CC(C)c1nn(CC(=O)NC[C@H](C)O)c(=O)c2cc3sc(Cl)cc3n12] | (S)-2-(2-Chloro-5-isopropyl-8-oxothieno[2',3':4,5]pyrrolo[1,2-d][1,2,4]triazin-7(8H)-yl)-N-(2-hydroxy propyl)acetamide | (400 MHz, DMSO-d6) δ (ppm) 7.99 (t, 1H), 7.80 (s, 1H), 7.46 (s, 1H), 4.68 (br s, 1H), 4.56 (s, 2H), 3.7-3.62 (m, 1H), 3.58 (sept, 1H), 3.03 (t, 2H), 1.28 (d, 6H), 1.01 (d, 3H). | Rt = 0.89 [M + H]⁺ 383.1 | 1 |
| Ex 70 | 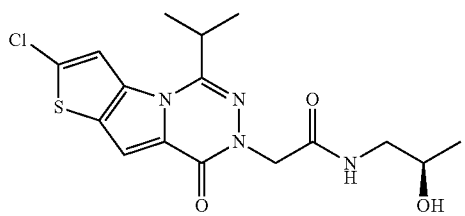 [SMILES: CC(C)c1nn(CC(=O)NC[C@@H](C)O)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(2-hydroxy propyl)acetamide | (400 MHz, DMSO-d6) δ (ppm) 7.98 (br t, 1H), 7.80 (s, 1H), 7.46 (s, 1H), 4.68 (br s, 1H), 4.56 (s, 2H), 3.7-3.62 (m, 1H), 3.58 (br sept, 1H), 3.03 (br t, 2H), 1.28 (d, 6H), 1.01 (d, 3H). | Rt = 0.89 [M + H]⁺ 383.1 | 1 |
| Ex 71 | 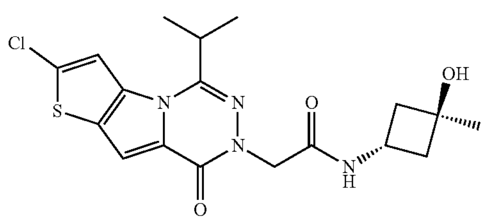 [SMILES: CC(C)c1nn(CC(=O)N[C@H]2C[C@](C)(O)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((1r,3r)-3-hydroxy-3-methylcyclobutyl)acetamide | (400 MHz, DMSO-d6) δ (ppm) 8.18 (d, 1H), 7.81 (s, 1H), 7.46 (s, 1H), 4.81 (s, 1H), 4.50 (s, 2H), 4.34-4.18 (m, 1H), 3.59 (sept, 1H), 2.26-2.15 (m, 2H), 1.94-1.85 (m, 2H), 1.28 (d, 6H), 1.24 (s, 3H). | Rt = 0.93 [M + H]⁺ 409.1 | 1 |
| Ex 72 | 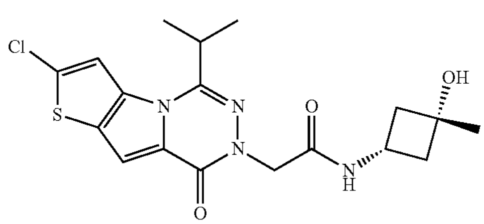 [SMILES: CC(C)c1nn(CC(=O)N[C@H]2C[C@@](C)(O)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((1s,3s)-3-hydroxy-3-methyl cyclobutyl)acetamide | (400 MHz, DMSO-d6) δ (ppm) 8.18 (d, 1H), 7.80 (s, 1H), 7.46 (s, 1H), 4.95 (s, 1H), 4.50 (s, 2H), 3.86-3.72 (m, 1H), 3.58 (sept, 1H), 2.28-2.15 (m, 2H), 2.00-1.88 (m, 2H), 1.28 (d, 6H), 1.21 (s, 3H). | Rt = 0.92 [M + H]⁺ 409.2 | 1 |
| Ex 73 | 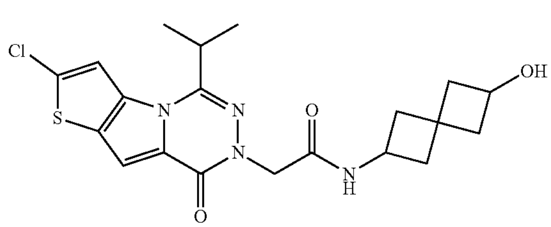 [SMILES: CC(C)c1nn(CC(=O)NC2CC3(CC(O)C3)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(6-hydroxyspiro[3.3]heptan-2-yl)acetamide | (400 MHz, DMSO-d6) δ (ppm) 8.15 (d, 1H), 7.80 (s, 1H), 7.46 (s, 1H), 4.95-4.79 (m, 1H), 4.47 (s, 2H), 4.21-4.03 (m, 2H), 4.00-3.86 (m, 1H), 3.64-3.52 (m, 1H), 2.39-2.05 (m, 4H), 2.00-1.65 (m, 4H), 1.28 (d, 6H). | Rt = 0.97 [M + H]⁺ 435.2 | 1 |

-continued

| Ex No. | Structure | Name | ¹H NMR | LC/MS (min; m/z) | Int |
|---|---|---|---|---|---|
| Ex 74 | 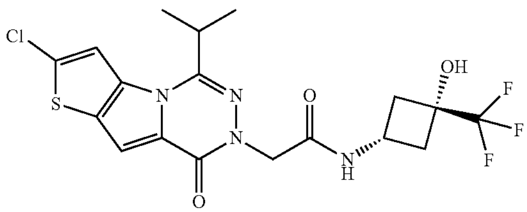 [SMILES: CC(C)c1nn(CC(=O)N[C@H]2C[C@](O)(C(F)(F)F)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((1s,3s)-3-hydroxy-3-(trifluoromethyl)cyclobutyl)acetamide | (400 MHz, DMSO-d6) δ (ppm) 8.42 (d, 1H), 7.81 (s, 1H), 7.47 (s, 1H), 6.63 (s, 1H), 4.52 (s, 2H), 4.02-3.89 (m, 1H), 3.59 (sept, 1H), 2.82-2.62 (m, 2H), 2.25 2.12 (m, 2H), 1.29 (d, 6H). | Rt = 1.04 [M + H]⁺ 463.0 | 1 |
| Ex 75 | 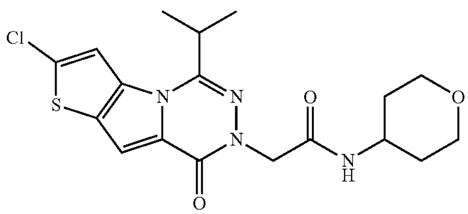 [SMILES: CC(C)c1nn(CC(=O)NC2CCOCC2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(tetrahydro-2H-pyran-4-yl)acetamide | (400 MHz, DMSO-d6) δ (ppm) 8.00 (d, 1H), 7.81 (s, 1H), 7.46 (s, 1H), 4.53 (s, 2H), 3.89-3.74 (m, 3H), 3.59 (sept, 1H), 3.38-3.33 (m, 2H), 1.73-1.63 (m, 2H), 1.48-1.35 (m, 2H), 1.28 (d, 6H). | Rt = 0.97 [M + H]⁺ 409.2 | 1 |
| Ex 76 | 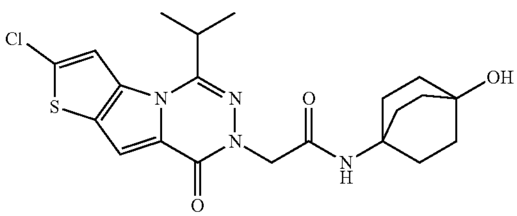 [SMILES: CC(C)c1nn(CC(=O)NC23CCC(O)(CC2)CC3)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(4-hydroxybicyclo[2.2.2]octan-1-yl)acetamide | (400 MHz, DMSO-d6) δ (ppm) 7.79 (s, 1H), 7.54 (s, 1H), 7.44 (s, 1H), 4.45 (s, 2H), 4.25 (s, 1H), 3.58 (sept, 1H), 1.93-1.84 (m, 6H), 1.60-1.51 (m, 6H), 1.27 (d, 6H). | Rt = 0.99 [M + H]⁺ 449.2 | 1 |
| Ex 77 | 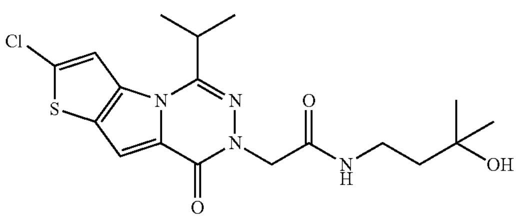 [SMILES: CC(C)c1nn(CC(=O)NCCC(C)(C)O)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(3-hydroxy-3-methylbutyl)acetamide | (400 MHz, DMSO-d6) δ (ppm) 7.87 (t, 1H), 7.81 (s, 1H), 7.46 (s, 1H), 4.50 (s, 2H), 4.24 (s, 1H), 3.58 (sept, 1H), 3.19-3.09 (m, 2H), 1.55-1.45 (m, 2H), 1.29 (d, 6H), 1.08 (s, 6H). | Rt = 0.96 [M + H]⁺ 411.1 | 1 |
| Ex 78 | 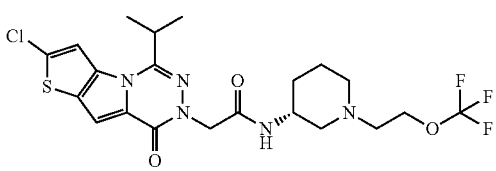 [SMILES: CC(C)c1nn(CC(=O)N[C@@H]2CCCN(CCOC(F)(F)F)C2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(1-(2-(trifluoromethoxy)ethyl)piperidin-3-yl)acetamide | (400 MHz, DMSO-d6) broad unresolved signals δ (ppm) 7.88 (s, 1H), 7.80 (s, 1H), 7.46 (s, 1H), 4.53 (s, 2H), 4.11 (s, 2H), 3.73 (s, 1H), 3.58 (s, 1H), 2.87-2.59 (m, 4H), 2.15-1.86 (m, 2H), 1.80-1.39 (m, 4H), 1.28 (s, 6H). | Rt = 0.93 [M + H]⁺ 520.1 | 1 |
| Ex 79 | 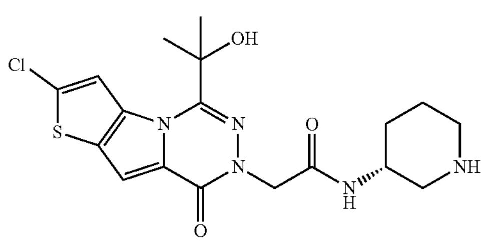 [SMILES: CC(C)(O)c1nn(CC(=O)N[C@@H]2CCCNC2)c(=O)c2cc3sc(Cl)cc3n12] | (R)-2-(2-Chloro-5-(2-hydroxypropan-2-yl)-8-oxothieno[2',3':4,5]pyrrolo[1,2-d][1,2,4]triazin-7(8H)-yl)-N-(piperidin-3-yl)acetamide | (400 MHz, DMSO-d6) δ (ppm) 8.00-7.88 (m, 2H), 7.53 (s, 1H), 6.08 (s, 1H), 4.54 (s, 2H), 3.65-3.55 (m, 1H), 2.96-2.66 (m, 2H), 2.45-2.22 (m, 2H), 1.81-1.71 (m, 1H), 1.58 (s, 6H), 1.48-1.14 (m, 3H). | Rt = 0.69 [M + H]⁺ 424.2 | 13 |
| Ex 80 | 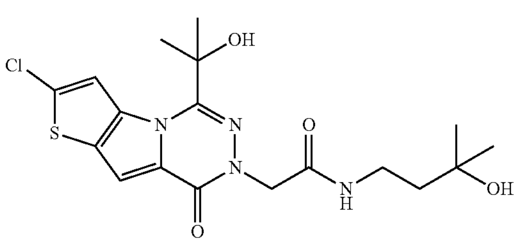 [SMILES: CC(C)(O)CCNC(=O)Cn1nc(C(C)(C)O)n2c(cc3sc(Cl)cc32)c1=O] | (2-(2-Chloro-5-(2-hydroxypropan-2-yl)-8-oxothieno[2',3':4,5]pyrrolo[1,2-d][1,2,4]triazin-7(8H)-yl)-N-(3-hydroxy-3-methylbutyl)acetamide | (400 MHz, DMSO-d6) δ (ppm) 7.98 (t, 1H), 7.92 (s, 1H), 7.53 (s, 1H), 6.16 (s, 1H), 4.51 (s, 2H), 4.27 (s, 1H), 3.19-3.08 (m, 2H), 1.58 (s, 6H), 1.53-1.49 (m, 2H), 1.08 (s, 6H). | Rt = 0.88 [M + H]⁺ 427.2 | 13 |

-continued

| Ex No. | Structure | Name | ¹H NMR | LC/MS (min; m/z) | Int |
|---|---|---|---|---|---|
| Ex 81 | 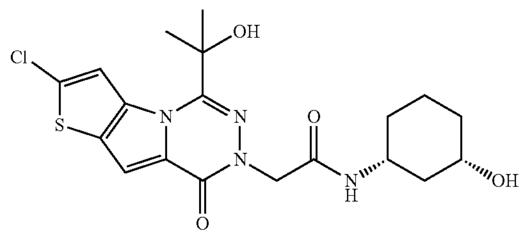 [SMILES: CC(C)(O)c1nn(CC(=O)N[C@@H]2CCC[C@H](O)C2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-((1R,3S)-3-hydroxycyclohexyl)acetamide | (400 MHz, DMSO-d6) δ (ppm) 8.12-7.85 (m, 2H), 7.53 (s, 1H), 6.07 (s, 1H), 4.63 (d, 1H), 4.51 (s, 2H), 3.71-3.50 (m, 2H), 2.04-1.47 (m, 10H), 1.33-0.84 (m, 4H). | Rt = 0.86 [M + H]⁺ 439.1 | 13 |
| Ex 82 | 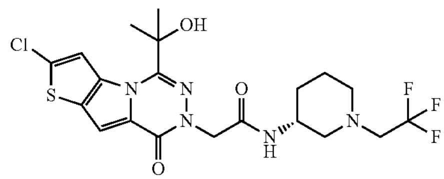 [SMILES: CC(C)(O)c1nn(CC(=O)N[C@@H]2CCCN(CC(F)(F)F)C2)c(=O)c2cc3sc(Cl)cc3n12] | (R)-2-(2-Chloro-5-(2-hydroxypropan-2-yl)-8-oxothieno[2',3':4,5]pyrrolo[1,2-d][1,2,4]triazin-7(8H)-yl)-N-(1-(2,2,2-trifluoroethyl)piperidin-3-yl)acetamide | (400 MHz, DMSO-d6) δ (ppm) 7.98 (d, 1H), 7.91 (s, 1H), 7.53 (s, 1H), 6.07 (s, 1H), 4.62-4.47 (m, 2H), 3.77-3.66 (m, 1H), 3.18 (q, 2H), 2.95-2.88 (m, 1H), 2.81-2.73 (m, 1H), 2.36-2.25 (m, 1H), 2.21-2.13 (m, 1H), 1.76-1.62 (m, 2H), 1.59 (s, 6H), 1.53-1.39 (m, 1H), 1.26-1.12 (m, 1H). | Rt = 1.1 [M + H]⁺ 506.1 | 13 |
| Ex 83 | 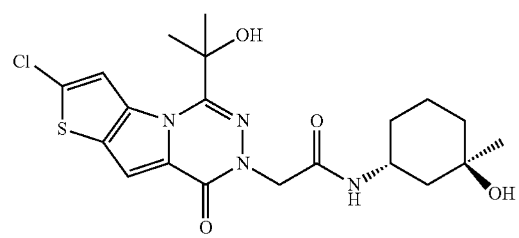 [SMILES: CC(C)(O)c1nn(CC(=O)N[C@@H]2CCC[C@@](C)(O)C2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-((1R,3R)-3-hydroxy-3-methylcyclohexyl)acetamide | (400 MHz, DMSO-d6) δ (ppm) 7.91 (s, 1H), 7.80 (d, 1H), 7.52 (s, 1H), 6.07 (s, 1H), 4.50 (s, 2H), 4.09 (s, 1H), 4.00-3.85 (m, 1H), 1.76-1.61 (m, 2H), 1.6 (s, 6H), 1.51-1.41 (m, 2H), 1.27-1.12 (m, 3H), 1.09 (s, 3H), 1.06-0.93 (m, 1H). | Rt = 0.93 [M + H]⁺ 453.1 | 13 |
| Ex 84 | 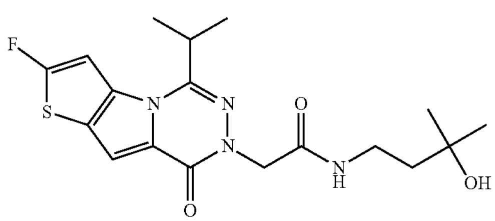 [SMILES: CC(C)c1nn(CC(=O)NCCC(C)(C)O)c(=O)c2cc3sc(F)cc3n12] | 2-(2-Fluoro-5-isopropyl-8-oxothieno[2',3':4,5]pyrrolo[1,2-d][1,2,4]triazin-7(8H)-yl)-N-(3-hydroxy-3-methylbutyl)acetamide | (400 MHz, DMSO-d6) broad unresolved signals 0 (ppm) 7.86 (s, 1H), 7.66-7.32 (m, 2H), 4.49 (s, 2H), 4.24 (s, 1H), 3.51 (s, 1H), 3.15 (s, 2H), 1.65-0.89 (m, 14H). | Rt = 0.90 [M + H]⁺ 395.1 | 24 |
| Ex 85 | 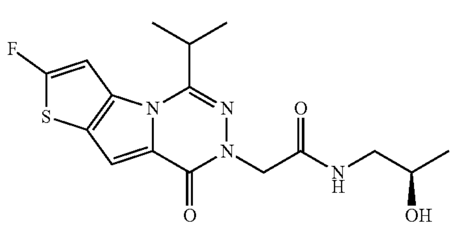 [SMILES: CC(C)c1nn(CC(=O)NC[C@@H](C)O)c(=O)c2cc3sc(F)cc3n12] | (R)-2-(2-Fluoro-5-isopropyl-8-oxothieno[2',3':4,5]pyrrolo[1,2-d][1,2,4]triazin-7(8H)-yl)-N-(2-hydroxypropyl)acetamide | (400 MHz, DMSO-d6) δ (ppm) 7.96 (t, 1H), 7.55 (d, 1H), 7.47 (s, 1H), 4.70-4.62 (m, 1H), 4.55 (s, 2H), 3.71-3.60 (m, 1H), 3.52 (sept, 1H), 3.07-2.97 (m, 2H) 1.28 (d, 6H), 1.01 (d, 3H). | Rt = 0.83 [M + H]⁺ 367.1 | 24 |
| Ex 86 | 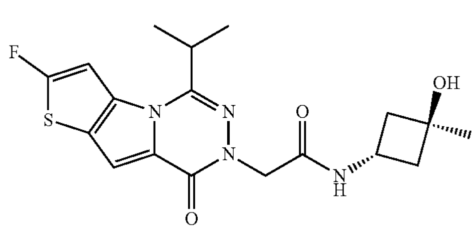 [SMILES: CC(C)c1nn(CC(=O)N[C@H]2C[C@](C)(O)C2)c(=O)c2cc3sc(F)cc3n12] | 2-(2-Fluoro-5-isopropyl-8-oxothieno[2',3':4,5]pyrrolo[1,2-d][1,2,4]triazin-7(8H)-yl)-N-((1r,3r)-3-hydroxy-3-methylcyclobutyl)acetamide | (400 MHz, DMSO-d6) δ (ppm) 8.17 (d, 1H), 7.55 (d, 1H), 7.47 (s, 1H), 4.81 (s, 1H), 4.49 (s, 2H), 4.33-4.21 (m, 1H), 3.52 (sept, 1H), 2.25-2.16 (m, 2H), 1.95-1.82 (m, 2H), 1.28 (d, 6H), 1.24 (s, 3H). | Rt = 0.86 [M + H]⁺ 393.2 | 24 |

| Ex No. | Structure | Name | ¹H NMR | LC/MS (min; m/z) | Int |
|---|---|---|---|---|---|
| Ex 87 | 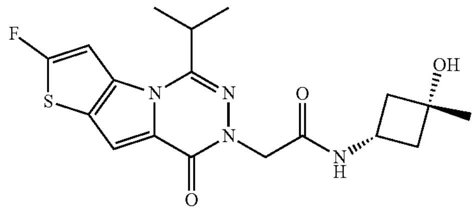 [SMILES: CC(C)c1nn(CC(=O)N[C@H]2C[C@@](C)(O)C2)c(=O)c2cc3sc(F)cc3n12] | 2-(2-Fluoro-5-isopropyl-8-oxothieno[2',3':4,5]pyrrolo[1,2-d][1,2,4]triazin-7(8H)-yl)-N-((1s,3s)-3-hydroxy-3-methylcyclobutyl)acetamide | (400 MHz, DMSO-d6) δ (ppm) 8.17 (d, 1H), 7.55 (d, 1H), 7.46 (s, 1H), 4.95 (s, 1H), 4.49 (s, 2H), 3.84-3.71 (m, 1H), 3.51 (sept, 1H), 2.27-2.16 (m, 2H), 2.01-1.86 (m, 2H), 1.28 (d, 6H), 1.21 (s, 3H). | Rt = 0.86 [M + H]⁺ 393.1 | 24 |
| Ex 88 | 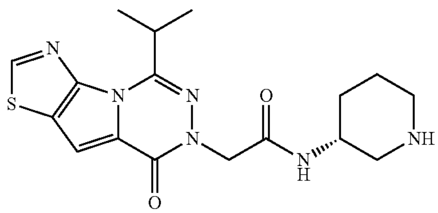 [SMILES: CC(C)c1nn(CC(=O)N[C@@H]2CCCNC2)c(=O)c2cc3scnc3n12] | (R)-2-(5-Isopropyl-8-oxothiazolo[5',4':4,5]pyrrolo[1,2-d][1,2,4]triazin-7(8H)-yl)-N-(piperidin-3-yl)acetamide | (400 MHz, DMSO-d6) δ (ppm) 9.31 (s, 1H), 7.84 (d, 1H), 7.51 (s, 1H), 4.61-4.51 (m, 2H), 4.22-4.12 (m, 1H), 3.65-3.56 (m, 1H), 2.90-2.83 (m, 1H), 2.78-2.69 (m, 1H), 2.44-2.18 (m, 3H), 1.79-1.70 (m, 1H), 1.63-1.52 (m, 1H), 1.37-1.28 (m, 8H). | Rt = 0.61 [M + H]⁺ 375.2 | 40 |
| Ex 89 | 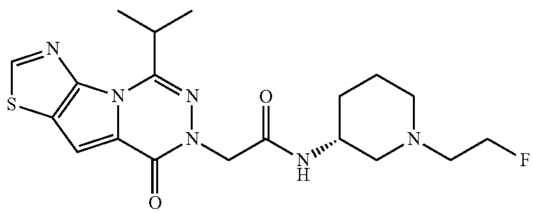 [SMILES: CC(C)c1nn(CC(=O)N[C@@H]2CCCN(CCF)C2)c(=O)c2cc3scnc3n12] | (R)-N-(1-(2-Fluoroethyl)piperidin-3-yl)-2-(5-isopropyl-8-oxothiazolo[5',4':4,5]pyrrolo[1,2-d][1,2,4]triazin-7(8H)-yl)acetamide | (400 MHz, DMSO-d6) δ (ppm) 9.31 (s, 1H), 7.88 (d, 1H), 7.51 (s, 1H), 4.62-4.49 (m, 3H), 4.48-4.38 (m, 1H), 4.25-4.13 (m, 1H), 3.81-3.66 (m, 1H), 2.86-2.77 (m, 1H), 2.74-2.54 (m, 3H), 2.08-1.97 (m, 1H), 1.97-1.88 (m, 1H), 1.74-1.60 (m, 2H), 1.52-1.40 (m, 1H), 1.33 (d, 6H), 1.26-1.13 (m, 1H) | Rt = 0.64 [M + H]⁺ 421.2 | 40 |
| Ex 90 | 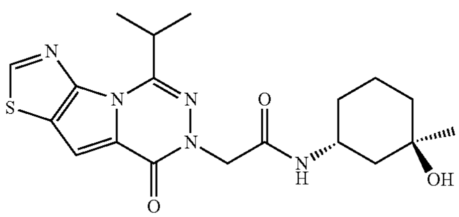 | N-((1R,3R)-3-Hydroxy-3-methylcyclohexyl)-2-(5-isopropyl-8-oxothiazolo[5',4':4,5]pyrrolo[1,2-d][1,2,4]triazin-7(8H)-yl)acetamide | (400 MHz, DMSO-d6) δ (ppm) 9.31 (s, 1H), 7.72 (d, 1H), 7.50 (s, 1H), 4.52 (s, 2H), 4.17 (sept, 1H), 4.00-3.87 (m, 1H), 1.76-1.54 (m, 3H), 1.50-1.39 (m, 2H), 1.33 (d, 6H), 1.19-0.94 (m, 3H) overlapping with 1.09 (s, 3H). OH-signal not observed. | Rt = 0.88 [M + H]⁺ 408.3 | 40 |
| Ex 91 | 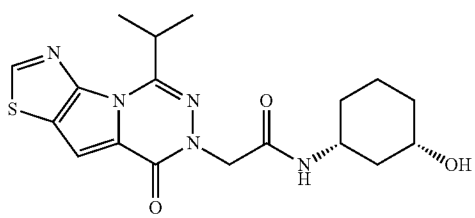 [SMILES: CC(C)c1nn(CC(=O)N[C@@H]2CCC[C@H](O)C2)c(=O)c2cc3scnc3n12] | N-((1R,3S)-3-Hydroxycyclohexyl)-2-(5-isopropyl-8-oxothiazolo[5',4':4,5]pyrrolo[1,2-d][1,2,4]triazin-7(8H)-yl)acetamide | (400 MHz, DMSO-d6) δ (ppm) 9.31 (s, 1H), 7.89 (d, 1H), 7.51 (s, 1H), 4.61 (d, 1H), 4.53 (s, 2H), 4.17 (sept, 1H), 3.65-3.53 (m, 1H), 3.45-3.33 (m, 1H), 1.98-1.90 (m, 1H), 1.79-1.60 (m, 3H), 1.33 (d, 6H), 1.27-0.94 (m, 4H). | Rt = 0.8 [M + H]⁺ 390.2 | 40 |
| Ex 92 | 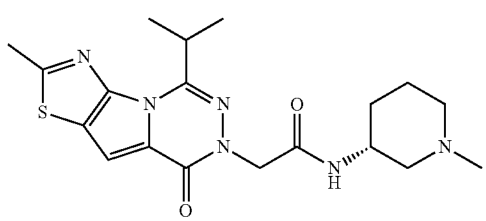 | (R)-2-(5-Isopropyl-2-methyl-8-oxothiazolo[5',4':4,5]pyrrolo[1,2-d][1,2,4]triazin-7(8H)-yl)-N-(1-methylpiperidin-3-yl)acetamide | (400 MHz, DMSO-d6) δ (ppm) 7.91 (d, 1H), 7.42 (s, 1H), 4.60-4.49 (m, 2H), 4.14 (sept, 1H), 3.80-3.69 (m, 1H), 2.85 (s, 3H), 2.67-2.58 (m, 1H), 2.14 (s, 3H), 1.96-1.75 (m, 2H), 1.70-1.58 (m, 2H), 1.53-1.39 (m, 1H), 1.32 (d, 6H), 1.27-1.13 (m, 2H). | Rt = 0.71 [M + H]⁺ 402.2 | 43 |
| Ex 93 | 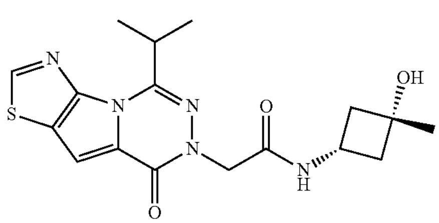 [SMILES: CC(C)c1nn(CC(=O)N[C@H]2C[C@@](C)(O)C2)c(=O)c2cc3scnc3n12] | N-((1s,3s)-3-Hydroxy-3-methylcyclobutyl)-2-(5-isopropyl-8-oxothiazolo[5',4':4,5]pyrrolo[1,2-d][1,2,4]triazin-7(8H)-yl)acetamide | (400 MHz, DMSO-d6) δ (ppm) 9.31 (s, 1H), 8.17 (d, 1H), 7.51 (s, 1H), 4.94 (s, 1H), 4.52 (s, 2H), 4.18 (sept, 1H), 3.85-3.74 (m, 1H), 2.27-2.17 (m, 2H), 2.01-1.86 (m, 2H), 1.33 (d, 6H), 1.21 (s, 3H). | Rt = 0.76 [M + H]⁺ 376.1 | 40 |

-continued

| Ex No. | Structure | Name | $^1$H NMR | LC/MS (min; m/z) | Int |
|---|---|---|---|---|---|
| Ex 94 | 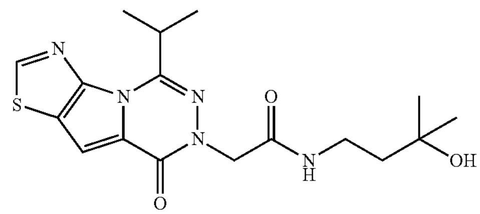 [SMILES: CC(C)c1nn(CC(=O)NCCC(C)(C)O)c(=O)c2cc3scnc3n12] | N-(3-Hydroxy-3-methylbutyl)-2-(5-isopropyl-8-oxothiazolo[5',4':4,5]pyrrolo[1,2-d][1,2,4]triazin-7(8H)-yl)acetamide | (400 MHz, DMSO-d6) δ (ppm) 9.31 (s, 1H), 7.87 (t, 1H), 7.51 (s, 1H), 4.52 (s, 2H), 4.25 (s, 1H), 4.22-4.13 (m, 1H), 3.20-3.10 (m, 2H), 1.56-1.46 (m, 2H), 1.33 (d, 6H), 1.08 (s, 6H). | Rt = 0.81 [M + H]$^+$ 378.1 | 40 |
| Ex 95 | 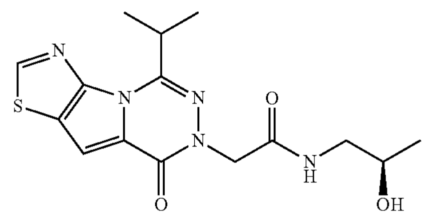 [SMILES: CC(C)c1nn(CC(=O)NC[C@@H](C)O)c(=O)c2cc3scnc3n12] | (R)-N-(2-Hydroxypropyl)-2-(5-isopropyl-8-oxothiazolo[5',4':4,5]pyrrolo[1,2-d][1,2,4]triazin-7(8H)-yl)acetamide | (400 MHz, DMSO-d6) δ (ppm) 9.31 (s, 1H), 7.97 (t, 1H), 7.51 (s, 1H), 4.66 (d, 1H), 4.64-4.53 (m, 2H), 4.17 (sept, 1H), 3.71-3.61 (m, 1H), 3.08-2.98 (m, 2H), 1.33 (d, 6H), 1.02 (d, 3H). | Rt = 0.73 [M + H]$^+$ 350.1 | 40 |
| Ex 96 | 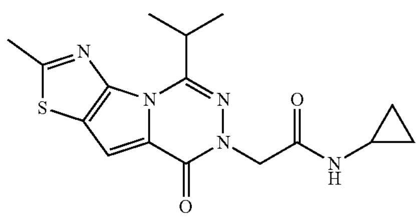 | N-Cyclopropyl-2-(5-isopropyl-2-methyl-8-oxothiazolo[5',4':4,5]pyrrolo[1,2-d][1,2,4]triazin-7(8H)-yl)acetamide | (400 MHz, DMSO-d6) broad unresolved signals δ (ppm) 8.08 (s, 1H), 7.42 (s, 1H), 4.49 (s, 2H), 4.14 (s, 1H), 2.85 (s, 3H), 2.64 (s, 1H), 1.31 (d, 6H), 0.66-0.55 (m, 2H), 0.41 (s, 2H). | Rt = 0.93 [M + H]$^+$ 346.2 | 43 |
| Ex 97 | 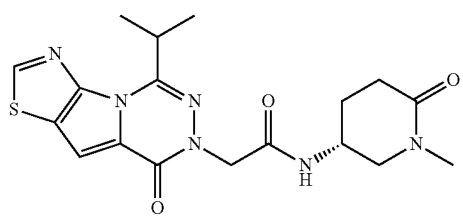 | (R)-2-(5-Isopropyl-8-oxothiazolo[5',4':4,5]pyrrolo[1,2-d][1,2,4]triazin-7(8H)-yl)-N-(1-methyl-6-oxopiperidin-3-yl)acetamide | (400 MHz, DMSO-d6) δ (ppm) 9.90 (s, 1H), 9.32 (s, 1H), 8.06 (s, 1H), 7.54 (s, 1H), 7.39 (d, 1H), 6.40 (d, 1H), 4.75 (s, 2H), 4.29-4.12 (m, 1H), 3.39 (s, 3H), 1.34 (d, 6H). | Rt = 0.75 [M + H]$^+$ 399.1 | 40 |
| Ex 98 | 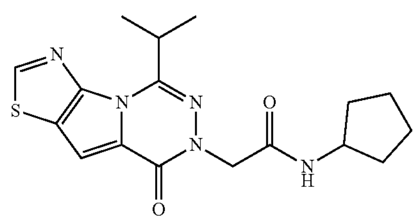 [SMILES: CC(C)c1nn(CC(=O)NC2CCCC2)c(=O)c2cc3scnc3n12] | N-Cyclopentyl-2-(5-isopropyl-8-oxothiazolo[5',4':4,5]pyrrolo[1,2-d][1,2,4]triazin-7(8H)-yl)acetamide | (400 MHz, DMSO-d6) 9.31 (s, 1H), 8.0 (d, 1H), 7.5 (s, 1H), 4.53 (s, 2H), 4.26-4.10 (m, 1H), 4.09-3.95 (m, 1H), 1.88-1.72 (m, 2H), 1.70-1.18 (m, 6H) overlapping with 1.33 (d, 6H). | Rt = 0.99 [M + H]$^+$ 360.3 | 40 |
| Ex 99 | 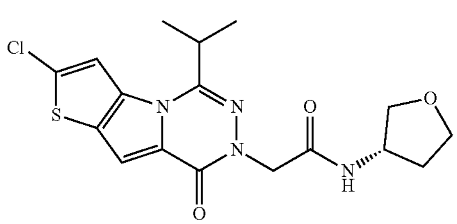 [SMILES: CC(C)c1nn(CC(=O)N[C@H]2CCOC2)c(=O)c2cc3sc(Cl)cc3n12] | (S)-2-(2-Chloro-5-isopropyl-8-oxothieno[2',3':4,5]pyrrolo[1,2-d][1,2,4]triazin-7(8H)-yl)-N-(tetrahydrofuran-3-yl)acetamide | (400 MHz, CDCl$_3$) 7.43 (s, 1H), 7.22 (s, 1H), 6.5 (d, 1H), 4.78-4.69 (m, 2H), 4.61-4.53 (m, 1H), 3.97-3.88 (m, 1H), 3.87-3.74 (m, 2H), 3.72-3.65 (m, 1H), 3.4 (sept, 1H), 2.34-2.19 (m, 1H), 1.90-1.78 (m, 1H), 1.45 (d, 6H). | Rt = 0.95 [M + H]$^+$ 395.1 | 1 |
| Ex 100 | 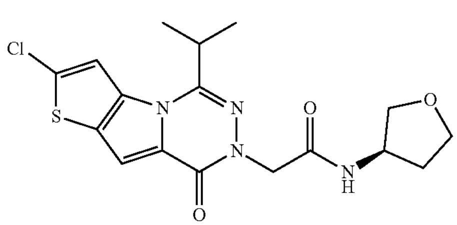 [SMILES: CC(C)c1nn(CC(=O)N[C@@H]2CCOC2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(tetrahydrofuran-3-yl)acetamide | (400 MHz, CDCl$_3$) 7.43 (s, 1H), 7.22 (s, 1H), 6.5 (d, 1H), 4.78-4.69 (m, 2H), 4.61-4.53 (m, 1H), 3.97-3.88 (m, 1H), 3.87-3.74 (m, 2H), 3.72-3.65 (m, 1H), 3.4 (sept, 1H), 2.34-2.19 (m, 1H), 1.90-1.78 (m, 1H), 1.45 (d, 6H). | Rt = 0.95 [M + H]$^+$ 395.1 | 1 |

-continued

| Ex No. | Structure | Name | ¹H NMR | LC/MS (min; m/z) | Int |
|---|---|---|---|---|---|
| Ex 101 | 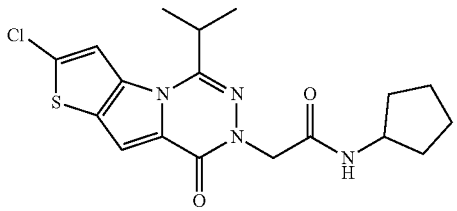 [SMILES: CC(C)c1nn(CC(=O)NC2CCCC2)c(=O)c2cc3sc(Cl)cc3n12] | 2-(2-chloro-5-Isopropyl-8-oxothieno[2',3':4,5]pyrrolo[1,2-d][1,2,4]triazin-7(8H)-yl)-N-cyclopentylacetamide | (400 MHz, DMSO-d6) 7.96 (d, 1H), 7.8 (s, 1H), 7.46 (s, 1H), 4.51 (s, 2H), 4.14-3.93 (m, 1H), 3.64-3.50 (m, 1H), 1.86-1.73 (m, 2H), 1.70-1.57 (m, 2H), 1.56-1.44 (m, 2H), 1.48-1.34 (m, 2H), 1.28 (d, 6H). | Rt = 1.14 [M + H]⁺ 393.2 | 1 |
| Ex 102 | 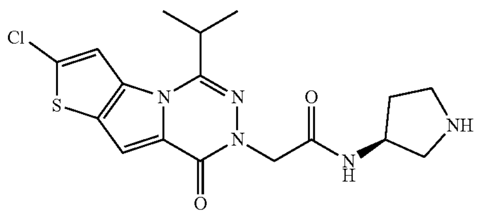 [SMILES: CC(C)c1nn(CC(=O)N[C@H]2CCNC2)c(=O)c2cc3sc(Cl)cc3n12] | (S)-2-(2-Chloro-5-isopropyl-8-oxothieno[2',3':4,5]pyrrolo[1,2-d][1,2,4]triazin-7(8H)-yl)-N-(pyrrolidin-3-yl)acetamide | (400 MHz, DMSO-d6) broad unresolved signals δ (ppm) 8.07 (s, 1H), 7.80 (s, 1H), 7.46 (s, 1H), 4.52 (s, 2H), 4.11 (s, 1H), 3.58 (d, 1H), 3.01-2.65 (m, 3H), 1.89 (s, 1H), 1.50 (s, 1H), 1.39-1.15 (m, 8H). | Rt = 0.74 [M + H]⁺ 394.1 | 1 |
| Ex 103 | 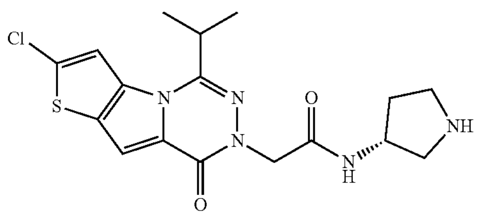 [SMILES: CC(C)c1nn(CC(=O)N[C@@H]2CCNC2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(pyrrolidin-3-yl)acetamide | (400 MHz, DMSO-d6) broad unresolved signals δ (ppm) 8.07 (s, 1H), 7.80 (s, 1H), 7.46 (s, 1H), 4.52 (s, 2H), 4.11 (s, 1H), 3.58 (d, 1H), 3.01-2.65 (m, 3H), 1.89 (s, 1H), 1.50 (s, 1H), 1.39-1.15 (m, 8H). | Rt = 0.74 [M + H]⁺ 394.1 | 1 |
| Ex 104 | 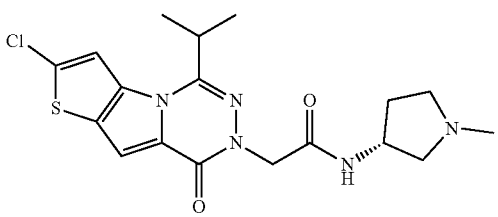 [SMILES: CC(C)c1nn(CC(=O)N[C@@H]2CCN(C)C2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(1-methylpyrrolidin-3-yl)acetamide | (400 MHz, DMSO-d6) δ (ppm) 8.2 (d, 1H), 7.79 (s, 1H), 7.45 (s, 1H), 4.58-4.45 (m, 2H), 4.26-4.13 (m, 1H), 3.65-3.54 (m, 1H), 2.62-2.51 (m, 2H), 2.37-2.27 (m, 2H), 2.22 (s, 3H), 2.14-2.03 (m, 1H), 1.62-1.51 (m, 1H), 1.28 (d, 6H). | Rt = 0.76 [M + H]⁺ 408.2 | 1 |
| Ex 105 | 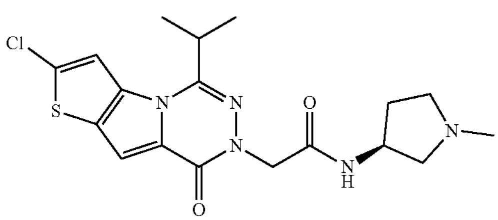 [SMILES: CC(C)c1nn(CC(=O)N[C@H]2CCN(C)C2)c(=O)c2cc3sc(Cl)cc3n12] | (S)-2-(2-Chloro-5-isopropyl-8-oxothieno[2',3':4,5]pyrrolo[1,2-d][1,2,4]triazin-7(8H)-yl)-N-(1-methylpyrrolidin-3-yl)acetamide | (400 MHz, DMSO-d6) δ (ppm) 8.2 (d, 1H), 7.79 (s, 1H), 7.45 (s, 1H), 4.58-4.45 (m, 2H), 4.26-4.13 (m, 1H), 3.65-3.54 (m, 1H), 2.62-2.51 (m, 2H), 2.37-2.27 (m, 2H), 2.22 (s, 3H), 2.14-2.03 (m, 1H), 1.62-1.51 (m, 1H), 1.28 (d, 6H). | Rt = 0.76 [M + H]⁺ 408.2 | 1 |
| Ex 106 | 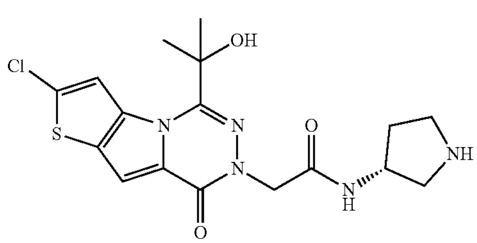 [SMILES: CC(C)(O)c1nn(CC(=O)N[C@@H]2CCNC2)c(=O)c2cc3sc(Cl)cc3n12] | (R)-2-(2-Chloro-5-(2-hydroxypropan-2-yl)-8-oxothieno[2',3':4,5]pyrrolo[1,2-d][1,2,4]triazin-7(8H)-yl)-N-(pyrrolidin-3-yl)acetamide | (400 MHz, DMSO-d6) broad unresolved signals δ (ppm) 8.12 (s, 1H), 7.91 (s, 1H), 7.53 (s, 1H), 6.08 (s, 1H), 4.52 (s, 2H), 4.1 (s, 1H), 3.74-3.47 (m, 3H), 2.98-2.63 (m, 2H), 1.9 (s, 1H), 1.67-1.44 (m, 7H). | Rt = 0.67 [M + H]⁺ 410.1 | 13 |

-continued

| Ex No. | Structure | Name | $^1$H NMR | LC/MS (min; m/z) | Int |
|---|---|---|---|---|---|
| Ex 107 | 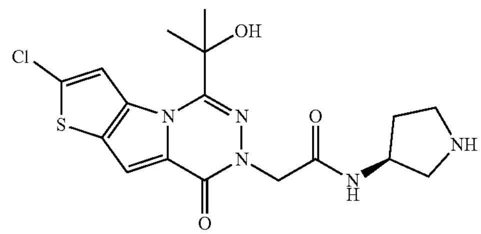 [SMILES: CC(C)(O)c1nn(CC(=O)N[C@H]2CCNC2)c(=O)c2cc3sc(Cl)cc3n12] | (S)-2-(2-Chloro-5-(2-hydroxypropan-2-yl)-8-oxothieno[2',3':4,5]pyrrolo[1,2-d][1,2,4]triazin-7(8H)-yl)-N-(pyrrolidin-3-yl)acetamide | (400 MHz, DMSO-d6) broad unresolved signals δ (ppm) 8.12 (s, 1H), 7.91 (s, 1H), 7.53 (s, 1H), 6.08 (s, 1H), 4.52 (s, 2H), 4.1 (s, 1H), 3.74-3.47 (m, 3H), 2.98-2.63 (m, 2H), 1.9 (s, 1H), 1.67-1.44 (m, 7H). | Rt = 0.67 [M + H]$^+$ 410.1 | 13 |
| Ex 108 | 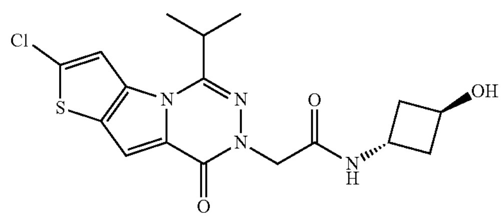 [SMILES: CC(C)c1nn(CC(=O)N[C@H]2C[C@H](O)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((1r,3r)-3-hydroxycyclobutyl)acetamide | (400 MHz, DMSO-d6) δ (ppm) 8.24 (d, 1H), 7.81 (s, 1H), 7.46 (s, 1H), 5.0 (d, 1H), 4.51 (s, 2H), 4.29-4.16 (m, 2H), 3.58 (sept, 1H), 2.16-2.06 (m, 4H), 1.28 (d, 6H). | Rt = 0.89 [M + H]$^+$ 395.0 | 1 |
| Ex 109 | 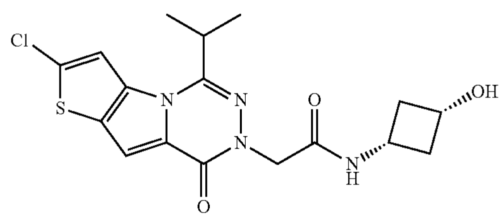 [SMILES: CC(C)c1nn(CC(=O)N[C@H]2C[C@@H](O)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((1s,3s)-3-hydroxycyclobutyl)acetamide | (400 MHz, DMSO-d6) δ (ppm) 8.16 (d, 1H), 7.81 (s, 1H), 7.46 (s, 1H), 5.07 (br s, 1H), 4.49 (s, 2H), 3.83-3.75 (m, 1H), 3.74-3.66 (m, 1H), 3.63-3.53 (m, 1H), 2.46 (m, 2H overlapping with DMSO signal), 1.80-1.69 (m, 2H), 1.29 (d, 6H). | Rt = 0.89 [M + H]$^+$ 395.1 | 1 |
| Ex 110 | 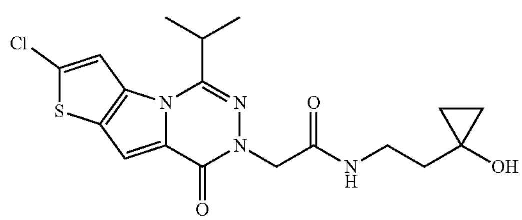 [SMILES: CC(C)c1nn(CC(=O)NCCC2(O)CC2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(2-(1-hydroxycyclopropyl)ethyl)acetamide | (400 MHz, DMSO-d6) broad signals δ 7.93 (s, 1H), 7.81 (s, 1H), 7.46 (s, 1H), 5.06 (s, 1H), 4.51 (s, 2H), 3.65-3.52 (m, 1H), 3.26 (m, 2H, overlapping with water signal), 1.64-1.50 (m, 2H), 1.29 (d, 6H), 0.59-0.45 (m, 2H), 0.40-0.25 (m, 2H). | Rt = 0.98 [M + H]$^+$ 409.1 | 1 |
| Ex 111 | 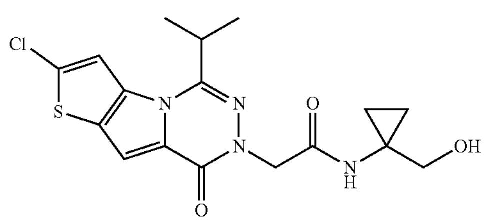 [SMILES: CC(C)c1nn(CC(=O)NC2(CO)CC2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(1-(hydroxymethyl)cyclopropyl)acetamide | (400 MHz, DMSO-d6) δ 8.30 (s, 1H), 7.80 (s, 1H), 7.46 (s, 1H), 4.66 (t, 1H), 4.48 (s, 2H), 3.58 (sept, 1H), 3.41 (d, 2H), 1.28 (d, 6H), 0.73-0.64 (m, 2H), 0.58-0.48 (m, 2H). | Rt = 0.91 [M + H]$^+$ 395.1 | 1 |
| Ex 112 | 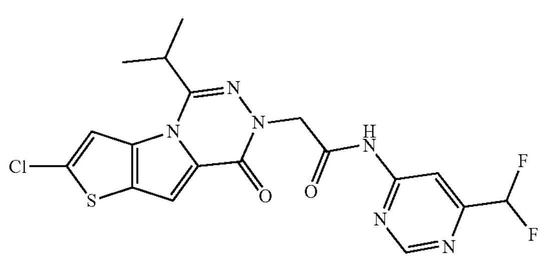 [SMILES: CC(C)c1nn(CC(=O)Nc2cc(C(F)F)ncn2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(6-(difluoromethyl)pyrimidin-4-yl)acetamide | (400 MHz, CDCl$_3$) δ 9.16 (br s, 1H), 8.90 (d, 1H), 8.44 (d, 1H), 7.48 (d, 1H), 7.21 (d, 1H), 6.51 (t, 1H), 4.94 (s, 2H), 3.40 (sept, 1H), 1.45 (d, 6H). | Rt = 1.14 [M + H]$^+$ 453.0 | 1 |

-continued

| Ex No. | Structure | Name | ¹H NMR | LC/MS (min; m/z) | Int |
|---|---|---|---|---|---|
| Ex 113 | 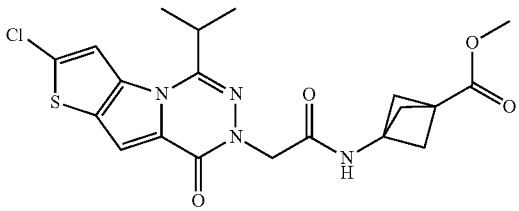 [SMILES: COC(=O)C12CC(NC(=O)Cn3nc(C(C)C)n4c(cc5sc(Cl)cc54)c3=O)(C1)C2] | Methyl 3-(2-(2-chloro-5-isopropyl-8-oxothieno[2',3':4,5]pyrrolo[1,2-d][1,2,4]triazin-7(8H)-yl)acetamido)bicyclo[1.1.1]pentane-1-carboxylate | (400 MHz, DMSO-d6) δ 8.70 (s, 1H), 7.81 (s, 1H), 7.46 (s, 1H), 4.48 (s, 2H), 3.64-3.53 (m, 1H) overlapping with 3.60 (s, 3H), 2.23 (s, 6H), 1.29 (d, 6H). | Rt = 1.08 [M + H]⁺ 449.1 | 1 |
| Ex 114 | 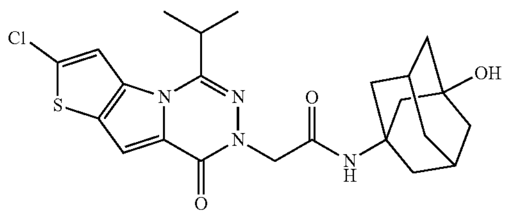 [SMILES: CC(C)c1nn(CC(=O)NC23CC4CC(CC(O)(C4)C2)C3)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((1S,3R,5S)-3-hydroxyadamantan-1-yl)acetamide | (400 MHz, DMSO-d6) δ (ppm): 7.80 (s, 1H), 7.63 (s, 1H), 7.45 (s, 1H), 4.49-4.46 (m, 3H), 3.59 (sept, 1H), 2.12 (b s, 2H), 1.87-1.74 (m, 6H), 1.55-1.47 (m, 4H), 1.46-1.39 (m, 2H), 1.28 (d, 6H). | Rt = 1.07; [M + H]⁺ 475.1 | 1 |
| Ex 115 | 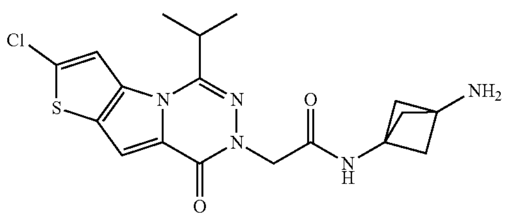 [SMILES: CC(C)c1nn(CC(=O)NC23CC(N)(C2)C3)c(=O)c2cc3sc(Cl)cc3n12] | N-(3-Aminobicyclo[1.1.1]pentan-1-yl)-2-(2-chloro-5-isopropyl-8-oxothieno[2',3':4,5]pyrrolo[1,2-d][1,2,4]triazin-7(8H)-yl)acetamide | (400 MHz, DMSO-d6) HCl-salt δ (ppm): 8.79 (s, 1H), 8.74 (br s, 3H), 7.81 (s, 1H), 7.47 (s, 1H), 4.51 (s, 2H), 3.65-3.53 (m, 1H), 2.21 (s, 6H), 1.28 (d, 6H). | Rt = 0.76; [M + H]⁺ 406.1 | 1 |
| Ex 116 | 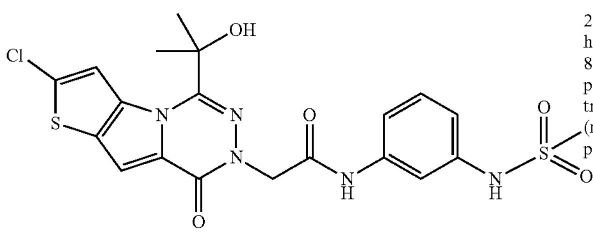 [SMILES: CC(C)(O)c1nn(CC(=O)Nc2cccc(NS(C)(=O)=O)c2)c(=O)c2cc3sc(Cl)cc3n12] | 2-(2-Chloro-5-(2-hydroxypropan-2-yl)-8-oxothieno[2',3':4,5]pyrrolo[1,2-d][1,2,4]triazin-7(8H)-yl)-N-(3-(methylsulfonamido)phenyl)acetamide | (400 MHz, DMSO-d6) δ (ppm): 10.29 (s, 1H), 9.77 (s, 1H), 7.93 (s, 1H), 7.56 (s, 1H), 7.52 (t, 1H), 7.33 (dt, 1H), 7.24 (t, 1H), 6.93-6.82 (m, 1H), 6.11 (s, 1H), 4.78 (s, 2H), 2.96 (s, 3H), 1.60 (s, 6H). | Rt = 0.97; [M + H]⁺ 508.1 | 13 |
| Ex 117 | 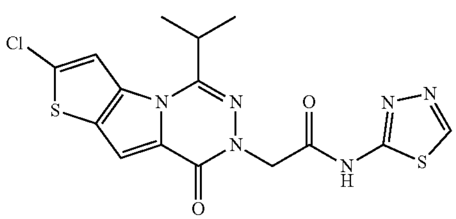 [SMILES: CC(C)c1nn(CC(=O)Nc2nncs2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-(1,3,4-thiadiazol-2-yl)acetamide | (400 MHz, CDCl₃) δ (ppm): 8.82 (s, 1H), 7.46 (s, 1H), 7.21 (s, 1H), 5.12 (s, 2H), 3.40 (sept, 1H), 1.44 (d, 6H). NH not observed. | Rt = 0.99; [M + H]⁺ 409.1 | 1 |
| Ex 118 | 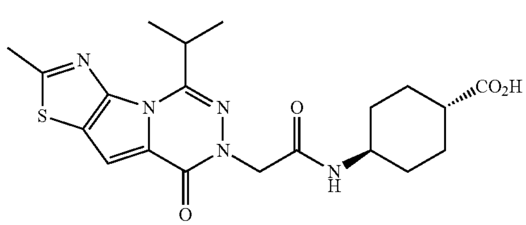 [SMILES: Cc1nc2c(cc3c(=O)n(CC(=O)N[C@H]4CC[C@H](C(=O)O)CC4)nc(C(C)C)n32)s1] | (1r,4r)-4-(2-(5-Isopropyl-2-methyl-8-oxothiazolo[5',4':4,5]pyrrolo[1,2-d][1,2,4]triazin-7(8H)-yl)acetamido)cyclohexane-1-carboxylic acid | (400 MHz, DMSO-d6) δ 12.05 (br s, 1H), 7.90 (d, 1H), 7.42 (s, 1H), 4.52 (s, 2H), 4.14 (sept, 1H), 3.57-3.48 (m, 1H), 2.85 (s, 3H), 2.18-2.07 (m, 1H), 1.93-1.74 (m, 4H), 1.38-1.15 (m, 4H) overlapping with 1.31 (d, 6H). | Rt = 0.91; [M + H]⁺ 432.3 | 43 |
| Ex 119 | 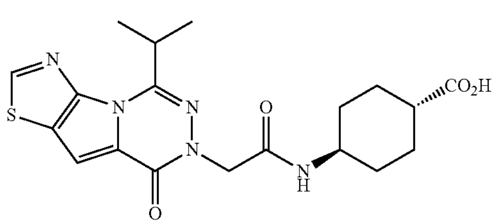 [SMILES: CC(C)c1nn(CC(=O)N[C@H]2CC[C@H](C(=O)O)CC2)c(=O)c2cc3scnc3n12] | (1r,4r)-4-(2-(5-Isopropyl-8-oxothiazolo[5',4':4,5]pyrrolo[1,2-d][1,2,4]triazin-7(8H)-yl)acetamido)cyclohexane-1-carboxylic acid | (400 MHz, DMSO-d6) δ 12.0 (br s, 1H), 9.30 (s, 1H), 7.89 (d, 1H), 7.50 (d, 1H), 4.53 (s, 2H), 4.17 (sept, 1H), 3.61-3.49 (m, 1H) overlapping with water signal, 2.19-2.06 (m, 1H), 1.97-1.73 (m, 4H), 1.39-1.12 (m, 4H) overlapping with 1.33 (d, 6H). | Rt = 0.82; [M + H]⁺ 418.3 | 40 |

| Ex No. | Structure | Name | ¹H NMR | LC/MS (min; m/z) | Int |
|---|---|---|---|---|---|
| Ex 120 | 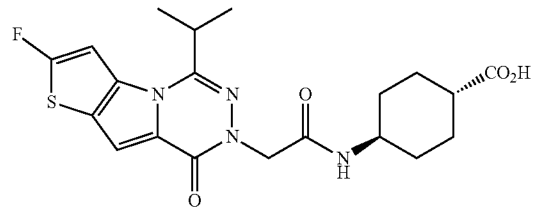 [SMILES: CC(C)c1nn(CC(=O)N[C@H]2CC[C@H](C(=O)O)CC2)c(=O)c2cc3sc(F)cc3n12] | (1r,4r)-4-(2-(2-Fluoro-5-isopropyl-8-oxothieno[2',3':4,5]pyrrolo[1,2-d][1,2,4]triazin-7(8H)-yl)acetamido)cyclohexane-1-carboxylic acid | (400 MHz, DMSO-d6) δ 12.04 (br s, 1H), 7.88 (brd, 1H), 7.55 (s, 1H), 7.46 (s, 1H), 4.50 (s, 2H), 3.58-3.49 (m, 2H, overlapping with water signal), 2.19-2.07 (m, 1H), 1.96-1.72 (m, 4H), 1.41-1.15 (m, 10H). | Rt = 0.91; [M + H]⁺ 435.3 | 24 |
| Ex 121 | 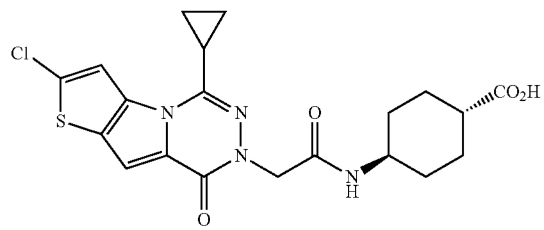 [SMILES: O=C(Cn1nc(C2CC2)n2c(cc3sc(Cl)cc32)c1=O)N[C@H]1CC[C@H](C(=O)O)CC1] | (1r,4r)-4-(2-(2-Chloro-5-cyclopropyl-8-oxothieno[2',3':4,5]pyrrolo[1,2-d][1,2,4]triazin-7(8H)-yl)acetamido)cyclohexane-1-carboxylic acid | (400 MHz, DMSO-d6) δ 8.19-7.75 (m, 2H), 7.44 (br s, 1H), 4.47 (br s, 2H), 3.5 (m, 1H, overlapping with water signal), 2.20-2.05 (m, 1H), 1.98-1.69 (m, 4H), 1.41-0.79 (m, 9H). COOH not observed. | Rt = 0.93; [M + H]+ 449.2 | 6 |
| Ex 122 | 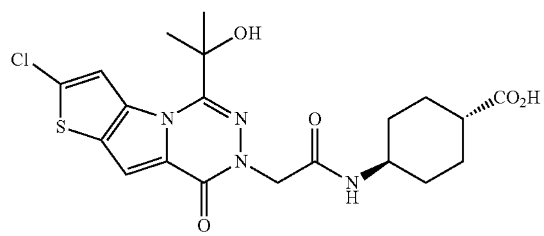 [SMILES: CC(C)(O)c1nn(CC(=O)N[C@H]2CC[C@H](C(=O)O)CC2)c(=O)c2cc3sc(Cl)cc3n12] | (1r,4r)-4-(2-(2-Chloro-5-(2-hydroxypropan-2-yl)-8-oxothieno[2',3':4,5]pyrrolo[1,2-d][1,2,4]triazin-7(8H)-yl)acetamido)cyclohexane-1-carboxylic acid | (400 MHz, DMSO-d6) δ 8.05-7.85 (m, 2H), 7.53 (br s, 1H), 6.08 (br s, 1H), 4.51 (br s, 2H), 3.18 (m, 1H, overlapping with water signal), 2.18-2.01 (m, 1H), 1.99-1.71 (m, 4H), 1.58 (s, 6H), 1.43-1.10 (m, 4H). COOH not observed. | Rt = 0.89; [M + H]⁺ 467.2 | 13 |
| Ex 123 | 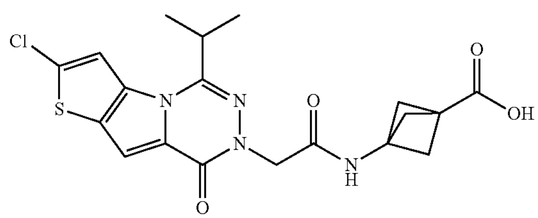 [SMILES: CC(C)c1nn(CC(=O)NC23CC(C(=O)O)(C2)C3)c(=O)c2cc3sc(Cl)cc3n12] | 3-(2-(2-Chloro-5-isopropyl-8-oxothieno[2',3':4,5]pyrrolo[1,2-d][1,2,4]triazin-7(8H)-yl)acetamido)bicyclo[1.1.1]pentane-1-carboxylic acid | (400 MHz, DMSO-d6) δ (ppm): 12.42 (br s, 1H), 8.66 (s, 1H), 7.81 (s, 1H), 7.46 (s, 1H), 4.48 (s, 2H), 3.59 (sept, 1H), 2.18 (s, 6H), 1.29 (d, 6H) | Rt = 0.94; [M + H]⁺ 435.2 | 1 |

Synthesis of Amine Building Blocks for the Above Examples (1R,3R)-3-Amino-1-methylcyclohexan-1-ol, Int 50

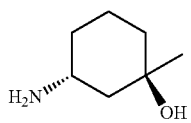

(1) Benzyl (R)-(3-oxocyclohexyl)carbamate, Int 51

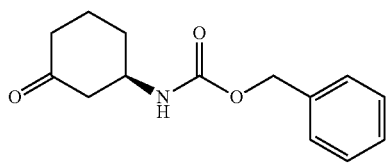 [SMILES: O=C1CCC[C@@H](NC(=O)OCc2ccccc2)C1]

Oxalyl chloride (0.386 mL, 4.41 mmol) was dissolved in DCM (15 mL) and cooled to −78° C. A solution of DMSO (0.626 mL, 8.82 mmol) in DCM (2 mL) was added dropwise at −78° C. and the mixture was stirred for 15 minutes. Then, benzyl ((1R,3S)-3-hydroxycyclohexyl)carbamate (1 g, 4.01 mmol) in DCM (10 mL) was added dropwise Stirring continued for 15 minutes, followed by addition of triethylamine (2.80 mL, 20.06 mmol). The mixture was stirred for 1 hour at −78° C., then at RT over the weekend. The reaction mixture was diluted with DCM and washed 3 times with brine. The organic layer was dried over $Na_2SO_4$, filtered and evaporated to give a colorless oil. The residue was purified by column chromatography on silica gel using cyclohexane and EtOAc (from 0% to 70%) provided the title compound as a colorless solid ¹H NMR (400 MHz, $CDCl_3$) δ (ppm) 7.45-7.32 (m, 5H), 5.12 (s, 2H), 4.76 (s, 1H), 4.02 (s, 1H), 2.74 (dd, 1H), 2.46-2.23 (m, 3H), 2.19-1.94 (m, 2H), 1.83-1.63 (m, 2H). LC-MS: Rt=0.85 min; MS m/z [M+H]⁺ 248.3

(2) Benzyl ((1R,3S)-3-hydroxy-3-methylcyclohexyl)carbamate, Int 52

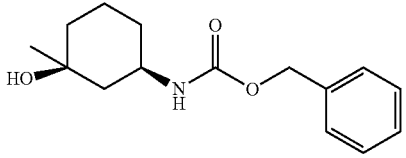 [SMILES: C[C@]1(O)CCC[C@@H](NC(=O)OCc2ccccc2)C1]

A solution of Int 51 (790 mg, 3.19 mmol) in THF (20 mL) was cooled to −78° C. Then, a solution of CH₃Li—LiBr complex (2.2M in Et₂O, 4.36 mL, 9.58 mmol) was added dropwise at this temperature. Stirring was continued for 3.5 hours before the reaction mixture was quenched with 10% NH₄Cl and allowed to reach RT. The mixture was partitioned between EtOAc and water. The organic layer was separated, dried over Na₂SO₄, filtered and evaporated. The crude was purified by column chromatography on silica gel using cyclohexane and EtOAc (from 0% to 60%) to provide the title compound as a colorless solid. ¹H NMR (400 MHz, DMSO-d6) δ (ppm) 7.47-7.23 (m, 5H), 7.04 (d, 1H), 5.05-4.93 (m, 2H), 4.06 (s, 1H), 3.69-3.57 (m, 1H), 1.79-1.53 (m, 3H), 1.49-1.41 (m, 2H), 1.15-1.05 (m, 5H), 1.05-0.91 (m, 1H). LC-MS: Rt=0.90 min; MS m/z [M+H]⁺ 264.3

(3) (1R,3R)-3-Amino-1-methylcyclohexan-1-ol, Int 50

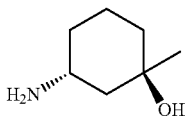

To a solution of Int 52 (550 mg, 2.089 mmol) in MeOH (50 mL) was added HCl (1.25M in MeOH, 1.671 mL, 2.089 mmol). The flask was purged with argon, then Pd/C (222 mg, 2.089 mmol) was added and the suspension was hydrogenated under atmospheric pressure for 1.5 hours. The reaction mixture was filtered through a pad of Hyflo, washed with more MeOH and evaporated to give the title compound as hydrochloride salt. ¹H NMR (400 MHz, DMSO-d6) δ (ppm) 3.85 (s, 3H), 3.18 (s, 1H), 2.99-2.86 (m, 1H), 1.83-1.37 (m, 5H), 1.17-0.86 (m, 6H). MS m/z [M+H]⁺ 130.2

(R)-1-(2-Fluoroethyl)piperidin-3-amine, Int 53

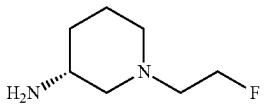

(1) Tert-Butyl (R)-(1-(2-fluoroethyl)piperidin-3-yl)carbamate, Int 54

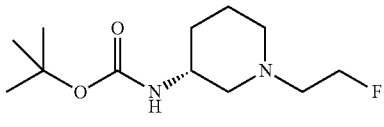 [SMILES: CC(C)(C)OC(=O)N[C@@H]1CCCN(CCF)C1]

A suspension of (R)-tert-butyl piperidin-3-ylcarbamate (500 mg, 2.497 mmol), 1-bromo-2-fluoroethane (0.200 mL, 2.497 mmol), TBAB (161 mg, 0.499 mmol) and K₂CO₃ (1725 mg, 12.48 mmol) in acetone (20 mL) was stirred at RT for 16 hours. The reaction mixture was evaporated and extracted with water and EtOAc. The organic layer was washed with brine, dried over Na₂SO₄, filtered and evaporated. The residue was purified by column chromatography on silica gel using cyclohexane and EtOAc (from 0% to 100%) to provide the title compound as colorless solid. ¹H NMR (400 MHz, DMSO-d6) δ (ppm) 6.65 (d, 1H), 4.56 (t, 1H), 4.44 (t, 1H), 3.41-3.33 (m, 1H), 2.88-2.76 (m, 1H), 2.75-2.67 (m, 1H), 2.63 (t, 1H), 2.56 (t, 1H), 1.99-1.90 (m, 1H), 1.87-1.77 (m, 1H), 1.72-1.57 (m, 2H), 1.44-1.36 (m, 10H), 1.19-1.07 (m, 1H). LC-MS: Rt=0.47 min; MS m/z [M+H]⁺ 247.3

(2) (R)-1-(2-Fluoroethyl)piperidin-3-amine, Int 53

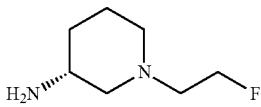

A solution of Int 54 (152 mg, 0.617 mmol) in DCM (5 mL) was treated with HCl (4M in dioxane, 1.543 mL, 6.17 mmol) and stirred at RT for 5 hours.
The reaction mixture was evaporated to give the title compound as crude hydrochloride salt. MS m/z [M+H]⁺ 147.1

(R)-1-(2-(Trifluoromethoxy)ethyl)piperidin-3-amine, Int 55

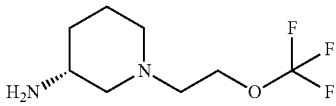 [SMILES: N[C@@H]1CCCN(CCOC(F)(F)F)C1]

(1) Tert-Butyl (R)-(1-(2-(trifluoromethoxy)ethyl)piperidin-3-yl)carbamate, Int 56

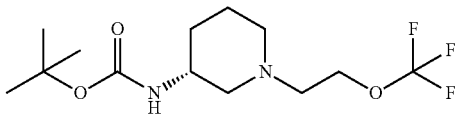 [SMILES: CC(C)(C)OC(=O)N[C@@H]1CCCN(CCOC(F)(F)F)C1]

A suspension of 1-bromo-2-(trifluoromethoxy)ethane (347 mg, 1.798 mmol) in EtOAc (1.5 mL) and water (1.5 mL) containing NaHCO$_3$ (629 mg, 7.49 mmol) was heated to 50° C. A solution of (R)-tert-butyl piperidin-3-ylcarbamate (300 mg, 1.498 mmol) in EtOAc (7 mL) was added dropwise over a period of 30 minutes. The suspension was stirred overnight. The reaction mixture was partitioned between water and EtOAc. The aqueous layer was extracted once more with EtOAc. The combined organic extracts were washed with brine, dried over Na$_2$SO$_4$, filtered and evaporated. The residue was purified by column chromatography on silica gel using cyclohexane and EtOAc (from 0% to 50%) to give the title compounds as a colorless oil. $^1$H NMR (400 MHz, DMSO-d6) δ (ppm) 6.66 (d, 1H), 4.17-4.05 (m, 2H), 2.82-2.57 (m, 4H), 2.00-1.90 (m, 1H), 1.89-1.77 (m, 1H), 1.73-1.56 (m, 2H), 1.47-1.39 (m, 1H), 1.37 (s, 9H), 1.19-1.04 (m, 1H). Piperidine-CH proton not observed.

(2) (R)-1-(2-(Trifluoromethoxy)ethyl)piperidin-3-amine, Int 55

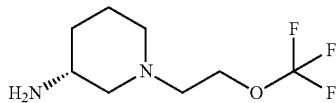

A solution of Int 56 (131 mg, 0.419 mmol) in DCM (5 mL) was treated with HCl (4M in dioxane, 1.049 mL, 4.19 mmol) and stirred at RT for 4 days. The suspension was evaporated to provide the title compound as hydrochloride salt. $^1$H NMR (400 MHz, DMSO-d6 plus D2O) broad unresolved signals δ (ppm) 4.42 (s, 2H), 3.69-3.32 (m, 5H), 3.12-2.83 (m, 2H), 2.13-1.85 (m, 2H), 1.86-1.42 (m, 2H). MS m/z [M+H]$^+$ 213.1

Example 124

(R)-2-(2-Chloro-5-isopropyl-8-oxothieno[2',3':4,5]pyrrolo[1,2-d][1,2,4]triazin-7(8H)-yl)-N-(1-cyclopropylpiperidin-3-yl)acetamide

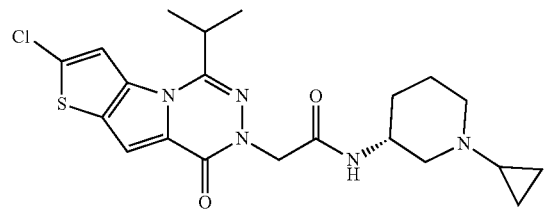 [SMILES: CC(C)c1nn(CC(=O)N[C@@H]2CCCN(C3CC3)C2)c(=O)c2cc3sc(Cl)cc3n12]

To a solution of Ex 10 (55 mg, 0.135 mmol) in MeOH (2.5 mL) was added AcOH (6 μL, 0.105 mmol) and (1-ethoxycyclopropoxy)trimethylsilane (149 μL, 0.742 mmol) followed by NaCNBH$_3$ (33.9 mg, 0.539 mmol). The solution was stirred at 45° C. overnight. The reaction mixture was diluted with DCM and washed with 10% NaHCO$_3$ solution. The organic extract was dried over Na$_2$SO$_4$, filtered and evaporated. The residue was purified via preparative RP chromatography to provide the title compound as TFA salt. The free base was obtained by partitioning between 10% Na$_2$CO$_3$ and DCM. The organic layer was dried and evaporated to give the title compound as a yellow solid. $^1$H NMR (400 MHz, DMSO-d6) δ (ppm) 7.86-7.78 (m, 2H), 7.47 (s, 1H), 4.53 (s, 2H), 3.70-3.52 (m, 2H), 2.88-2.80 (m, 1H), 2.75-2.64 (m, 1H), 2.21-2.11 (m, 1H), 2.08-1.98 (m, 1H), 1.70-1.52 (m, 3H), 1.47-1.32 (m, 1H), 1.29 (d, 6H), 1.26-1.17 (m, 1H), 0.44-0.32 (m, 2H), 0.29-0.19 (m, 2H). LC-MS: Rt=0.8 min; MS m/z [M+H]$^+$ 448.2

The following examples were synthesized analogous to the above reductive amination procedure using the previously described piperidine derivatives (Example 10, Example 79 or Example 88) and the appropriate ketones:

| Ex No. | Structure | Name | $^1$H NMR | LC/MS (min; m/z) |
|---|---|---|---|---|
| Ex 125 | 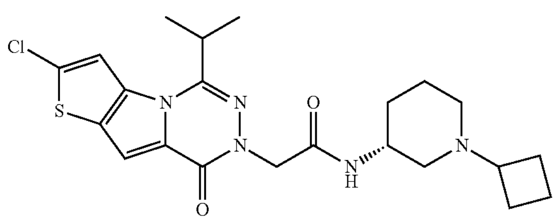 [SMILES: CC(C)c1nn(CC(=O)N[C@@H]2CCCN(C3CCC3)C2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(1-cyclobutylpiperidin-3-yl)acetamide | (400 MHZ, CDCl$_3$) δ (ppm) 7.36 (s, 1H), 7.13 (s, 1H), 6.52 (s, 1H), 4.77-4.57 (m, 2H), 4.04-3.94 (m, 1H), 3.36-3.23 (m, 1H), 2.57-2.46 (m, 1H), 2.40-1.99 (m, 3H), 1.91-1.74 (m, 3H), 1.62-1.31 (m, 14H). | Rt = 0.83 [M + H]$^+$ 462.2 |
| Ex 126 | 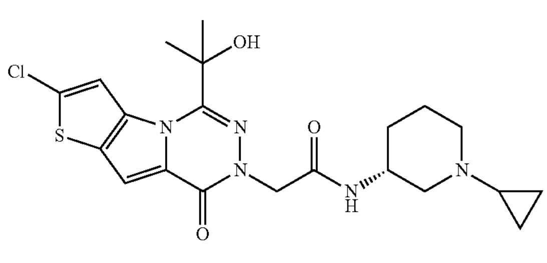 [SMILES: CC(C)(O)c1nn(CC(=O)N[C@@H]2CCCN(C3CC3)C2)c(=O)c2cc3sc(Cl)cc3n12] | (R)-2-(2-Chloro-5-(2-hydroxypropan-2-yl)-8-oxothieno[2', 3':4,5]pyrrolo[1,2-d][1,2,4]triazin-7(8H)-yl)-N-(1-cyclopropylpiperidin-3-yl)acetamide | (400 MHZ, DMSO-d6) δ (ppm) 7.95-7.87 (m, 2H), 7.53 (s, 1H), 6.08 (s, 1H), 4.53 (s, 2H), 3.72-3.61 (m, 1H), 3.19-3.14 (m, 1H), 2.89-2.82 (m, 1H), 2.75-2.66 (m, 1H), 2.21-2.10 (m, 1H), 2.10-1.98 (m, 1H), 1.72-1.61 (m, 2H), 1.58 (s, 6H), 1.45-1.32 (m, 1H), 1.28-1.15 (m, 1H), 0.42-0.34 (m, 2H), 0.30-0.20 (m, 2H). | Rt = 0.74 [M + H]$^+$ 464.1 |

| Ex No. | Structure | Name | ¹H NMR | LC/MS (min; m/z) |
|---|---|---|---|---|
| Ex 127 | 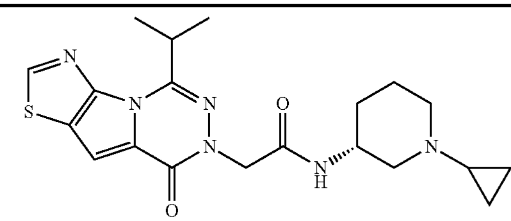 | (R)-N-(1-Cyclopropylpiperidin-3-yl)-2-(5-isopropyl-8-oxothiazolo[5',4':4,5]pyrrolo[1,2-d][1,2,4]triazin-7(8H)-yl)acetamide | (400 MHZ, DMSO-d6) broad unresolved signals δ (ppm) 9.31 (s, 1H), 7.82 (d, 1H), 7.51 (s, 1H), 4.55 (s, 2H), 4.26-4.10 (m, 1H), 3.66 (s, 1H), 2.92-2.77 (m, 1H), 2.77-2.62 (m, 1H), 2.25-1.96 (m, 2H), 1.78-1.51 (m, 3H), 1.46-1.13 (m, 8H), 0.47-0.14 (m, 4H). | Rt = 0.66 [M + H]⁺ 415.2 |

Example 128

2-(2-Chloro-5-isopropyl-8-oxothieno[2',3':4,5]pyrrolo[1,2-d][1,2,4]triazin-7(8H)-yl)-N—((R)-1-((R)-2-hydroxypropyl)piperidin-3-yl)acetamide

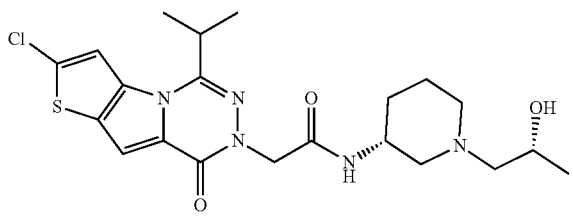 [SMILES: CC(C)c1nn(CC(=O)N[C@@H]2CCCN(C[C@@H](C)O)C2)c(=O)c2cc3sc(Cl)cc3n12]

A solution of Example 10 (50 mg, 0.123 mmol) and (R)-2-methyloxirane (0.058 mL, 0.981 mmol) in a mixture of OCM (2 ml-) and MeOH (2 ml-) was stirred at 55° C. over the weekend. The mixture was diluted with EtOAc and washed with water. The organic layer was dried over Na₂SO₄, filtered and evaporated to give the title compound as a white solid ¹H NMR (400 MHz, DMSO-d6) δ (ppm) 7.88 (d, 1H), 7.80 (s, 1H), 7.47 (s, 1H), 4.60-4.48 (m, 2H), 4.26 (d, 1H), 3.81-3.66 (m, 2H), 3.6 (sept, 1H), 2.70-2.62 (m, 1H), 2.61-2.53 (m, 1H), 2.24-1.94 (m, 4H), 1.68-1.58 (m, 2H), 1.50-1.38 (m, 1H), 1.29 (d, 6H), 1.26-1.19 (m, 1H), 0.98 (d, 3H). LC-MS: Rt=0.76 min; MS m/z [M+H]⁺ 466.2

The following examples were synthesized analogous to the procedure of Example 128 using the previously described piperidine derivative (Example 10) and the appropriate oxiranes:

| Ex No. | Structure | Name | ¹H NMR | LC/MS (min; m/z) |
|---|---|---|---|---|
| Ex 129 | 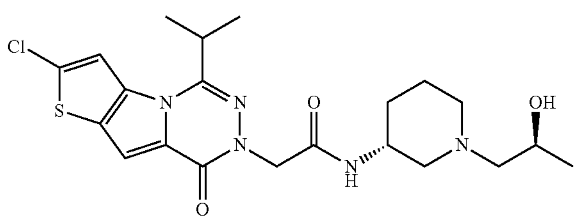 [SMILES: CC(C)c1nn(CC(=O)N[C@@H]2CCCN(C[C@H](C)O)C2)c(=O)c2cc3sc(Cl)cc3n12] | 2-(2-Chloro-5-isopropyl-8-oxothieno[2',3':4,5]pyrrolo[1,2-d][1,2,4]triazin-7(8H)-yl)-N-((R)-1-((S)-2-hydroxypropyl)piperidin-3-yl)acetamide | (400 MHZ, DMSO-d6) δ (ppm) 7.88 (d, 1H), 7.80 (s, 1H), 7.47 (s, 1H), 4.60-4.48 (m, 2H), 4.26 (d, 1H), 3.81-3.66 (m, 2H), 3.6 (sept, 1H), 2.70-2.62 (m, 1H), 2.61-2.53 (m, 1H), 2.24-1.94 (m, 4H), 1.68-1.58 (m, 2H), 1.50-1.38 (m, 1H), 1.29 (d, 6H), 1.26-1.19 (m, 1H), 0.98 (d, 3H). | Rt = 0.76 [M + H]⁺ 466.2 |
| Ex 130 | 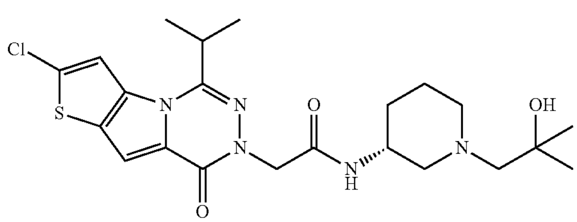 [SMILES: CC(C)c1nn(CC(=O)N[C@@H]2CCCN(CC(C)(C)O)C2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(1-(2-hydroxy-2-methylpropyl)piperidin-3-yl)acetamide | (400 MHZ, CDCl₃) δ (ppm) 7.49 (s, 1H), 7.35 (br s, 1H), 7.23 (s, 1H), 4.75 (s, 2H), 4.10-4.02 (m, 1H), 3.41 (sept, 1H), 2.77-2.51 (m, 3H), 2.41-2.29 (m, 1H), 2.24 (s, 2H), 1.76-1.58 (m, 3H), 1.56-1.47 (m, 2H), 1.46 (d, 3H), 1.44 (d, 3H), 1.10 (s, 3H), 1.00 (s, 3H). | Rt = 0.79 [M + H]⁺ 480.2 |
| Ex 131 | 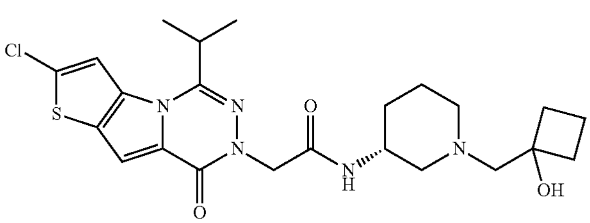 [SMILES: CC(C)c1nn(CC(=O)N[C@@H]2CCCN(CC3(O)CCC3)C2)c(=O)c2cc3sc(Cl)cc3n12] | (R)-2-(2-Chloro-5-isopropyl-8-oxothieno[2',3':4,5]pyrrolo[1,2-d][1,2,4]triazin-7(8H)-yl)-N-(1-((1-hydroxycyclobutyl)methyl)piperidin-3-yl)acetamide | (400 MHZ, CDCl₃) δ (ppm) 7.50 (s, 1H), 7.23 (s, 1H), 7.02 (br s, 1H), 4.79-4.69 (m, 2H), 4.11-4.02 (m, 1H), 3.41 (sept, 1H), 2.65-2.41 (m, 5H), 2.39-2.29 (m, 1H), 2.13-1.90 (m, 4H), 1.83-1.49 (m, 7H), 1.45 (d, 6H). | Rt = 0.81 [M + H]⁺ 492.2 |

Example 132

(R)-2-(2-Chloro-5-(2-hydroxypropan-2-yl)-8-oxothieno[2',3':4,5]pyrrolo[1,2-d][1,2,4]triazin-7(8H)-yl)-N-(1-ethylpiperidin-3-yl)acetamide

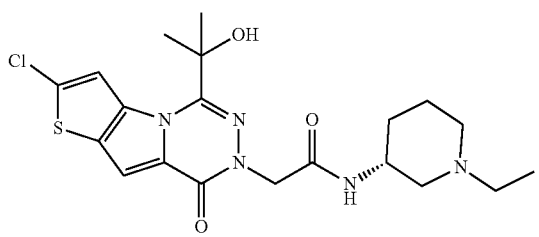 [SMILES: CCN1CCC[C@@H](NC(=O)Cn2nc(C(C)(C)O)n3c(cc4sc(Cl)cc43)c2=O)C1]

A mixture of Example 79 (35 mg, 0.083 mmol), Na$_2$CO$_3$ (26.3 mg, 0.248 mmol) and bromoethane (8.01 μL, 0.107 mmol) in acetonitrile (3 ml-) was stirred at 60° C. overnight. More bromoethane (20 μL) was added and the reaction mixture was stirred for another 6 hours. It was partitioned between EtOAc and 10% NaHCO$_3$ solution. The organic layer was dried over Na$_2$SO$_4$, filtered and evaporated. The crude was purified by column chromatography on silica gel using DCM and MeOH (from 0% to 25%) to provide the title compound. $^1$H NMR (400 MHz, DMSO-d6) broad, unresolved signals δ (ppm) 8.02-7.85 (m, 2H), 7.53 (s, 1H), 6.08 (s, 7H), 4.64-4.40 (s, 2H), 3.80-3.65 (m, 1H), 2.81-2.58 (m, 2H), 2.39-2.23 (m, 2H), 2.01-1.76 (m, 2H), 1.73-1.39 (m, 8H), 1.31-1.17 (m, 2H), 1.03-0.89 (m, 3H). LC-MS: Rt=0.72 min; MS m-z [M+H]$^+$ 452.3

The following examples were synthesized analogous to the procedure of Example 132 using the previously described piperidine derivative (Example 10) and the appropriate alkyl bromides:

Biological Assays and Data

The activity of a compound according to the present invention can be assessed by the following in vitro methods. A compound of formula (I), or a pharmaceutically acceptable salt thereof, exhibits valuable pharmacological properties, e.g. properties susceptible to inhibit NLRP3 activity, e.g. as indicated in tests as provided in the next sections, and are therefore indicated for therapy related to NLRP3 inflammasome activity.

IL-1β Secretion Assay:

Monocytic THP-1 cells (ATCC: TIB-202) were maintained according to providers' instructions in RPMI media (RPMI/Hepes+10% fetal bovine serum+Sodium Pyruvate+ 0.05 mM Beta-mercaptoethanol (1000× stock)+Pen-Strep). Cells were differentiated in bulk with 0.5 μM phorbol 12-myristate 13-acetate (PMA; Sigma #P8139) for 3 hours, media was exchanged, and cells were plated at 50,000 cells per well in a 384-well flat-bottom cell culture plates (Greiner, #781986), and allowed to differentiate overnight. Compound in a 1:3.16 serial dilution series in DMSO was added 1:100 to the cells and incubated for 1 hour. The NLRP3 inflammasome was activated with the addition of 15 μM (final concentration) Nigericin (Enzo Life Sciences, #BML-CA421-0005), and cells were incubated for 3 hours. 10 μL supernatant was removed, and IL-1p levels were monitored using an HTRF assay (CisBio, #62IL1PEC) according to manufacturers' instructions. Viability and pyroptosis was monitored with the addition of PrestoBlue cell viability reagent (Life Technologies, #A13261) directly to the cell culture plate.

TNF-α Secretion Assay:

Monocytic THP-1 cells were maintained according to providers' instructions in RPMI media as described above. Undifferentiated cells were plated at 50,000 cells per well in a 384-well flat-bottom cell culture plates (Greiner, #781986), and allowed to rest overnight. Experimental compounds were prepared and added as described above. TNF-α

| Ex No. | Structure | Name | $^1$H NMR | LC/MS (min; m/z) |
|---|---|---|---|---|
| Ex 133 | 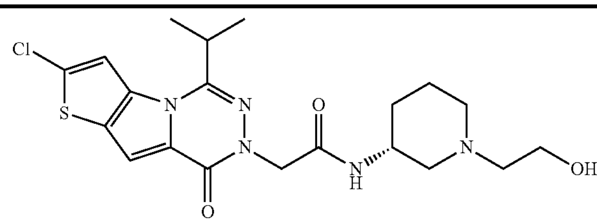 | (R)-2-(2-Chloro-5-isopropyl-8-oxothieno[2',3':4,5]pyrrolo[1,2-d][1,2,4]triazin-7(8H)-yl)-N-(1-(2-hydroxyethyl)piperidin-3-yl)acetamide | (400 MHZ, DMSO-d6) δ (ppm) 7.88 (d, 1H), 7.80 (s, 1H), 7.46 (s, 1H), 4.59-4.50 (m, 2H), 4.37-4.30 (m, 1H), 3.79-3.67 (m, 1H), 3.59 (sept, 1H), 3.50-3.42 (m, 2H), 2.76-2.69 (m, 1H), 2.63-2.57 (m, 1H), 2.39-2.31 (m, 2H), 2.08-1.98 (m, 1H), 1.96-1.88 (m, 1H), 1.71-1.58 (m, 2H), 1.51-1.39 (m, 1H), 1.29 (d, 6H), 1.25-1.15 (m, 1H). | Rt = 0.74 [M + H]$^+$ 452.1 |
| Ex 134 | | (R)-2-(2-Chloro-5-isopropyl-8-oxothieno[2',3':4,5]pyrrolo[1,2-d][1,2,4]triazin-7(8H)-yl)-N-(1-(cyclopropylmethyl)piperidin-3-yl)acetamide | (400 MHZ, DMSO-d6) δ (ppm) 7.87 (d, 1H), 7.80 (s, 1H), 7.46 (s, 1H), 4.60-4.48 (m, 2H), 3.80-3.70 (m, 1H), 3.59 (sept, 1H), 2.88-2.77 (m, 1H), 2.75-2.65 (m, 1H), 2.21-2.11 (m, 2H), 2.04-1.93 (m, 1H), 1.91-1.81 (m, 1H), 1.72-1.60 (m, 2H), 1.51-1.40 (m, 1H), 1.28 (d, 6H), 1.26-1.14 (m, 1H), 0.84-0.71 (m, 1H), 0.47-0.38 (m, 2H), 0.09-0.0 (m, 2H). | Rt = 0.83 [M + H]$^+$ 462.2 | secretion was triggered by the addition of either 1 μg/mL LPS (Sigma, #L4391) or 100 ng/mL Pam3CSK4 (Invivogen, #tlrl-pms) depending on the experiment, and cells were incubated for 3 hours. 10 μL supernatant was removed, and TNF-α levels were monitored using an HTRF assay (Cis-Bio, #62TNFPEC) according to manufacturers' instructions. Viability was monitored as described above.

Data Interpretation:

IC$_{50}$ values were calculated from the plot of percentage of inhibition versus the inhibitor concentration by a logistics fit according to:

$$y = A2 + (A1-A2)/(1+(x/IC_{50})^p)$$

where y is the %-inhibition at the inhibitor concentration, x. A1 is the lowest inhibition value, i.e. 0%, and A2 the maximum inhibition value, i.e. 100%. The exponent, p, is the Hill coefficient. The curve fitting was conducted with an internally developed software suite.

NLRP3-dependent IL-1β secretion was stimulated in PMA-differentiated THP-1 cells by the addition of nigericin, and cytokines were measured in the serum after 3 hours. As discussed above, activation of the NLRP3 inflammasome requires both an NF-kB-dependent priming step and the addition of a NLRP3 activator. To ensure that the inhibitors did not interfere with the priming step, Pam3CSK4-stimulated, NF-kB-dependent TNF-α secretion was monitored as a counterscreen. Data for the inhibitory effect (IC$_{50}$) of the compounds of the invention for both assays are given in the table below.

| Ex. No. | IL-1β IC$_{50}$ [μM] | TNF-α IC$_{50}$ [μM] |
|---|---|---|
| 1 | 0.0202 | >100 |
| 2 | 0.0442 | >100 |
| 3 | 0.2276 | >100 |
| 4 | 0.2199 | >100 |
| 5 | 0.0629 | >100 |
| 6 | 0.0065 | >100 |
| 7 | 0.2541 | >100 |
| 8 | 0.0874 | >100 |
| 9 | 0.0079 | >100 |
| 10 | 0.0562 | >100 |
| 11 | 0.0625 | |
| 12 | 0.0237 | |
| 13 | 0.0940 | |
| 14 | 0.0906 | |
| 15 | 0.0054 | |
| 16 | 0.0573 | |
| 17 | 0.0250 | >100 |
| 18 | 1.1295 | >100 |
| 19 | 0.0486 | >100 |
| 20 | 0.0598 | >100 |
| 21 | 0.0325 | >100 |
| 22 | 0.4081 | |
| 23 | 0.4523 | |
| 24 | 0.0395 | >100 |
| 25 | 0.0785 | >100 |
| 26 | 0.0464 | >100 |
| 27 | 0.0180 | >100 |
| 28 | 0.0133 | >100 |
| 29 | 0.0357 | >100 |
| 30 | 0.0525 | >100 |
| 31 | 0.0905 | >100 |
| 32 | 0.0076 | >100 |
| 33 | 0.1077 | >100 |
| 34 | 0.0803 | >100 |
| 35 | 0.0481 | 40 |
| 36 | 0.1091 | >100 |
| 37 | 0.1014 | >100 |
| 38 | 0.0880 | >100 |
| 39 | 0.5403 | >100 |
| 40 | 0.0563 | >100 |
| 41 | 1.1719 | >100 |
| 42 | 1.1015 | >100 |
| 43 | 2.0474 | >100 |
| 44 | 0.1119 | >100 |
| 45 | 0.2441 | >100 |
| 46 | 0.0508 | >100 |
| 47 | 0.0091 | >100 |
| 48 | 0.0471 | >100 |
| 49 | 0.0264 | >100 |
| 50 | 0.1082 | >100 |
| 51 | 0.1384 | >100 |
| 52 | 0.6604 | >100 |
| 53 | 0.0342 | >100 |
| 54 | 0.5620 | >100 |
| 55 | 0.8430 | >100 |
| 56 | >0.33* | >100 |
| 57 | 0.0615 | |
| 58 | 0.176 | >100 |
| 59 | 0.201 | >100 |
| 60 | 0.0152 | >100 |
| 61 | 0.0594 | |
| 62 | 0.0761 | >100 |
| 63 | 0.0017 | |
| 64 | 0.0034 | >100 |
| 65 | 0.0062 | |
| 66 | 0.0078 | |
| 67 | 0.2124 | |
| 68 | 0.0452 | >100 |
| 69 | 0.0588 | >100 |
| 70 | 0.0349 | >100 |
| 71 | 0.0159 | |
| 72 | 0.0004 | >100 |
| 73 | 0.0145 | |
| 74 | 0.0044 | |
| 75 | 0.0374 | >100 |
| 76 | 0.0451 | >100 |
| 77 | 0.0140 | >100 |
| 78 | 0.0714 | |
| 79 | 0.2436 | >100 |
| 80 | 0.0607 | |
| 81 | 0.0039 | >100 |
| 82 | 0.0422 | >100 |
| 83 | 0.0162 | >100 |
| 84 | 0.0129 | |
| 85 | 0.1302 | |
| 86 | 0.0412 | |
| 87 | 0.0010 | |
| 88 | 0.0275 | >100 |
| 89 | 0.0248 | >100 |
| 90 | 0.0608 | >100 |
| 91 | 0.0019 | >100 |
| 92 | 0.0652 | |
| 93 | 0.0008 | |
| 94 | 0.0649 | |
| 95 | 0.2461 | |
| 96 | 1.0450 | >33 |
| 97 | 0.0183 | |
| 98 | 0.2706 | |
| 99 | 0.5374 | >100 |
| 100 | 0.1819 | >100 |
| 101 | 0.3812 | |
| 102 | 0.8860 | |
| 103 | 0.1905 | >100 |
| 104 | 0.2545 | |
| 105 | 0.8382 | |
| 106 | 2.1799 | |
| 107 | 4.3994 | |
| 108 | 0.1010 | |
| 109 | 0.2210 | |
| 110 | 0.1150 | |
| 111 | 0.1110 | >100 |
| 112 | 0.2530 | |
| 113 | 0.0058 | >100 |
| 114 | 0.298 | >11 |
| 115 | 0.172 | >100 |

-continued

| Ex. No. | IL-1β IC$_{50}$ [μM] | TNF-α IC$_{50}$ [μM] |
|---|---|---|
| 116 | 0.4* | |
| 117 | 6.0* | |
| 118 | 0.0788 | |
| 119 | 0.0405 | |
| 120 | 0.0172 | |
| 121 | 0.0441 | |
| 122 | 0.2670 | |
| 123 | 2.080 | |
| 124 | 0.0009 | >100 |
| 125 | 0.0003 | >33 |
| 126 | 0.0006 | |
| 127 | 0.0042 | >100 |
| 128 | 0.0045 | >100 |
| 129 | 0.0031 | >100 |
| 130 | 0.0204 | >100 |
| 131 | 0.0179 | >33 |
| 132 | 0.0008 | |
| 133 | 0.0205 | >100 |
| 134 | 0.0007 | >100 |

*readout of pyroptosis

The invention claimed is:

1. A compound of Formula (I):

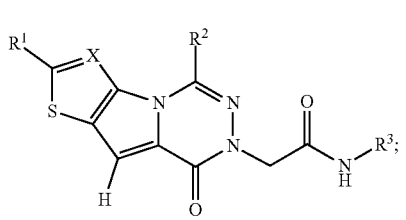

or a pharmaceutically acceptable salt thereof wherein:
$R^1$ is H, halo, or methyl;
$R^2$ is ethyl substituted with —OH, $C_1$-$C_4$alkoxy, or with one or more halo groups; or
$R^2$ is $C_3$-$C_6$alkyl optionally substituted with OH, halo or $C_{1-4}$alkoxy; or
$R^2$ is $C_3$-$C_6$cycloalkyl;
$R^3$ is $C_2$-$C_8$alkyl optionally substituted with 1 to 3 substituents independently selected from —NH$_2$, —NH($C_1$-$C_4$alkyl), —NHC(O)O($C_1$-$C_4$alkyl), —NHC(O)($C_1$-$C_4$alkyl), —OH, $C_1$-$C_4$alkoxy, halo$C_1$-$C_4$alkoxy, halo and $C_3$-$C_5$cycloalkyl which is further optionally substituted with OH or halo; or
$R^3$ is $C_3$-$C_{10}$cycloalkyl or $C_3$-$C_5$cycloalkyl-CH$_2$, each of which is optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —NH($C_1$-$C_4$alkyl), —CO$_2$H; or
$R^3$ is mono or bicyclic aryl, or a mono or bicyclic heteroaryl, each of which is optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —SO$_2$NH$_2$, —SO$_2$NH($C_1$-$C_4$alkyl), —NHSO$_2$($C_1$-$C_4$alkyl), —NH($C_1$-$C_4$alkyl), —C(O)NH$_2$, C(O)$C_1$-$C_4$alkyl, —CO$_2$H; or $R^3$ is a mono or bicyclic heterocyclyl optionally substituted with 1 to 3 substituents independently selected from —OH, oxo, $C_3$-$C_6$cycloalkyl, halo, —C(O)O—$C_1$-$C_4$alkyl, —C(O)$C_1$-$C_4$alkyl, and $C_1$-$C_4$alkyl which is further optionally substituted with 1 to 4 substituents independently selected from $C_3$-$C_6$cycloalkyl, halo, $C_1$-$C_4$alkoxy, halo$C_1$-$C_4$alkoxy and OH;
X is N or CH.

2. The compound according to claim 1, or a pharmaceutically acceptable salt thereof, having Formula (II):

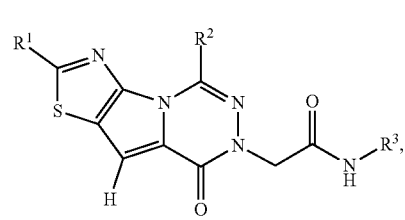

wherein $R^1$ is methyl, or H or Formula (III):

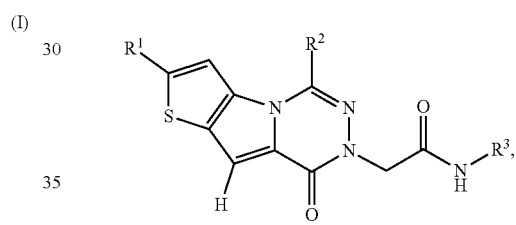

wherein $R^1$ is methyl, or halo.

3. The compound according to claim 1, or a pharmaceutically acceptable salt thereof, wherein $R^3$ is $C_2$-$C_8$alkyl optionally substituted with 1 to 3 substituents independently selected from NH$_2$, NH($C_1$-$C_4$alkyl), NHC(O)O($C_1$-$C_4$alkyl), NHC(O)($C_1$-$C_4$alkyl), OH, $C_1$-$C_4$alkoxy, halo$C_1$-$C_4$alkoxy, halo and $C_3$-$C_5$cycloalkyl which is optionally further substituted with OH or halo.

4. The compound according to claim 3, or a pharmaceutically acceptable salt thereof, wherein $R^3$ is $C_2$-$C_8$alkyl optionally substituted with 1 to 2 substituents independently selected from OH, NH$_2$, NHC(O)($C_1$-$C_4$alkyl), halo and $C_3$-$C_5$cycloalkyl which is optionally further substituted with OH or halo.

5. The compound according to claim 1, or a pharmaceutically acceptable salt thereof, wherein $R^3$ is $C_3$-$C_{10}$cycloalkyl or $C_3$-$C_5$cycloalkyl-CH$_2$ optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —NH($C_1$-$C_4$alkyl) and CO$_2$H.

6. The compound according to claim 5, or a pharmaceutically acceptable salt thereof, wherein $R^3$ is selected from the following:

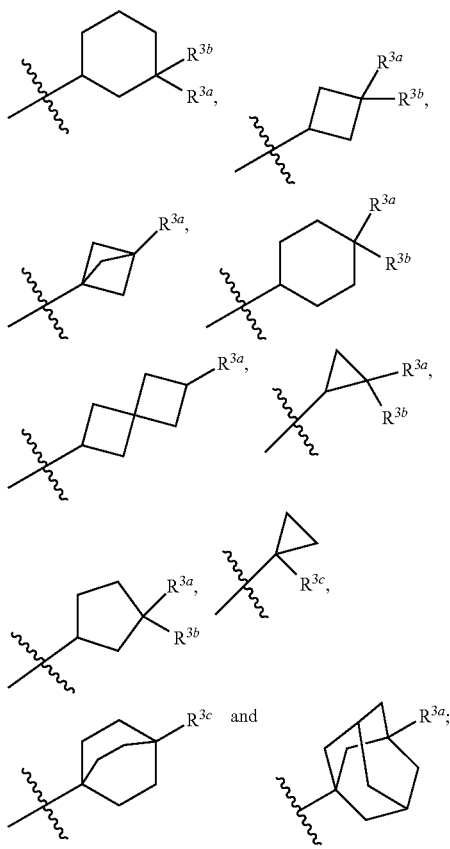

wherein $R^{3a}$, $R^{3b}$ and $R^{3c}$ are independently selected from H, —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —NH($C_1$-$C_4$alkyl) and $CO_2H$.

7. The compound according to claim 1, or a pharmaceutically acceptable salt thereof, wherein $R^3$ is mono or bicyclic aryl, a mono or bicyclic heteroaryl, each of which is optionally substituted with 1 to 3 substituents independently selected from —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —SO$_2$NH$_2$, —SO$_2$NH($C_1$-$C_4$alkyl), —NHSO$_2$($C_1$-$C_4$alkyl), —NH($C_1$-$C_4$alkyl), —C(O)NH$_2$, C(O)$C_1$-$C_4$alkyl and —CO$_2$H.

8. The compound according to claim 7, or a pharmaceutically acceptable salt thereof, wherein $R^3$ is selected from the following:

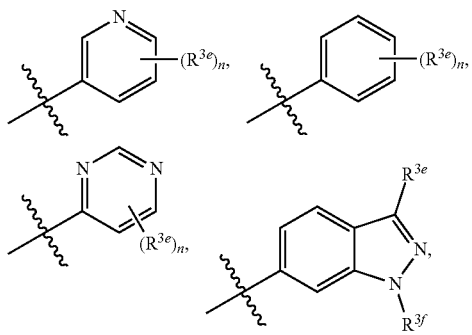

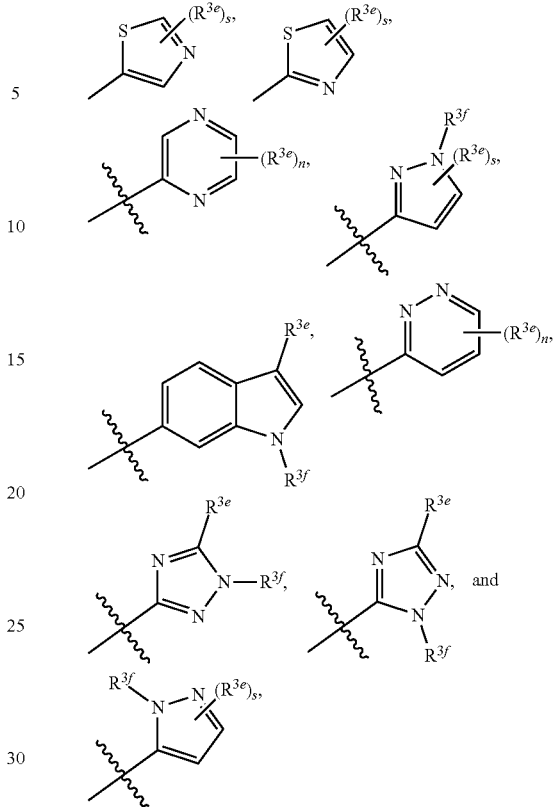

wherein $R^{3e}$ is independently selected from H, —OH, $C_1$-$C_4$alkyl, $C_3$-$C_6$cycloalkyl, halo, —OC(O)($C_1$-$C_4$alkyl), halo$C_1$-$C_4$alkyl, —C(O)O($C_1$-$C_4$alkyl), hydroxy$C_1$-$C_4$alkyl, $C_1$-$C_4$alkoxy, halo$C_1$-$C_4$alkoxy, —NH$_2$, —SO$_2$NH$_2$, —SO$_2$NH($C_1$-$C_4$alkyl), —NHSO$_2$($C_1$-$C_4$alkyl), —NH($C_1$-$C_4$alkyl), —C(O)NH$_2$, C(O)$C_1$-$C_4$alkyl, and —CO$_2$H; $R^{31}$ is H or $C_1$-$C_4$alkyl; n is 1, 2 or 3; and s is 1 or 2.

9. The compound according to claim 1, or a pharmaceutically acceptable salt thereof, wherein $R^3$ is a mono or bicyclic heterocyclyl optionally substituted with 1 to 3 substituents independently selected from —OH, oxo, $C_3$-$C_6$cycloalkyl, halo, —C(O)O—$C_1$-$C_4$alkyl, —C(O)$C_1$-$C_4$alkyl, and $C_1$-$C_4$alkyl which is further optionally substituted with 1 to 4 substituents independently selected from $C_3$-$C_6$cycloalkyl, halo, $C_1$-$C_4$alkoxy, halo$C_1$-$C_4$alkoxy and OH.

10. The compound according to claim 9, or a pharmaceutically acceptable salt thereof, wherein $R^3$ is selected from the following:

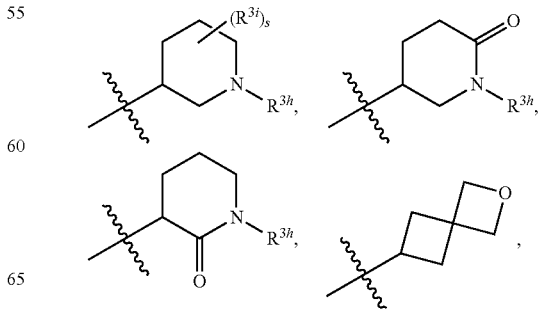

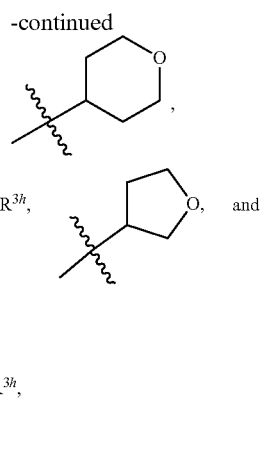

wherein R³ʰ is selected from H, C₃-C₆cycloalkyl, —C(O)O—C₁-C₄alkyl, —C(O)C₁-C₄alkyl, and C₁-C₄alkyl which is further optionally substituted with 1 to 4 substituents independently selected from C₃-C₆cycloalkyl, halo, C₁-C₄alkoxy, haloC₁-C₄alkoxy and OH, and wherein R³ⁱ is H, halo, OH or alkyl, and wherein s is 1 or 2.

11. The compound according to claim 1, wherein R¹ is chloro, or a pharmaceutically acceptable salt thereof.

12. The compound according to claim 1, or a pharmaceutically acceptable salt thereof, wherein R² is selected from:

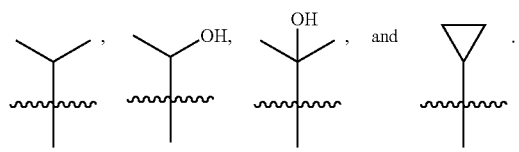

13. The compound according to claim 1, or pharmaceutically acceptable salt thereof, wherein the compound is selected from:
- 2-(2-Chloro-5-isopropyl-8-oxothieno[2',3':4,5]pyrrolo[1,2-d][1,2,4]triazin-7(8H)-yl)-N-(pyrimidin-4-yl)acetamide;
- 2-(2-Chloro-5-isopropyl-8-oxothieno[2',3':4,5]pyrrolo[1,2-d][1,2,4]triazin-7(8H)-yl)-N-(pyridin-3-yl)acetamide;
- 2-(2-Chloro-5-(1-hydroxyethyl)-8-oxothieno[2',3':4,5]pyrrolo[1,2-d][1,2,4]triazin-7(8H)-yl)-N-(pyrimidin-4-yl)acetamide;
- 2-(5-Cyclopropyl-8-oxothiazolo[5',4':4,5]pyrrolo[1,2-d][1,2,4]triazin-7(8H)-yl)-N-(pyridin-3-yl)acetamide;
- 2-(2-Fluoro-5-isopropyl-8-oxothieno[2',3':4,5]pyrrolo[1,2-d][1,2,4]triazin-7(8H)-yl)-N-(pyridin-3-yl)acetamide;
- 2-(2-Fluoro-5-isopropyl-8-oxothieno[2',3':4,5]pyrrolo[1,2-d][1,2,4]triazin-7(8H)-yl)-N-(pyrimidin-4-yl)acetamide;
- 2-(5-Isopropyl-2-methyl-8-oxothieno[2',3':4,5]pyrrolo[1,2-d][1,2,4]triazin-7(8H)-yl)-N-(pyridin-3-yl)acetamide;
- 2-(2-Chloro-5-(2-hydroxypropan-2-yl)-8-oxothieno[2',3':4,5]pyrrolo[1,2-d][1,2,4]triazin-7(8H)-yl)-N-(pyridin-3-yl)acetamide;
- 2-(2-Chloro-5-(2-hydroxypropan-2-yl)-8-oxothieno[2',3':4,5]pyrrolo[1,2-d][1,2,4]triazin-7(8H)-yl)-N-(pyrimidin-4-yl)acetamide;
- (R)-2-(2-Chloro-5-isopropyl-8-oxothieno[2',3':4,5]pyrrolo[1,2-d][1,2,4]triazin-7(8H)-yl)-N-(piperidin-3-yl)acetamide;
- 2-(2-Chloro-5-isopropyl-8-oxothieno[2',3':4,5]pyrrolo[1,2-d][1,2,4]triazin-7(8H)-yl)-N-(thiazol-2-yl)acetamide;
- 2-(2-Chloro-5-isopropyl-8-oxothieno[2',3':4,5]pyrrolo[1,2-d][1,2,4]triazin-7(8H)-yl)-N-(thiazol-5-yl)acetamide;
- 2-(2-Chloro-5-isopropyl-8-oxothieno[2',3':4,5]pyrrolo[1,2-d][1,2,4]triazin-7(8H)-yl)-N-(2-chloropyridin-3-yl)acetamide;
- 2-(2-Chloro-5-isopropyl-8-oxothieno[2',3':4,5]pyrrolo[1,2-d][1,2,4]triazin-7(8H)-yl)-N-(6-fluoropyridin-3-yl)acetamide;
- 2-(2-Chloro-5-isopropyl-8-oxothieno[2',3':4,5]pyrrolo[1,2-d][1,2,4]triazin-7(8H)-yl)-N-(5-fluoropyrimidin-4-yl)acetamide;
- 2-(2-Chloro-5-isopropyl-8-oxothieno[2',3':4,5]pyrrolo[1,2-d][1,2,4]triazin-7(8H)-yl)-N-(5-chloropyrimidin-4-yl)acetamide;
- (R)-2-(2-Chloro-5-isopropyl-8-oxothieno[2',3':4,5]pyrrolo[1,2-d][1,2,4]triazin-7(8H)-yl)-N-(1-methylpiperidin-3-yl)acetamide;
- (S)-2-(2-Chloro-5-isopropyl-8-oxothieno[2',3':4,5]pyrrolo[1,2-d][1,2,4]triazin-7(8H)-yl)-N-(1-methylpiperidin-3-yl)acetamide;
- (R)-2-(2-Chloro-5-isopropyl-8-oxothieno[2',3':4,5]pyrrolo[1,2-d][1,2,4]triazin-7(8H)-yl)-N-(6-oxopiperidin-3-yl)acetamide;
- 2-(2-Chloro-5-isopropyl-8-oxothieno[2',3':4,5]pyrrolo[1,2-d][1,2,4]triazin-7(8H)-yl)-N-(3-hydroxy-2,2-dimethylpropyl)acetamide;
- 2-(2-Chloro-5-isopropyl-8-oxothieno[2',3':4,5]pyrrolo[1,2-d][1,2,4]triazin-7(8H)-yl)-N-((1R,3R)-3-hydroxycyclohexyl)acetamide;
- N-((1R,3R)-3-Aminocyclopentyl)-2-(2-chloro-5-isopropyl-8-oxothieno[2',3':4,5]pyrrolo[1,2-d][1,2,4]triazin-7(8H)-yl)acetamide;
- 2-(2-Chloro-5-isopropyl-8-oxothieno[2',3':4,5]pyrrolo[1,2-d][1,2,4]triazin-7(8H)-yl)-N-((1r,3r)-3-hydroxy-1-methylcyclobutyl) acetamide;
- 2-(2-Chloro-5-isopropyl-8-oxothieno[2',3':4,5]pyrrolo[1,2-d][1,2,4]triazin-7(8H)-yl)-N-(2-oxaspiro[3.3]heptan-6-yl)acetamide;
- 2-(2-Chloro-5-(2-hydroxypropan-2-yl)-8-oxothieno[2',3':4,5]pyrrolo[1,2-d][1,2,4]triazin-7(8H)-yl)-N-(3,3-dimethylcyclobutyl)acetamide;
- 2-(2-Chloro-5-(2-hydroxypropan-2-yl)-8-oxothieno[2',3':4,5]pyrrolo[1,2-d][1,2,4]triazin-7(8H)-yl)-N-(2-oxaspiro[3.3]heptan-6-yl)acetamide;
- 2-(2-Chloro-5-isopropyl-8-oxothieno[2',3':4,5]pyrrolo[1,2-d][1,2,4]triazin-7(8H)-yl)-N-((1R,3R)-3-hydroxy-3-methylcyclohexyl)acetamide;
- (R)-2-(2-Chloro-5-isopropyl-8-oxothieno[2',3':4,5]pyrrolo[1,2-d][1,2,4]triazin-7(8H)-yl)-N-(1-(2-fluoroethyl)piperidin-3-yl)acetamide;
- (R)-2-(2-Chloro-5-(2-hydroxypropan-2-yl)-8-oxothieno[2',3':4,5]pyrrolo[1,2-d][1,2,4]triazin-7(8H)-yl)-N-(1-methyl-6-oxopiperidin-3-yl)acetamide;
- (R)-2-(2-Chloro-5-(2-hydroxypropan-2-yl)-8-oxothieno[2',3':4,5]pyrrolo[1,2-d][1,2,4]triazin-7(8H)-yl)-N-(1-(2-fluoroethyl)piperidin-3-yl)acetamide;

(R)-2-(2-Fluoro-5-isopropyl-8-oxothieno[2',3':4,5]pyrrolo[1,2-d][1,2,4]triazin-7(8H)-yl)-N-(piperidin-3-yl)acetamide hydrochloride;

(R)-2-(2-Fluoro-5-isopropyl-8-oxothieno[2',3':4,5]pyrrolo[1,2-d][1,2,4]triazin-7(8H)-yl)-N-(1-methylpiperidin-3-yl)acetamide;

(R)-2-(2-Fluoro-5-isopropyl-8-oxothieno[2',3':4,5]pyrrolo[1,2-d][1,2,4]triazin-7(8H)-yl)-N-(6-oxopiperidin-3-yl)acetamide;

(R)-2-(5-Cyclopropyl-2-fluoro-8-oxothieno[2',3':4,5]pyrrolo[1,2-d][1,2,4]triazin-7(8H)-yl)-N-(piperidin-3-yl)acetamide;

(R)-2-(5-Cyclopropyl-2-fluoro-8-oxothieno[2',3':4,5]pyrrolo[1,2-d][1,2,4]triazin-7(8H)-yl)-N-(1-methylpiperidin-3-yl)acetamide;

(R)-2-(2-Chloro-5-cyclopropyl-8-oxothieno[2',3':4,5]pyrrolo[1,2-d][1,2,4]triazin-7(8H)-yl)-N-(piperidin-3-yl)acetamide hydrochloride;

(R)-2-(2-Chloro-5-cyclopropyl-8-oxothieno[2',3':4,5]pyrrolo[1,2-d][1,2,4]triazin-7(8H)-yl)-N-(1-methylpiperidin-3-yl)acetamide;

(R)-2-(5-Isopropyl-2-methyl-8-oxothieno[2',3':4,5]pyrrolo[1,2-d][1,2,4]triazin-7(8H)-yl)-N-(piperidin-3-yl)acetamide;

(R)-2-(5-Isopropyl-2-methyl-8-oxothieno[2',3':4,5]pyrrolo[1,2-d][1,2,4]triazin-7(8H)-yl)-N-(6-oxopiperidin-3-yl)acetamide;

(R)-2-(5-Isopropyl-2-methyl-8-oxothieno[2',3':4,5]pyrrolo[1,2-d][1,2,4]triazin-7(8H)-yl)-N-(1-methylpiperidin-3-yl)acetamide;

N-Cyclopropyl-2-(5-isopropyl-2-methyl-8-oxothieno[2',3':4,5]pyrrolo[1,2-d][1,2,4]triazin-7(8H)-yl)acetamide;

2-(2-Chloro-5-(1-hydroxyethyl)-8-oxothieno[2',3':4,5]pyrrolo[1,2-d][1,2,4]triazin-7(8H)-yl)-N-(pyridin-3-yl)acetamide;

2-(2-Chloro-5-(1-hydroxyethyl)-8-oxothieno[2',3':4,5]pyrrolo[1,2-d][1,2,4]triazin-7(8H)-yl)-N—((R)-piperidin-3-yl)acetamide hydrochloride;

2-(2-Chloro-5-(1-hydroxyethyl)-8-oxothieno[2',3':4,5]pyrrolo[1,2-d][1,2,4]triazin-7(8H)-yl)-N—((R)-1-methylpiperidin-3-yl)acetamide;

2-(2-Chloro-5-(1-hydroxyethyl)-8-oxothieno[2',3':4,5]pyrrolo[1,2-d][1,2,4]triazin-7(8H)-yl)-N-((1R,3R)-3-hydroxy-3-methylcyclohexyl)acetamide;

(R)-2-(5-Isopropyl-8-oxothiazolo[5',4':4,5]pyrrolo[1,2-d][1,2,4]triazin-7(8H)-yl)-N-(6-oxopiperidin-3-yl)acetamide;

N-((1R,3R)-3-Hydroxycyclohexyl)-2-(5-isopropyl-8-oxothiazolo[5',4':4,5]pyrrolo[1 2-d][1,2,4]triazin-7(8H)-yl)acetamide;

(R)-2-(5-Isopropyl-8-oxothiazolo[5',4':4,5]pyrrolo[1,2-d][1,2,4]triazin-7(8H)-yl)-N-(1-methylpiperidin-3-yl)acetamide;

(R)-2-(5-Isopropyl-8-oxothiazolo[5',4':4,5]pyrrolo[1,2-d][1,2,4]triazin-7(8H)-yl)-N-(1-methyl-6-oxopiperidin-3-yl)acetamide;

(R)-2-(5-Isopropyl-2-methyl-8-oxothiazolo[5',4':4,5]pyrrolo[1,2-d][1,2,4]triazin-7(8H)-yl)-N-(piperidin-3-yl)acetamide;

N-Cyclopropyl-2-(5-isopropyl-8-oxothiazolo[5',4':4,5]pyrrolo[1,2-d][1,2,4]triazin-7(8H)-yl)acetamide;

2-(2-Chloro-5-isopropyl-8-oxothieno[2',3':4,5]pyrrolo[1,2-d][1,2,4]triazin-7(8H)-yl)-N-((1R,2S)-2-fluorocyclopropyl)acetamide;

(1r,4r)-4-(2-(2-Chloro-5-isopropyl-8-oxothieno[2',3':4,5]pyrrolo[1,2-d][1,2,4]triazin-7(8H)-yl)acetamido)cyclohexane-1-carboxylic acid;

(1s,4s)-4-(2-(2-Chloro-5-isopropyl-8-oxothieno[2',3':4,5]pyrrolo[1,2-d][1,2,4]triazin-7(8H)-yl)acetamido)cyclohexane-1-carboxylic acid;

(1R,3S)-3-(2-(2-Chloro-5-isopropyl-8-oxothieno[2',3':4,5]pyrrolo[1,2-d][1,2,4]triazin-7(8H)-yl)acetamido)cyclohexane-1-carboxylic acid;

tert-Butyl ((1R,3S)-3-(2-(2-chloro-5-isopropyl-8-oxothieno[2',3':4,5]pyrrolo[1,2-d][1,2,4]triazin-7(8H)-yl)acetamido)cyclohexyl)carbamate;

2-(2-Chloro-5-isopropyl-8-oxothieno[2',3':4,5]pyrrolo[1,2-d][1,2,4]triazin-7(8H)-yl)-N-(1-methyl-1H-pyrazol-5-yl)acetamide;

2-(2-Chloro-5-isopropyl-8-oxothieno[2',3':4,5]pyrrolo[1,2-d][1,2,4]triazin-7(8H)-yl)-N-(2,4-difluorophenyl)acetamide;

(R)-2-(2-Chloro-5-isopropyl-8-oxothieno[2',3':4,5]pyrrolo[1,2-d][1,2,4]triazin-7(8H)-yl)-N-(tetrahydro-2H-pyran-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-methylpiperidin-3-yl)acetamide;

2-(2-Chloro-5-(2-hydroxypropan-2-yl)-8-oxothieno[2',3':4,5] pyrrolo[1,2-d][1,2,4]triazin-7(8H)-yl)-N-((1 r,3r)-3-hydroxy-3-methylcyclobutyl)acetamide;

2-(2-Chloro-5-(2-hydroxypropan-2-yl)-8-oxothieno[2',3':4,5]pyrrolo[1,2-d][1,2,4]triazin-7(8H)-yl)-N-cyclopropylacetamide;

2-(2-Chloro-5-(2-hydroxypropan-2-yl)-8-oxothieno[2',3':4,5]pyrrolo[1,2-d][1,2,4]triazin-7(8H)-yl)-N-((1s,3s)-3-hydroxy-3-methyl cyclobutyl) acetamide;

2-(2-Chloro-5-(2-hydroxypropan-2-yl)-8-oxothieno[2',3':4,5]pyrrolo[1,2-d][1,2,4]triazin-7(8H)-yl)-N-((1R,3R)-3-hydroxy cyclohexyl)acetamide;

2-(2-Chloro-5-(2-hydroxypropan-2-yl)-8-oxothieno[2',3':4,5]pyrrolo[1,2-d][1,2,4]triazin-7(8H)-yl)-N-(1H-indazol-6-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-(3-methyl-1H-indazol-6-yl)acetamide;

2-(2-Chloro-5-(2-hydroxypropan-2-yl)-8-oxothieno[2',3':4,5]pyrrolo[1,2-d][1 2,4]triazin-7(8H)-yl)-N-(1H-indol-6-yl)acetamide;

2-(2-Chloro-5-isopropyl-8-oxothieno[2',3':4,5]pyrrolo[1,2-d][1,2,4]triazin-7(8H)-yl)-N-(2-hydroxyethyl) acetamide;

(S)-2-(2-Chloro-5-isopropyl-8-oxothieno[2',3':4,5]pyrrolo[1,2-d][1,2,4]triazin-7(8H)-yl)-N-(2-hydroxy propyl)acetamide;

(R)-2-(2-Chloro-5-isopropyl-8-oxothieno[2',3':4,5]pyrrolo[1,2-d][1,2,4]triazin-7(8H)-yl)-N-(2-hydroxypropyl)acetamide;

2-(2-Chloro-5-isopropyl-8-oxothieno[2',3':4,5]pyrrolo[1,2-d][1,2,4]triazin-7(8H)-yl)-N-((1 r,3r)-3-hydroxy-3-methylcyclobutyl)acetamide;

2-(2-Chloro-5-isopropyl-8-oxothieno[2',3':4,5]pyrrolo[1,2-d][1,2,4]triazin-7(8H)-yl)-N-((1s,3s)-3-hydroxy-3-methylcyclobutyl)acetamide;

2-(2-Chloro-5-isopropyl-8-oxothieno[2',3':4,5]pyrrolo[1,2-d][1,2,4]triazin-7(8H)-yl)-N-(6-hydroxyspiro[3.3]heptan-2-yl)acetamide;

2-(2-Chloro-5-isopropyl-8-oxothieno[2',3':4,5]pyrrolo[1,2-d][1,2,4]triazin-7(8H)-yl)-N-((1s,3s)-3-hydroxy-3-(trifluoromethyl)cyclobutyl)acetamide;

2-(2-Chloro-5-isopropyl-8-oxothieno[2',3':4,5]pyrrolo[1,2-d][1,2,4]triazin-7(8H)-yl)-N-(tetrahydro-2H-pyran-4-yl)acetamide;

2-(2-Chloro-5-isopropyl-8-oxothieno[2',3':4,5]pyrrolo[1,2-d][1,2,4]triazin-7(8H)-yl)-N-(4-hydroxybicyclo[2.2.2]octan-1-yl)acetamide;

2-(2-Chloro-5-isopropyl-8-oxothieno[2',3':4,5]pyrrolo[1,2-d][1,2,4]triazin-7(8H)-yl)-N-(3-hydroxy-3-methylbutyl)acetamide;

(R)-2-(2-Chloro-5-isopropyl-8-oxothieno[2',3':4,5]pyrrolo[1,2-d][1,2,4]triazin-7(8H)-yl)-N-(1-(2-(trifluoromethoxy) ethyl)piperidin-3-yl)acetamide;

(R)-2-(2-Chloro-5-(2-hydroxypropan-2-yl)-8-oxothieno[2',3':4,5]pyrrolo[1 2-d][1,2,4]triazin-7(8H)-yl)-N-(piperidin-3-yl)acetamide;

(2-(2-Chloro-5-(2-hydroxypropan-2-yl)-8-oxothieno[2',3':4,5]pyrrolo[1,2-d][1,2,4]triazin-7(8H)-yl)-N-(3-hydroxy-3-methylbutyl)acetamide;

2-(2-Chloro-5-(2-hydroxypropan-2-yl)-8-oxothieno[2',3':4,5]pyrrolo[1,2-d][1,2,4]triazin-7(8H)-yl)-N-((1R,3S)-3-hydroxycyclohexyl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-(2,2,2-trifluoroethyl)piperidin-3-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-((1R,3R)-3-hydroxy-3-methyl cyclohexyl)acetamide;

2-(2-Fluoro-5-isopropyl-8-oxothieno[2',3':4,5]pyrrolo[1,2-d][1,2,4]triazin-7(8H)-yl)-N-(3-hydroxy-3-methylbutyl)acetamide;

(R)-2-(2-Fluoro-5-isopropyl-8-oxothieno[2',3':4,5]pyrrolo[1,2-d][1,2,4]triazin-7(8H)-yl)-N-(2-hydroxy propyl)acetamide;

2-(2-Fluoro-5-isopropyl-8-oxothieno[2',3':4,5]pyrrolo[1,2-d][1,2,4]triazin-7(8H)-yl)-N-((1 r,3r)-3-hydroxy-3-methylcyclobutyl)acetamide;

2-(2-Fluoro-5-isopropyl-8-oxothieno[2',3':4,5]pyrrolo[1,2-d][1,2,4]triazin-7(8H)-yl)-N-((1s,3s)-3-hydroxy-3-methyl cyclobutyl)acetamide;

(R)-2-(5-Isopropyl-8-oxothiazolo[5',4':4,5]pyrrolo[1,2-d][1,2,4]triazin-7(8H)-yl)-N-(piperidin-3-yl)acetamide;

(R)—N-(1-(2-Fluoroethyl)piperidin-3-yl)-2-(5-isopropyl-8-oxothiazolo[5',4':4,5]pyrrolo[1,2-d][1,2,4]triazin-7(8H)-yl)acetamide;

N-((1R,3R)-3-Hydroxy-3-methylcyclohexyl)-2-(5-isopropyl-8-oxothiazolo[5',4':4,5]pyrrolo[1,2-d][1,2,4]triazin-7(8H)-yl)acetamide;

N-((1R,3S)-3-Hydroxycyclohexyl)-2-(5-isopropyl-8-oxothiazolo[5',4':4,5]pyrrolo[1 2-d][1,2,4]triazin-7(8H)-yl)acetamide;

(R)-2-(5-Isopropyl-2-methyl-8-oxothiazolo[5',4':4,5]pyrrolo[1,2-d][1,2,4]triazin-7(8H)-yl)-N-(1-methylpiperidin-3-yl)acetamide;

N-((1s,3s)-3-Hydroxy-3-methylcyclobutyl)-2-(5-isopropyl-8-oxothiazolo[5',4':4,5]pyrrolo[1,2-d][1,2,4]triazin-7(8H)-yl)acetamide;

N-(3-Hydroxy-3-methylbutyl)-2-(5-isopropyl-8-oxothiazolo[5',4':4,5]pyrrolo[1,2-d][1,2,4]triazin-7(8H)-yl)acetamide;

(R)—N-(2-Hydroxypropyl)-2-(5-isopropyl-8-oxothiazolo[5',4':4,5]pyrrolo[1,2-d][1,2,4]triazin-7(8H)-yl)acetamide;

N-Cyclopropyl-2-(5-isopropyl-2-methyl-8-oxothiazolo[5',4':4,5]pyrrolo[1,2-d][1,2,4]triazin-7(8H)-yl)acetamide;

(R)-2-(5-Isopropyl-8-oxothiazolo[5',4':4,5]pyrrolo[1,2-d][1,2,4]triazin-7(8H)-yl)-N-(1-methyl-6-oxopiperidin-3-yl)acetamide;

N-Cyclopentyl-2-(5-isopropyl-8-oxothiazolo[5',4':4,5]pyrrolo[1,2-d][1,2,4]triazin-7(8H)-yl)acetamide;

(S)-2-(2-Chloro-5-isopropyl-8-oxothieno[2',3':4,5]pyrrolo[1,2-d][1,2,4]triazin-7(8H)-yl)-N-(tetrahydrofuran-3-yl)acetamide;

(R)-2-(2-Chloro-5-isopropyl-8-oxothieno[2',3':4,5]pyrrolo[1,2-d][1,2,4]triazin-7(8H)-yl)-N-(tetrahydrofuran-3-yl)acetamide;

2-(2-Chloro-5-Isopropyl-8-oxothieno[2',3':4,5]pyrrolo[1,2-d][1,2,4]triazin-7(8H)-yl)-N-cyclopentylacetamide;

(S)-2-(2-Chloro-5-isopropyl-8-oxothieno[2',3':4,5]pyrrolo[1,2-d][1,2,4]triazin-7(8H)-yl)-N-(pyrrolidin-3-yl)acetamide;

(R)-2-(2-Chloro-5-isopropyl-8-oxothieno[2',3':4,5]pyrrolo[1,2-d][1,2,4]triazin-7(8H)-yl)-N-(pyrrolidin-3-yl)acetamide;

(R)-2-(2-Chloro-5-isopropyl-8-oxothieno[2',3':4,5]pyrrolo[1,2-d][1,2,4]triazin-7(8H)-yl)-N-(1-methylpyrrolidin-3-yl)acetamide;

(S)-2-(2-Chloro-5-isopropyl-8-oxothieno[2',3':4,5]pyrrolo[1,2-d][1,2,4]triazin-7(8H)-yl)-N-(1-methylpyrrolidin-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(pyrrolidin-3-yl)acetamide;

(S)-2-(2-Chloro-5-(2-hydroxypropan-2-yl)-8-oxothieno[2',3':4,5]pyrrolo[1,2-d][1,2,4]triazin-7(8H)-yl)-N-(pyrrolidin-3-yl)acetamide;

2-(2-Chloro-5-isopropyl-8-oxothieno[2',3':4,5]pyrrolo[1,2-d][1,2,4]triazin-7(8H)-yl)-N-((1 r,3r)-3-hydroxycyclobutyl)acetamide;

2-(2-Chloro-5-isopropyl-8-oxothieno[2',3':4,5]pyrrolo[1,2-d][1,2,4]triazin-7(8H)-yl)-N-((1s,3s)-3-hydroxycyclobutyl)acetamide;

2-(2-Chloro-5-isopropyl-8-oxothieno[2',3':4,5]pyrrolo[1,2-d][1,2,4]triazin-7(8H)-yl)-N-(2-(1-hydroxycyclopropyl)ethyl)acetamide;

2-(2-Chloro-5-isopropyl-8-oxothieno[2',3':4,5]pyrrolo[1,2-d][1,2,4]triazin-7(8H)-yl)-N-(1-(hydroxymethyl)cyclopropyl)acetamide;

2-(2-Chloro-5-isopropyl-8-oxothieno[2',3':4,5]pyrrolo[1,2-d][1,2,4]triazin-7(8H)-yl)-N-(6-(difluoromethyl)pyrimidin-4-yl)acetamide;

Methyl 3-(2-(2-chloro-5-isopropyl-8-oxothieno[2',3':4,5]pyrrolo[1,2-d][1,2,4]triazin-7(8H)-yl)acetamido)bicyclo[1.1.1]pentane-1-carboxylate;

2-(2-Chloro-5-isopropyl-8-oxothieno[2',3':4,5]pyrrolo[1,2-d][1,2,4]triazin-7(8H)-yl)-N-((1 S,3R,5S)-3-hydroxyadamantan-1-yl)acetamide;

N-(3-Aminobicyclo[1.1.1]pentan-1-yl)-2-(2-chloro-5-isopropyl-8-oxothieno[2',3':4,5]pyrrolo[1,2-d][1,2,4]triazin-7(8H)-yl)acetamide;

2-(2-Chloro-5-(2-hydroxypropan-2-yl)-8-oxothieno[2',3':4,5]pyrrolo[1,2-d][1,2,4]triazin-7(8H)-yl)-N-(3-(methylsulfonamido)phenyl)acetamide;

2-(2-Chloro-5-isopropyl-8-oxothieno[2',3':4,5]pyrrolo[1,2-d][1,2,4]triazin-7(8H)-yl)-N-(1,3,4-thiadiazol-2-yl)acetamide;

(1r,4r)-4-(2-(5-Isopropyl-2-methyl-8-oxothiazolo[5',4':4,5]pyrrolo[1,2-d][1,2,4]triazin-7(8H)-yl)acetamido)cyclohexane-1-carboxylic acid;

(1r,4r)-4-(2-(5-Isopropyl-8-oxothiazolo[5',4':4,5]pyrrolo[1,2-d][1,2,4]triazin-7(8H)-yl)acetamido)cyclohexane-1-carboxylic acid;

(1r,4r)-4-(2-(2-Fluoro-5-isopropyl-8-oxothieno[2',3':4,5]pyrrolo[1,2-d][1,2,4]triazin-7(8H)-yl)acetamido)cyclohexane-1-carboxylic acid;

(1r,4r)-4-(2-(2-Chloro-5-cyclopropyl-8-oxothieno[2',3':4,5]pyrrolo[1,2-d][1,2,4]triazin-7(8H)-yl)acetamido)cyclohexane-1-carboxylic acid;

(1r,4r)-4-(2-(2-Chloro-5-(2-hydroxypropan-2-yl)-8-oxothieno[2',3':4,5]pyrrolo[1 2-d][1,2,4]triazin-7(8H)-yl)acetamido)cyclohexane-1-carboxylic acid;

3-(2-(2-Chloro-5-isopropyl-8-oxothieno[2',3':4,5]pyrrolo[1,2-d][1,2,4]triazin-7(8H)-yl)acetamido)bicyclo[1.1.1]pentane-1-carboxylic acid;

(R)-2-(2-Chloro-5-isopropyl-8-oxothieno[2',3':4,5]pyrrolo[1,2-d][1,2,4]triazin-7(8H)-yl)-N-(1-cyclopropylpiperidin-3-yl)acetamide;

(R)-2-(2-Chloro-5-isopropyl-8-oxothieno[2',3':4,5]pyrrolo[1,2-d][1,2,4]triazin-7(8H)-yl)-N-(1-cyclobutylpiperidin-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-cyclopropylpiperidin-3-yl)acetamide;

(R)—N-(1-Cyclopropylpiperidin-3-yl)-2-(5-isopropyl-8-oxothiazolo[5',4':4,5]pyrrolo[1,2-d][1,2,4]triazin-7(8H)-yl)acetamide;

2-(2-Chloro-5-isopropyl-8-oxothieno[2',3':4,5]pyrrolo[1,2-d][1,2,4]triazin-7(8H)-yl)-N—((R)-1-((R)-2-hydroxypropyl)piperidin-3-yl)acetamide;

2-(2-Chloro-5-isopropyl-8-oxothieno[2',3':4,5]pyrrolo[1,2-d][1,2,4]triazin-7(8H)-yl)-N—((R)-1-((S)-2-hydroxypropyl)piperidin-3-yl)acetamide;

(R)-2-(2-Chloro-5-isopropyl-8-oxothieno[2',3':4,5]pyrrolo[1,2-d][1,2,4]triazin-7(8H)-yl)-N-(1-(2-hydroxy-2-methylpropyl)piperidin-3-yl)acetamide;

(R)-2-(2-Chloro-5-isopropyl-8-oxothieno[2',3':4,5]pyrrolo[1,2-d][1,2,4]triazin-7(8H)-yl)-N-(1-((1-hydroxycyclobutyl)methyl)piperidin-3-yl)acetamide;

(R)-2-(2-Chloro-5-(2-hydroxypropan-2-yl)-8-oxothieno[2',3':4,5]pyrrolo[1,2-d][1,2,4]triazin-7(8H)-yl)-N-(1-ethylpiperidin-3-yl)acetamide;

(R)-2-(2-Chloro-5-isopropyl-8-oxothieno[2',3':4,5]pyrrolo[1,2-d][1,2,4]triazin-7(8H)-yl)-N-(1-(2-hydroxyethyl)piperidin-3-yl)acetamide; and (R)-2-(2-Chloro-5-isopropyl-8-oxothieno[2',3':4,5]pyrrolo[1,2-d][1,2,4]triazin-7(8H)-yl)-N-(1-(cyclopropylmethyl)piperidin-3-yl)acetamide.

14. A pharmaceutical composition comprising a therapeutically effective amount of a compound according to claim 1, or a pharmaceutically acceptable salt thereof, and one or more pharmaceutically acceptable carriers.

15. A combination comprising a therapeutically effective amount of a compound according to claim 1, or a pharmaceutically acceptable salt thereof, and one or more therapeutic agents.

16. The combination according to claim 15, wherein one or more therapeutic agents are independently selected from farnesoid X receptor (FXR) agonists; anti-steatotics; anti-fibrotics; JAK inhibitors; checkpoint inhibitors; chemotherapy, radiation therapy and surgical procedures; urate-lowering therapies; anabolics and cartilage regenerative therapy; blockade of IL-17; complement inhibitors; Bruton's tyrosine Kinase inhibitors (BTK inhibitors); Toll Like receptor inhibitors (TLR7/8 inhibitors); CAR-T therapy; anti-hypertensive agents; cholesterol lowering agents; leukotriene A4 hydrolase (LTAH4) inhibitors; SGLT2 inhibitors; β2-agonists; anti-inflammatory agents; nonsteroidal anti-inflammatory drugs ("NSAIDs"); acetylsalicylic acid drugs (ASA); regenerative therapy treatments; cystic fibrosis treatments; and atherosclerotic treatment.

17. A method of treating a disease or disorder in which NLRP3 signaling contributes to the pathology, and/or symptoms, and/or progression, of said disease or disorder, comprising administering a therapeutically effective amount of a compound according to claim 1, or a pharmaceutically acceptable salt thereof.

18. The method of treating according to claim 17, wherein the disease or disorder is selected from inflammasome-related diseases/disorders, immune diseases, inflammatory diseases, auto-immune diseases, or auto-inflammatory diseases, liver related diseases/disorders, inflammatory arthritis related disorders kidney related diseases, neuroinflammation-related diseases, cardiovascular/metabolic diseases/disorders, inflammatory skin diseases, wound healing and scar formation, asthma, sarcoidosis, age-related macular degeneration, and cancer related diseases/disorders.

19. A method of inhibiting the NLRP3 inflammasome activity in a subject in need thereof, the method comprising administering to a subject in need thereof a therapeutically effective amount of a compound according to claim 1, or a pharmaceutically acceptable salt thereof.

* * * * *